US009132182B2

(12) United States Patent
Zlotnick et al.

(10) Patent No.: US 9,132,182 B2
(45) **Date of Patent: *Sep. 15, 2015**

(54) IMMUNOGENIC COMPOSITIONS FOR THE PREVENTION AND TREATMENT OF MENINGOCOCCAL DISEASE

(75) Inventors: Gary W. Zlotnick, New Windsor, NY (US); Leah Diane Fletcher, Geneseo, NY (US); John Erwin Farley, Chapel Hill, NC (US); Liesel A. Bernfield, Pittsford, NY (US); Robert J. Zagursky, Victor, NY (US); Benjamin J. Metcalf, Rochester, NY (US)

(73) Assignee: Wyeth Holdings LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/455,268

(22) Filed: Apr. 25, 2012

(65) Prior Publication Data

US 2012/0294880 A1 Nov. 22, 2012

Related U.S. Application Data

(60) Continuation of application No. 13/333,123, filed on Dec. 21, 2011, now Pat. No. 8,563,006, which is a division of application No. 10/492,427, filed as application No. PCT/US02/32369 on Oct. 11, 2002, now Pat. No. 8,101,194.

(60) Provisional application No. 60/328,101, filed on Oct. 11, 2001, provisional application No. 60/406,934, filed on Aug. 30, 2002.

(51) Int. Cl.

| | |
|---|---|
| ***A61K 39/095*** | (2006.01) |
| ***A61P 37/04*** | (2006.01) |
| ***C07K 14/22*** | (2006.01) |
| ***C07K 16/12*** | (2006.01) |
| ***G01N 33/569*** | (2006.01) |
| ***C12N 9/28*** | (2006.01) |
| ***C12N 9/40*** | (2006.01) |
| ***C12N 9/38*** | (2006.01) |
| *A61K 39/00* | (2006.01) |

(52) U.S. Cl.

CPC ............... *A61K 39/095* (2013.01); *C07K 14/22* (2013.01); *C07K 16/1217* (2013.01); *C12N 9/2417* (2013.01); *C12N 9/2465* (2013.01); *C12N 9/2471* (2013.01); *G01N 33/56911* (2013.01); *A61K 39/00* (2013.01); *A61K 2039/505* (2013.01); *A61K 2039/53* (2013.01); *A61K 2039/55577* (2013.01); *G01N 2333/22* (2013.01); *Y10S 530/825* (2013.01)

(58) Field of Classification Search

None

See application file for complete search history.

(56) References Cited

U.S. PATENT DOCUMENTS

| | | | |
|---|---|---|---|
| 4,376,110 | A | 3/1983 | David et al. |
| 4,554,101 | A | 11/1985 | Hopp |
| 4,650,764 | A | 3/1987 | Temin et al. |
| 4,666,829 | A | 5/1987 | Glenner et al. |
| 4,797,368 | A | 1/1989 | Carter et al. |
| 4,861,719 | A | 8/1989 | Miller |
| 4,912,094 | A | 3/1990 | Myers et al. |
| 4,925,792 | A | 5/1990 | Rappuoli |
| 4,980,289 | A | 12/1990 | Temin et al. |
| 5,057,540 | A | 10/1991 | Kensil et al. |
| 5,078,996 | A | 1/1992 | Conlon, III et al. |
| 5,124,263 | A | 6/1992 | Temin et al. |
| 5,139,941 | A | 8/1992 | Muzyczka et al. |
| 5,254,339 | A | 10/1993 | Morein |
| 5,399,346 | A | 3/1995 | Anderson et al. |
| 5,459,127 | A | 10/1995 | Felgner et al. |
| 5,514,581 | A | 5/1996 | Ferrari et al. |
| 5,550,213 | A | 8/1996 | Anderson et al. |
| 5,565,204 | A | 10/1996 | Kuo et al. |
| 5,580,859 | A | 12/1996 | Felgner et al. |
| 5,583,038 | A | 12/1996 | Stover |
| 5,589,466 | A | 12/1996 | Felgner et al. |
| 5,614,382 | A | 3/1997 | Metcalf |
| 5,668,004 | A | 9/1997 | O'Donnell |
| 5,723,127 | A | 3/1998 | Scott et al. |
| 5,739,118 | A | 4/1998 | Carrano et al. |
| 5,955,580 | A | 9/1999 | Green et al. |
| 6,113,918 | A | 9/2000 | Johnson et al. |
| 6,130,085 | A | 10/2000 | Hamers et al. |

(Continued)

FOREIGN PATENT DOCUMENTS

| | | |
|---|---|---|
| CA | 2012311 C | 6/2003 |
| EP | 0125023 B1 | 11/1984 |

(Continued)

OTHER PUBLICATIONS

GenBank No. EF108319.1, O'Leary, M. M. et al., *Neisseria meningitidis* strain NM452 FHBP/GNA1870 variant (GNA1870) gene, complete cds, Nov. 8, 2006, accessed Sep. 5, 2012.

*Neisseria gonorrhoeae* FA 1090 chromosome Entire clone gono strain FA1090, complete sequence. GenBank Accession gono AE004969, 2153894 bp, Sep. 26, 2000.

Pannekoek et al, "Construction of recombinant neisserial Hsp60 proteins and mapping of antigenic domains", Molecular Microbiology 15(2):277-285 (1995).

(Continued)

*Primary Examiner* — S. Devi

(74) *Attorney, Agent, or Firm* — Anna C. Chau

(57) ABSTRACT

The present invention relates to *Neisseria* ORF2086 proteins, crossreactive immunogenic proteins which can be isolated from nesserial strains or prepared recombinantly, including immunogenic portions thereof, biological equivalents thereof, antibodies that immunospecifically bind to the foregoing and nucleic acid sequences encoding each of the foregoing, as well as the use of same in immunogenic compositions that are effective against infection by *Neisseria meningitidis* serogroup B.

14 Claims, 20 Drawing Sheets

(56) References Cited

U.S. PATENT DOCUMENTS

| | | | |
|---|---|---|---|
| 6,207,646 B1 | 3/2001 | Krieg et al. | |
| 6,245,892 B1 | 6/2001 | Oaks et al. | |
| 6,270,775 B1 | 8/2001 | Cleary | |
| 6,355,253 B1 | 3/2002 | Zlotnick | |
| 6,355,255 B1 | 3/2002 | Cleary et al. | |
| 6,951,653 B2 | 10/2005 | Cleary et al. | |
| 7,118,757 B1 | 10/2006 | Seid et al. | |
| 7,576,176 B1 | 8/2009 | Fraser et al. | |
| 7,785,608 B2 | 8/2010 | Zlotnick et al. | |
| 7,803,387 B2 | 9/2010 | Arico et al. | |
| 8,039,007 B2 | 10/2011 | Rappuoli et al. | |
| 8,101,194 B2 | 1/2012 | Zlotnick et al. | |
| 8,273,360 B2 | 9/2012 | Pizza et al. | |
| 8,398,988 B2 | 3/2013 | Contorni et al. | |
| 2004/0110670 A1 | 6/2004 | Arico et al. | |
| 2004/0249125 A1 | 12/2004 | Pizza et al. | |
| 2006/0251670 A1 | 11/2006 | Comanducci et al. | |
| 2007/0020622 A1 | 1/2007 | Lee et al. | |
| 2007/0148729 A1* | 6/2007 | Farley et al. | 435/69.1 |
| 2009/0035328 A1 | 2/2009 | Granoff | |
| 2009/0202593 A1 | 8/2009 | Zlotnick et al. | |
| 2011/0076299 A1 | 3/2011 | Zlotnick et al. | |
| 2011/0189187 A1 | 8/2011 | Zlotnick | |
| 2012/0034261 A1 | 2/2012 | Zlotnick et al. | |
| 2012/0093852 A1 | 4/2012 | Anderson et al. | |
| 2012/0107339 A1* | 5/2012 | Granoff et al. | 424/190.1 |

FOREIGN PATENT DOCUMENTS

| | | | |
|---|---|---|---|
| EP | 0171496 | B1 | 2/1986 |
| EP | 0173494 | A2 | 3/1986 |
| EP | 0178220 | A2 | 4/1986 |
| EP | 0184187 | A2 | 6/1986 |
| EP | 0185573 | B1 | 6/1986 |
| EP | 0453242 | A1 | 10/1991 |
| EP | 0467714 | A1 | 1/1992 |
| EP | 0488528 | A1 | 6/1992 |
| EP | 1296713 | B1 | 9/2003 |
| EP | 1326634 | B1 | 4/2006 |
| EP | 2351767 | A2 | 8/2011 |
| JP | 1144977 | A | 6/1989 |
| WO | WO 86/01533 | A1 | 3/1986 |
| WO | WO 87/01130 | | 2/1987 |
| WO | WO 87/02671 | A1 | 5/1987 |
| WO | WO 89/07150 | A1 | 8/1989 |
| WO | WO 90/02806 | A1 | 3/1990 |
| WO | 9010458 | | 9/1990 |
| WO | WO 91/18088 | A1 | 11/1991 |
| WO | WO 92/05263 | A1 | 4/1992 |
| WO | WO 92/19265 | | 11/1992 |
| WO | WO 93/09239 | A1 | 5/1993 |
| WO | WO 94/12649 | A2 | 6/1994 |
| WO | WO 94/21807 | A2 | 9/1994 |
| WO | WO 94/26914 | A1 | 11/1994 |
| WO | WO 94/28152 | A1 | 12/1994 |
| WO | WO 94/28938 | A1 | 12/1994 |
| WO | WO 95/02697 | A1 | 1/1995 |
| WO | WO 95/07358 | A1 | 3/1995 |
| WO | WO 95/18863 | A1 | 7/1995 |
| WO | WO 95/21931 | A1 | 8/1995 |
| WO | WO 95/22617 | A1 | 8/1995 |
| WO | WO 95/26411 | A2 | 10/1995 |
| WO | WO 95/28494 | A1 | 10/1995 |
| WO | WO 96/10038 | A1 | 4/1996 |
| WO | 96/14086 | A1 | 5/1996 |
| WO | WO 96/17823 | A1 | 6/1996 |
| WO | WO 96/22378 | A1 | 7/1996 |
| WO | WO 96/25508 | A1 | 8/1996 |
| WO | 9629412 | | 9/1996 |
| WO | 9640718 | | 12/1996 |
| WO | WO 96/39036 | A1 | 12/1996 |
| WO | WO 97/19182 | A1 | 5/1997 |
| WO | 98/08543 | A1 | 3/1998 |
| WO | 98/08874 | A1 | 3/1998 |
| WO | 9817805 | | 4/1998 |
| WO | WO 99/01157 | A1 | 1/1999 |
| WO | WO 99/01158 | A1 | 1/1999 |
| WO | WO 99/01175 | A1 | 1/1999 |
| WO | 99/10372 | A1 | 3/1999 |
| WO | WO 99/24578 | | 5/1999 |
| WO | WO 99/27944 | | 6/1999 |
| WO | 99/36544 | A2 | 7/1999 |
| WO | 9940200 | | 8/1999 |
| WO | 99/48525 | A1 | 9/1999 |
| WO | 99/55730 | A2 | 11/1999 |
| WO | 9955872 | | 11/1999 |
| WO | WO 99/57280 | | 11/1999 |
| WO | 99/61053 | A1 | 12/1999 |
| WO | WO 00/18434 | A1 | 4/2000 |
| WO | WO 00/22430 | | 4/2000 |
| WO | 0042192 | | 7/2000 |
| WO | 0043518 | | 7/2000 |
| WO | 00/45841 | A2 | 8/2000 |
| WO | 00/50075 | A2 | 8/2000 |
| WO | WO 00/44890 | A1 | 8/2000 |
| WO | 00/57906 | A1 | 10/2000 |
| WO | 00/66741 | A2 | 11/2000 |
| WO | 00/71574 | A2 | 11/2000 |
| WO | 0071725 | A2 | 11/2000 |
| WO | WO 00/66791 | | 11/2000 |
| WO | 01/04316 | A2 | 1/2001 |
| WO | 01/31019 | A2 | 5/2001 |
| WO | 01/38350 | A2 | 5/2001 |
| WO | 0137863 | A2 | 5/2001 |
| WO | 01/41800 | A2 | 6/2001 |
| WO | 01/52885 | A1 | 7/2001 |
| WO | WO 01/64920 | A2 | 9/2001 |
| WO | WO 01/64922 | A2 | 9/2001 |
| WO | 02/058737 | A2 | 8/2002 |
| WO | 02/083710 | A2 | 10/2002 |
| WO | 02/083711 | A2 | 10/2002 |
| WO | 02079246 | A2 | 10/2002 |
| WO | WO 02/079243 | A2 | 10/2002 |
| WO | WO 02/098368 | A2 | 12/2002 |
| WO | WO 02/098369 | A2 | 12/2002 |
| WO | 03/007985 | A2 | 1/2003 |
| WO | 03/009869 | A1 | 2/2003 |
| WO | WO 03/020756 | A2 | 3/2003 |
| WO | WO 03/063766 | A2 | 8/2003 |
| WO | 2004032958 | A1 | 4/2004 |
| WO | 2004048404 | A2 | 6/2004 |
| WO | 2004/065603 | A2 | 8/2004 |
| WO | 2004067030 | A2 | 8/2004 |
| WO | WO 2004/083251 | A2 | 9/2004 |
| WO | WO 2004/094596 | A2 | 11/2004 |
| WO | WO 2005/108580 | A1 | 11/2005 |
| WO | 2006024954 | A2 | 3/2006 |
| WO | 2006/081259 | A2 | 8/2006 |
| WO | 2007060548 | A2 | 5/2007 |
| WO | 2008001224 | A2 | 1/2008 |
| WO | 2009/050586 | A1 | 4/2009 |
| WO | 2009/104097 | A2 | 8/2009 |
| WO | 2009/158142 | A1 | 12/2009 |
| WO | 2010/109323 | A1 | 9/2010 |
| WO | 2011/161653 | A1 | 12/2011 |

OTHER PUBLICATIONS

Poolman et al, "Colony variants of *Neisseria meningitidis* strain 2996 (B-2b:P1.2): influence of class-5 outer membrane proteins and lipopolysaccharides", J Med Microbiol 19(2):203-209 (1985).

Bantam Medical Dictionary, Third Edition, p. 302, 2000.

Biocomputing: Informatics and Genome Projects, Smith, D. W., ed., Academic Press, New York, 1993.

BLAST Manual, Altschul, S., et al., NCBI NLM NIH Bethesda, Md. 20894, 1990.

Computer Analysis of Sequence Data, Part I, Griffin, A. M., and Griffin, H. G., eds., Humana Press, New Jersey, 1994.

Current Protocols in Molecular Biology, 1995, F.M. Ausubel et al., eds., John Wiley & Sons, Inc., sections 2.10 and 6.3-6.4.

Database Geneseq 'Online' "*N. gonorrhoeae* amino acid sequence SEQ ID 1586", XP002320505, Mar. 7, 2003.

(56) References Cited

OTHER PUBLICATIONS

Database Geneseq 'Online' "*Neisseria meningitidis* ORF 741 protein sequence SEQ ID 2536", XP002320506, Mar. 21, 2000.
Database Geneseq 'Online' "*Neisseria meningitidis* ORF 741 protein sequence SEQ ID 2534", XP002320504, Mar. 21, 2000.
Database UniProt 'Online', "Hypothetical Protein NMB1870", XP00230811, Oct. 1, 2000.
Database UniProt 'Online', "Putative lipoprotein *N meningitidis* (Serotype A)", XP003220503, Oct. 1, 2000.
Database Geneseq Online Jan. 29, 2004, "*Neisseria meningitides* ORF2086 protein-encoding gene SeqID61", (AAY75530 and AAZ54292-NT).
Gribskov, M. and Devereux, J., eds. *Sequence Analysis Primer*, Stockton Press, New York, 1991.
The Illustrated *Steadman's Medical Dictionary*, 24th Edition, Williams & Wilkins, Baltimore, p. 707, 1982.
Lesk, A. M., ed. *Computational Molecular Biology*, Oxford University Press, New York, 1988.
CDC, MMWR (Morbidity and Mortality Weekly Report), Case Definitions for Infectious Conditions Udner Public Health Surveillance, Recommendations and Reports, May 2, 1997, vol. 46., No. RR-10.
The Random House Dictionary, Random House, New York, p. 546, 1984.
Sambrook, J., E.F. Fritsch, and T. Maniatis, 1989, Molecular Cloning: A Laboratory Manual, Cold Spring Harbor Laboratory Press, Cold Spring Harbor, NY, chapters 9 and 11.
Sambrook, J. and D. W. Russell. Current Protocols in Molecular Biology. John Wiley & Sons, Inc., New York (1995).
Sambrook, J. et al. 2001. Molecular cloning a laboratory manual, Third ed, vol. 3. Cold Spring Harbor Laboratory Press, Cold Spring Harbor, New York.
Sanger Centre FTP files [online], [retrieved on May 16, 2003]. Retieved from the Internet<URL:ftp://ftp.sanger.ac.uk/pub/pathogens/nm/.
Sequence Analysis in Molecular Biology, von Heinje, G., Academic Press, 1987.
University of Oklahoma *Neisseria gonorrhoeae* genome [online], [retrieved Mar. 25, 2005]. Retrieved from the Internet<URL:http://dna1.chem.ou.edu/gono.html.
The Webster's II *New Riverside University Dictionary*, The Riverside Publishing Company, p. 933, 1984.
Achtman, Mark "Epidemic spread and antigenic variability of *Neisseria meningitidis*," 1995, Trends in Microbiology, vol. 3(5), pp. 186-192.
Ambrosch, F. et al., "Immunogenicity and side-effects of a new tetravalent meningococcal polysaccharide vaccine," 1983, Bulletin of the World Health Organization, vol. 61(2), pp. 317-323.
Abdillahi, Hussein and Poolman, Jan T., Whole-cell ELISA for typing *Neisseria meningitides* with monoclonal antibodies, 1987, FEMS Microbiology Letters, vol. 48, pp. 367-371.
Abdillahi, Hussein and Poolman, Jan T., "*Neisseria meningitides* group B serosubtyping using monoclonal antibodies in whole-cell Elisa," 1988, Microbial Pathogenesis, vol. 4(1), pp. 27-32.
Alm, R. A., et al., "Genomic-sequence comparison of two unrelated isolates of the human gastric pathogen *Helicobacter pylori*," [published erratum appears in Nature Feb. 25, 1999;397(6721):719], 1999, Nature, vol. 397, pp. 176-180.
Altschul, S. F. et al., "Basic local alignment search tool," 1990, Journal of Molecular Biology, vol. 215, pp. 403-410.
Altschul, S. F. et al., "Protein database searches for multiple alignments," Jul. 1990, Proceedings of the National Academy Science, vol. 87, pp. 5509-5513.
Altschul, S. F. et al., "Gapped BLAST and PSI-BLAST: a new generation of protein database search programs," 1997, Nucleic Acids Research, vol. 25, pp. 3389-3402.
Anderson, T. F., "Techniques for the preservation of three-dimensional structure in preparing specimens for the electron microscope," 1951, Transactions of the N.Y. Academy Sciences, vol. 13, pp. 130-134.
Bateman, A. T., "The Pfam protein families database," 2000, Nucleic Acids Research, vol. 28, pp. 263-266.
Barbour, A.G., et al., "New Tricks of Tick-Borne Pathogen", Nature, vol. 390, pp. 553 & 555 (1997).
Beard, Clayton W. et al., "Transcription Mapping of Mouse Adenovirus Type 1 Early Region 3," 1990, Virology, vol. 75, pp. 81-90.
Beuvery, E. Coen et al., "Preparation and Physicochemical and Immunological Characterization of Polysaccharide-Outer Membrane Protein Complexes of *Neisseria meningitidis*," 1983, Infection and Immunity, vol. 40, pp. 369-380.
Bender, Michael A. et al., "Evidence that the Packaging Signal of Moloney Murine Leukemia Virus Extends into the *gag* Region," 1987, Journal of Virology, vol. 61, pp. 1639-1646.
Benson, Gary, "Tandem repeats finder: a program to analyze DNA sequences," 1999, Nucleic Acids Research, vol. 27, pp. 573-580.
Bernstein, Alan et al., "Gene Transfer With Retrovirus Vectors," 1985, Genet. Eng., vol. 7, pp. 235-281.
Better, Marc et al., *Escherichia coli* Secretion of an Active Chimeric Antibody Fragment, 1988, Science, vol. 240, pp. 1041-1043.
Boulianne, Gabrielle L. et al., "Production of functional chimaeric mouse/human antibody," 1984, Nature, vol. 312, pp. 643-646.
Cabilly, Shmuel et al., "Generation of antibody activity from immunoglobulin polypeptide chains produced in *Escherichia coli*," 1984, Proceedings of the National Academy of Science USA, vol. 81, pp. 3273-3277.
Carillo, H., and Lipman, D., "The Multiple Sequence alignment Problem in Biology," 1988, SIAM Journal of Applied Math, vol. 48, pp. 1073-1082.
Chao, et al., "Endocarditis due to *Neisseria sicca*: Report of One Case," 1997, Dept. of Pediatrics, Chang Gung Children's Hospital, vol. 38, pp. 229-231.
Chen, C. C. et al., "Cloning and expression of the streptococcal C5a peptidase gene in *Escherichia coli*: linkage to the type 12 M protein gene," 1989, Infection and Immunity, vol. 57, pp. 1740-1745.
Chmouryguina, Ilona, A. et al., "Conservation of the C5a peptidase genes in group A and B streptococci," 1996, Infection and Immunity, vol. 64, pp. 2387-2390.
Cockerill, F. R., III et al., "Molecular, serological, and clinical features of 16 consecutive cases of invasive streptococcal disease," Southeastern Minnesota Streptococcal Working Group, 1998, Clinical Infectious Diseases, vol. 26, pp. 1448-1458.
Courtney, Harry S. et al., "Cloning, sequencing, and expression of a fibronectin/fibrinogen-binding protein from group A streptococci," 1994, Infection and Immunity, vol. 62, pp. 3937-3946.
Cserzo, M. et al., "Prediction of transmembrane alpha-helices in prokaryotic membrane proteins: the dense alignment surface method," 1997, Protein Engineering, vol. 10, pp. 673-676.
Cunningham, Madeleine W. and Quinn, Anthony, "Immunological crossreactivity between the class I epitope of streptococcal M protein and myosin," 1997, Adv. Exp. Med. Biol., vol. 418, pp. 887-892.
Curiel, David T. et al., "High-Efficiency Gene Transfer Mediated by Adenovirus Coupled to DNA-Polylysine Complexes," 1992, Human Gene Therapy, vol. 3, pp. 147-154.
Dale, James B. et al., "Passive protection of mice against group A streptococcal pharyngeal infection by lipoteichoic acid," 1994, Journal of Infectious Diseases, vol. 169, pp. 319-323.
Dale, James B. et al., "Recombinant, octavalent group A streptococcal M protein vaccine," 1996, Vaccine, vol. 14, pp. 944-948.
Dale, James B. et al., "Hyaluronate capsule and surface M protein in resistance to opsonization of group A streptococci," 1996, Infection and Immunity, vol. 64, pp. 1495-1501.
De, B. K. et al., "Purification and characterization of *Streptococcus pneumoniae* palmitoylated pneumococcal surface adhesin A expressed in *Escherichia coli*," 2000, Vaccine, Mar. 6; vol. 18(17), pp. 1811-1821.
Devereux, J. et al., "A comprehensive set of sequence analysis programs for the VAX," 1984, Nucleic Acids Research, vol. 12(1), p. 387.
Eddy, Sean R., "Hidden Markov models," 1996, Current Opinion in Structural Biology, vol. 6, pp. 361-365.
Ellen, R. P. and Gibbons R. J., "M protein-associated adherence of *Streptococcus pyogenes* to epithelial surfaces: prerequisite for virulence," 1972, Infection and Immunity, vol. 5, pp. 826-830.

(56) References Cited

OTHER PUBLICATIONS

Ellis, R. W., "New Technologies for Making Vaccines," 1988, Vaccines, (eds) Plotkin et al.; W.B. Sauders Company, Philadephia, Chapter 29, pp. 568-575.
Eng, Jimmy K. et al., "An approach to correlate tandem mass-spectral data of peptides with amino-acid-sequences in a protein database," 1994, American Society for Mass Spectrometry, vol. 5, pp. 976-989.
Erdile, Lorne F. et al., "Role of attached lipid in immunogenicity of *Borrelia burgdorferi* OspA.," Jan. 1993, Infection and Immunity, vol. 61(1), pp. 81-90.
Feigner, Philip L. et al., "Lipofection: A highly efficient, lipid-mediated DNA-transfection procedure," 1987, Proceedings of the National Academy of Science U.S.A., vol. 84, pp. 7413-7417.
Feigner, P. L. and Ringold, G. M., "Cationic liposome-mediated transfection," Nature Science, 1989, vol. 337, pp. 387-388.
Fletcher, et al., "Vaccine Potential of the *Neisseria meningitidis* 2086 Lipoprotein," 2004, Infection and Immunity, vol. 72, No. 4, pp. 2088-2100.
Fischetti, V. A. et al., "Conservation of a hexapeptide sequence in the anchor region of surface proteins from gram-positive cocci," 1990, Journal of Microbiology, vol. 4, pp. 1603-1605.
Fogg, G. C. et al., "Constitutive expression of fibronectin binding in *Streptococcus pyogenes* as a result of anaerobic activation of *rofA*," 1997, Journal Bacteriol. vol. 179, pp. 6172-6180.
Foster, Timothy J. and Hook, Magnus, "Surface protein adhesins of *Staphylococcus aureus*,"1998, Trends in Microbiology, vol. 6, pp. 484-488.
Fraser, Claire M. et al., "Genomic sequence of a Lyme disease spirochaete, *Borrelia burgdorferi*," 1997, Nature, vol. 390, pp. 580-586.
Gentz, Reiner et al., "Bioassay for trans-activation using purified human immunodeficiency virus *tat*-encoded protein: trans-activation requires mRNA synthesis," 1989, Proceedings of the National Academy of Science, vol. 86, pp. 821-824.
Goldschneider, Irving et al., "Human immunity to the *meningococcus*. I. The role of humoral antibodies," 1969, Journal of Experimental Medicine, vol. 129(6), pp. 1307-1326.
Goldschneider, Irving et al., Human immunity to the *meningococcus*. II. Development of natural immunity, 1969, Journal of Experimental Medicine, vol. 129(6), pp. 1327-1348.
Gomez et al., Nucleotide the *Bacillus subtilis* lipoprotein LplA causes cell lysis when expressed in *Escherichia coli*, Aug. 1994, Microbiology, vol. 140 (Pt 8), pp. 1839-1845.
Gotschlich, E. C. et al., "Human immunity to the *meningococcus*. IV. Immunogenicity of group A and group C meningococcal polysaccharides in human volunteers," 1969, Journal of Experimental Medicine, vol. 129(6), pp. 1367-1384.
Gotschlich, E. C. et al., "Human immunity to the *meningococcus*. V. The effect of immunization with meningococcal group C polysaccharide on the carrier state," 1969, Journal of Experimental Medicine, vol. 129(6), pp. 1385-1395.
Graham, F. L., "Covalently closed circles of human adenovirus DNA are infectious," 1984, EMBO Journal, vol. 3, pp. 2917-2922.
Graham, F. L. et al., "Characteristics of a Human Cell Line Transformed by DNA from Human Adenovirus Type 5," 1977, Journal Gen. Virology, vol. 36, pp. 59-72.
Green, B. A. et al., "The *e* (P4) Outer Membrane Protein of *Haemophilus influenzae*: Biologic Activity of Anti-*e* Serum and Cloning and Sequencing of the Structural Gene," 1991, Infection and Immunity, vol. 59, pp. 3191-3198.
Greenspan, et al., "Defining epitopes: It's not as easy as it seems", Nature Biotechnology, 17:936-937 (1999).
Guzman, L-M et al., "Tight Regulation, Modulation, and High-Level Expression by Vectors Containing the Arabinose $P_{BAD}$ Promoter," 1995, Journal of Bacteriology, vol. 177, pp. 4121-4130.
Hacker, J. et al., Pathogenicity islands of virulent bacteria: structure, function and impact on microbial evolution. 1997, Mol Microbiol., vol. 23, pp. 1089-1097.
Hanski, E. et al., "Expression of protein F, the fibronectin-binding protein of *Streptococcus pyogenes* JRS4, in heterologous streptococcal and enterococcal strains promotes their adherence to respiratory epithelial cells," 1992, Infect Immun., vol. 60, pp. 5119-5125.
Hanski, E. et al. Protein F, a fibronectin-binding protein, is an adhesion of the group A streptococcus *Streptococcus pyogenes*, 1992, Proceedings of the National Academy of Science USA, vol. 89, pp. 6172-6176.
Hansson et al., "Expression of truncated and full-length forms of the Lyme disease *Borrelia* outer surface protein A in *Escherichia coli*," Feb. 1995, Protein Expr. Purif., vol. 6(1), pp. 15-24.
Hayashi et al., "Lipoproteins in bacteria," Jun. 1990, J. Bioenerg. Biomembr.; vol. 22(3), pp. 451-471.
Hernandez-Sanchez, J. et al., "lambda bar minigene-mediated inhibition of protein synthesis involves accumulation of peptidyl-tRNA and starvation for tRNA" 1998, EMBO Journal, vol. 17, pp. 3758-3765.
Hornyik, Galina et al., "Cerebrospinal Fluid Shunt Infection by *Neisseria sicca*", 1994, Petidatri. Neurosurg., vol. 21, pp. 189-191.
Huang, T. T. et al., "The streptokinase gene of group A streptococci: cloning, expression in *Escherichia coli*, and sequence analysis," 1989, Mol Microbiol., vol. 3, pp. 197-205.
Hynes, W. L. et al., "Analysis of a second bacteriophage hyaluronidase gene from *Streptococcus pyogenes*: evidence for a third hyaluronidase involved in extracellular enzymatic activity," 1995, Infect Immun., vol. 63, pp. 3015-3020.
Hynes, W. L. et al. 2000. The extracellular hyaluronidase gene (*hylA*) of *Streptococcus pyogenes*. FEMS Microbiol Letters, vol. 184, pp. 109-112.
Isberg, R. R. et al., "Binding and internalization of microorganisms by integrin receptors," 1994, Trends Microbio., vol. 2: pp. 10-14.
Jones, K. F. et al., "The importance of the location of antibody binding on the M6 protein for opsonization and phagocytosis of group A M6 streptococci," 1988, Journal of Exp Med., vol. 167, pp. 1114-1123.
Kafri, Tal et al., "A Packaging Cell Line for Lentivirus Vectors," 1999, Journal of Virology, vol. 73, pp. 576-584.
Kaplitt, Michael G. et al., "Expression of a Functional Goreign Gene in Adult Mammalian Brain following in Vivo Transfer via a Herpes Simplex Virus type 1 Defective Viral Vector," 1991, Molecular and Cellular Neurosciences, vol. 2, pp. 320-330.
Kihlberg, B. M. et al. "Protein H, an antiphagocytic surface protein in *Streptococcus pyogenes*," 1999, Infection and Immunity, vol. 67, pp. 1708-1714.
Klein et al., "Distinctive properties of signal sequences from bacterial lipoproteins," Apr. 1988, Protein Engineering, vol. 2(1), pp. 15-20.
Koebnik, R., "Proposal for a peptidoglycan-associating alpha-helical motif in the C-terminal regions of some bacterial cell-surface proteins," [letter; comment], 1995, Molecular Microbiology, vol. 16, pp. 1269-1270.
Kohler and Milstein, "Continuous cultures of fused cells secreting antibody of predefined specificity" 1975, Nature, vol. 256, pp. 495-497.
Kuipers, O. P., et al., "Improved site-directed mutagenesis method using PCR," 1991, Nucleic Acids Research, vol. 19, p. 4558.
Kuo, Ming-Ling et al., "Efficient Gene Transfer Into Primary Murine Lymphocytes Obviating the Need for Drug Selection," 1993, Blood, vol. 82, pp. 845-852.
Kyte, J. et al., "A simple method for displaying the hydropathic character of a protein," 1982, Journal of Molecular Biology, vol. 157, pp. 105-132.
Landt, O. et al., "A general method for rapid site-directed mutagenesis using the polymerase chain reaction," 1990, Gene, vol. 96, pp. 125-128.
La Salle, G. Le Gal et al., "An Adenovirus Vector for Gene Transfer into Neurons and Glia in the Brain," 1993, Science, vol. 259, pp. 988-990.
Lebkowski, Jane S. et al., Adeno-Associated Virus: a Vector System for Efficient Introduction and Integration of DNA into a Variety of Mammalian Cell Types, 1988, Molecular and Cellular Biology, vol. 8, pp. 3988-3996.
Levrero, Massimo et al., "Defective and nondefective adenovirus vectors for expressing foreign genes in vitro and in vivo," 1991, Gene, vol. 101, pp. 195-202.

(56) References Cited

OTHER PUBLICATIONS

Liu, Alvin Y. et al., "Chimeric mouse-human IgG1 antibody that can mediate lysis of cancer cells," 1987, Proceedings of the National Academy of Science USA, vol. 84, pp. 3439-3443.
Loessner, Martin J. et al, "Evidence for a holin-like protein gene fully embedded out of frame in the endolysin gene of *Staphylococcus aureus* bacteriophage 187," Journal of Bacteriology, vol. 181, pp. 4452-4460.
Lukashin, A. V. et al., "GeneMark.hmm: new solutions for gene finding," 1998, Nucleic Acids Research, vol. 26, pp. 1107-1115.
Lukomski, S. et al., "Extracellular cysteine protease produced by *Streptococcus pyogenes* participates in the pathogenesis of invasive skin infection and dissemination in mice," 1999, Infection and Immunity, vol. 67, pp. 1779-1788.
Lunn et al., "Effects of prolipoprotein signal peptide mutations on secretion of hybrid prolipo-beta-lactamase in *Escherichia coli*," Jun. 15, 1987, Journal Biol. Chem., vol. 262(17), pp. 8318-8324.
Machy, Patrick et al., "Gene transfer from targeted liposomes to specific lymphoid cells by electroporation," 1988, Proceedings of the National Academy of Science U.S.A., vol. 85, pp. 8027-8031.
Madore, Dace V., "Characterization of immune response as an indicator of *Haemophilus influenzae* type b vaccine efficacy," 1998, Pediatric Infectious Disease Journal, vol. 17, pp. S207-S210.
Mann, Richard et al., "Construction of a Retrovirus Packaging Mutant and Its Use to Produce Helper-Free Defective Retrovirus," 1983, Cell, vol. 33, pp. 153-159.
Markowitz, Dina et al., "A Safe Packaging Line for Gene Transfer: Separating Viral Genes on Two Different Plasmids," 1988, Journal of Virology, vol. 62, pp. 1120-1124.
Martin et al., "Highly Conserved *Neisseria meningitidis* Surface Protein Confers Protection Against Experimental Injection," 1985, Journal of Experimental Medicine, vol. 185, No. 7, pp. 1173-1183.
Matsuka, Yury V. et al., "Fibrinogen cleavage by the *Streptococcus pyogenes* extracellular cysteine protease and generation of antibodies that inhibit enzyme proteolytic activity," 1999, Infection and Immunity, vol. 67, pp. 4326-4333.
Mazmanian, S. K. et al., "*Staphylococcus aureus* sortase, an enzyme that anchors surface proteins to the cell wall," 1999, Science, vol. 285, pp. 760-763.
McAtee, C. P. et al., "Identification of potential diagnostic and vaccine candidates of *Helicobacter pylori* by "proteome" technologies," 1998, Helicobacter., vol. 3, pp. 163-169.
McAtee, C. P. et al., "Identification of potential diagnostic and vaccine candidates of *Helicobacter pylori* by two-dimensional gel electrophoresis, sequence analysis, and serum profiling," 1998, Clinical Diagnosis Lab Immunol., vol. 5, pp. 537-542.
McAtee, C. P. et al., "Characterization of a *Helicobacter pylori* vaccine candidate by proteome techniques," 1998, Journal Chromatogr B Biomed Sci Appl., vol. 714, pp. 325-333.
McCormick, Douglas, "Human Gene Therapy: The First Round," 1985, BioTechnology, vol. 3, pp. 689-693.
McGuiness, et al., Mol. Microbiol. 7:505-514 (1993).
Mejlhede, N. et al., "Ribosomal -1 frameshifting during decoding of *Bacillus subtilis* cdd occurs at the sequence CGA AAG," 1999, Journal of Bacteriology, vol. 181, pp. 2930-2937.
Miller, A. Dusty and Rosman, Guy J., "Improved Retroviral Vectors for Gene Transfer and Expression," 1992, BioTechniques, vol. 7, pp. 980-990.
Mir, Lluis M. et al., "Long-term, high level in vivo gene expression after electric pulse-mediated gene transfer into skeletal muscle," 1988, C.P. Acad. Sci., vol. 321, pp. 893-899.
Molinari, G. et al., "The Fibronectin-Binding Protein of *Streptococcus pyogenes*, Sfbl, Is Involved in the Internalization of Group A Streptococci by Epithelial Cells," 1997, Infection and Immunity, vol. 65, pp. 1357-1363.
Morrison, Sherie L. et al., "Chimeric human antibody molecules: Mouse antigen-binding domains with human constant region domains," 1984, Proceedings of the National Academy of Science USA, vol. 81, pp. 6851-6855.
Mountzouros, K. T. et al., "Detection of complement-mediated antibody-dependent bactericidal activity in a fluorescence-based serum bactericidal assay for group B *Neisseria meningitides*," 2000, Journal of Clinical Microbiology, vol. 38(8), pp. 2878-2884.
Nakai, K. et al., "Expert system for predicting protein localization sites in gram-negative bacteria," 1991, Proteins, vol. 11, pp. 95-110.
Naldini, Luigi, "Lentiviruses as gene transfer agents for delivery to non-dividing cells," 1998, Current Opinion in Biotechnology, vol. 9, pp. 457-463.
Navarre, W. W. et al., "Surface proteins of gram-positive bacteria and mechanisms of their targeting to the cell wall envelope," 1999, Microbiology and Molecular Biology Reviews, vol. 63, pp. 174-229.
Nielsen, H., J. Engelbrecht, S. Brunak, and G. von Heijne, "Identification of prokaryotic and eukaryotic signal peptides and prediction of their cleavage sites," 1997, Protein Engineering, vol. 10, pp. 1-6.
Nizet, V. et al., "Genetic locus for streptolysin S production by group A *streptococcus*," 2000, Infection and Immunity, vol. 68, pp. 4245-4254.
Nordstrand, A. et al., "Allele substitution of the streptokinase gene reduces the nephritogenic capacity of group A streptococcal strain NZ131," 2000, Infection and Immunity, vol. 68, pp. 1019-1025.
Olmsted, S. B. et al., "High-resolution visualization by field emission scanning electron microscopy of *Enterococcus faecalis* surface proteins encoded by the pheromone-inducible conjugative plasmid pCF10," 1993, Journal of Bacteriology, vol. 175, pp. 6229-6237.
Oudega et al., "A lipoprotein signal peptide plus a cysteine residue at the amino-terminal end of the periplasmic protein β-lactamase is sufficient for its lipid modification, processing and membrane localization in *Escherichia coli*," 1993, FEMS Microbiology Letters, vol. 108, pp. 353-360.
Oudega et al., "*Escherichia coli* SecB, SecA, and SecY proteins are required for expression and membrane insertion of the bacteriocin release protein, a small lipoprotein," Mar. 1993, Journal of Bacteriology, vol. 175(5), pp. 1543-1547.
Park, J. et al., "DIVCLUS: an automatic method in the GEANFAMMER package that finds homologous domains in single- and multi-domain proteins," 1998, Bioinformatics, vol. 14, pp. 144-150.
Parkhill, J. et al., Complete DNA sequence of a serogroup A strain of *Neisseria meningitidis* Z2491 [see comments], 2000, Nature, vol. 404, pp. 502-506.
Perrett, Kirsten P. et al., "Towards an improved serogroup B *Neisseria meningitidis* vaccine," 2005, Expert Opinion Biological Therapy, vol. 5, pp. 1611-1625.
Phillips, A., "The challenge of gene therapy and DNA delivery," 2001, Journal of Pharmacy and Pharmacology, vol. 53, pp. 1169-1174.
Pierschbacher, M. D. et al., "Influence of stereochemistry of the sequence Arg-Gly-Asp-Xaa on binding specificity in cell adhesion," 1987, Journal of Biol Chem., vol. 262, pp. 17294-17298.
Pizza, M. et al., "Identification of vaccine candidates against serogroup B *meningococcus* by whole-genome sequencing," 2000, Science, vol. 287(5459), pp. 1816-1820.
Podbielski, A. et al., "The group A streptococcal virR49 gene controls expression of four structural vir regulon genes," 1995, Infection and Immunity, vol. 63, pp. 9-20.
Pollitt et al., "Effect of amino acid substitutions at the signal peptide cleavage site of the *Escherichia coli* major outer membrane lipoprotein," Feb. 5, 1986, Journal of Biol. Chem., vol. 261(4), pp. 1835-1837.
Poolman, J. T., "Bacterial outer membrane protein vaccines. The meningococcal example." 1996, Advances in Experimental Medicine & Biology, vol. 397, pp. 73-77.
Proft, T. et al., Identification and Characterization of Novel Superantigens from *Streptococcus pyogenes*, 1999, Journal of Exp Med., vol. 189, pp. 89-102.
Pugsley, A. P., "The complete general secretory pathway in gram-negative bacteria," 1993, Microbiological Review, vol. 57, pp. 50-108.
Quinn, A. et al., "Immunological relationship between the class I epitope of streptococcal M protein and myosin," 1998, Infection and Immunity, vol. 66, pp. 4418-4424.
Reda, K. B. et al., Phylogenetic distribution of streptococcal superantigen SSA allelic variants provides evidence for horizontal

(56) References Cited

OTHER PUBLICATIONS transfer of ssa within *Streptococcus pyogenes*, 1996, Infection and Immunity, vol. 64, pp. 1161-1165.
Sahagan, Barbara G. et al., "A Genetically Engineered Murine/Human Chimeric Antibody Retains Specificity for Human Tumor-Associated Antigen," 1986, Journal of Immunology, vol. 137, pp. 1066-1074.
Salzberg, S. L. et al., "Microbial gene identification using interpolated Markov models," 1998, Nucleic Acids Res, vol. 26, pp. 544-548.
Samulski, Richard Jude et al., "A Recombinant Plasmid from Which an Infectious Adeno-Associated Virus Genome Can Be Excised In Vitro and Its Use to Study Viral Replication," 1987, Journal of Virology, vol. 61, pp. 3096-3101.
Samulski, Richard Jude et al., Helper-Free Stocks of Recombinant Adeno-Associated Viruses: Normal Integration Does Not Require Viral Gene Expression, 1989, Journal of Virology, vol. 63, pp. 3822-3828.
Sankaran, Krishnan et al., "Modification of bacterial lipoproteins," 1995, Methods in Enzymology, vol. 250, pp. 683-697.
Saukkonen, Kirsi, et al., "Protective efficacy of monoclonal antibodies to class 1 and class 3 outer membrane proteins of *Neisseria meningitides* B:15:P1.16 in infant rat infection model: new prospects for vaccine development," 1987, Microbial Pathogenesis, vol. 3(4), pp. 261-267.
Sedegah, Martha et al., Protection against malaria by immunization with plasmid DNA encoding circumsporozoite protein, 1994, Proc. National Academy of Science USA, Immunology, vol. 91, pp. 9866-9870.
Sedegah, M. et al., Improving Protective Immunity Induced by DNA-based immunization: Priming with Antigen and GM-CSF-encoding plasmid DNA and Boosting with Antigen-Expressing Recombinant Poxvirus, 2000, Journal of Immunology, vol. 164, pp. 5905-5912.
Snapper, C.M. et al., "IL-3 and granulocyte-macrophage colony-stimulating factor strongly induce Ig secretion by sort-purified murine B cells activated through the membrane Ig, but not the CD40, signaling pathway," 1995, The Journal of Immunology, vol. 154, pp. 5842-5850.
Snapper, Clifford et al., "Bacterial Lipoproteins May Substitute for Cytokines in the Humoral Immune Response to T Cell-Independent Type II antigens," 1995, Journal of Immunology, vol. 155(12), pp. 5582-5589.
Sonnenberg, M. G. et al., Definition of *Mycobacterium tuberculosis* culture filtrate proteins by two-dimensional polyacrylamide gel electrophoresis, N-terminal amino acid sequencing, and electrospray mass spectrometry, 1997, Infect Immun., vol. 65, pp. 4515-4524.
Sonnhammer, E. L. et al., "Pfam: a comprehensive database of protein domain families based on seed alignments," 1997, Proteins, vol. 28, pp. 405-420.
Stevens, D. L., "Streptococcal toxic-shock syndrome: spectrum of disease, pathogenesis, and new concepts in treatment," 1995, Emerg Infectious Disease, vol. 1, pp. 69-78.
Stockbauer, K. E. et al., "A natural variant of the cysteine protease virulence factor of group A *streptococcus* with an arginine-glycine-aspartic acid (RGD) motif preferentially binds human integrins alphavbeta3 and alphallbbeta3," 1999, Proc Natl Acad Sci., USA., vol. 96, pp. 242-247.
Stratford-Perricaudet, Leslie D. et al., "Widespread Long-term Gene Transfer to Mouse Skeletal Muscles and Heart," 1992, Journal of Clin. Invest., vol. 90, pp. 626-630.
Sun, Lee K. et al., "Chimeric antibody with human constant regions and mouse variable regions directed against carcinoma-associated antigen 17-1A," 1987, Proceedings of the National Academy of Science USA, vol. 84, pp. 214-218.
Tarkka, Eveliina et al., "Antibody production to a meningococcal outer membrane protein cloned into live *Salmonella typhimurium* aroA vaccine strain," May 1989, Micrb. Pathogen, vol. 6, pp. 327-335.
Tettelin, H. et al., Complete genome sequence of *Neisseria meningitidis* serogroup B strain MC58, 2000, Science, vol. 287(5459), pp. 1809-1815.
Ton-That, H., G. Liu, S. K. Mazmanian, K. F. Faull, and O. Schneewind, Purification and characterization of sortase, the transpeptidase that cleaves surface proteins of *Staphylococcus aureus* at the LPXTG motif, 1999, Proc Natl Acad Sci USA, vol. 96, pp. 12424-12429.
Ulmer, Jeffrey B. et al., "Heterologous Protection Against Influenza by Injection of DNA Encoding a Viral Protein," 1993, Science, vol. 259, pp. 1745-1748.
Wahl, Richard L. et al., "Improved Radioimaging and Tumor Localization with Monoclonal $F(ab')_2$," 1983, Journal of Nuclear Medicine, vol. 24, pp. 316-325.
Weldingh, K. et al., "Two-dimensional electrophoresis for analysis of *Mycobacterium tuberculosis* culture filtrate and purification and characterization of six novel proteins," 1998, Infect Immun., vol. 66, pp. 3492-3500.
Williams, R. Sanders et al., "Introduction of foreign genes into tissues of living mice by DNA-coated microprojectiles," 1991, Proceedings of the National Academy of Science USA, vol. 88, pp. 2726-2730.
Wilson, James M. et al., "Hepatocyte-directed Gene Transfer in Vivo Leads to Transient Improvement of Hypercholesterolemia in Low Density Lipoprotein receptor-deficient Rabbits," 1992, Journal of Biological Chemistry, vol. 267, pp. 963-967.
Wolff, Jon A. et al., "Direct Gene Transfer into Mouse Muscle in Vivo," 1990, Science, vol. 247, pp. 1465-1468.
Wu, George Y. and Wu, Catherine H., "Receptor-mediated in Vitro Gene Transformation by a Soluble DNA Carrier System," 1987, Journal of Biological Chemistry, vol. 262, pp. 4429-4432.
Wu, George Y. and Wu, Catherine H., "Receptor-mediated Gene Delivery and Expression in Vivo," 1988, Journal of Biological Chemistry, vol. 263, pp. 14621-14624.
Wu et al., "Hepatocyte-directed gene transfer in vivo leads to transient improvement of hypercholesterolemia in low density lipoprotein receptor-deficient rabbits," 1992, Journal Biol. Chem., vol. 267(2), pp. 963-967.
Yakushi et al., Lethality of the covalent linkage between mislocalized major outer membrane lipoprotein and the peptidoglycan of *Escherichia coli*, May 1997, Journal of Bacteriology, vol. 179(9), pp. 2857-2862.
Yakushi et al., "A new ABC transporter mediating the detachment of lipid modified proteins from membranes," Apr. 2000, Nat Cell Biol., vol. 2(4), pp. 212-218.
Yutsudo, T. et al., "The gene encoding a new mitogenic factor in a *Streptococcus pyogenes* strain is distributed only in group A streptococci," 1994, Infection and Immunity, vol. 62, pp. 4000-4004.
Zagursky, R.J. et al., "Bioinformatics: Use in Bacterial Vaccine Discovery," 2001, BioTechniques, vol. 31, pp. 636-659.
Zavascki, Alexandre Prehn et al., "First Case Report of *Neisseria lactamica* Causing Cavitary Lung Disease in an Adult Organ Transplant Recipient," 2006, Journal of Clinical Microbiology, vol. 44, pp. 2666-2668.
Zufferey, Romain et al., "Self-Inactivating Lentivirus Vector for Safe and Efficient In Vivo Gene Delivery," 1998, Journal of Virology, vol. 72, pp. 9873-9880.
Annex to Form PCT/ISA/206, Communication Relating to the Results of the Partial International Search, PCT/US2007/026238.
International Search Report for PCT/US2007/026238, date of mailing of the ISR Feb. 23, 2009.
Aasel, A., et al., Abstract from the 11th International Pathogenic Neisseria Conference, Nice, France, pp. 37-38 (Nov. 1-6, 1998).
Bernfield, L, et al., "Identification of a novel vaccine candidate for group B *Neisseria meningitidis*", Abstract from the Thirteenth International Pathogenic Neisseria Conference, Oslo, Norway, p. 116 (Sep. 1-6, 2002).
Bjune, G., et al., "Effect of outer membrane vesicle vaccine against group B meningococcal disease in Norway", The Lancet, 338(8775):1093-1096 (1991).
Boslego, J. W., et al., "Chapter 17: Gonorrhea Vaccines", Vaccines and Immunotherapy, S.J. Cryz, Jr. ed., Pergamon Press, pp. 17:211-17:223 (1991).

(56) References Cited

OTHER PUBLICATIONS

Cannon, J.G., "Conserved Lipoproteins of Pathogenic Neisseria Species Bearing the H.8 Epitope: Lipid-Modified Azurin and H.8 Outer Membrane Protein", Clinical Microbiology Reviews, 2:S1-S4 (1989).
Cantini, F., et al., "Solution Structure of the Immunodominant Domain of Protective Antigen GNA1870 of *Neisseria meningitidis*", Journal of Biological Chemistry, 281(11):7220-7227 (2006).
Chen, H., et al., "Determination of the optimal aligned spacing between the Shine-Dalgarno sequence and the translation initiation codon of *Escherichia coli* mRNAs", Nucleic Acids Research, 22(23):4953-4957 (1994).
Curriculum Vitae of Professor Paul M. Dunman, Ph.D., submitted in Opposition Proceedings against Novartis EP 1 645 631 on Sep. 14, 2011.
Database EMBL [Online] EBI, Kohara, Y., "*Caenorhabditis elegans* cDNA clone yk26f2: 5' end, single read," Database accession No. D35881 (Aug. 13, 1994).
Declaration by Dr. Julian Parkhill, submitted in Opposition Proceedings against Novartis EP 1 645 631 on Jul. 23, 2008.
Declaration by Professor Paul Dunman, submitted in Opposition Proceedings against Novartis EP 1 645 631 on Sep. 14, 2011.
Declaration of Dr. Ellen Murphy, submitted in Opposition Proceedings against Novartis EP 1 645 631 on Sep. 14, 2011.
Declaration of Emilio A. Emini, Ph.D., submitted in Opposition Proceedings against Novartis EP 1 645 631 on Nov. 3, 2011.
Definition of "epitope" from Henderson's Dictionary of Biological Terms, Eleventh Edition, Eleanor Lawrence ed., pp. 37, 184 and cover pages (1997).
Delgado, M., et al., "Lipoprotein NMB0928 from *Neisseria meningitidis* serogroup B as a novel vaccine candidate", Vaccine 25:8420-8431 (2007).
Dempsey, J.A.F., et al., "The Physical Map of the Chromosome of a Serogroup A Strain of *Neisseria meningitidis* Shows Complex Rearrangements Relative to the Chromosomes of the Two Mapped Strains of the Closely Related Species *N. gonorrhoeae*", Journal of Bacteriology, 177(22):6390-6400 (1995).
EP Appln. No. 07075161.5 Response to Communication submitted Oct. 28, 2009.
Farley, J., et al., "Characterization, cloning and expression of different subfamilies of the ORF 2086 gene from *Neisseria meningitidis*", Abstract from the Thirteenth International Pathogenic Neisseria Conference, Oslo, Norway, p. 124 (Sep. 1-6, 2002).
Feavers, I.M., et al., "Meningococcal protein antigens and vaccines", Vaccine, 275:B42-B50 (2009).
Final Written Submission in Preparation of Oral Proceedings in Opposition against Novartis EP 1 645 631 submitted Sep. 14, 2011.
Fleischmann, R.D, et al., "Whole-Genome Random Sequencing and Assembly of *Haemophilus influenzae* Rd", Science, 269:496-512 (1995).
Fontana, M.R., et al., "A genomic approach to identify vaccine candidates against *gonococcus*", Abstract from the Thirteenth International Pathogenic Neisseria Conference, Oslo, Norway, p. 248, (Sep. 1-6, 2002).
Giuliani, M.M., et al., "The Region Comprising Amino Acids 100 to 255 of *Neisseria meningitidis* Lipoprotein GNA 1870 Elicits Bactericidal Antibodies", Infection and Immunity, 73(2):1151-1160 (2005).
Giuliani, M.M., et al., "A universal vaccine for serogroup B *meningococcus*", Proc. Natl. Acad. Sci., 103 (29):10834-10839 (2006).
Gold, L., et al., "Chapter 78: Translation Initiation", *Escherichia coli* and *Salmonella typhimurium*: Cellular and Molecular Biology, F.C. Neidhardt ed., vol. 2, pp. 1302-1307 (1987).
Grandi, G., et al., "Reverse vaccinology: a critical analysis", Encyclopedia of Genetics, Genomics, Proteomics and Bioinformatics, pp. 1320-1330 (2005).
Hung, M.C., et al., "The *Neisseria meningitidis* Macrophage Infectivity Potentiator Protein Induces Cross-Strain Serum Bactericidal Activity and Is a Potential Serogroup B Vaccine Candidate", Infection and Immunity, 79 (9):3784-3791 (2011).
Interlocutory Decision of the Opposition Division in Opposition against Novartis EP 1 645 631 dated May 21, 2012.
Jiang, H.Q., et al., "Broad vaccine coverage predicted for a bivalent recombinant factor H binding protein based vaccine to prevent serogroup B meningococcal disease", Vaccine, 28:6086-6093 (2010).
Johnson, A.S., et al., "Analysis of the human Ig isotype response to lactoferrin binding protein A from *Neisseria meningitidis*", FEMS Immunology and Medical Microbiology, 25(4):349-354 (1999).
JVCI-CMR website showing Z2491 Sanger sequence (http://cmr.jvci.org/tigr-scripts/CMR/shared/Genomes.cgi and links) printed on Jul. 1, 2010.
Masignani, V., et al., "Vaccination against *Neisseria meningitidis* Using Three Variants of the Lipoprotein GNA1870", J. Exp. Med., 197(6):789-799 (2003).
Milagres, L.G., et al., "Specificity of Bactericidal Antibody Response to Serogroup B Meningococcal Strains in Brazilian Children after Immunization with an Outer Membrane Vaccine", Infection and Immunity, 66(10):4755-4761 (1998).
Minutes of Oral Proceedings in Opposition against Novartis EP 1 645 631 dated Mar. 5, 2012.
Moreno, C., et al., "Immunity and Protection of Mice Against *Neisseria meningitidis* Group B by Vaccination, Using Polysaccharide Complexed with Outer Membrane Proteins: A Comparison with Purified B Polysaccharide", Infection and Immunity, 47(2):527-533 (1985).
Morley, S.L., et al., "Vaccine prevention of meningococcal disease, coming soon?", Vaccine, 20:666-687 (2002).
Moxon, R.E., "Applications of molecular microbiology to vaccinology", The Lancet, 350(9086):1240-1244 (1997).
Munkley, A., et al., "Blocking of bactericidal killing of *Neisseria meningitidis* by antibodies directed against class 4 outer membrane protein", Microbial Pathogenesis, 11:447-452 (1991).
Murphy, E., et al., "Sequence Diversity of the Factor H Binding Protein Vaccine Candidate in Epidemiologically Relevant Strains of Serogroup B *Neisseria meningitidis*", The Journal of Infectious Diseases, 200:379-389 (2009).
Nassif, X., "A Furtive Pathogen Revealed", Science, 287:1767-1768 (2000).
Notice of Opposition against Novartis EP 1 645 631 submitted Jul. 23, 2008.
Novartis submits Bexsero®, a multi-component meningococcal B vaccine, for regulatory review in Europe, Novartis Media Release (Dec. 23, 2010).
Opponent's Further Submission in Preparation of Oral Proceedings in Opposition against Novartis EP 1 645 631 submitted Nov. 3, 2011.
Patentees' Further Submission Under Rule 116 EPC in Opposition against Novartis EP 1 645 631 submitted Oct. 14, 2011.
Patentees' Response to Opposition against Novartis EP 1 645 631 submitted May 8, 2009.
Patentees' Submissions Under Rule 116 EPC in Opposition against Novartis EP 1 645 631 submitted Sep. 13, 2011.
Pettersson, A., et al., "The meningococcal lactoferrin receptor", IPNC Abstract (1998).
Pettersson, A., et al., "Vaccine potential of the *Neisseria meningitidis* lactoferrin-binding proteins LbpA and LbpB", Vaccine, 24(17):3545-3557 (2006).
Phase II clinical results for Novartis vaccine, Novartis Media Release (Oct. 9, 2008).
Pizza, M.G., et al., "Preparation of Meningococcal Antigens" (Feb. 2, 2005), available at: http://cordis.europa.eu/search/index.cfm?fuseaction=result.document&RSLANG=EN&RSRCN=7461241&q=.
Poolman, J.T., "Development of a Meningococcal Vaccine", Infectious Agents and Disease, 4(1):13-28 (1995).
Parkhill, J., "*Campylobacter jejuni* genome sequence at the Sanger Centre", (May 8, 1998), available at: http://www.bio.net/bionet/mm/bionews/1998-May/00442.html.
Preliminary Opinion of the Opposition Division in Opposition against Novartis EP 1 645 631 dated Jun. 24, 2011.

(56) References Cited

OTHER PUBLICATIONS

Progress through the Sanger Institute FTP Server, submitted in Opposition Proceedings against Novartis EP 1 645 631 on May 8, 2009.
PSORT analysis of 200 of the sequences disclosed in PCT/US99/09346, submitted in Opposition Proceedings against Novartis EP 1 645 631 on May 25, 2010.
PSORT analysis of SEQ ID Nos. 4 and 6, and of 'Contig295' 300mer, submitted in Opposition Proceedings against Novartis EP 1 645 631 on May 8, 2009.
PSORT prediction result for SEQ ID No. 2, submitted in Opposition Proceedings against Novartis EP 1 645 631 on May 25, 2010.
Rinaudo, C.D., et al., "Vaccinology in the genome era", The Journal of Clinical Investigation, 119(9):2515-2525 (2009).
Romero, J.D., et al., "Current Status of Meningococcal Group B Vaccine Candidates: Capsular of Noncapsular?", Clinical Microbiology Reviews, 7(4):559-575 (1994).
Ross, B.C.., et al., "Identification of vaccine candidate antigens from a genomic analysis of *Porphyromonas gingivalis*", Vaccine, 19:4135-4142 (2001).
Sanger Centre's "Projects" website as of Dec. 12, 1997 as retrievable via http://web.archive.org.
Sequence for "Putative Lipoprotein [*Neisseria miningitidis* Z2491]", NCBI Reference Sequence: YP_002342062.1.
Serruto, D., et al., "Genome-based approaches to develop vaccines against bacterial pathogens", Vaccine, 27:3245-3250 (2009).
Smith, C.J., et al., "Nucleotide Sequence Determination and Genetic Analysis of the Bacteroides Plasmid, pBI143", Plasmid, 34(3):211-222 (1995).
Supplementary Declaration by Dr. Julian Parkhill submitted in Opposition Proceedings against Novartis EP 1 645 631 on May 25, 2010.
Supplementary Submission in Opposition Proceedings against Novartis EP 1 645 631 submitted May 25, 2010.
Sutcliffe, I.C., et al., "Lipoproteins of Gram-Positive Bacteria", Journal of Bacteriology, 177(5):1123-1128 (1995).
Sworn Statement from Dr. Rino Rappuoli submitted in Opposition Prceedings against Novartis EP 1 645 631 on Oct. 14, 2011.
Telford, J.L., et al., "Chapter 1: Genomics and Proteomics in Vaccine Design", New Bacterial Vaccines, Kleweur Academic/Plenum Publishers, USA, pp. 1-11 (2003).
Jackson, J.W., et al., U.S. Appl. No. 60/098,685, filed Sep. 1, 1998.
Van Der Ley, P., et al., "Construction of *Neisseria meningitidis* strains carrying multiple chromosomal copies of the por A gene for use in the production of a multivalent outer membrane vesicle vaccine", Vaccine, 13(4):401-407 (1995).
Welsch, J.A., et al., "Protective Activity of Monoclonal Antibodies to Genome-Derived Neisserial Antigen 1870, a *Neisseria meningitidis* Candidate Vaccine", The Journal of Immunology, 172:5606-5615 (2004).
Woods, J.P., "Resistance to Meningococcemia Apparently Conferred by Anti-H.8 Monoclonal Antibody Is Due to Contaminating Endotoxin and Not to Specific Immunoprotection", Infection and Immunity, 55(8):1927-1928 (1987).
Zollinger, W.D., "New and Improved Vaccines Against Meningococcal Disease", New Generation Vaccines, 2nd Edition, Myron M. Levine, et al. eds., Marcel Dekker, Inc., New York, NY, pp. 469-488 (1997).
Prosecution history of U.S. Appl. No. 13/455,326, dated Apr. 26, 2013.
Tappero et al, "Immunogenicity of 2 Serogroup B Outer-Membrane Protein Meningococcal Vaccines", JAMA 281 (16):1520-1527 (1999).
US Patent No. 8,398,988 B2 Prosecution History (Feb. 23, 2012-Feb. 27, 2013).
Fukasawa et al, "*Neisseria meningitidis* serogroup C polysaccharide and serogroup B outer membrane vesicle conjugate as a bivalent *meningococcus* vaccine candidate", Vaccine 17:2951-2958 (1999).
Rosenqvist et al, "Human Antibody Responses to Meningococcal Outer Membrane Antigens after Three Doses of the Norwegian Group B Meningococcal Vaccine", Infection and Immunity 63(12):4642-4652 (1995).
Van Der Ende et al, "Multiple Mechanisms of Phase Variation of PorA in *Neisseria meningitidis*", Infection and Immunity 68(12):6685-6690 (2000).
Andersen, et al, "Immune Responses to Meningococcal Outer Membrane Vesicles After Intranasal Immunisation", Twelfth International Pathogenic Neisseria Conference, Nov. 12-17, 2000, Galveston, Texas (Abstract #057).
Beuvery et al, "Preparation and Immunochemical Characterization of Meningococcal Group C Polysaccharide-Tetanus Toxoid Conjugates as a New Generation of Vaccines", Infection and Immunity 40(1):39-45 (1983).
Curriculum Vitae of Lakshmi Khandke, Ph.D., submitted in Opposition Proceedings against Novartis EP1409013 on Nov. 18, 2011.
Datasheet for MENCEVAX™, International Data Sheet version 2.1 (May 15, 2000).
Datasheet for MENOMUNE™, product information as of Feb. 2001.
Datasheet for MeNZB® vaccine product prepared Jun. 23, 2009.
Declaration of Lakshmi Khandke, Ph.D., submitted in Opposition Proceedings against Novartis EP1409013 on Dec. 21, 2011.
Fredriksen et al, "Production, Characterization and Control of MenB-Vaccine <<Folkehelsa>>: An Outer Membrane Vesicle Vaccine Against Group B Meningococcal Disease", NIPH Annals 14(2):67-80 (1991).
Gupta, "Aluminum compounds as vaccine adjuvants", Advanced Drug Delivery Reviews 32(3):155-172 (1998).
Hem et al, "Chapter 9: Structure and Properties of Aluminum-Containing Adjuvants", Vaccine Design: The Subunit and Adjuvant Approach, Plenum Press, New York, pp. 249-276 (1995).
Houghten, "General Method for the rapid solid-phase synthesis of large numbers of peptides: Specificity of antigen-antibody interaction at the level of individual amino acids", Proceedings of the National Academy of Sciences of USA 82:5131-5135 (1985).
Koeberling at el, "Bactericidal Antibody Responses Elicited by a Meningococcal Outer Membrane Vesicle Vaccine with Overexpressed Factor H-binding Protein and Genetically Attenuated Endotoxin", The Journal of Infectious Diseases 198:262-270 (2008).
NCBI GenBank No. AAF42204.1, Tettelin, H. et al., "Hypothetical protein [*Neisseria meningitidis*]", Feb. 25, 2000, accessed Jul. 12, 2012.
NCBI GenBank: ACB38141.1, factor H-binding protein [*Neisseria meningitidis*] (Jun. 4, 2010).
NCBI GenBank: FJ184233.1, "*Neisseria meningitidis* factor H binding protein variant B09_004 (fhbp) gene, partial cds" (Aug. 4, 2009).
Rosenstein et al, "Meningococcal Vaccines", Infectious Disease Clinics of North America 15(1):155-169 (2001).
Sepelyak et al, "Adsorption of Pepsin by Aluminum Hydroxide I: Adsorption Mechanism", Journal of Pharmaceutical Sciences 73(11):1514-1517 (1984).
Sworn Statement from Dr. Giovanna Campanella submitted in Opposition Proceedings against Novartis EP1409013 on Nov. 10, 2011.
Tondella et al, "Distribution of *Neisseria meningitidis* Serogroup B Serosubtypes and Serotypes Circulating in the United States", Journal of Clinical Microbiology 38(9):3323-3328 (2000).
Beernink, P.T., et al., "The modular architecture of meningococcal factor H-binding protein", Microbiology, 155:2873-2883 (2009).
Van Der Ende, A., et al., "Deletion of porA by Recombination between Clusters of Repetitive Extragenic Palindromic Sequences in *Neisseria meningitidis*", Infection and Immunity, 67(6):2928-2934 (1999).
Callahan, P.M., et al., "The Importance of Surface Charge in the Optimization of Antigen-Adjuvant Interactions", Pharmaceutical Research, 8(7):851-858 (1991).

* cited by examiner

IDENTIFICATION OF COMPONENTS IN THE UNABSORBED TMAE FRACTION: SDS-PAGE ISOLATION OF PEPTIDES (CNBr CLEAVAGE OF UNABSORBED TMAE FRACTION FOLLOWED BY SDS-PAGE AND N-TERM SEQUENCING OF FRAGMENTS FROM PVDF BLOT)

1 - TMAE UNABSORBED UNDIGESTED
2 - TMAE UNABSORBED LysC DIGEST
3 - TMAE UNABSORBED CNBR CLEAVAGE

IDENTIFICATION OF COMPONENTS IN THE UNABSORBED TMAE FRACTION: REVERSE PHASE ISOLATION OF PEPTIDES

ENZYMATIC DIGESTION OF UNABSORBED TMAE FRACTION FOLLOWED BY REVERSE PHASE CHROMATOGRAPHY SEPARATION OF PEPTIDES AND DIRECT N-TERMINAL SEQUENCING

| ENZYMATIC DIGEST | RETENTION TIME OF PEPTIDE (min) | MOLECULAR WEIGHT OF PEPTIDE (d) | N-TERM. ID |
|---|---|---|---|
| GluC (V8) | 6.716 | 2069.7 | P5163 |
| LysC | 13.800 | 3351.2 | P4431 |
| LysC | 13.800 | 3351.2 | P2086 |
| ArgC | 6.860 | 2278.9 | P5163 |

P4431 (SEQ ID NO: 327)
PREDICTED mw 36,775

P2086 (SEQ ID NO: 212)
PREDICTED mw 27,100

P5163 (SEQ ID NO: 328)
PREDICTED mw 7,081

FIG. 1B

IDENTIFICATION OF COMPONENTS IN THE UNABSORBED TMAE FRACTION: LC-MS/MS

SDS-PAGE FOLLOWED BY GEL EXCISION, PROTEOLYTIC DIGESTION, AND LC-MS/MS ANALYSIS (LIQUID CHROMATOGRAPHY TANDEM MASS SPECTROMETRY)

10-20% SDS-PAGE
COOMASSIE STAIN

```
                     10                  20                  30
1  C S S G G G G - - - - - V A A D I G A G L A D A L T A P L D 8529 mat.pro  (N-Terminal Domain of SEQ ID NO: 212)
1  C S S G G G G - - - - - V A A D I G A G L A D A L T A P L D 2996 mat.pro  (N-Terminal Domain of SEQ ID NO: 110)
1  C S S G G G G S G G G G V T A D I G T G L A D A L T A P L D 1573 mat.pro  (N-Terminal Domain of SEQ ID NO: 248)
                 5 AMINO ACID REPEAT
```

FIG. 8

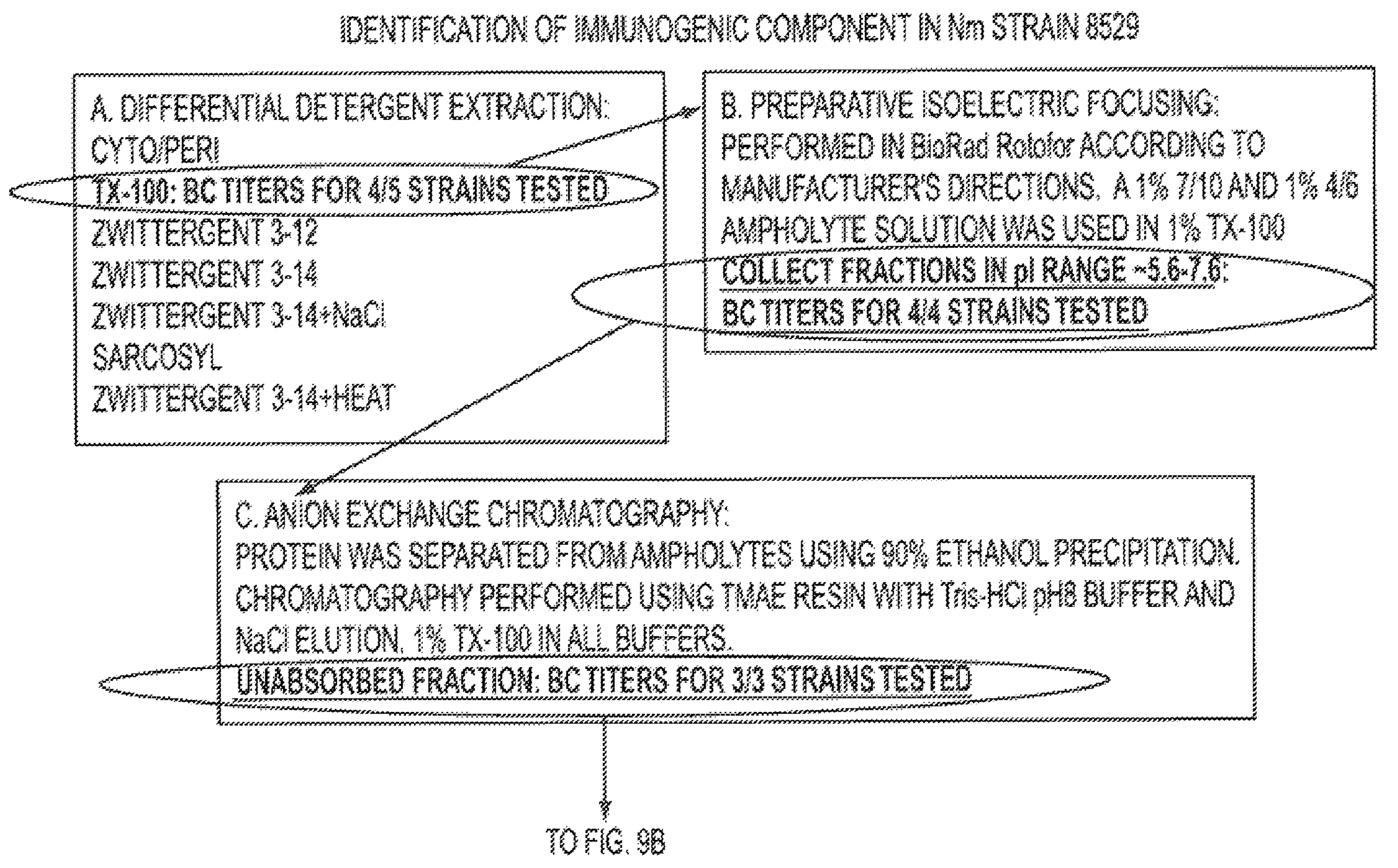

FIG. 9A

IDENTIFICATION OF IMMUNOGENIC COMPONENT IN Mn STRAIN 8529

A. DIFFERENTIAL DETERGENT EXTRACTION:
CYTO/PERI
TX-100: *BC TITERS FOR 4/5 STRAINS TESTED*
ZWITTERGENT 3-12
ZWITTERGENT 3-14
ZWITTERGENT 3-14+NaCl
SARCOSYL
ZWITTERGENT 3-14+HEAT

B. PREPARATIVE ISOELECTRIC FOCUSING:
PERFORMED IN BioRad Rotofor ACCORDING TO MANUFACTURER'S DIRECTIONS. A 1% 7/10 AND 1% 4/6 AMPHOLYTE SOLUTION WAS USED IN 1% TX-100.
*COLLECT FRACTIONS IN pI RANGE ~5.6-7.6:*
*BC TITERS FOR 4/4 STRAINS TESTED*

C. ANION EXCHANGE CHROMATOGRAPHY:
PROTEIN WAS SEPARATED FROM AMPHOLYTES US

LIPIDATED rP2086
pBAD18-ARABINOSE PROMOTER

NON-LIPIDATED rP2086
pET9a-T7 PROMOTER
8529, CDC-1573 AND 2996

WESTERN BLOT REACTIVITY OF rLP2086 MOUSE ANTISERA TO P2086 SUBFAMILY B *N. meningitidis* WHOLE CELL LYSATES 1 - MOLECULAR WEIGHT MARKER (kDa)
2 - M97 251985
3 - CDC937
4 - 6940
5 - M97 251926
6 - CDC1573
7 - CDC1359
8 - CDC1658
9 - M97 252026
10 - M97 252029
11 - M982

SUBFAMILY B P2086 CELL LYSATES ARE ALL GROUP B *N. meningitidis*

WESTERN BLOT REACTIVITY OF rLP2086 MOUSE ANTISERA TO P2086 SUBFAMILY A *N. meningitidis* AND *N. lactamica* WHOLE CELL LYSATES 1 - MOLECULAR WEIGHT MARKERS (kDa)
2 - GROUP A *N. meningitidis* A4 (P2086 SUBFAMILY B)
3 - GROUP C *N. meningitidis* - C11
4 - GROUP Y *N. meningitidis* - ATCC35561
5 - GROUP W135 *N. meningitidis* - ATCC35559
6 - *N. lactamica* - UR5

GROUP B *N. meningitidis*:
7 - CDC1034
8 - M98 250732
9 - NmB
10 - 6557
11 - CDC1521
12 - M97 252153

IMMUNOGENIC COMPOSITIONS FOR THE PREVENTION AND TREATMENT OF MENINGOCOCCAL DISEASE

CROSS-REFERENCE TO RELATED APPLICATIONS

This application is a continuation of U.S. application Ser. No. 13/333,123, now U.S. Pat. No. 8,563,006, filed Dec. 21, 2011, which is a divisional of U.S. application Ser. No. 10/492,427, filed Oct. 7, 2004, now U.S. Pat. No. 8,101,194, which is a National Stage of International Application No. PCT/US02/32369, filed Oct. 11, 2002, which claims the benefit of U.S. Provisional Application No. 60/328,101, filed Oct. 11, 2001, and U.S. Provisional Application No. 60/406,934, filed Aug. 30, 2002, all of which are incorporated herein by reference.

FIELD OF THE INVENTION

The present invention relates to *Neisseria* ORF2086 proteins (Subfamily A and Subfamily B), which may be isolated from bacterial strains such as those of *Neisseria* species, including strains of *Neisseria meningitidis* (serogroups A, B, C, D, W-135, X, Y, Z and 29E), *Neisseria gonorrhoeae*, and *Neisseria lactamica*, as well as immunogenic portions and/or biological equivalents of said proteins. The present invention also relates to antibodies that immunospecifically bind to said proteins, immunogenic portions and/or biological equivalents. Further, the present invention relates to isolated polynucleotides comprising nucleic acid sequences encoding any of the foregoing proteins, immunogenic portions, biological equivalents and/or antibodies. Additionally, the present invention relates to immunogenic compositions and their use in preventing, treating and/or diagnosing meningococcal infection caused by *N. meningitidis*, and in particular meningococcal disease caused by *N. meningitidis* serogroup B, as well as methods for preparing said compositions. This invention relates to both recombinant forms and forms isolated from a natural source, as well as both lipidated and non-lipidated forms.

BACKGROUND OF THE INVENTION

Meningococcal meningitis is a devastating disease that can kill children and young adults within hours despite the availability of antibiotics. Pizza et al., 2000, *Science* 287:1816-1820. Meningitis is characterized as an inflammation of the meninges resulting in an intense headache, fever, loss of appetite, intolerance to light and sound, rigidity of muscles, especially in the neck, and in severe cases convulsions, vomiting and delirium leading to death. The symptoms of meningococcal meningitis appear suddenly and culminate in meningococcal septicemia with its characteristic hemorrhagic rash. A rapid diagnosis and immediate treatment with large doses of antibiotics is critical if there is to be any chance of survival. 2000. *Bantam Medical Dictionary, Third Edition* 302.

Meningococcal meningitis is caused by *Neisseria meningitidis* (the meningococcus), a Gram-negative, capsulated bacterium that has been classified into several pathogenic serogroups including A, B, C, D, W-135, X, Y, Z and 29E. Serogroup B strains of *N. meningitidis* are a major cause of meningococcal disease throughout the world. For example, it is reported in the medical literature that serogroup B is responsible for about 50% of bacterial meningitis in infants and children residing in the United States and Europe. No vaccine currently exists to prevent meningococcal disease caused by *N. meningitidis* serogroup B.

Developing an immunogenic composition for the prevention of serogroup B meningococcal disease has been a challenge to researchers since the work of Goldschneider et al. over thirty years ago. Goldschneider et al., 1969, *J. Exp. Med* 129(6):1307-26; Goldschneider et al, 1969, *J. Exp. Med* 129 (6):1327-48; Gotschlich et al., 1969, *J. Exp. Med.* 129(6): 1385-95; and Gotschlich et al., 1969, *J. Exp. Med.* 129(6): 1367-84. Unlike serogroup A disease, which virtually disappeared from North America after World War II, Achtman, M., 1995, *Trends in Microbiology* 3(5):186-92, disease caused by serogroup B and C organisms remains endemic throughout much of the economically developed world. The incidence of disease varies from <1/100,000 where endemic disease is rare to 200/100,000 in high risk populations during epidemics.

Vaccines based on polysaccharide conjugates have been developed against *N. meningitidis* serogroups A and C and appear to be effective in preventing disease. Currently, an immunogenic composition made of capsular polysaccharide from serogroups A, C, Y, & W-135 is available. Ambrosch et al., 1983, Immunogenicity and side-effects of a new tetravalent. *Bulletin of the World Health Organization* 61(2):317-23. However, this immunogenic composition elicits a T-cell independent immune response, is not effective in young children, and provides no coverage for serogroup B strains, which cause upwards of 50% of meningococcal disease.

Others have also attempted to develop immunogenic compositions using capsular polysaccharides. Recently, immunogenic compositions for serogroup C disease prepared by conjugating the serogroup C capsular material to proteins have been licensed for use in Europe. However, the serogroup B capsule may be unsuitable as a vaccine candidate because the capsule polysaccharide is composed of polysialic acid which bears a similarity to carbohydrate moieties on developing human neural tissues. This sugar moiety is recognized as a self-antigen and is thus poorly immunogenic in humans.

Outer membrane proteins (OMP's) have been developed as alternative vaccine antigens for serogroup B disease. Monoclonal antibody binding to the two variable regions of PorA define the serosubtyping scheme for meningococci. PorA proteins thus serve as the serosubtyping antigens (Abdillahi et al., 1988, *Microbial Pathogenesis* 4(1):27-32) for meningococcal strains and are being actively investigated as components of a serogroup B immunogenic composition (Poolman, 1996, *Adv. Exp. Med. Biol.* 397:73-7), since they can elicit bactericidal antibodies (Saukkonen, 1987, *Microbial Pathogenesis* 3(4):261-7). Bactericidal antibodies are thought to be an indicator of protection and any new immunogenic composition candidate should elicit these functional antibodies.

Studies in humans as well as animals indicate that the serosubtyping antigen, PorA, elicits bactericidal antibodies. However, the immune response to Por A is generally serosubtype specific. In particular, serosubtyping data indicate that an immunogenic composition made of PorAs may require a PorA for each serosubtype to be covered by such an immunogenic composition, perhaps as many as six to nine. Therefore, 6-9 PorAs will be needed to cover 70-80% of serogroup B strains. Thus, the variable nature of this protein requires a multivalent vaccine composition to protect against a sufficient number of meningococcal serosubtype clinical isolates.

Developing an immunogenic composition for serogroup B meningococci has been so difficult that recently several groups have sequenced the genomes from strains representing both serogroups A and B to assist in identifying new immunogenic composition candidates. Tettelin, 2000, *Science,* 287(5459):1809-15; Pizza et al., 2000, *Science* 287:1816-1820. Identifying new immunogenic composition candidates, even with the knowledge of the neisserial genome, is a challenging process for which adequate mathematical algorithms do not currently exist. In fact, a recent report indicates that despite identifying hundreds of open reading frames ("ORFs") containing theoretical membrane spanning domains, problems with expression, purification, and inducing surface reactive, and functionally active antibodies have led investigators to only seven candidates for a serogroup B meningococcal immunogenic composition. See Id. One of these was previously known.

Accordingly, there remains a need for immunogenic compositions that (1) elicit bactericidal antibodies to multiple neisserial strains; (2) react with the surface of multiple strains; (3) confer passive protection against a live challenge; and/or (4) prevent colonization.

SUMMARY OF THE INVENTION

To meet these and other needs, and in view of its purposes, the present invention provides *Neisseria* ORF2086 proteins ("2086 proteins"), including 2086 Subfamily A proteins and 2086 Subfamily B proteins. Each of the 2086 proteins are proteins that can be isolated from native neisserial strains, including strains of *Neisseria meningitidis* (serogroups A, B, C, D, W-135, X, Y, Z and 29E), *Neisseria gonorrhoeae*, and *Neisseria lactamica*. The 2086 proteins may also be prepared using recombinant technology.

In particular, the present invention provides the 2086 proteins, immunogenic portions thereof, and/or biological equivalents thereof, antibodies that immunospecifically bind to any of the foregoing, and polynucleotides comprising nucleic acid sequences that encode any of the foregoing. The present invention includes compositions, immunogenic compositions and their use in preventing, treating and/or diagnosing meningococcal infection, and in particular meningococcal disease caused by *N. meningitidis*, as well as methods for preparing said compositions. The 2086 proteins herein include recombinant forms and forms isolated from a natural source, as well as both lipidated and non-lipidated forms.

The present invention unexpectedly and advantageously provides compositions that (1) elicit bactericidal antibodies to multiple neisserial strains, such as strains of *N. meningitidis, N. gonorrhoeae*, and/or *N. lactamica*; (2) react with the surface of multiple strains; (3) confer passive protection against a live challenge; and/or (4) prevent colonization, as well as methods of using said compositions and methods of preparing said compositions. Various embodiments of the invention are described below.

BRIEF DESCRIPTION OF THE DRAWINGS

FIG. 1B depicts the results from the experiments from the identification of the two major proteins by analysis of TMAE Flow Through components by protease digestion and reverse Phase N-terminal sequencing.

FIG. 8 illustrates N-terminal regions of 2086 gene from various strains. The amino acid sequence shown for strain 8529 depicts the N-terminal region of the 2086 ORF as shown in SEQ ID NO:212. The amino acid sequence shown for strain 2996 depicts the N-terminal region of the 2086 ORF as shown in SEQ ID NO:110. The amino acid sequence shown for strain 1573 depicts the N-terminal region of the 2086 ORF as shown in SEQ ID NO:248.

FIG. 9A is a flow chart showing the preliminary steps in the identification of an immunogenic component in a nesserial strain.

SEQUENCE SUMMARY

Figure 1A:
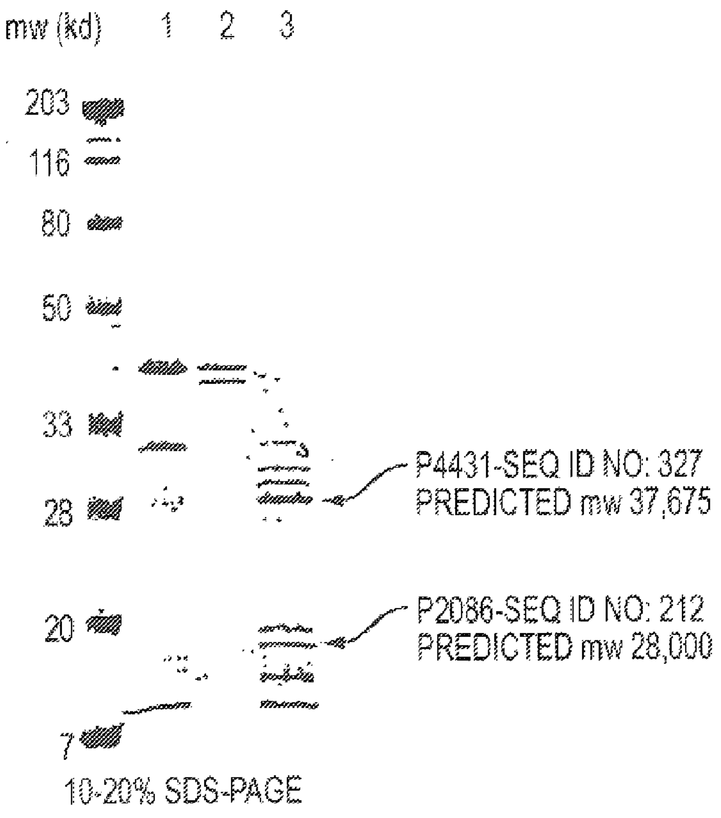
FIG. 1A depicts an SDS-PAGE gel that depicts the two major proteins of the protein fractions obtained from the experiments for identifying neisserial membrane protein extract that is capable of eliciting bactericidal antibodies against heterologous strains.

SEQ ID NOS. For Studied Sequences:

SEQ ID NO:1 nucleic acid sequence encoding amino acid sequence for mature 2086 protein from L3 6275 strain when combined with a native leader sequence.

SEQ ID NO:2 amino acid sequence for mature 2086 protein from L3 6275 strain prepared using a native leader sequence.

SEQ ID NO:3 nucleic acid sequence for encoding amino acid sequence for mature 2086 protein from L3 6275 when combined with a P4 leader sequence.

SEQ ID NO:4 amino acid sequence for mature 2086 protein from L3 6275 strain prepared using a P4 leader sequence.

SEQ ID NO:5 nucleic acid sequence encoding amino acid sequence for mature 2086 protein from L3 6275 strain.

SEQ ID NO:6 amino acid sequence for mature 2086 protein from L3 6275 strain.

SEQ ID NO:7 nucleic acid sequence encoding amino acid sequence for mature 2086 protein from CDC2369 strain when combined with a native leader sequence.

SEQ ID NO:8 amino acid sequence for mature 2086 protein from CDC2369 strain prepared using a native leader sequence.

SEQ ID NO:9 nucleic acid sequence for encoding amino acid sequence for mature 2086 protein from CDC2369 when combined with a P4 leader sequence.

SEQ ID NO:10 amino acid sequence for mature 2086 protein from CDC2369 strain prepared using a P4 leader sequence.

SEQ ID NO:11 nucleic acid sequence encoding amino acid sequence for mature 2086 protein from CDC2369 strain.

SEQ ID NO:12 amino acid sequence for mature 2086 protein from CDC2369 strain.

SEQ ID NO:13 nucleic acid sequence encoding amino acid sequence for mature 2086 protein from CDC1034 strain when combined with a native leader sequence.

SEQ ID NO:14 amino acid sequence for mature 2086 protein from CDC1034 strain prepared using a native leader sequence.

SEQ ID NO:15 nucleic acid sequence for encoding amino acid sequence for mature 2086 protein from CDC1034 when combined with a P4 leader sequence.

SEQ ID NO:16 amino acid sequence for mature 2086 protein from CDC1034 strain prepared using a P4 leader sequence.

SEQ ID NO:17 nucleic acid sequence encoding amino acid sequence for mature 2086 protein from CDC1034 strain.

SEQ ID NO:18 amino acid sequence for mature 2086 protein from CDC1034 strain.

SEQ ID NO:19 nucleic acid sequence encoding amino acid sequence for mature 2086 protein from L4 891 strain when combined with a native leader sequence.

SEQ ID NO:20 amino acid sequence for mature 2086 protein from L4 891 strain prepared using a native leader sequence.

SEQ ID NO:21 nucleic acid sequence for encoding amino acid sequence for mature 2086 protein from L4 891 when combined with a P4 leader sequence.

SEQ ID NO:22 amino acid sequence for mature 2086 protein from L4 891 strain prepared using a P4 leader sequence.

SEQ ID NO:23 nucleic acid sequence encoding amino acid sequence for mature 2086 protein from L4 891 strain.

SEQ ID NO:24 amino acid sequence for mature 2086 protein from L4 891 strain.

SEQ ID NO:25 nucleic acid sequence encoding amino acid sequence for mature 2086 protein from B16B6 strain when combined with a native leader sequence.

SEQ ID NO:26 amino acid sequence for mature 2086 protein from B16B6 strain prepared using a native leader sequence.

SEQ ID NO:27 nucleic acid sequence for encoding amino acid sequence for mature 2086 protein from B16B6 when combined with a P4 leader sequence.

SEQ ID NO:28 amino acid sequence for mature 2086 protein from B16B6 strain prepared using a P4 leader sequence.

SEQ ID NO:29 nucleic acid sequence encoding amino acid sequence for mature 2086 protein from B16B6 strain.

SEQ ID NO:30 amino acid sequence for mature 2086 protein from B16B6 strain.

SEQ ID NO:31 nucleic acid sequence encoding amino acid sequence for mature 2086 protein from W135 (ATCC35559) strain when combined with a native leader sequence.

SEQ ID NO:32 amino acid sequence for mature 2086 protein from W135 (ATCC35559) strain prepared using a native leader sequence.

SEQ ID NO:33 nucleic acid sequence for encoding amino acid sequence for mature 2086 protein from W135 (ATCC35559) when combined with a P4 leader sequence.

SEQ ID NO:34 amino acid sequence for mature 2086 protein from W135 (ATCC35559) strain prepared using a P4 leader sequence.

SEQ ID NO:35 nucleic acid sequence encoding amino acid sequence for mature 2086 protein from W135 (ATCC35559) strain.

SEQ ID NO:36 amino acid sequence for mature 2086 protein from W135 (ATCC35559) strain.

SEQ ID NO:37 nucleic acid sequence encoding amino acid sequence for mature 2086 protein from C11 strain when combined with a native leader sequence.

SEQ ID NO:38 amino acid sequence for mature 2086 protein from C11 strain prepared using a native leader sequence.

SEQ ID NO:39 nucleic acid sequence for encoding amino acid sequence for mature 2086 protein from C11 when combined with a P4 leader sequence.

SEQ ID NO:40 amino acid sequence for mature 2086 protein from C11 strain prepared using a P4 leader sequence.

SEQ ID NO:41 nucleic acid sequence encoding amino acid sequence for mature 2086 protein from C11 strain.

SEQ ID NO:42 amino acid sequence for mature 2086 protein from C11 strain.

SEQ ID NO:43 nucleic acid sequence encoding amino acid sequence for mature 2086 protein from Y (ATCC35561) strain when combined with a native leader sequence.

SEQ ID NO:44 amino acid sequence for mature 2086 protein from Y (ATCC35561) strain prepared using a native leader sequence.

SEQ ID NO:45 nucleic acid sequence for encoding amino acid sequence for mature 2086 protein from Y (ATCC35561) when combined with a P4 leader sequence.

SEQ ID NO:46 amino acid sequence for mature 2086 protein from Y (ATCC35561) strain prepared using a P4 leader sequence.

SEQ ID NO:47 nucleic acid sequence encoding amino acid sequence for mature 2086 protein from Y (ATCC35561) strain.

SEQ ID NO:48 amino acid sequence for mature 2086 protein from Y (ATCC35561) strain.

SEQ ID NO:49 nucleic acid sequence encoding amino acid sequence for mature 2086 protein from M98 250732 strain when combined with a native leader sequence.

SEQ ID NO:50 amino acid sequence for mature 2086 protein from M98 250732 strain prepared using a native leader sequence.

SEQ ID NO:51 nucleic acid sequence for encoding amino acid sequence for mature 2086 protein from M98 250732 when combined with a P4 leader sequence.

SEQ ID NO:52 amino acid sequence for mature 2086 protein from M98 250732 strain prepared using a P4 leader sequence.

SEQ ID NO:53 nucleic acid sequence encoding amino acid sequence for mature 2086 protein from M98 250732 strain.

SEQ ID NO:54 amino acid sequence for mature 2086 protein from M98 250732 strain.

SEQ ID NO:55 nucleic acid sequence encoding amino acid sequence for mature 2086 protein from M98 250771 strain when combined with a native leader sequence.

SEQ ID NO:56 amino acid sequence for mature 2086 protein from M98 250771 strain prepared using a native leader sequence.

SEQ ID NO:57 nucleic acid sequence for encoding amino acid sequence for mature 2086 protein from M98 250771 when combined with a P4 leader sequence.

SEQ ID NO:58 amino acid sequence for mature 2086 protein from M98 250771 strain prepared using a P4 leader sequence.

SEQ ID NO:59 nucleic acid sequence encoding amino acid sequence for mature 2086 protein from M98 250771 strain.

SEQ ID NO:60 amino acid sequence for mature 2086 protein from M98 250771 strain.

SEQ ID NO:61 nucleic acid sequence encoding amino acid sequence for mature 2086 protein from CDC1135 strain when combined with a native leader sequence.

SEQ ID NO:62 amino acid sequence for mature 2086 protein from CDC1135 strain prepared using a native leader sequence.

SEQ ID NO:63 nucleic acid sequence for encoding amino acid sequence for mature 2086 protein from CDC1135 when combined with a P4 leader sequence.

SEQ ID NO:64 amino acid sequence for mature 2086 protein from CDC1135 strain prepared using a P4 leader sequence.

SEQ ID NO:65 nucleic acid sequence encoding amino acid sequence for mature 2086 protein from CDC1135 strain.

SEQ ID NO:66 amino acid sequence for mature 2086 protein from CDC1135 strain.

SEQ ID NO:67 nucleic acid sequence encoding amino acid sequence for mature 2086 protein from M97 252153 strain when combined with a native leader sequence.

SEQ ID NO:68 amino acid sequence for mature 2086 protein from M97 252153 strain prepared using a native leader sequence.

SEQ ID NO:69 nucleic acid sequence for encoding amino acid sequence for mature 2086 protein from M97 252153 when combined with a P4 leader sequence.

SEQ ID NO:70 amino acid sequence for mature 2086 protein from M97 252153 strain prepared using a P4 leader sequence.

SEQ ID NO:71 nucleic acid sequence encoding amino acid sequence for mature 2086 protein from M97 252153 strain.

SEQ ID NO:72 amino acid sequence for mature 2086 protein from M97 252153 strain.

SEQ ID NO:73 nucleic acid sequence encoding amino acid sequence for mature 2086 protein from CDC1610 strain when combined with a native leader sequence.

SEQ ID NO:74 amino acid sequence for mature 2086 protein from CDC1610 strain prepared using a native leader sequence.

SEQ ID NO:75 nucleic acid sequence for encoding amino acid sequence for mature 2086 protein from CDC1610 when combined with a P4 leader sequence.

SEQ ID NO:76 amino acid sequence for mature 2086 protein from CDC1610 strain prepared using a P4 leader sequence.

SEQ ID NO:77 nucleic acid sequence encoding amino acid sequence for mature 2086 protein from CDC1610 strain.

SEQ ID NO:78 amino acid sequence for mature 2086 protein from CDC1610 strain.

SEQ ID NO:79 nucleic acid sequence encoding amino acid sequence for mature 2086 protein from CDC1492 strain when combined with a native leader sequence.

SEQ ID NO:80 amino acid sequence for mature 2086 protein from CDC1492 strain prepared using a native leader sequence.

SEQ ID NO:81 nucleic acid sequence for encoding amino acid sequence for mature 2086 protein from CDC1492 when combined with a P4 leader sequence.

SEQ ID NO:82 amino acid sequence for mature 2086 protein from CDC1492 strain prepared using a P4 leader sequence.

SEQ ID NO:83 nucleic acid sequence encoding amino acid sequence for mature 2086 protein from CDC1492 strain.

SEQ ID NO:84 amino acid sequence for mature 2086 protein from CDC1492 strain.

SEQ ID NO:85 nucleic acid sequence encoding amino acid sequence for mature 2086 protein from L8 M978 strain when combined with a native leader sequence.

SEQ ID NO:86 amino acid sequence for mature 2086 protein from L8 M978 strain prepared using a native leader sequence.

SEQ ID NO:87 nucleic acid sequence for encoding amino acid sequence for mature 2086 protein from L8 M978 when combined with a P4 leader sequence.

SEQ ID NO:88 amino acid sequence for mature 2086 protein from L8 M978 strain prepared using a P4 leader sequence.

SEQ ID NO:89 nucleic acid sequence encoding amino acid sequence for mature 2086 protein from L8 M978 strain.

SEQ ID NO:90 amino acid sequence for mature 2086 protein from L8 M978 strain.

SEQ ID NO:91 nucleic acid sequence encoding amino acid sequence for mature 2086 protein from M97 252988 strain when combined with a native leader sequence.

SEQ ID NO:92 amino acid sequence for mature 2086 protein from M97 252988 strain prepared using a native leader sequence.

SEQ ID NO:93 nucleic acid sequence for encoding amino acid sequence for mature 2086 protein from M97 252988 when combined with a P4 leader sequence.

SEQ ID NO:94 amino acid sequence for mature 2086 protein from M97 252988 strain prepared using a P4 leader sequence.

SEQ ID NO:95 nucleic acid sequence encoding amino acid sequence for mature 2086 protein from M97 252988 strain.

SEQ ID NO:96 amino acid sequence for mature 2086 protein from M97 252988 strain.

SEQ ID NO:97 nucleic acid sequence encoding amino acid sequence for mature 2086 protein from M97 252697 strain when combined with a native leader sequence.

SEQ ID NO:98 amino acid sequence for mature 2086 protein from M97 252697 strain prepared using a native leader sequence.

SEQ ID NO:99 nucleic acid sequence for encoding amino acid sequence for mature 2086 protein from M97 252697 when combined with a P4 leader sequence.

SEQ ID NO:100 amino acid sequence for mature 2086 protein from M97 252697 strain prepared using a P4 leader sequence.

SEQ ID NO:101 nucleic acid sequence encoding amino acid sequence for mature 2086 protein from M97 252697 strain.

SEQ ID NO:102 amino acid sequence for mature 2086 protein from M97 252697 strain.

SEQ ID NO:103 nucleic acid sequence encoding amino acid sequence for mature 2086 protein from 6557 strain when combined with a native leader sequence.

SEQ ID NO:104 amino acid sequence for mature 2086 protein from 6557 strain prepared using a native leader sequence.

SEQ ID NO:105 nucleic acid sequence for encoding amino acid sequence for mature 2086 protein from 6557 when combined with a P4 leader sequence.

SEQ ID NO:106 amino acid sequence for mature 2086 protein from 6557 strain prepared using a P4 leader sequence.

SEQ ID NO:107 nucleic acid sequence encoding amino acid sequence for mature 2086 protein from 6557 strain.

SEQ ID NO:108 amino acid sequence for mature 2086 protein from 6557 strain.

SEQ ID NO:109 nucleic acid sequence encoding amino acid sequence for mature 2086 protein from 2996 strain when combined with a native leader sequence.

SEQ ID NO:110 amino acid sequence for mature 2086 protein from 2996 strain prepared using a native leader sequence.

SEQ ID NO:111 nucleic acid sequence for encoding amino acid sequence for mature 2086 protein from 2996 when combined with a P4 leader sequence.

SEQ ID NO:112 amino acid sequence for mature 2086 protein from 2996 strain prepared using a P4 leader sequence.

SEQ ID NO:113 nucleic acid sequence encoding amino acid sequence for mature 2086 protein from 2996 strain.

SEQ ID NO:114 amino acid sequence for mature 2086 protein from 2996 strain.

SEQ ID NO:115 nucleic acid sequence encoding amino acid sequence for mature 2086 protein from M97 252976 strain when combined with a native leader sequence.

SEQ ID NO:116 amino acid sequence for mature 2086 protein from M97 252976 strain prepared using a native leader sequence.

SEQ ID NO:117 nucleic acid sequence for encoding amino acid sequence for mature 2086 protein from M97 252976 when combined with a P4 leader sequence.

SEQ ID NO:118 amino acid sequence for mature 2086 protein from M97 252976 strain prepared using a P4 leader sequence.

SEQ ID NO:119 nucleic acid sequence encoding amino acid sequence for mature 2086 protein from M97 252976 strain.

SEQ ID NO:120 amino acid sequence for mature 2086 protein from M97 252976 strain.

SEQ ID NO:121 nucleic acid sequence encoding amino acid sequence for mature 2086 protein from M97 251854 strain when combined with a native leader sequence.

SEQ ID NO:122 amino acid sequence for mature 2086 protein from M97 251854 strain prepared using a native leader sequence.

SEQ ID NO:123 nucleic acid sequence for encoding amino acid sequence for mature 2086 protein from M97 251854 when combined with a P4 leader sequence.

SEQ ID NO:124 amino acid sequence for mature 2086 protein from M97 251854 strain prepared using a P4 leader sequence.

SEQ ID NO:125 nucleic acid sequence encoding amino acid sequence for mature 2086 protein from M97 251854 strain.

SEQ ID NO:126 amino acid sequence for mature 2086 protein from M97 251854 strain.

SEQ ID NO:127 nucleic acid sequence encoding amino acid sequence for mature 2086 protein from CDC1521 strain when combined with a native leader sequence.

SEQ ID NO:128 amino acid sequence for mature 2086 protein from CDC1521 strain prepared using a native leader sequence.

SEQ ID NO:129 nucleic acid sequence for encoding amino acid sequence for mature 2086 protein from CDC1521 when combined with a P4 leader sequence.

SEQ ID NO:130 amino acid sequence for mature 2086 protein from CDC1521 strain prepared using a P4 leader sequence.

SEQ ID NO:131 nucleic acid sequence encoding amino acid sequence for mature 2086 protein from CDC1521 strain.

SEQ ID NO:132 amino acid sequence for mature 2086 protein from CDC1521 strain.

SEQ ID NO:133 nucleic acid sequence encoding amino acid sequence for mature 2086 protein from M98 250622 strain when combined with a native leader sequence.

SEQ ID NO:134 amino acid sequence for mature 2086 protein from M98 250622 strain prepared using a native leader sequence.

SEQ ID NO:135 nucleic acid sequence for encoding amino acid sequence for mature 2086 protein from M98 250622 when combined with a P4 leader sequence.

SEQ ID NO:136 amino acid sequence for mature 2086 protein from M98 250622 strain prepared using a P4 leader sequence.

SEQ ID NO:137 nucleic acid sequence encoding amino acid sequence for mature 2086 protein from M98 250622 strain.

SEQ ID NO:138 amino acid sequence for mature 2086 protein from M98 250622 strain.

SEQ ID NO:139 nucleic acid sequence encoding amino acid sequence for mature 2086 protein from 870446 strain when combined with a native leader sequence.

SEQ ID NO:140 amino acid sequence for mature 2086 protein from 870446 strain prepared using a native leader sequence.

SEQ ID NO:141 nucleic acid sequence for encoding amino acid sequence for mature 2086 protein from 870446 when combined with a P4 leader sequence.

SEQ ID NO:142 amino acid sequence for mature 2086 protein from 870446 strain prepared using a P4 leader sequence.

SEQ ID NO:143 nucleic acid sequence encoding amino acid sequence for mature 2086 protein from 870446 strain.

SEQ ID NO:144 amino acid sequence for mature 2086 protein from 870446 strain.

SEQ ID NO:145 nucleic acid sequence encoding amino acid sequence for mature 2086 protein from M97 253248 strain when combined with a native leader sequence.

SEQ ID NO:146 amino acid sequence for mature 2086 protein from M97 253248 strain prepared using a native leader sequence.

SEQ ID NO:147 nucleic acid sequence for encoding amino acid sequence for mature 2086 protein from M97 253248 when combined with a P4 leader sequence.

SEQ ID NO:148 amino acid sequence for mature 2086 protein from M97 253248 strain prepared using a P4 leader sequence.

SEQ ID NO:149 nucleic acid sequence encoding amino acid sequence for mature 2086 protein from M97 253248 strain.

SEQ ID NO:150 amino acid sequence for mature 2086 protein from M97 253248 strain.

SEQ ID NO:151 nucleic acid sequence encoding amino acid sequence for mature 2086 protein from M98 250809 strain when combined with a native leader sequence.

SEQ ID NO:152 amino acid sequence for mature 2086 protein from M98 250809 strain prepared using a native leader sequence.

SEQ ID NO:153 nucleic acid sequence for encoding amino acid sequence for mature 2086 protein from M98 250809 when combined with a P4 leader sequence.

SEQ ID NO:154 amino acid sequence for mature 2086 protein from M98 250809 strain prepared using a P4 leader sequence.

SEQ ID NO:155 nucleic acid sequence encoding amino acid sequence for mature 2086 protein from M98 250809 strain.

SEQ ID NO:156 amino acid sequence for mature 2086 protein from M98 250809 strain.

SEQ ID NO:157 nucleic acid sequence encoding amino acid sequence for mature 2086 protein from L5 M981 strain when combined with a native leader sequence.

SEQ ID NO:158 amino acid sequence for mature 2086 protein from L5 M981 strain prepared using a native leader sequence.

SEQ ID NO:159 nucleic acid sequence for encoding amino acid sequence for mature 2086 protein from L5 M981 when combined with a P4 leader sequence.

SEQ ID NO:160 amino acid sequence for mature 2086 protein from L5 M981 strain prepared using a P4 leader sequence.

SEQ ID NO:161 nucleic acid sequence encoding amino acid sequence for mature 2086 protein from L5 M981 strain.

SEQ ID NO:162 amino acid sequence for mature 2086 protein from L5 M981 strain.

SEQ ID NO:163 nucleic acid sequence encoding amino acid sequence for mature 2086 protein from NMB strain when combined with a native leader sequence.

SEQ ID NO:164 amino acid sequence for mature 2086 protein from NMB strain prepared using a native leader sequence.

SEQ ID NO:165 nucleic acid sequence for encoding amino acid sequence for mature 2086 protein from NMB when combined with a P4 leader sequence.

SEQ ID NO:166 amino acid sequence for mature 2086 protein from NMB strain prepared using a P4 leader sequence.

SEQ ID NO:167 nucleic acid sequence encoding amino acid sequence for mature 2086 protein from NMB strain.

SEQ ID NO:168 amino acid sequence for mature 2086 protein from NMB strain.

SEQ ID NO:169 nucleic acid sequence encoding amino acid sequence for mature 2086 protein from M98 250572 strain when combined with a native leader sequence.

SEQ ID NO:170 amino acid sequence for mature 2086 protein from M98 250572 strain prepared using a native leader sequence.

SEQ ID NO:171 nucleic acid sequence for encoding amino acid sequence for mature 2086 protein from M98 250572 when combined with a P4 leader sequence.

SEQ ID NO:172 amino acid sequence for mature 2086 protein from M98 250572 strain prepared using a P4 leader sequence.

SEQ ID NO:173 nucleic acid sequence encoding amino acid sequence for mature 2086 protein from M98 250572 strain.

SEQ ID NO:174 amino acid sequence for mature 2086 protein from M98 250572 strain.

SEQ ID NO:175 nucleic acid sequence encoding amino acid sequence for mature 2086 protein from A4 Sanford; M97 251836 PART; M97 251957; M97 251985; M97 252060; M97 251870; M97 251994; M98 250024; M97 251905; M97 251876; M97 251898; or M97 251830 strain when combined with a native leader sequence.

SEQ ID NO:176 amino acid sequence for mature 2086 protein from A4 Sanford; M97 251836 PART; M97 251957; M97 251985; M97 252060; M97 251870; M97 251994; M98 250024; M97 251905; M97 251876; M97 251898; or M97 251830 strain prepared using a native leader sequence.

SEQ ID NO:177 nucleic acid sequence for encoding amino acid sequence for mature 2086 protein from A4 Sanford; M97 251836 PART; M97 251957; M97 251985; M97 252060; M97 251870; M97 251994; M98 250024; M97 251905; M97 251876; M97 251898; or M97 251830 when combined with a P4 leader sequence.

SEQ ID NO:178 amino acid sequence for mature 2086 protein from A4 Sanford; M97 251836 PART; M97 251957; M97 251985; M97 252060; M97 251870; M97 251994; M98 250024; M97 251905; M97 251876; M97 251898; or M97 251830 strain prepared using a P4 leader sequence.

SEQ ID NO:179 nucleic acid sequence encoding amino acid sequence for mature 2086 protein from A4 Sanford; M97 251836 part; M97 251957; M97 251985; M97 252060; M97 251870; M97 251994; M98 250024; M97 251905; M97 251876; M97 251898; or M97 251830 strain.

SEQ ID NO:180 amino acid sequence for mature 2086 protein from A4 Sanford; M97 251836 PART; M97 251957; M97 251985; M97 252060; M97 251870; M97 251994; M98 250024; M97 251905; M97 251876; M97 251898; or M97 251830 strain.

SEQ ID NO:181 nucleic acid sequence encoding partial amino acid sequence for mature 2086 protein from CDC937 strain when combined with a native leader sequence.

SEQ ID NO:182 amino acid sequence for mature 2086 protein from CDC937 strain prepared using a native leader sequence.

SEQ ID NO:183 nucleic acid sequence for encoding partial amino acid sequence for mature 2086 protein from CDC937 when combined with a P4 leader sequence.

SEQ ID NO:184 amino acid sequence for mature 2086 protein from CDC937 strain prepared using a P4 leader sequence.

SEQ ID NO:185 nucleic acid sequence encoding partial amino acid sequence for mature 2086 protein from CDC937 strain.

SEQ ID NO:186 amino acid sequence for mature 2086 protein from CDC937 strain.

SEQ ID NO:187 nucleic acid sequence encoding partial amino acid sequence for mature 2086 protein from M97 252097 strain when combined with a native leader sequence.

SEQ ID NO:188 amino acid sequence for mature 2086 protein from M97 252097 strain prepared using a native leader sequence.

SEQ ID NO:189 nucleic acid sequence for encoding partial amino acid sequence for mature 2086 protein from M97 252097 when combined with a P4 leader sequence.

SEQ ID NO:190 amino acid sequence for mature 2086 protein from M97 252097 strain prepared using a P4 leader sequence.

SEQ ID NO:191 nucleic acid sequence encoding partial amino acid sequence for mature 2086 protein from M97 252097 strain.

SEQ ID NO:192 amino acid sequence for mature 2086 protein from M97 252097 strain.

SEQ ID NO:193 nucleic acid sequence encoding amino acid sequence for mature 2086 protein from 870227 strain when combined with a native leader sequence.

SEQ ID NO:194 amino acid sequence for mature 2086 protein from 870227 strain prepared using a native leader sequence.

SEQ ID NO:195 nucleic acid sequence for encoding amino acid sequence for mature 2086 protein from 870227 when combined with a P4 leader sequence.

SEQ ID NO:196 amino acid sequence for mature 2086 protein from 870227 strain prepared using a P4 leader sequence.

SEQ ID NO:197 nucleic acid sequence encoding amino acid sequence for mature 2086 protein from 870227 strain.

SEQ ID NO:198 amino acid sequence for mature 2086 protein from 870227 strain.

SEQ ID NO:199 nucleic acid sequence encoding amino acid sequence for mature 2086 protein from H355 strain when combined with a native leader sequence.

SEQ ID NO:200 amino acid sequence for mature 2086 protein from H355 strain prepared using a native leader sequence.

SEQ ID NO:201 nucleic acid sequence for encoding amino acid sequence for mature 2086 protein from H355 when combined with a P4 leader sequence.

SEQ ID NO:202 amino acid sequence for mature 2086 protein from H355 strain prepared using a P4 leader sequence.

SEQ ID NO:203 nucleic acid sequence encoding amino acid sequence for mature 2086 protein from H355 strain.

SEQ ID NO:204 amino acid sequence for mature 2086 protein from H355 strain.

SEQ ID NO:205 nucleic acid sequence encoding amino acid sequence for mature 2086 protein from H44_76 strain when combined with a native leader sequence.

SEQ ID NO:206 amino acid sequence for mature 2086 protein from H44_76 strain prepared using a native leader sequence.

SEQ ID NO:207 amino acid sequence for mature 2086 protein from H44_76 strain prepared using a P4 leader sequence.

SEQ ID NO:208 nucleic acid sequence encoding amino acid sequence for mature 2086 protein from H44_76 strain.

SEQ ID NO:209 nucleic acid sequence for encoding amino acid sequence for mature 2086 protein from H44_76 when combined with a P4 leader sequence.

SEQ ID NO:210 amino acid sequence for mature 2086 protein from H44_76 strain.

SEQ ID NO:211 nucleic acid sequence encoding amino acid sequence for mature 2086 protein from 8529 strain when combined with a native leader sequence.

SEQ ID NO:212 amino acid sequence for mature 2086 protein from 8529 strain prepared using a native leader sequence.

SEQ ID NO:213 nucleic acid sequence for encoding amino acid sequence for mature 2086 protein from 8529 when combined with a P4 leader sequence.

SEQ ID NO:214 amino acid sequence for mature 2086 protein from 8529 strain prepared using a P4 leader sequence.

SEQ ID NO:215 nucleic acid sequence encoding amino acid sequence for mature 2086 protein from 8529 strain.

SEQ ID NO:216 amino acid sequence for mature 2086 protein from 8529 strain.

SEQ ID NO:217 nucleic acid sequence encoding amino acid sequence for mature 2086 protein from 6940 strain when combined with a native leader sequence.

SEQ ID NO:218 amino acid sequence for mature 2086 protein from 6940 strain prepared using a native leader sequence.

SEQ ID NO:219 nucleic acid sequence for encoding amino acid sequence for mature 2086 protein from 6940 when combined with a P4 leader sequence.

SEQ ID NO:220 amino acid sequence for mature 2086 protein from 6940 strain prepared using a P4 leader sequence.

SEQ ID NO:221 nucleic acid sequence encoding amino acid sequence for mature 2086 protein from 6940 strain.

SEQ ID NO:222 amino acid sequence for mature 2086 protein from 6940 strain.

SEQ ID NO:223 nucleic acid sequence encoding amino acid sequence for mature 2086 protein from M982 strain when combined with a native leader sequence.

SEQ ID NO:224 amino acid sequence for mature 2086 protein from M982 strain prepared using a native leader sequence.

SEQ ID NO:225 nucleic acid sequence for encoding amino acid sequence for mature 2086 protein from M982 when combined with a P4 leader sequence.

SEQ ID NO:226 amino acid sequence for mature 2086 protein from M982 strain prepared using a P4 leader sequence.

SEQ ID NO:227 nucleic acid sequence encoding amino acid sequence for mature 2086 protein from M982 strain.

SEQ ID NO:228 amino acid sequence for mature 2086 protein from M982 strain.

SEQ ID NO:229 nucleic acid sequence encoding amino acid sequence for mature 2086 protein from 880049 strain when combined with a native leader sequence.

SEQ ID NO:230 amino acid sequence for mature 2086 protein from 880049 strain prepared using a native leader sequence.

SEQ ID NO:231 nucleic acid sequence for encoding amino acid sequence for mature 2086 protein from 880049 when combined with a P4 leader sequence.

SEQ ID NO:232 amino acid sequence for mature 2086 protein from 880049 strain prepared using a P4 leader sequence.

SEQ ID NO:233 nucleic acid sequence encoding amino acid sequence for mature 2086 protein from 880049 strain.

SEQ ID NO:234 amino acid sequence for mature 2086 protein from 880049 strain.

SEQ ID NO:235 nucleic acid sequence encoding amino acid sequence for mature 2086 protein from M97 253524, M97 251885, and M97 251926 strains when combined with a native leader sequence.

SEQ ID NO:236 amino acid sequence for mature 2086 protein from M97 253524, M97 251885, and M97 251926 strains prepared using a native leader sequence.

SEQ ID NO:237 nucleic acid sequence for encoding amino acid sequence for mature 2086 protein from M97 253524, M97 251885, and M97 251926 strains when combined with a P4 leader sequence.

SEQ ID NO:238 amino acid sequence for mature 2086 protein from M97 253524, M97 251885, and M97 251926 strains prepared using a P4 leader sequence.

SEQ ID NO:239 nucleic acid sequence encoding amino acid sequence for mature 2086 protein from M97 253524, M97 251885, and M97 251926 strains.

SEQ ID NO:240 amino acid sequence for mature 2086 protein from M97 253524, M97 251885, and M97 251926 strains.

SEQ ID NO:241 nucleic acid sequence encoding amino acid sequence for mature 2086 protein from M98 250670 strain when combined with a native leader sequence.

SEQ ID NO:242 amino acid sequence for mature 2086 protein from M98 250670 strain prepared using a native leader sequence.

SEQ ID NO:243 nucleic acid sequence for encoding amino acid sequence for mature 2086 protein from M98 250670 when combined with a P4 leader sequence.

SEQ ID NO:244 amino acid sequence for mature 2086 protein from M98 250670 strain prepared using a P4 leader sequence.

SEQ ID NO:245 nucleic acid sequence encoding amino acid sequence for mature 2086 protein from M98 250670 strain.

SEQ ID NO:246 amino acid sequence for mature 2086 protein from M98 250670 strain.

SEQ ID NO:247 nucleic acid sequence encoding amino acid sequence for mature 2086 protein from CDC1573 strain when combined with a native leader sequence.

SEQ ID NO:248 amino acid sequence for mature 2086 protein from CDC1573 strain prepared using a native leader sequence.

SEQ ID NO:249 nucleic acid sequence for encoding amino acid sequence for mature 2086 protein from CDC1573 when combined with a P4 leader sequence.

SEQ ID NO:250 amino acid sequence for mature 2086 protein from CDC1573 strain prepared using a P4 leader sequence.

SEQ ID NO:251 nucleic acid sequence encoding amino acid sequence for mature 2086 protein from CDC1573 strain.

SEQ ID NO:252 amino acid sequence for mature 2086 protein from CDC1573 strain.

SEQ ID NO:253 partial nucleic acid sequence encoding amino acid sequence for 2086 protein from a strain of *Neisseria lactamica*.

SEQ ID NOS:254 to 259 amino acid sequences associated with proteins of 2086 family of proteins.

SEQ ID NOS:260 to 278 amino acid sequences associated with proteins of 2086 Subfamily A.

SEQ ID NOS:279 to 299 amino acid sequences associated with proteins of 2086 Subfamily B.

SEQ ID NO:300 is the amino acid consensus sequence corresponding to the 2086 protein family ("2086 proteins") according to an embodiment of the present invention.

SEQ ID NO:301 is the amino acid consensus sequence corresponding to the 2086 protein Subfamily A according to an embodiment of the present invention.

SEQ ID NO:302 is the amino acid consensus sequence corresponding to the 2086 protein Subfamily B according to an embodiment of the present invention.

SEQ ID NO:303 nucleic acid sequence for a reverse primer with BamHI restriction site (Compound No. 4623).

SEQ ID NO:304 nucleic acid sequence for a forward primer with NdeI restriction site (Compound No. 4624).

SEQ ID NO:305 nucleic acid sequence for a forward primer (Compound No. 4625).

SEQ ID NO:306 nucleic acid sequence for a forward primer (Compound No. 5005). SEQ ID NO:307 nucleic acid sequence for a reverse primer (Compound No. 5007).

SEQ ID NO:308 nucleic acid sequence for a reverse primer with BglII restriction site (Compound No. 5135).

SEQ ID NO:309 nucleic acid sequence for a forward primer with BamHI restriction site (Compound No. 5658).

SEQ ID NO:310 nucleic acid sequence for a reverse primer with SphI restriction site (Compound No. 5660).

SEQ ID NO:311 nucleic acid sequence for a forward primer with BamHI restriction site (Compound No. 6385).

SEQ ID NO:312 nucleic acid sequence for a forward primer with BglII and NdeI restriction sites (Compound No. 6406).

SEQ ID NO:313 nucleic acid sequence for a forward primer (Compound No. 6470).

SEQ ID NO:314 nucleic acid sequence for a reverse primer (Compound No. 6472).

SEQ ID NO:315 nucleic acid sequence for a forward primer with BamHI restriction site (Compound 6473).

SEQ ID NO:316 nucleic acid sequence for a forward primer with BglII and NdeI restriction sites (Compound No. 6474).

SEQ ID NO:317 nucleic acid sequence for a forward primer (Compound No. 6495).

SEQ ID NO:318 nucleic acid sequence for a reverse primer (Compound No. 6496).

SEQ ID NO:319 nucleic acid sequence for a reverse primer with SphI restriction site (Compound No. 6543).

SEQ ID NO:320 nucleic acid sequence for a reverse primer with BglII restriction site (Compound No. 6605).

SEQ ID NO:321 nucleic acid sequence for a forward primer with BglII and NdeI restriction sites (Compound No. 6721).

SEQ ID NO:322 nucleic acid sequence for the P4 leader sequence.

SEQ ID NO:323 nucleic acid sequence for native 2086 leader variant 1.

SEQ ID NO:324 nucleic acid sequence for native 2086 leader variant 2.

SEQ ID NO:325 nucleic acid sequence for native 2086 leader variant 3.

SEQ ID NO:326 nucleic acid sequence for native 2086 leader variant 4.

SEQ ID NO:327 is the amino acid sequence of P4431.

SEQ ID NO:328 is the amino acid sequence of P5163.

SEQ ID NO:329 is an amino acid sequence according to an embodiment of the present invention.

DETAILED DESCRIPTION OF THE INVENTION

A new class of antigens with cross-functional bactericidal activity against *Neisseria meningitidis* serogroup B would obviate the need for a multi-valent PorA approach to immunization against infection. Such an antigen has been unexpectedly identified and is described and claimed herein. The presence of one such antigen was first observed in a complex mixture of soluble outer membrane proteins (sOMPs) from a meningococcal strain. The bactericidal activity of this antigen was followed through a series of fractionation and protein purification steps until the protein mixture of interest contained just a few proteins. The major proteins in this mixture were identified by N-terminal amino acid sequencing and peptide mapping. The protein of interest exhibiting bactericidal activity was identified as ORF2086 protein, a lipidated protein (also more specifically referred to as LP2086). "ORF2086 protein" refers to a protein encoded by open reading frame 2086 (ORF2086) of *Neisseria* species.

As described herein, new immunogenic composition candidates based on *Neisseria* species ORF2086 protein (also referred to as "2086 protein" or "ORF2086" protein, used interchangably herein, or P2086 for the non-lipated proteins and LP2086 for the lipidated version of the proteins) isolated from *N. meningitidis* were identified by combining cell fractionation, differential detergent extraction, protein purification, with the preparation of antisera, and a bactericidal activity assay utilizing multiple strains. As an alternative to potential immunogenic compositions and diagnostics disclosed in the references cited above, this invention relates to compositions and methods of treating and/or preventing meningococcal infection through the use of proteins, immunogenic portions thereof and biological equivalents thereof, as well as genes encoding said polypeptides, portions and equivalents, and antibodies that immunospecifically bind to same.

According to an embodiment of the present invention, immunogenic agents based on 2086 protein, including isolated polypeptides, immunogenic portions thereof and/or biological equivalents thereof were unexpectedly identified as immunogenic candidates based on the ability of said agents to exhibit cross-reactivity or non-strain specificity. In particular, candidates were identified that unexpectedly demonstrate the ability to (1) elicit bactericidal antibodies to multiple neisserial and/or gonococcal strains; (2) react with the surface of multiple strains; (3) confer passive protection against a live challenge; and/or (4) prevent colonization. Accordingly, the present invention provides immunogenic compositions comprising said immunogenic agents, including isolated polypeptides, immunogenic portions thereof, and/or biological equivalents thereof, as well as methods for using same against infection by *N. meningitidis*. (See Example 1 herein for the methodology used in the identification of the 2086 protein.)

As used herein, the term "non-strain specific" refers to the characteristic of an antigen to elicit an immune response effective against more than one strain of *N. meningitidis* (e.g., heterologous meningococcal strains). The term "cross-reactive" as it is used herein is used interchangeably with the term "non-strain specific". The term "immunogenic non-strain specific *N. meningitidis* antigen," as used herein, describes an antigen that can be isolated from *N. meningitidis*, although it can also be isolated from another bacterium (e.g., other neisserial strains, such as gonococcal strains, for example), or prepared using recombinant technology.

The 2086 proteins of the present invention include lipidated and non-lipidated proteins. Further, the present invention also contemplates the use of the immature proteins or preproteins that correspond to each protein as intermediate compounds/compositions.

The present invention also provides antibodies that immunospecifically bind to the foregoing immunogenic agents, according to implementations of the invention. Further, the present invention relates to isolated polynucleotides comprising nucleic acid sequences encoding any of the foregoing. Additionally, the present invention provides compositions and/or immunogenic compositions and their use in preventing, treating and/or diagnosing meningococcal meningitis, in particular serogroup B meningococcal disease, as well as methods for preparing said compositions.

The compositions of the present invention have been shown to be highly immunogenic and capable of eliciting the production of bactericidal antibodies. These antibodies are cross-reactive to serogroup, serotype and serosubtype heterologous meningococcal strains. Accordingly, the present compositions overcome the deficiencies of previous *N. meningitidis* vaccine attempts by exhibiting the ability to elicit bactericidal antibodies to heterologous neisserial strains. Thus, among other advantages, the present invention provides immunogenic compositions that can be compounded with fewer components to elicit protection comparable to previously used agents. The compositions or immunogenic agents therein (e.g., polypeptides, immunogenic portions or fragments, and biological equivalents, etc., without limitation) can be used alone or in combination with other antigens or agents to elicit immunological protection from meningococcal infection and disease, as well as to elicit immunological protection from infection and/or disease caused by other pathogens. This simplifies the design of an immunogenic composition for use against meningococcal infection by reducing the number of antigens required for protection against multiple strains. In fact, purified 2086 protein will dramatically and unexpectedly reduce the number of proteins required to provide adequate immunogenic coverage of the strains responsible for meningococcal disease. The 2086 protein can be recombinantly expressed in *E. coli* as a lipoprotein, which is the wild type form of the protein, at levels much higher than in the native meningococci.

Because antibodies directed against the 2086 protein from a single strain were found to kill unrelated (i.e., heterologous) strains, an attempt was made to characterize a large number of heterologous strains for the presence of a "2086 homolog", and to determine the level of sequence conservation. While about 70% of the strains tested by PCR had 2086 homologs that could be amplified using the primers that amplified the original 2086 gene from strain 8529, the remaining approximately 30% were negative by this test. These remaining approximately 30% were found to contain a 2086 homolog that has only about 60% amino acid sequence homology to the original 8529 derived 2086 gene. Other primers were identified that could amplify a 2086 homolog from these approximately 30% of strains. The *N. meningitidis* strains tested have been designated as belonging to Subfamily A or Subfamily B depending on which primer set can amplify a 2086 homolog. The details of these experiments are outlined in Example 5 below.

The Presence of a 2086 Protein in Numerous Serosubtypes.

To determine the level of sequence conservation of the 2086 gene between *N. meningitidis* strains, several representatives from Subfamilies A and B were cloned as full length genes and submitted for DNA sequence analysis. Using primers as disclosed herein, see, for example, Table IV, twenty four serogroup B meningococcal strains were identified, which express different serosubtype antigens and also express a shared protein, P2086. Examples of these sequences are provided herein and are shown as mature DNA sequences (i.e., all lipoprotein signal sequences have been cleaved at the cysteine residue). See, for example, the amino acid sequences of even numbered SEQ ID NOS: 2-252, without limitation.

Although the 2086 protein is not present in large amounts in wild type strains, it is a target for bactericidal antibodies. These antibodies, unlike those produced in response to the PorAs, are capable of killing strains expressing heterologous serosubtypes.

Antibodies to the 2086 protein also passively protect infant rats from challenge with meningococci. (see Table VII) Recombinant expression of 2086 protein enables the use of 2086 protein as an immunogenic composition for the prevention of meningococcal disease. All of the recent meningococcal immunogenic composition candidates in clinical trials have been complex mixtures or outer membrane protein preparations containing many different proteins. The PorA protein, that provides serosubtype specificity, will require the inclusion of 6 to 9 variants in an immunogenic composition to provide about 70-80% coverage of disease related serosubtypes. In contrast, it is clearly demonstrated herein that antisera to a single 2086 protein alone is able to kill representatives of six serosubtypes responsible for about 65% of the disease isolates in western Europe and the United States. Therefore, purified 2086 protein has the potential to reduce the number of proteins required to provide adequate immunogenic composition coverage of the serosubtypes responsible for meningococcal disease.

Proteins, Immunogenic Portions and Biological Equivalents

The 2086 proteins provided by the present invention are isolated proteins. The term "isolated" means altered by the hand of man from the natural state. If an "isolated" composition or substance occurs in nature, it has been changed or removed from its original environment, or both. For example, a polypeptide or a polynucleotide naturally present in a living animal is not "isolated," but the same polypeptide or polynucleotide separated from the coexisting materials of its natural state is "isolated", as the term is employed herein. Accordingly, as used herein, the term "isolated protein" encompasses proteins isolated from a natural source and proteins prepared using recombinant technology, as well as such proteins when combined with other antigens and/or additives, such as pharmaceutically acceptable carriers, buffers, adjuvants, etc., for example.

A 2086 protein, immunogenic portion thereof and/or a biological equivalent thereof, according an embodiment of the invention, comprises any of the following amino acid sequences:

(SEQ ID NO: 254)
ADIGxGLADA, wherein x is any amino acid;

(SEQ ID NO: 255)
IGxGLADALT, wherein x is any amino acid;

(SEQ ID NO: 256)
SLNTGKLKND;

(SEQ ID NO: 257)
SLNTGKLKNDKxSRFDF, wherein x is any amino acid;

(SEQ ID NO: 258)
SGEFQxYKQ, wherein x is any amino acid; or (SEQ ID NO: 259)
IEHLKxPE, wherein x is any amino acid.

A 2086 Subfamily A protein, immunogenic portion thereof and/or biological equivalent thereof comprises any of the following amino acid sequences, in accordance with an embodiment of the present invention:

(SEQ ID NO: 260)
GGGVAADIGx, wherein x is any amino acid;

(SEQ ID NO: 261)
SGEFQIYKQ;

(SEQ ID NO: 262)
HSAVVALQIE;

(SEQ ID NO: 263)
EKINNPDKID;

(SEQ ID NO: 264)
SLINQRSFLV;

(SEQ ID NO: 265)
SGLGGEHTAF;

(SEQ ID NO: 266)
GEHTAFNQLP;

(SEQ ID NO: 267)
SFLVSGLGGEH;

(SEQ ID NO: 268)
EKINNPDKIDSLINQRSFLVSGLGGEHTAFNQLP;

(SEQ ID NO: 269)
GKAEYHGKAF;

(SEQ ID NO: 270)
YHGKAFSSDD;

(SEQ ID NO: 271)
GKAEYHGKAFSSDD;

(SEQ ID NO: 272)
IEHLKTPEQN;

(SEQ ID NO: 273)
KTPEQNVELA;

(SEQ ID NO: 274)
IEHLKTPEQNVELA;

(SEQ ID NO: 275)
AELKADEKSH;

(SEQ ID NO: 276)
AVILGDTRYG;

(SEQ ID NO: 277)
AELKADEKSHAVILGDTRYG;
or (SEQ ID NO: 278)
EEKGTYHLAL.

A 2086 Subfamily B protein, immunogenic portion thereof and/or biological equivalent thereof comprises any of the following amino acid sequences, in accordance with an embodiment embodiment of the present invention:

(SEQ ID NO: 279)
LITLESGEFQ;

(SEQ ID NO: 280)
SALTALQTEQ;

(SEQ ID NO: 281)
FQVYKQSHSA;

(SEQ ID NO: 282)
LITLESGEFQVYKQSHSALTALQTEQ;

(SEQ ID NO: 283)
IGDIAGEHTS;

-continued (SEQ IDNO: 284)
EHTSFDKLPK;

(SEQ ID NO: 285)
IGDIAGEHTSFDKLPK;

(SEQ ID NO: 286)
ATYRGTAFGS;

(SEQ ID NO: 287)
DDAGGKLTYT;

(SEQ ID NO: 288)
IDFAAKQGHG;

(SEQ ID NO: 289)
KIEHLKSPEL;

(SEQ ID NO: 290)
ATYRGTAFGSDDAGGKLTYTIDFAAKQGHGKIEHLKSPELNV;

(SEQ ID NO: 291)
HAVISGSVLY;

(SEQ IDNO: 292)
KGSYSLGIFG;

(SEQ ID NO: 293)
VLYNQDEKGS;

(SEQ ID NO: 294)
HAVISGSVLYNQDEKGSYSLGIFG;

(SEQ ID NO: 295)
AQEVAGSAEV;

(SEQ ID NO: 296)
IHHIGLAAKQ;

(SEQ ID NO: 297)
VETANGIHHI;

(SEQ ID NO: 298)
AQEVAGSAEVETANGIHHIGLAAKQ;
or (SEQ ID NO: 299)
VAGSAEVETANGIHHIGLAAKQ.

The 2086 protein comprises the following consensus sequence and/or immunogenic portions thereof in accordance with an embodiment of the present invention.

2086 Protein Consensus Sequence (SEQ ID NO: 300):

CSSG-----GGGVxADIGxGLADALTxPxDxKDKxLxSLTLxxSxxxNxx
LxLxAQGAEKTxxxGD---SLNTGKLKNDKxSRFDFxxxIxVDGxxITLx
SGEFQxYKQxHSAxxALQxExxxxxxxxxxxxxxRxFxxxxxxGEHTxFx
xLPxx-xAxYxGxAFxSDDxxGxLxYxIDFxxKQGxGxIEHLKxPExNVx
LAxxxxKxDEKxHAVIxGxxxYxxxEKGxYxLxxxGxxAQExAGxAxVxx
xxxxHxIxxAxKQ In the foregoing consensus sequence, the "x" represents any amino acid, the region from amino acid position 5 to amino acid position 9 is any of 0 to 5 amino acids, the region from amino acid position 67 to amino acid position 69 is any of 0 to 3 amino acids, and amino acid position 156 is any of 0 to 1 amino acid. The region from amino acid position 5 to amino acid position 9 preferably comprises 0, 4 or 5 amino acids. The region from amino acid position 67 to amino acid position 69 preferably comprises 0 or 3 amino acids. It should be particularly noted that this consensus sequence illustrates the high variability of the 2086 proteins. By way of theory, without intending to be bound thereto, it is believed that this high variability provides the advantageous and unexpected cross-reactivity.

According to an implementation of the present invention, the 2086 proteins are characterized as being immunogenic, nonpathogenic and non-strain specific. Moreover, according to a further implementation of the present invention, these proteins unexpectedly exhibit immunogenicity while being about 2% to about 40% nonconserved.

As used herein, the term "nonconserved" refers to the number of amino acids that may undergo insertions, substitution and/or deletions as a percentage of the total number of amino acids in a protein. For example, if a protein is 40% nonconserved and has, for example, 263 amino acids, then there are 105 amino acid positions in the protein at which amino acids may undergo substitution. Likewise, if a protein is 10% nonconserved and has, for example, about 280 amino acids, then there are 28 amino acid positions at which amino acids may undergo substitution. The 2086 proteins may also undergo deletion of amino acid residues without compromising the immunogenicity of the proteins.

Further, the 2086 proteins may be divided into subfamilies based upon homology at various regions. For example, without intending to be limited thereto, the consensus sequences for two such subfamilies, Subfamily A and Subfamily B, are provided below:

2086 Subfamily A Sequence (SEQ ID 301)

```
CSSG----GGGVAADIGxGLADALTxPxDxKDKxLxSLTLxxSxxxNxxL

xLxAQGAEKTxxxGD---SLNTGKLKNDKxSRFDFxxxIxVDGQxITLxS

GEFQIYKQxHSAVVALQIEKINNPDKIDSLINQRSFLVSGLGGEHTAFNQ

LPxGKAEYHGKAFSSDDxxGxLxYxIDFxxKQGxGxIEHLKTPEQNVELA

xAELKADEKSHAVILGDTRYGxEEKGTYHLALxGDRAQEIAGxATVKIxE

KVHEIxIAxKQ

The reference "x" is any amino acid.
```

The reference "x" is any amino acid.

The region from amino acid position 5 to amino acid position 8 is any of 0 to 4 amino acids.

The region from amino acid position 66 to amino acid position 68 is any of 0 to 3 amino acids.

The region from amino acid position 5 to amino acid position 8 preferably comprises 0 or 4 amino acids. The region from amino acid position 66 to amino acid position 68 preferably comprises 0 or 3 amino acids.

2086 Subfamily B (SEQ ID 302)

```
CSSGGGG-----VxADIGxGLADALTAPLDHKDKxLxSLTLxxSxxxNxx

LxLxAQGAEKTYGNGDSLNTGKLKNDKVSRFDFIRQIEVDGxLITLESGE

FQVYKQSHSALTALQTEQxQDxExSxKMVAKRxFxIGDIAGEHTSFDKLP

KxxxATYRGTAFGSDDAGGKLTYTIDFAAKQGHGKIEHLKSPELNVxLAx

xYIKPDEKxHAVISGSVLYNQDEKGSYSLGIFGxxAQEVAGSAEVETANG

IHHIGLAAKQ

The reference "x" is any amino acid.
```

The reference "x" is any amino acid.

The region from amino acid position 8 to amino acid position 12 is any of 0 to 5 amino acids.

The region from amino acid position 8 to amino acid position 12 preferably comprises 0 or 5 amino acids.

According to implementations of the present invention, the 2086 protein subfamilies may be further subdivided into clusters. For example, according to an implementation of the present invention, the following clusters are provided: even numbered SEQ ID NOS:2-12; even numbered SEQ ID NOS: 14-24; even numbered SEQ ID NOS:26-42; even numbered SEQ ID NOS:50-60; even numbered SEQ ID NOS:62-108; even numbered SEQ ID NOS:110-138; even numbered SEQ ID NOS:140-156; even numbered SEQ ID NOS:158-174; and even numbered SEQ ID NOS: 224-252.

A polypeptide sequence of the invention may be identical to the reference sequence of even numbered SEQ ID NOS: 2-252, that is, 100% identical, or it may include a number of amino acid alterations as compared to the reference sequence such that the % identity is less than 100%. Such alterations include at least one amino acid deletion, substitution, including conservative and non-conservative substitution, or insertion. The alterations may occur at the amino- or carboxy-terminal positions of the reference polypeptide sequence or anywhere between those terminal positions, interspersed either individually among the amino acids in the reference amino acid sequence or in one or more contiguous groups within the reference amino acid sequence.

Thus, the invention also provides proteins having sequence identity to the amino acid sequences contained in the Sequence Listing (i.e., even numbered SEQ ID NOS: 2-252). Depending on the particular sequence, the degree of sequence identity is preferably greater than 60% (e.g., 60%, 70%, 80%, 90%, 95%, 97%, 99%, 99.9% or more). These homologous proteins include mutants and allelic variants.

In preferred embodiments of the invention, the 2086 proteins or other 2086 polypeptides (e.g., immunological portions and biological equivalents) generate bactericidal antibodies to homologous and at least one heterologous strain of meningococci. Specifically, the antibodies to the 2086 polypeptides passively protect infant rats from challenge, such as intranasal, with meningococci. In further preferred embodiments, the 2086 polypeptides exhibit such protection for infants rats for homologous strains and at least one heterologous strain. The polypeptide may be selected from the Sequence Summary above, as set forth in the even numbered SEQ ID NOS: 2-252, or the polypeptide may be any immunological fragment or biological equivalent of the listed polypeptides. Preferably, the polypeptide is selected from any of the even numbered SEQ ID NOS: 2-252 in the Sequence Summary above.

This invention also relates to allelic or other variants of the 2086 polypeptides, which are biological equivalents. Suitable biological equivalents will exhibit the ability to (1) elicit bactericidal antibodies to homologous strains and at least one heterologous neisserial strain and/or gonococcal strain; (2) react with the surface of homologous strains and at least one heterologous neisserial and/or gonococcal strain; (3) confer passive protection against a live challenge; and/or (4) prevent colonization.

Suitable biological equivalents have at least about 60%, preferably at least about 70%, more preferably at least about 75%, even more preferably about 80%, even more preferably about 85%, even more preferably about 90%, even more preferably 95% or even more preferably 98%, or even more preferably 99% similarity to one of the 2086 polypeptides specified herein (i.e., the even numbered SEQ ID NOS: 2-252), provided the equivalent is capable of eliciting substantially the same immunogenic properties as one of the 2086 proteins of this invention.

Alternatively, the biological equivalents have substantially the same immunogenic properties of one of the 2086 protein in the even numbered SEQ ID NOS: 2-252. According to embodiments of the present invention, the biological equivalents have the same immunogenic properties as the even numbered SEQ ID NOS 2-252.

The biological equivalents are obtained by generating variants and modifications to the proteins of this invention. These variants and modifications to the proteins are obtained by altering the amino acid sequences by insertion, deletion or substitution of one or more amino acids. The amino acid sequence is modified, for example by substitution in order to create a polypeptide having substantially the same or improved qualities. A preferred means of introducing alterations comprises making predetermined mutations of the nucleic acid sequence of the polypeptide by site-directed mutagenesis.

Modifications and changes can be made in the structure of a polypeptide of the present invention and still obtain a molecule having *N. meningitidis* immunogencity. For example, without limitation, certain amino acids can be substituted for other amino acids, including nonconserved and conserved substitution, in a sequence without appreciable loss of immunogenicity. Because it is the interactive capacity and nature of a polypeptide that defines that polypeptide's biological functional activity, a number of amino acid sequence substitutions can be made in a polypeptide sequence (or, of course, its underlying DNA coding sequence) and nevertheless obtain a polypeptide with like properties. The present invention contemplates any changes to the structure of the polypeptides herein, as well as the nucleic acid sequences encoding said polypeptides, wherein the polypeptide retains immunogenicity. A person of ordinary skill in the art would be readily able to modify the disclosed polypeptides and polynucleotides accordingly, based upon the guidance provided herein.

For example, certain variable regions have been identified where substitution or deletion is permissible The 2086 consensus sequence, as previously discussed, shows conserved and nonconserved regions of the 2086 family of proteins according to an implementation of the present invention.

In making such changes, any techniques known to persons of skill in the art may be utilized. For example, without intending to be limited thereto, the hydropathic index of amino acids can be considered. The importance of the hydropathic amino acid index in conferring interactive biologic function on a polypeptide is generally understood in the art. Kyte et al. 1982. *J. Mol. Bio.* 157:105-132.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity, i.e. with a biological property of the polypeptide.

Biological equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. Such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a phage vector which can exist in both a single stranded and double stranded form. Typically, site-directed mutagenesis in accordance herewith is performed by first obtaining a single-stranded vector which includes within its sequence a DNA sequence which encodes all or a portion of the *N. meningitidis* polypeptide sequence selected. An oligonucleotide primer bearing the desired mutated sequence is prepared (e.g., synthetically). This primer is then annealed to the single-stranded vector, and extended by the use of enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as *E. coli* cells and clones are selected which include recombinant vectors bearing the mutation. Commercially available kits come with all the reagents necessary, except the oligonucleotide primers.

2086 polypeptides include any protein or polypeptide comprising substantial sequence similarity and/or biological equivalence to a 2086 protein having an amino acid sequence from one of the even numbered SEQ ID NOS 2-252. In addition, a 2086 polypeptide of the invention is not limited to a particular source. Thus, the invention provides for the general detection and isolation of the polypeptides from a variety of sources. Also, the 2086 polypeptides can be prepared recombinantly, as is well within the skill in the art, based upon the guidance provided herein, or in any other synthetic manner, as known in the art.

It is contemplated in the present invention, that a 2086 polypeptide may advantageously be cleaved into fragments for use in further structural or functional analysis, or in the generation of reagents such as 2086-related polypeptides and 2086-specific antibodies. This can be accomplished by treating purified or unpurified *N. meningitidis* polypeptides with a peptidase such as endoproteinase glu-C (Boehringer, Indianapolis, Ind.). Treatment with CNBr is another method by which peptide fragments may be produced from natural *N. meningitidis* 2086 polypeptides. Recombinant techniques also can be used to produce specific fragments of a 2086 protein.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical (i.e., biologically equivalent). A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. *Applied Math.,* 48:1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al 1984), BLASTP, BLASTN, and FASTA (Altschul, S. F., et al., 1990). The BLASTX program is publicly available from NCBI and other sources (BLAST Manual, Altschul, S., et al., NCBI NLM NIH Bethesda, Md. 20894; Altschul, S., et al., 1990). The well known Smith Waterman algorithm may also be used to determine identity.

By way of example, without intending to be limited thereto, an amino acid sequence of the present invention may be identical to the reference sequences, even numbered SEQ ID NOS: 2-252; that is be 100% identical, or it may include a number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NOS:2-252 by the numerical percent of the respective percent identity (divided by 100) and then subtracting that product from said total number of amino acids in any of SEQ ID NOS:2-252, or:

$$n_a = x_a - (x_a \cdot y),$$

wherein $n_a$ is the number of amino acid alterations, $x_a$ is the total number of amino acids in SEQ ID NOS:2-252, and y is, for instance 0.70 for 70%, 0.80 for 80%, 0.85 for 85% etc., and wherein any non-integer product of x.sub.a and y is rounded down to the nearest integer prior to subtracting it from $x_a$.

In preferred embodiments, the polypeptide above is selected from the proteins set forth in the even numbered SEQ ID NOS 2-252, such as mature processed form of a 2086 protein. The 2086 proteins or equivalents, etc. may be lipidated or non-lipidated.

ORF 2086 is expressible in *E. coli* with the native ORF 2086 signal sequence. However, it is desirable to find means to improve the expression of proteins. According to an embodiment of the present invention, a leader sequence produces a lipidated form of the protein. For example, the following describes the use of the signal sequence of the non-typable *Haemophilus influenzae* P4 protein to enhance expression.

The processing of bacterial lipoproteins begins with the synthesis of a precursor or prolipoprotein containing a signal sequence, which in turn contains a consensus lipoprotein processing/modification site. This prolipoprotein initially passes through the common Sec system on the inner membrane of Gram negative bacteria or on the membrane in Gram positive bacteria. Once placed in the membrane by the Sec system, the prolipoprotein is cleaved by signal peptidase II at the consensus site and the exposed N-terminal cysteine residue is glycerated and acylated. Hayashi et al. 1990. Lipoproteins in bacteria. *J. Bioenerg. Biomembr.* June; 22(3):451-71; Oudega et al. 1993. *Escherichia coli* SecB, SecA, and SecY proteins are required for expression and membrane insertion of the bacteriocin release protein, a small lipoprotein. *J. Bacteriol.* March; 175(5):1543-7; Sankaran et al. 1995. Modification of bacterial lipoproteins. *Methods Enzymol.* 250:683-97.

In Gram negative bacteria, transport of the lipidated protein to the outer membrane is mediated by a unique ABC transporter system with membrane specificity depending on a sorting signal at position 2 of the lipoprotein. Yakushi et al. 2000. A new ABC transporter mediating the detachment of lipid modified proteins from membranes. *Nat Cell Biol.* April; 2(4):212-8.

Fusion with bacterial lipoproteins and their signal sequences has been used to display recombinant proteins on the surface of bacteria. U.S. Pat. Nos. 5,583,038 and 6,130,085. Exchanging lipoprotein signal sequences can increase the production of the lipoprotein. De et al. 2000. Purification and characterization of *Streptococcus pneumoniae* palmitoylated pneumococcal surface adhesin A expressed in *Escherichia coli. Vaccine.* March 6; 18(17):1811-21.

Bacterial lipidation of proteins is known to increase or modify the immunological response to proteins. Erdile et al. 1993. Role of attached lipid in immunogenicity of *Borrelia burgdorferi* OspA. *Infect. Immun.* January; 61(1):81-90; Snapper et al. 1995. Bacterial lipoproteins may substitute for cytokines in the humoral immune response to T cell-independent type II antigens. *J. Immunol.* December 15; 155(12):5582-9. However, bacterial lipoprotein expression can be complicated by the stringency of the processing. Pollitt et al. 1986. Effect of amino acid substitutions at the signal peptide cleavage site of the *Escherichia coli* major outer membrane lipoprotein. *J. Biol. Chem.* February 5; 261(4):1835-7; Lunn et al. 1987. Effects of prolipoprotein signal peptide mutations on secretion of hybrid prolipo-beta-lactamase in *Escherichia coli. J. Biol. Chem.* June 15; 262(17):8318-24; Klein et al. 1988. Distinctive properties of signal sequences from bacterial lipoproteins. *Protein Eng.* April; 2(1):15-20. Bacterial lipoprotein expression is also complicated by other problems such as toxicity and low expression levels. Gomez et al. 1994.

Nucleotide The *Bacillus subtilis* lipoprotein LplA causes cell lysis when expressed in *Escherichia coli. Microbiology*. August; 140 (Pt 8):1839-45; Hansson et al. 1995. Expression of truncated and full-length forms of the Lyme disease *Borrelia* outer surface protein A in *Escherichia coli. Protein Expr. Pur* February; 6(1):15-24; Yakushi et al. 1997. Lethality of the covalent linkage between mislocalized major outer membrane lipoprotein and the peptidoglycan of *Escherichia coli. J. Bacteriol*. May; 179(9):2857-62.

The nontypable *Haemophilus influenzae* bacterium expresses a lipoprotein designated P4 (also known as protein "e"). The recombinant form of the P4 protein is highly expressed in *E. coli* using the native P4 signal sequence. U.S. Pat. No. 5,955,580. When the native P4 signal sequence is substituted for the native ORF 2086 signal sequence in an expression vector in *E. coli*, the level of expression of ORF2086 is increased.

This concept of using the heterologous P4 signal sequence to increase expression is extendible to other bacterial lipoproteins. In particular, analysis of bacterial genomes leads to the identification of many ORFs as being of possible interest. Attempting to express each ORF with its native signal sequence in a heterologous host cell, such as *E. coli*, gives rise to a variety of problems inherent in using a variety of signal sequences, including stability, compatibility and so forth. To minimize these problems, the P4 signal sequence is used to express each ORF of interest. As described above, the P4 signal sequence improves the expression of the heterologous 2086 ORF. An expression vector is constructed by deleting the native signal sequence of the ORF of interest, and ligating the P4 signal sequence to the ORF. A suitable host cell is then transformed, transfected or infected with the expression vector, and expression of the ORF is increased in comparison to expression using the native signal sequence of the ORF.

The non-lipidated form is produced by a protein lacking the original leader sequence or a by a leader sequence which is replaced with a portion of sequence that does not specify a site for fatty acid acylation in a host cell.

The various forms of the 2086 proteins of this invention are referred to herein as "2086" protein, unless otherwise specifically noted. Also "2086 polypeptide" refers to the 2086 proteins as well as immunogenic portions or biological equivalents thereof as noted above, unless otherwise noted.

The full length isolated and purified *N. meningitidis* 2086 protein has an apparent molecular weight of about 28 to 35 kDa as measured on a 10% to 20% gradient SDS polyacrylamide gel (SDS-PAGE). More specifically, this protein has a molecular weight of about 26,000 to 30,000 daltons as measured by mass spectrometry.

Preferably, the 2086 polypeptides and nucleic acids encoding such polypeptides are used for preventing or ameliorating infection caused by *N. meningitidis* and/or other species.

Antibodies

The proteins of the invention, including the amino acid sequences of SEQ ID NOS: 2-252, their fragments, and analogs thereof, or cells expressing them, are also used as immunogens to produce antibodies immunospecific for the polypeptides of the invention. The invention includes antibodies to immunospecific polypeptides and the use of such antibodies to detect the presence of *N. meningitidis*, provide passive protection or measure the quantity or concentration of the polypeptides in a cell, a cell or tissue extract, or a biological fluid.

The antibodies of the invention include polyclonal antibodies, monoclonal antibodies, chimeric antibodies, and anti-idiotypic antibodies. Polyclonal antibodies are heterogeneous populations of antibody molecules derived from the sera of animals immunized with an antigen. Monoclonal antibodies are a substantially homogeneous population of antibodies to specific antigens. Monoclonal antibodies may be obtained by methods known to those skilled in the art, e.g., Kohler and Milstein, 1975, *Nature* 256:495-497 and U.S. Pat. No. 4,376,110. Such antibodies may be of any immunoglobulin class including IgG, IgM, IgE, IgA, GILD and any subclass thereof.

Chimeric antibodies are molecules, different portions of which are derived from different animal species, such as those having variable region derived from a murine monoclonal antibody and a human immunoglobulin constant region. Chimeric antibodies and methods for their production are known in the art (Cabilly et al., 1984, *Proc. Natl. Acad. Sci. USA* 81:3273-3277; Morrison et al., 1984, *Proc. Natl. Acad. Sci. USA* 81:6851-6855; Boulianne et al., 1984, *Nature* 312:643-646; Cabilly et al., European Patent Application 125023 (published Nov. 14, 1984); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Morrison et al., European Patent Application 173494 (published Mar. 5, 1986); Sahagan et al., 1986, *J. Immunol.* 137:1066-1074; Robinson et al., PCT/US86/02269 (published May 7, 1987); Liu et al., 1987, *Proc. Natl. Acad. Sci. USA* 84:3439-3443; Sun et al., 1987, *Proc. Natl. Acad. Sci. USA* 84:214-218; Better et al., 1988, *Science* 240:1041-1043). These references are hereby incorporated by reference in their entirety.

An anti-idiotypic (anti-Id) antibody is an antibody which recognizes unique determinants generally associated with the antigen-binding site of an antibody. An anti-Id antibody is prepared by immunizing an animal of the same species and genetic type (e.g., mouse strain) as the source of the monoclonal antibody with the monoclonal antibody to which an anti-Id is being prepared. The immunized animal will recognize and respond to the idiotypic determinants of the immunizing antibody by producing an antibody to these isotypic determinants (the anti-Id antibody).

Accordingly, monoclonal antibodies generated against the polypeptides of the present invention may be used to induce anti-Id antibodies in suitable animals. Spleen cells from such immunized mice can be used to produce anti-Id hybridomas secreting anti-Id monoclonal antibodies. Further, the anti-Id antibodies can be coupled to a carrier such as keyhole limpet hemocyanin (KLH) and used to immunize additional BALB/c mice. Sera from these mice will contain anti-anti-Id antibodies that have the binding properties of the final mAb specific for an R-PTPase epitope. The anti-Id antibodies thus have their idiotypic epitopes, or "idiotopes" structurally similar to the epitope being evaluated, such as *Streptococcus pyogenes* polypeptides.

The term "antibody" is also meant to include both intact molecules as well as fragments such as Fab which are capable of binding antigen. Fab fragments lack the Fc fragment of intact antibody, clear more rapidly from the circulation, and may have less non-specific tissue binding than an intact antibody (Wahl et al., 1983, *J. Nucl. Med.* 24:316-325). It will be appreciated that Fab and other fragments of the antibodies useful in the present invention may be used for the detection and quantitation of *N. meningitidis* polypeptides according to the methods for intact antibody molecules.

The antibodies of this invention, such as anti-iodiotypic ("anti-Id") antibodies, can be employed in a method for the treatment or prevention of *Neisseria* infection in mammalian hosts, which comprises administration of an immunologically effective amount of antibody, specific for a polypeptide as described above. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

The antibodies are used in a variety of ways, e.g., for confirmation that a protein is expressed, or to confirm where a protein is expressed. Labeled antibody (e.g., fluorescent labeling for FACS) can be incubated with intact bacteria and the presence of the label on the bacterial surface confirms the location of the protein, for instance.

Antibodies generated against the polypeptides of the invention can be obtained by administering the polypeptides or epitope-bearing fragments, analogs, or cells to an animal using routine protocols. For preparing monoclonal antibodies, any technique which provides antibodies produced by continuous cell line cultures are used.

Polynucleotides

As with the proteins of the present invention, a polynucleotide of the present invention may comprise a nucleic acid sequence that is identical to any of the reference sequences of odd numbered SEQ ID NOS:1-253, that is be 100% identical, or it may include up to a number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in any of odd numbered SEQ ID NOS:1-253 by the numerical percent of the respective percent identity (divided by 100) and subtracting that product from said total number of nucleotides in said sequence.

By way of example, without intending to be limited thereto, an isolated *N. meningitidis* polynucleotide comprising a polynucleotide sequence that has at least 70% identity to any nucleic acid sequence of SEQ ID NOS:1-253; a degenerate variant thereof or a fragment thereof, wherein the polynucleotide sequence may include up to $n_n$ nucleic acid alterations over the entire polynucleotide region of the nucleic acid sequence of SEQ ID NOS:1-253, wherein $n_n$ is the maximum number of alterations and is calculated by the formula:

$$n_n = x_n - (x_n \cdot y),$$

in which $x_n$ is the total number of nucleic acids of any of SEQ ID NOS:1-253 and y has a value of 0.70, wherein any non-integer product of $x_n$ and y is rounded down to the nearest integer prior to subtracting such product from $x_n$. Of course, y may also have a value of 0.80 for 80%, 0.85 for 85%, 0.90 for 90% 0.95 for 95%, etc. Alterations of a polynucleotide sequence encoding the polypeptides comprising amino acid sequences of any of SEQ ID NOS:2-252 may create nonsense, missense or frameshift mutations in this coding sequence and thereby alter the polypeptide encoded by the polynucleotide following such alterations.

Certain embodiments of the present invention relate to polynucleotides (herein referred to as the "2086 polynucleotides" or "ORF2086 polynucleotides") which encode the 2086 proteins and antibodies made against the 2086 proteins. In preferred embodiments, an isolated polynucleotide of the present invention is a polynucleotide comprising a nucleotide sequence having at least about 95% identity to a nucleotide sequence chosen from one of the odd numbered SEQ ID NO: 1 and SEQ ID NOS: 253, a degenerate variant thereof, or a fragment thereof. As defined herein, a "degenerate variant" is defined as a polynucleotide that differs from the nucleotide sequence shown in the odd numbered SEQ ID NOS:1 and SEQ ID NOS:253 (and fragments thereof) due to degeneracy of the genetic code, but still encodes the same 2086 protein (i.e., the even numbered SEQ ID NOS: 2-252) as that encoded by the nucleotide sequence shown in the odd numbered SEQ ID NOS: 1-253.

In other embodiments, the polynucleotide is a complement to a nucleotide sequence chosen from one of the odd numbered SEQ ID NOS: 1-253, a degenerate variant thereof, or a fragment thereof. In yet other embodiments, the polynucleotide is selected from the group consisting of DNA, chromosomal DNA, cDNA and RNA and may further comprises heterologous nucleotides. In another embodiment, an isolated polynucleotide hybridizes to a nucleotide sequence chosen from one of SEQ ID NOS: 1-253, a complement thereof, a degenerate variant thereof, or a fragment thereof, under high stringency hybridization conditions. In yet other embodiments, the polynucleotide hybridizes under intermediate stringency hybridization conditions.

It will be appreciated that the 2086 polynucleotides may be obtained from natural, synthetic or semi-synthetic sources; furthermore, the nucleotide sequence may be a naturally occurring sequence, or it may be related by mutation, including single or multiple base substitutions, deletions, insertions and inversions, to such a naturally occurring sequence, provided always that the nucleic acid molecule comprising such a sequence is capable of being expressed as 2086 immunogenic polypeptide as described above. The nucleic acid molecule may be RNA, DNA, single stranded or double stranded, linear or covalently closed circular form. The nucleotide sequence may have expression control sequences positioned adjacent to it, such control sequences usually being derived from a heterologous source. Generally, recombinant expression of the nucleic acid sequence of this invention will use a stop codon sequence, such as TAA, at the end of the nucleic acid sequence.

The invention also includes polynucleotides capable of hybridizing under reduced stringency conditions, more preferably stringent conditions, and most preferably highly stringent conditions, to polynucleotides described herein. Examples of stringency conditions are shown in the Stringency Conditions Table below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE I

STRINGENCY CONDITIONS

| Stringency Condition | Polynucleotide Hybrid | Hybrid Length (bp)[I] | Hybridization Temperature and Buffer[H] | Wash Temperature and Buffer[H] |
|---|---|---|---|---|
| A | DNA:DNA | >50 | 65EC; 1xSSC -or- 42EC; 1xSSC, 50% formamide | 65EC; 0.3xSSC |
| B | DNA:DNA | <50 | $T_B$; 1xSSC | $T_B$; 1xSSC |
| C | DNA:RNA | >50 | 67EC; 1xSSC -or- 45EC; 1xSSC, 50% formamide | 67EC; 0.3xSSC |

TABLE I-continued

| STRINGENCY CONDITIONS | | | | |
|---|---|---|---|---|
| Stringency Condition | Polynucleotide Hybrid | Hybrid Length (bp)$^I$ | Hybridization Temperature and Buffer$^H$ | Wash Temperature and Buffer$^H$ |
| D | DNA:RNA | <50 | $T_D$; 1xSSC | $T_D$; 1xSSC |
| E | RNA:RNA | >50 | 70EC; 1xSSC -or- 50EC; 1xSSC, 50% formamide | 70EC; 0.3xSSC |
| F | RNA:RNA | <50 | $T_F$; 1xSSC | $T_f$; 1xSSC |
| G | DNA:DNA | >50 | 65EC; 4xSSC -or- 42EC; 4xSSC, 50% formamide | 65EC; 1xSSC |
| H | DNA:DNA | <50 | $T_H$; 4xSSC | $T_H$; 4xSSC |
| I | DNA:RNA | >50 | 67EC; 4xSSC -or- 45EC; 4xSSC, 50% formamide | 67EC; 1xSSC |
| J | DNA:RNA | <50 | $T_J$; 4xSSC | $T_J$; 4xSSC |
| K | RNA:RNA | >50 | 70EC; 4xSSC -or- 50EC; 4xSSC, 50% formamide | 67EC; 1xSSC |
| L | RNA:RNA | <50 | $T_L$; 2xSSC | $T_L$; 2xSSC |
| M | DNA:DNA | >50 | 50EC; 4xSSC -or- 40EC; 6xSSC, 50% formamide | 50EC; 2xSSC |
| N | DNA:DNA | <50 | $T_N$; 6xSSC | $T_N$; 6xSSC |
| O | DNA:RNA | >50 | 55EC; 4xSSC -or- 42EC; 6xSSC, 50% formamide | 55EC; 2xSSC |
| P | DNA:RNA | <50 | $T_P$; 6xSSC | $T_P$; 6xSSC |
| Q | RNA:RNA | >50 | 60EC; 4xSSC -or- 45EC; 6xSSC, 50% formamide | 60EC; 2xSSC |
| R | RNA:RNA | <50 | $T_R$; 4xSSC | $T_R$; 4xSSC |

bp$^I$: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarities.

buffer$^H$: SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes after hybridization is complete.

$T_B$ through $T_R$: The hybridization temperature for hybrids anticipated to be less than 50 base pairs in length should be 5-10 EC less than the melting temperature ($T_m$) of the hybrid, where $T_m$ is determined according to the following equations. For hybrids less than 18 base pairs in length, $T_m$(EC)=2(# of A+T bases)+4(# of G+C bases). For hybrids between 18 and 49 base pairs in length, $T_m$(EC)=81.5+16.6($\log_{10}$[$Na^+$])+0.41(% G+C)−(600/N), where N is the number of bases in the hybrid, and [$Na^+$] is the concentration of sodium ions in the hybridization buffer ([$Na^+$] for 1×SSC=0.165 M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology,* 1995, F. M. Ausubel et al., eds., John Wiley & Sons, Inc., sections 2.10 and 6.3-6.4, incorporated herein by reference.

The invention also provides polynucleotides that are fully complementary to these polynucleotides and also provides antisense sequences. The antisense sequences of the invention, also referred to as antisense oligonucleotides, include both internally generated and externally administered sequences that block expression of polynucleotides encoding the polypeptides of the invention. The antisense sequences of the invention comprise, for example, about 15-20 base pairs. The antisense sequences can be designed, for example, to inhibit transcription by preventing promoter binding to an upstream nontranslated sequence or by preventing translation of a transcript encoding a polypeptide of the invention by preventing the ribosome from binding.

The polynucleotides of the invention are prepared in many ways (e.g., by chemical synthesis, from DNA libraries, from the organism itself) and can take various forms (e.g., single-stranded, double-stranded, vectors, probes, primers). The term "polynucleotide" includes DNA and RNA, and also their analogs, such as those containing modified backbones.

According to further implementations of the present invention, the polynucleotides of the present invention comprise a DNA library, such as a cDNA library.

Fusion Proteins

The present invention also relates to fusion proteins. A "fusion protein" refers to a protein encoded by two, often unrelated, fused genes or fragments thereof. For example, fusion proteins comprising various portions of constant region of immunoglobulin molecules together with another immunogenic protein or part thereof. In many cases, employing an immunoglobulin Fc region as a part of a fusion protein is advantageous for use in therapy and diagnosis resulting in, for example, improved pharmacokinetic properties (see, e.g., EP 0 232 262 A1). On the other hand, for some uses it would be desirable to be able to delete the Fc part after the fusion protein has been expressed, detected and purified. The 2086 polynucleotides of the invention are used for the recombinant production of polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of a 2086 polypeptide or fused polypeptide can be encoded (see Gentz et al., 1989, incorporated herein by reference in its entirety). Thus, contemplated in an implementation of the present invention is the preparation of polynucleotides encoding fusion polypeptides permitting His-tag purification of expression products. The polynucleotide may also contain non-coding 5' and 3' sequences, such as transcribed, non-translated sequences, splicing and polyadenylation signals. Such a fused polypeptide can be produced by a host cell transformed/transfected or infected or infected with a recombinant DNA cloning vehicle as described below and it can be subsequently isolated from the host cell to provide the fused polypeptide substantially free of other host cell proteins.

Immunogenic Compositions

One aspect of the present invention provides immunogenic compositions which comprise at least one 2086 proteins or a nucleic acid encoding said proteins. The foregoing have the ability to (1) elicit bactericidal antibodies to multiple strains; (2) react with the surface of multiple strains; (3) confer passive protection against a live challenge; and/or (4) prevent colonization.

The formulation of such immunogenic compositions is well known to persons skilled in this field. Immunogenic compositions of the invention preferably include a pharmaceutically acceptable carrier. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the antibody. The preparation and use of pharmaceutically acceptable carriers is well known in the art. Except insofar as any conventional media or agent is incompatible with the active ingredient, use thereof in the immunogenic compositions of the present invention is contemplated.

Such immunogenic compositions can be administered parenterally, e.g., by injection, either subcutaneously or intramuscularly, as well as orally or intranasally. Methods for intramuscular immunization are described by Wolff et al. and by Sedegah et al. Other modes of administration employ oral formulations, pulmonary formulations, suppositories, and transdermal applications, for example, without limitation. Oral formulations, for example, include such normally employed excipients as, for example, pharmaceutical grades of mannitol, lactose, starch, magnesium stearate, sodium saccharine, cellulose, magnesium carbonate, and the like, without limitation.

The immunogenic compositions of the invention can include one or more adjuvants, including, but not limited to aluminum hydroxide; aluminum phosphate; STIMULON™ QS-21 (Aquila Biopharmaceuticals, Inc., Framingham, Mass.); MPL™ (3-O-deacylated monophosphoryl lipid A; Corixa, Hamilton, Mont.), 529 (an amino alkyl glucosamine phosphate compound, Corixa, Hamilton, Mont.), IL-12 (Genetics Institute, Cambridge, Mass.); GM-CSF (Immunex Corp., Seattle, Wash.); N-acetyl-muramyl-L-theronyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3-hydroxyphosphoryloxy-ethylamine) (CGP 19835A, referred to as MTP-PE); and cholera toxin. Others which may be used are non-toxic derivatives of cholera toxin, including its A subunit, and/or conjugates or genetically engineered fusions of the *N. meningitidis* polypeptide with cholera toxin or its B subunit ("CTB"), procholeragenoid, fungal polysaccharides, including schizophyllan, muramyl dipeptide, muramyl dipeptide ("MDP") derivatives, phorbol esters, the heat labile toxin of *E. coli*, block polymers or saponins.

In certain preferred embodiments, the proteins of this invention are used in an immunogenic composition for oral administration which includes a mucosal adjuvant and used for the treatment or prevention of *N. meningitidis* infection in a human host. The mucosal adjuvant can be a cholera toxin; however, preferably, mucosal adjuvants other than cholera toxin which may be used in accordance with the present invention include non-toxic derivatives of a cholera holotoxin, wherein the A subunit is mutagenized, chemically modified cholera toxin, or related proteins produced by modification of the cholera toxin amino acid sequence. For a specific cholera toxin which may be particularly useful in preparing immunogenic compositions of this invention, see the mutant cholera holotoxin E29H, as disclosed in Published International Application WO 00/18434, which is hereby incorporated herein by reference in its entirety. These may be added to, or conjugated with, the polypeptides of this invention. The same techniques can be applied to other molecules with mucosal adjuvant or delivery properties such as *Escherichia coli* heat labile toxin (LT). Other compounds with mucosal adjuvant or delivery activity may be used such as bile; polycations such as DEAE-dextran and polyornithine; detergents such as sodium dodecyl benzene sulphate; lipid-conjugated materials; antibiotics such as streptomycin; vitamin A; and other compounds that alter the structural or functional integrity of mucosal surfaces. Other mucosally active compounds include derivatives of microbial structures such as MDP; acridine and cimetidine. STIMULON™ QS-21, MPL, and IL-12, as described above, may also be used.

The immunogenic compositions of this invention may be delivered in the form of ISCOMS (immune stimulating complexes), ISCOMS containing CTB, liposomes or encapsulated in compounds such as acrylates or poly(DL-lactide-co-glycoside) to form microspheres of a size suited to adsorption. The proteins of this invention may also be incorporated into oily emulsions.

Multiple Antigens

The immunogenic agents, including proteins, polynucleotides and equivalents of the present invention may be administered as the sole active immunogen in a immunogenic composition, or alternatively, the composition may include other active immunogens, including other *Neisseria* sp. immunogenic polypeptides, or immunologically-active proteins of one or more other microbial pathogens (e.g. virus, prion, bacterium, or fungus, without limitation) or capsular polysaccharide. The compositions may comprise one or more desired proteins, fragments or pharmaceutical compounds as desired for a chosen indication. In the same manner, the compositions of this invention which employ one or more nucleic acids in the immunogenic composition may also include nucleic acids which encode the same diverse group of proteins, as noted above.

Any multi-antigen or multi-valent immunogenic composition is contemplated by the present invention. For example, the compositions of the present invention may a comprise combinations of two or more 2086 proteins, a combination of 2086 protein with one or more Por A proteins, a combination of 2086 protein with meningococcus serogroup A, C, Y and W135 polysaccharides and/or polysaccharide conjugates, a combination of 2086 protein with meningococcus and pneumococcus combinations, or a combination of any of the foregoing in a form suitable for mucosal delivery. Persons of skill in the art would be readily able to formulate such multi-antigen or multi-valent immunologic compositions.

The present invention also contemplates multi-immunization regimens wherein any composition useful against a pathogen may be combined therein or therewith the compositions of the present invention. For example, without limitation, a patient may be administered the immunogenic composition of the present invention and another immununological composition for immunizing against *S. Pneumoniae*, as part of a multi-immunization regimen. Persons of skill in the art would be readily able to select immunogenic compositions for use in conjunction with the immunogenic compositions of the present invention for the purposes of developing and implementing multi-immunization regimens.

Specific embodiments of this invention relate to the use of one or more polypeptides of this invention, or nucleic acids encoding such, in a composition or as part of a treatment regimen for the prevention or amelioration of *S. pneumonaie* infection. One can combine the 2086 polypeptides or 2086 polynucleotides with any immunogenic composition for use against *S. pneumonaie* infection. One can also combine the 2086 polypeptides or 2086 polynucleotides with any other protein or polysaccharide-based meningococcal vaccine.

The 2086 polypeptides, fragments and equivalents can be used as part of a conjugate immunogenic composition; wherein one or more proteins or polypeptides are conjugated to a carrier in order to generate a composition that has immunogenic properties against several serotypes and/or against several diseases. Alternatively, one of the 2086 polypeptides can be used as a carrier protein for other immunogenic polypeptides.

The present invention also relates to a method of inducing immune responses in a mammal comprising the step of providing to said mammal an immunogenic composition of this invention. The immunogenic composition is a composition which is antigenic in the treated animal or human such that the immunologically effective amount of the polypeptide(s) contained in such composition brings about the desired immune response against *N. meningitidis* infection. Preferred embodiments relate to a method for the treatment, including amelioration, or prevention of *N. meningitidis* infection in a human comprising administering to a human an immunologically effective amount of the composition.

The phrase "immunologically effective amount," as used herein, refers to the administration of that amount to a mammalian host (preferably human), either in a single dose or as part of a series of doses, sufficient to at least cause the immune system of the individual treated to generate a response that reduces the clinical impact of the bacterial infection. This may range from a minimal decrease in bacterial burden to prevention of the infection. Ideally, the treated individual will not exhibit the more serious clinical manifestations of the bacterial infection. The dosage amount can vary depending upon specific conditions of the individual. This amount can be determined in routine trials or otherwise by means known to those skilled in the art.

Another specific aspect of the present invention relates to using as the immunogenic composition a vector or plasmid which expresses an protein of this invention, or an immunogenic portion thereof. Accordingly, a further aspect this invention provides a method of inducing an immune response in a mammal, which comprises providing to a mammal a vector or plasmid expressing at least one isolated 2086 polypeptide. The protein of the present invention can be delivered to the mammal using a live vector, in particular using live recombinant bacteria, viruses or other live agents, containing the genetic material necessary for the expression of the polypeptide or immunogenic portion as a foreign polypeptide.

According to a further implementation of the present invention, a method is provided for diagnosing bacterial meningitis in a mammal comprising: detecting the presence of immune complexes in the mammal or a tissue sample from said mammal, said mammal or tissue sample being contacted with an antibody composition comprising antibodies that immunospecifically bind with at least one polypeptide comprising the amino acid sequence of any of the even numbered SEQ ID NOS: 2-252; wherein the mammal or tissue sample is contacted with the antibody composition under conditions suitable for the formation of the immune complexes.

Viral and Non-Viral Vectors

Preferred vectors, particularly for cellular assays in vitro and in vivo, are viral vectors, such as lentiviruses, retroviruses, herpes viruses, adenoviruses, adeno-associated viruses, vaccinia virus, baculovirus, and other recombinant viruses with desirable cellular tropism. Thus, a nucleic acid encoding a 2086 protein or immunogenic fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication No. WO 95/28494, which is incorporated herein by reference in its entirety.

Viral vectors commonly used for in vivo or ex vivo targeting and therapy procedures are DNA-based vectors and retroviral vectors. Methods for constructing and using viral vectors are known in the art (e.g., Miller and Rosman, *BioTechniques,* 1992, 7:980-990). Preferably, the viral vectors are replication-defective, that is, they are unable to replicate autonomously in the target cell. Preferably, the replication defective virus is a minimal virus, i.e., it retains only the sequences of its genome which are necessary for encapsulating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., *Molec. Cell. Neurosci.,* 1991, 2:320-330), defective herpes virus vector lacking a glycoprotein L gene, or other defective herpes virus vectors (PCT Publication Nos. WO 94/21807 and WO 92/05263); an attenuated adenovirus vector, such as the vector described by Stratford-Perricaudet et al. (*J. Clin. Invest.,* 1992, 90:626-630; see also La Salle et al., *Science,* 1993, 259:988-990); and a defective adeno-associated virus vector (Samulski et al., J. Virol., 1987, 61:3096-3101; Samulski et al., *J. Virol.,* 1989, 63:3822-3828; Lebkowski et al., *Mol. Cell. Biol.,* 1988, 8:3988-3996), each of which is incorporated by reference herein in its entirety.

Various companies produce viral vectors commercially, including, but not limited to, Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors), incorporated by reference herein in its entirety.

Adenovirus Vectors.

Adenoviruses are eukaryotic DNA viruses that can be modified to efficiently deliver a nucleic acid of this invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see PCT Publication No. WO 94/26914). Those adenoviruses of animal origin which can be used within the scope of the present invention include adenoviruses of canine, bovine, murine (example: Mav1, Beard et al., Virology, 1990, 75-81), ovine, porcine, avian, and simian (example: SAV) origin. Preferably, the adenovirus of animal origin is a canine adenovirus, more preferably a CAV2 adenovirus (e.g., Manhattan or A26/61 strain, ATCC VR-800, for example). Various replication defective adenovirus and minimum adenovirus vectors have been described (PCT Publication Nos. WO 94/26914, WO 95/02697, WO 94/28938, WO 94/28152, WO 94/12649, WO 95/02697, WO 96/22378). The replication defective recombinant adenoviruses according to the invention can be prepared by any technique known to the person skilled in the art (Levrero et al., *Gene,* 1991, 101:195; European Publication No. EP 185 573; Graham, EMBO J., 1984, 3:2917; Graham et al., *J. Gen. Virol.,* 1977, 36:59). Recombinant adenoviruses are recovered and purified using standard molecular biological techniques, which are well known to persons of ordinary skill in the art.

Adeno-Associated Viruses.

The adeno-associated viruses (AAV) are DNA viruses of relatively small size that can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see, PCT Publication Nos. WO 91/18088 and WO 93/09239; U.S. Pat. Nos. 4,797,368 and 5,139,941; European Publication No. EP 488 528). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (for example an adenovirus). The AAV recombinants which are produced are then purified by standard techniques.

Retrovirus Vectors.

In another implementation of the present invention, the nucleic acid can be introduced in a retroviral vector, e.g., as described in U.S. Pat. No. 5,399,346; Mann et al., *Cell,* 1983, 33:153; U.S. Pat. Nos. 4,650,764 and 4,980,289; Markowitz et al., *J. Virol.,* 1988, 62:1120; U.S. Pat. No. 5,124,263; European Publication Nos. EP 453 242 and EP178 220; Bernstein et al., *Genet. Eng.,* 1985, 7:235; McCormick, *BioTechnology,* 1985, 3:689; PCT Publication No. WO 95/07358; and Kuo et al., *Blood,* 1993, 82:845, each of which is incorporated by reference in its entirety. The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukaemia virus" MSV ("murine Moloney sarcoma virus"), HaSV ("Harvey sarcoma virus"); SNV ("spleen necrosis virus"); RSV ("Rous sarcoma virus") and Friend virus. Suitable packaging cell lines have been described in the prior art, in particular the cell line PA317 (U.S. Pat. No. 4,861,719); the PsiCRIP cell line (PCT Publication No. WO 90/02806) and the GP+envAm-12 cell line (PCT Publication No. WO 89/07150). In addition, the recombinant retroviral vectors can contain modifications within the LTRs for suppressing transcriptional activity as well as extensive encapsidation sequences which may include a part of the gag gene (Bender et al., *J. Virol.,* 1987, 61:1639). Recombinant retroviral vectors are purified by standard techniques known to those having ordinary skill in the art.

Retroviral vectors can be constructed to function as infectious particles or to undergo a single round of transfection. In the former case, the virus is modified to retain all of its genes except for those responsible for oncogenic transformation properties, and to express the heterologous gene. Non-infectious viral vectors are manipulated to destroy the viral packaging signal, but retain the structural genes required to package the co-introduced virus engineered to contain the heterologous gene and the packaging signals. Thus, the viral particles that are produced are not capable of producing additional virus.

Retrovirus vectors can also be introduced by DNA viruses, which permits one cycle of retroviral replication and amplifies transfection efficiency (see PCT Publication Nos. WO 95/22617, WO 95/26411, WO 96/39036 and WO 97/19182).

Lentivirus Vectors.

In another implementation of the present invention, lentiviral vectors can be used as agents for the direct delivery and sustained expression of a transgene in several tissue types, including brain, retina, muscle, liver and blood. The vectors can efficiently transduce dividing and nondividing cells in these tissues, and effect long-term expression of the gene of interest. For a review, see, Naldini, Curr. Opin. Biotechnol., 1998, 9:457-63; see also Zufferey, et al., *J. Virol.,* 1998, 72:9873-80). Lentiviral packaging cell lines are available and known generally in the art. They facilitate the production of high-titer lentivirus vectors for gene therapy. An example is a tetracycline-inducible VSV-G pseudotyped lentivirus packaging cell line that can generate virus particles at titers greater than 106 IU/mL for at least 3 to 4 days (Kafri, et al., *J. Virol.,* 1999, 73: 576-584). The vector produced by the inducible cell line can be concentrated as needed for efficiently transducing non-dividing cells in vitro and in vivo.

Non-Viral Vectors.

In another implementation of the present invention, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner, et. al., Proc. Natl. Acad. Sci. U.S.A., 1987, 84:7413-7417; Felgner and Ringold, Science, 1989, 337:387-388; see Mackey, et al., *Proc. Natl. Acad. Sci. U.S.A.,* 1988, 85:8027-8031; Ulmer et al., *Science,* 1993, 259:1745-1748). Useful lipid compounds and compositions for transfer of nucleic acids are described in PCT Patent Publication Nos. WO 95/18863 and WO 96/17823, and in U.S. Pat. No. 5,459, 127. Lipids may be chemically coupled to other molecules for the purpose of targeting (see Mackey, et. al., supra). Targeted peptides, e.g., hormones or neurotransmitters, and proteins such as antibodies, or non-peptide molecules could be coupled to liposomes chemically.

Other molecules are also useful for facilitating transfection of a nucleic acid in vivo, such as a cationic oligopeptide (e.g., PCT Patent Publication No. WO 95/21931), peptides derived from DNA binding proteins (e.g., PCT Patent Publication No. WO 96/25508), or a cationic polymer (e.g., PCT Patent Publication No. WO 95/21931).

It is also possible to introduce the vector in vivo as a naked DNA plasmid. Naked DNA vectors for vaccine purposes or gene therapy can be introduced into the desired host cells by methods known in the art, e.g., electroporation, microinjection, cell fusion, DEAE dextran, calcium phosphate precipitation, use of a gene gun, or use of a DNA vector transporter (e.g., Wu et al., *J. Biol. Chem.,* 1992, 267:963-967; Wu and Wu, *J. Biol. Chem.,* 1988, 263:14621-14624; Canadian Patent Application No. 2,012,311; Williams et al., Proc. Natl. Acad. Sci. USA, 1991, 88:2726-2730). Receptor-mediated DNA delivery approaches can also be used (Curiel et al., *Hum. Gene Ther.,* 1992, 3:147-154; Wu and Wu, *J. Biol. Chem.,* 1987, 262:4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., *C.P. Acad. Sci.,* 1988, 321:893; PCT Publication Nos. WO 99/01157; WO 99/01158; WO 99/01175). Accordingly, additional embodiments of the present invention relates to a method of inducing an immune response in a human comprising administering to said human an amount of a DNA molecule encoding a 2086 polypeptide of this invention, optionally with a transfection-facilitating agent, where said polypeptide, when expressed, retains immunogenicity and, when incorporated into an immunogenic composition and administered to a human, provides protection without inducing enhanced disease upon subsequent infection of the human with *Neisseria* sp. pathogen, such as *N. meningitidis*. Transfection-facilitating agents are known in the art and include bupivicaine, and other local anesthetics (for examples see U.S. Pat. No. 5,739,118) and cationic polyamines (as published in International Patent Application WO 96/10038), which are hereby incorporated by reference.

The present invention also relates to an antibody, which may either be a monoclonal or polyclonal antibody, specific for 2086 polypeptides as described above. Such antibodies may be produced by methods which are well known to those skilled in the art.

Bacterial Expression Systems and Plasmids

This invention also provides a recombinant DNA molecule, such as a vector or plasmid, comprising an expression control sequence having promoter sequences and initiator sequences and a nucleotide sequence which codes for a polypeptide of this invention, the nucleotide sequence being located 3' to the promoter and initiator sequences. In yet another aspect, the invention provides a recombinant DNA cloning vehicle capable of expressing a 2086 polypeptide comprising an expression control sequence having promoter sequences and initiator sequences, and a nucleotide sequence which codes for a 2086 polypeptide, the nucleotide sequence being located 3' to the promoter and initiator sequences. In a further aspect, there is provided a host cell containing a recombinant DNA cloning vehicle and/or a recombinant DNA molecule as described above. Suitable expression control sequences and host cell/cloning vehicle combinations are well known in the art, and are described by way of example, in Sambrook et al. (1989).

Once recombinant DNA cloning vehicles and/or host cells expressing a desired a polypeptide of this invention have been constructed by transforming, transfecting or infecting such cloning vehicles or host cells with plasmids containing the corresponding 2086 polynucleotide, cloning vehicles or host cells are cultured under conditions such that the polypeptides are expressed. The polypeptide is then isolated substantially free of contaminating host cell components by techniques well known to those skilled in the art.

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in view of the present disclosure, appreciate that many changes can be made in the specific embodiments which are disclosed and still obtain a like or similar result without departing from the spirit and scope of the invention.

EXAMPLES

Example 1

Identification of a Neisserial Membrane Protein Extract Capable of Eliciting Bactericidal Antibodies Against Heterologous Strains Referring to Table II below, LOS-depleted outer membrane protein preparations have been shown to elicit bactericidal antibodies. These antibodies are often directed towards the PorA of the respective strain. LOS-depleted outer membrane preparations from serogroup B meningococcal strain 8529 (B:15:P1.7b,3) are unusual in this manner because they unexpectedly elicit bactericidal antibodies to several heterologous strains.

TABLE II

BC Activity of Anti-sOMPS Against Different Strains of *N. meningitidis*

| Anti-serum Week 6 | H44/76 | 5315 | H355 | M982 | 880049 | 8529* | NMB |
|---|---|---|---|---|---|---|---|
| Serosubtype | P1.7, 16 | P1.5 | P1.15 | P1.9 | P1.4 | P1.3 | P1.5, 2 |
| sOMPs H44/76 25 μg QS-21 20 μg | 1,000 | <50 | <50 | <50 | <50 | 980 | <50 |
| sOMPs 5315 25 μg QS-21 20 μg | 50 | <50 | <50 | <50 | <50 | 2170 | <50 |
| sOMPs H355 25 μg QS-21 20 μg | <50 | <50 | 450 | <50 | <50 | 860 | <50 |
| sOMPs M982 25 μg QS-21 20 μg | 92 | <50 | <50 | 300 | <50 | 1100 | <50 |
| sOMPs 880049 25 μg QS-21 20 μg | 50 | <50 | <50 | <50 | <50 | 1190 | <50 |
| sOMPs 8529 25 μg QS-21 20 μg | 1,000 | <50 | 450 | 50 | 215 | >4050 (81.7) | <50 |
| sOMPs 2996 25 μg QS-21 20 μg | <50 | <50 | <50 | <50 | <50 | 790 | 148 |
| Whole-cell control serum 25 μg 3DMPL 25 μg | 450 | 50 | 100 | 500 | 150 | >1350 (66.0) | 952 |

To facilitate the isolation and characterization of the antigen(s) responsible for eliciting heterologous bactericidal antibodies, we sought to identify which detergent optimally extracted the antigen(s)

Strains and Culture Conditions.

*N. meningitidis* strain 8529 from a frozen vial was streaked onto a GC plate. (The meningococcal strain 8529 was received from The RIVM, Bilthoven, The Netherlands). The plate was incubated at 36 C/5% $CO_2$ for 7.5 h. Several colonies were used to inoculate a flask containing 50 mL of modified Frantz medium+GC supplement. The flask was incubated in an air shaker at 36° C. and agitated at 200 RPM for 4.5 h. 5 mL was used to inoculate a Fernbach flask containing 450 mL of modified Frantz medium+GC supplement. The flask was incubated in an air shaker at 36° C. and agitated at 100 RPM for 11 h. The entire 450 mL was used to inoculate 8.5 L of modified Frantz medium+GC supplement in a 10 L fermentor.

Composition of Modified Frantz Medium:

| | |
|---|---|
| Glutamic acid | 1.3 g/L |
| Cysteine | 0.02 |
| Sodium phosphate, dibasic, 7 hydrate | 10 |
| Potassium chloride | 0.09 |
| Sodium chloride | 6 |
| Ammonium chloride | 1.25 |
| Dialyzed yeast extract (YE) | 40 ml |

(25% YE soln. dialyzed against 5 volumes of $dH_2O$ overnight, then autoclaved)
GC Supplement 100×, Filter Sterilize

| | |
|---|---|
| Dextrose | 400 g/L |
| Glutamic acid | 10 |
| Cocarboxylase | 0.02 |
| Ferric nitrate | 0.5 |

The following parameters were controlled during fermentation: Temperature=36° C.; pH=7.4; Dissolved Oxygen=20%. Several drops of P-2000 antifoam were added to control foaming. The culture was grown to stationary phase. Cells were harvested by centrifugation at OD650=5.25. A total of 100-300 grams of wet cell paste is typically harvested from ~8.5 L of culture.

Partial Purification of Outer Membrane Protein Fractions from Meningococci which Elicit Heterologous Bactericidal Antibodies:

100 gms wet weight of cells were suspended, to a volume five times the wet weight, with 10 mM HEPES-NaOH, pH 7.4, 1 mM Na2EDTA and lysed by passage through a 110Y microfluidizer equipped with a chamber at ~18,000 psi. The cell lysate was clarified and the cell envelope isolated by centrifugation at 300,000×g for 1 hour at 10° C. The cell envelopes were washed 2× with the same buffer by suspension with a homogenizer followed by centrifugation as above. The cell envelopes were then extracted with 320 mL of 1% (w/v) TRITON X-100 in 10 mM HEPES-NaOH, pH 7.4, 1 mM $MgCl_2$. Referring to Table III below, results from sequential differential detergent extraction using TRITON X-100 and ZWITTERGENT 3-14 followed by immunization of mice, allowed us to determine that the TRITON extracts optimally extracted the candidate(s) of interest. This TRITON X-100 extract, eliciting bactericidal antibody response against 4 out of five strains listed in table III, was then fractionated by preparative isoelectric focusing (IEF) in a BioRad Rotophor unit. Ampholyte concentrations were 1% pH 3-10 mixed with 1% pH 4-6. As shown in Table III, several fractions were found to elicit a heterologous bactericidal response. The fractions obtained from IEF, which focused in the pH range of 5.5-7.8, elicited a heterologous response to the most strains as determined by the bactericidal assay. The pooled IEF fractions were concentrated and the ampholytes removed by ethanol precipitation. A further purification was achieved by adsorbing some of the proteins obtained in the pH range of about 5.5-7.8 on an anion exchange column and comparing the bactericidal activity obtained after immunizing mice with the adsorbed and unadsorbed proteins. Referring again to Table II, while many proteins were adsorbed to the anion exchange resin, the proteins which were not adsorbed by the column elicited more heterologous bactericidal antibodies.

TABLE III

| | | $BC_{50}$ Target Strain | | | | |
|---|---|---|---|---|---|---|
| Method | Fraction | H44/76 | 880049 | H355 | 539* | M982 |
| LOS-depleted | sOMPs | 1,000 | 215 | 450 | NC | 50 |
| Detergent | Cytoplasmic Extract | 200 | NT | NT | NT | NT |
| Extractions | TX-100 | >800 | >800 | >800 | >800 | <25 |
| | ZWITTERGENT 3-12 | 400 | >25 | 100 | 400 | <25 |
| | ZWITTERGENT 3-14 | <25 | NT | NT | NT | NT |
| | Zw. 3-14 + NaCl | <25 | NT | NT | NT | NT |
| | Sarcosyl | <25 | NT | NT | NT | NT |
| | Zw. 3-14 + heat | <25 | NT | NT | NT | NT |
| Preparative | Fractions 1-3 (pH 2.3-3.9) | 50 | NT | NT | NT | NT |
| IEF | Fraction 4 (pH 4.1) | >800 | <25 | 100 | <25 | NT |
| | Fraction 5 (pH 4.3) | >800 | <25 | 100 | 200 | NT |
| | Fraction 6 (pH 4.5) | 400 | NT | NT | NT | NT |
| | Fraction 7 (pH 4.8) | <25 | NT | NT | NT | NT |
| | Fractions 8-9 (pH 5.0-5.3) | <25 | NT | NT | NT | NT |
| | Fractions 10-17 (pH 5.5-7.8) | >800 | 200 | <800 | <800 | NT |
| Anion | Adsorbed | 400 | NT | 100 | 100 | NT |
| Exchange | Unadsorbed | >6,400 | NT | <800 | <800 | NT |

NT: not tested
*Clinical isolate 539 is a homologous strain to 8529, isolated from the same outbreak As shown in FIG. 1A, two major proteins were present in the unadsorbed fraction as determined by SDS-PAGE. To identify these proteins, two types of analysis were performed. One analysis was to perform limited proteolytic degradation (See FIG. 1A, and FIG. 1B) followed by isolation of peptides and direct protein sequencing. The other analysis was to perform SDS-PAGE followed by gel excision, proteolytic digestion, and LC-MS/MS (Liquid Chromatography tandem Mass Spectrometry), (see FIG. 3) to obtain mass spectral information on the components of the preparations of interest. (See peptide mapping and sequencing methods described later in this section)

The *N. meningitidis* A Sanger genomic sequence was analyzed using the methods and algorithms described in Zagursky and Russell, 2001, *BioTechniques,* 31:636-659. This mining analysis yielded over 12,000 possible Open Reading Frames (ORFs). Both the direct sequence data and the mass spectral data described above indicated that the major components of the unadsorbed fraction were the products of several ORFs present in an analysis of the Sanger database. The three predominant proteins identified by this methodology correspond to ORFs 4431, 5163 and 2086, (see FIGS. 1B and 3).

Although ORF 4431 was the most predominant protein identified in the fractions, mouse antibodies to recombinant lipidated 4431 were not bactericidal and did not provide a protective response in an animal model. Additional analysis of ORF 5163 is in progress.

The second most predominant component of the preparations described herein corresponds to the product of ORF 2086.

Immunogenicity Methods:

Preparation of Antisera:

Except where noted, protein compositions/vaccines were formulated with 25 μg of total protein and were adjuvanted with 20 μg QS-21. A 0.2 mL dose was administered by subcutaneous (rump) injection to 6-8 week old female Swiss-Webster mice at week 0 and 4. Bleeds were collected at week 0 and 4, and a final exsanguination bleed was performed on week 6.

Bactericidal Assay:

Bactericidal assays were performed essentially as described (See Mountzouros and Howell, 2000, *J. Clin. Microbiol.* 38(8):2878-2884). Complement-mediated antibody-dependent bactericidal titers for the SBA were expressed as the reciprocal of the highest dilution of test serum that killed ≥50% of the target cells introduced into the assays ($BC_{50}$ titer).

Methods Used to Identify 2086 Protein:

Cyanogen Bromide Cleavage and Direct Sequencing of Fragments:

Cyanogen Bromide cleavage of Anion Exchange Unadsorbed Fraction (AEUF). The AEUF was precipitated with 90% cold ethanol and was solubilized with 10 mg/mL cyanogen bromide in 70% formic acid to a protein concentration of 1 mg/mL. The reaction was performed overnight at room temperature in the dark. The cleaved products were dried down by speed vacuum, and the pellet was solubilized with HE/0.1% reduced TX-100. SDS-PAGE followed by N-terminal amino acid sequencing were used to identify the components of this fraction.

Protease Digestion/Reverse Phase/N-Terminal Sequencing to Identify Components:

The AEUF was digested with either GluC (V8), LysC or ArgC. The protein to enzyme ratio was 30 μg protein to 1 μg enzyme. The digestion was carried out at 37° C. overnight. The digested protein mixture (30 μg) was passed over a seven micron AQUAPORE RF-300 column and was eluted with a gradient of 10-95% acetonitrile in 0.1% trifluoroacetic acid, and peaks were collected manually. A no protein blank was also run, and the peaks from this were subtracted from the sample chromatogram. Peaks occurring only in the sample run were analyzed by mass spectrometer, and those samples giving a clear mass were analyzed for N-terminal amino acid sequencing.

N-Terminal Amino Acid Sequencing:

For bands excised from a blot, the protein sample is transferred from an SDS gel to a PVDF membrane, stained with AMIDO BLACK (10% acetic acid, 0.1% AMIDO BLACK in deionized water) and destained in 10% acetic acid. The desired protein band is then excised from all ten lanes using a methanol cleaned scalpel or mini-Exacto knife and placed in the reaction cartridge of the Applied Biosystems 477A Protein Sequencer. For direct sequencing of samples in solution, the Prosorb cartridge is assembled and the PVDF wetted with 60 μL of methanol. The PVDF is rinsed with 50 μL of deionized water and the sample (50 μL) is loaded to the PVDF. After 50 μL of deionized water is used to rinse the sample, the Prosorb PVDF is punched out, dried, and placed in the reaction cartridge of the Applied Biosystems 477A Protein Sequencer. For both methods, the Applied Biosystems N-terminal Sequencer is then run under optimal blot conditions for 12 or more cycles (1 cycle Blank, 1 cycle Standard, and 10 or more cycles for desired residue identification) and PTH-amino acid detection is done on the Applied Biosystems 120A PTH Analyzer. The cycles are collected both on an analog chart recorder and digitally via the instrument software. Amino acid assignment is done using the analog and digital data by comparison of a standard set of PTH-amino acids and their respective retention times on the analyzer (cysteine residues are destroyed during conversion and are not detected). Multiple sequence information can be obtained from a single residue and primary versus secondary assignments are made based on signal intensity.

LC-MS/MS

Protein samples purified by IEF were further analyzed by SDS-polyacrylamide gel electrophoresis. Proteins were visualized by COOMASSIE BLUE staining, and bands of interest were excised manually, then reduced, alkylated and digested with trypsin (Promega, Madison, Wis.) in situ using an automated in-gel tryptic digestion robot (1). After digestion, peptide extracts were concentrated to a final volume of 10-20 μL using a Savant Speed Vac Concentrator (ThermoQuest, Holdbrook, N.Y.).

Peptide extracts were analyzed on an automated microelectrospray reversed phase HPLC. In brief, the microelectrospray interface consisted of a Picofrit fused silica spray needle, 50 cm length by 75 um ID, 8 um orifice diameter (New Objective, Cambridge Mass.) packed with 10 um C18 reversed-phase beads (YMC, Wilmington, N.C.) to a length of 10 cm. The Picofrit needle was mounted in a fiber optic holder (Melles Griot, Irvine, Calif.) held on a home-built base positioned at the front of the mass spectrometer detector. The rear of the column was plumbed through a titanium union to supply an electrical connection for the electrospray interface. The union was connected with a length of fused silica capillary (FSC) tubing to a FAMOS autosampler (LC-Packings, San Francisco, Calif.) that was connected to an HPLC solvent pump (ABI 140C, Perkin-Elmer, Norwalk, Conn.). The HPLC solvent pump delivered a flow of 50 μL/min which was reduced to 250 nL/min using a PEEK microtight splitting tee (Upchurch Scientific, Oak Harbor, Wash.), and then delivered to the autosampler using an FSC transfer line. The LC pump and autosampler were each controlled using their internal user programs. Samples were inserted into plastic autosampler vials, sealed, and injected using a 54 sample loop.

Figure 3:
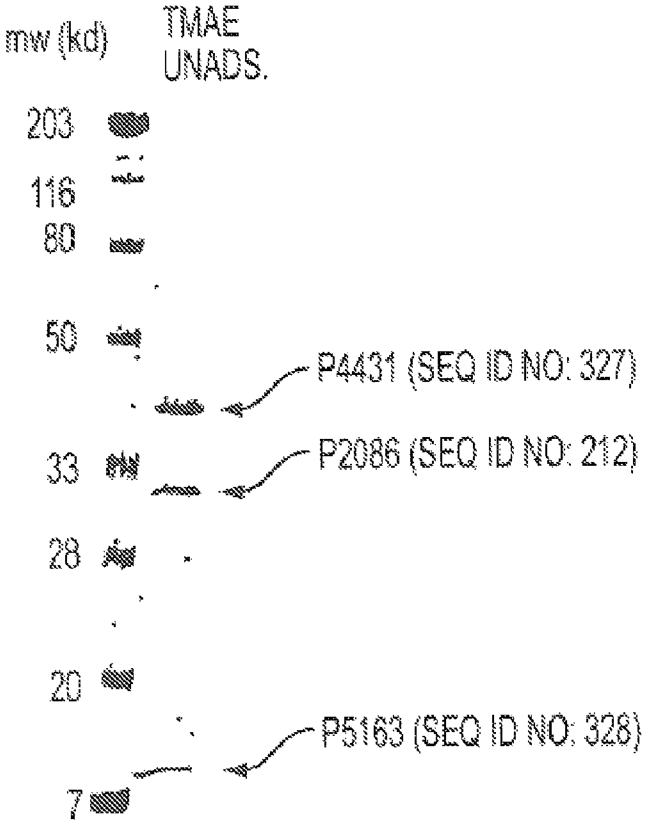
FIG. 3 depicts the results from the experiments from the identification of the two major proteins and one minor protein by analysis of TMAE Flow Through components by LC-MS/MS and the corresponding SDS-PAGE.

Microcapillary HPLC-Mass Spectrometry:

Extracted peptides from in-gel digests were separated by the microelectrospray HPLC system using a 50 minute gradient of 0-50% solvent B (A: 0.1M HoAc, B: 90% MeCN/0.1M HoAc). Peptide analyses were done on a Finnigan LCQ ion trap mass spectrometer (ThermoQuest, San Jose, Calif.) operating at a spray voltage of 1.5 kV, and using a heated capillary temperature of 150° C. Data were acquired in automated MS/MS mode using the data acquisition software provided with the instrument. The acquisition method included 1 MS scan (375-1200 m/z) followed by MS/MS scans of the top 3 most abundant ions in the MS scan. The dynamic exclusion and isotope exclusion functions were employed to increase the number of peptide ions that were analyzed (settings: 3 amu=exclusion width, 3 min=exclusion duration, 30 secs=pre-exclusion duration, 3 amu=isotope exclusion width). Automated analysis of MS/MS data was performed using the SEQUEST computer algorithm incorporated into the Finnigan Bioworks data analysis package (ThermoQuest, San Jose, Calif.) using the database of proteins derived from the complete genome of *N. meningitidis* (from Sanger). The results of the study are illustrated in FIG. 3.

Example 2

Cloning of Recombinant Lipidated P2086 (rLP2086)

A.) Native Leader Sequence:

Source Materials:

The ORF 2086 gene was amplified by PCR from a clinical isolate of a serogroup B *Neisseria meningitidis* strain designated 8529. The serogroup, serotype and serosubtype of this strain is shown in parentheses; 8529 (B:15, P1:7b,3). This meningococcal strain was received from The RIVM, Bilthoven, The Netherlands. The mature 2086 protein gene sequence from meningococcal strain 8529 is provided herein as SEQ ID. NO. 212.

PCR Amplification and Cloning Strategy:

A visual inspection of ORF 2086 indicated that this gene had a potential lipoprotein signal sequence. Additional analysis using a proprietary Hidden Markov Model Lipoprotein algorithm confirmed that ORF 2086 contains a lipoprotein signal sequence. In order to recombinantly express P2086 in a more native-like conformation, oligonucleotide primers were designed to amplify the full length gene with the lipoprotein signal sequence intact and were based on an analysis of the Sanger sequence for *N. meningitidis* A ORF 2086, (5' primer—CT ATT CTG CAT ATG ACT AGG AGC and 3' primer—GCGC GGATCC TTA CTG CTT GGC GGC AAG ACC), which are SEQ ID NO. 304 (Compound No. 4624) and SEQ ID NO. 303 (Compound No. 4623), respectively (See also Table IV herein). The 2086 gene was amplified by polymerase chain reaction (PCR) [ABI 2400 thermal cycler, Applied Biosystems, Foster City, Calif.] from *N. meningitidis* strain 8529. The correct size amplified product was ligated and cloned into pCR2.1-TOPO (Invitrogen). The plasmid DNA was restriction digested with NdeI and BamHI, gel purified and ligated into pET-27b(+) vector (Novagen).

Oligonucleotide primers described herein, were synthesized on a PerSeptive Biosystems oligonucleotide synthesizer, Applied Biosystems, Foster City Calif., using β-Cyanoethylphosphoramidite chemistry, Applied Biosystems, Foster City Calif. The primers used for PCR amplification of the ORF 2086 gene families are listed in Table IV, which shows non-limiting examples of primers of the present invention.

TABLE IV

PRIMERS

| SEQ ID NO. (Compound No.) | Primer | Sequence | Restriction sites |
|---|---|---|---|
| 303 (4623) | Reverse | GCGCGGATCCTTACTGCTTGGCGGCAAGACC | BamHI |
| 304 (4624) | Forward | CTATTCTGCATATGACTAGGAGC | NdeI |
| 305 (4625) | Forward | AGCAGCGGAGGCGGCGGTGTC | |
| 306 (5005) | Forward | TGCCGATGCACTAACCGCACC | |
| 307 (5007) | Reverse | CGTTTCGCAACCATCTTCCCG | |
| 308 (5135) | Reverse | GAGATCTCACTCACTCATTACTGCTTGGCGGCAAGACCGATATG | BglII |
| 309 (5658) | Forward | GCGGATCCAGCGGAGGGGGTGGTGTCGCC | BamHI |
| 310 (5660) | Reverse | GCGCATGCTTACTGCTTGGCGGCAAGACCGATATG | SphI |
| 311 (6385) | Forward | GCGGATCCAGCGGAGGCGGCGGAAGC | BamHI |
| 312 (6406) | Forward | GCGCAGATCTCATATGAGCAGCGGAGGGGGTGGTGTCGCCGCCGAYATWGGTGCGGGGCTTGCCG | BglII and NdeI |
| 313 (6470) | Forward | CTATTCTGCGTATGACTAG | |
| 314 (6472) | Reverse | GTCCGAACGGTAAATTATCGTG | |

TABLE IV-continued

Figure 4:
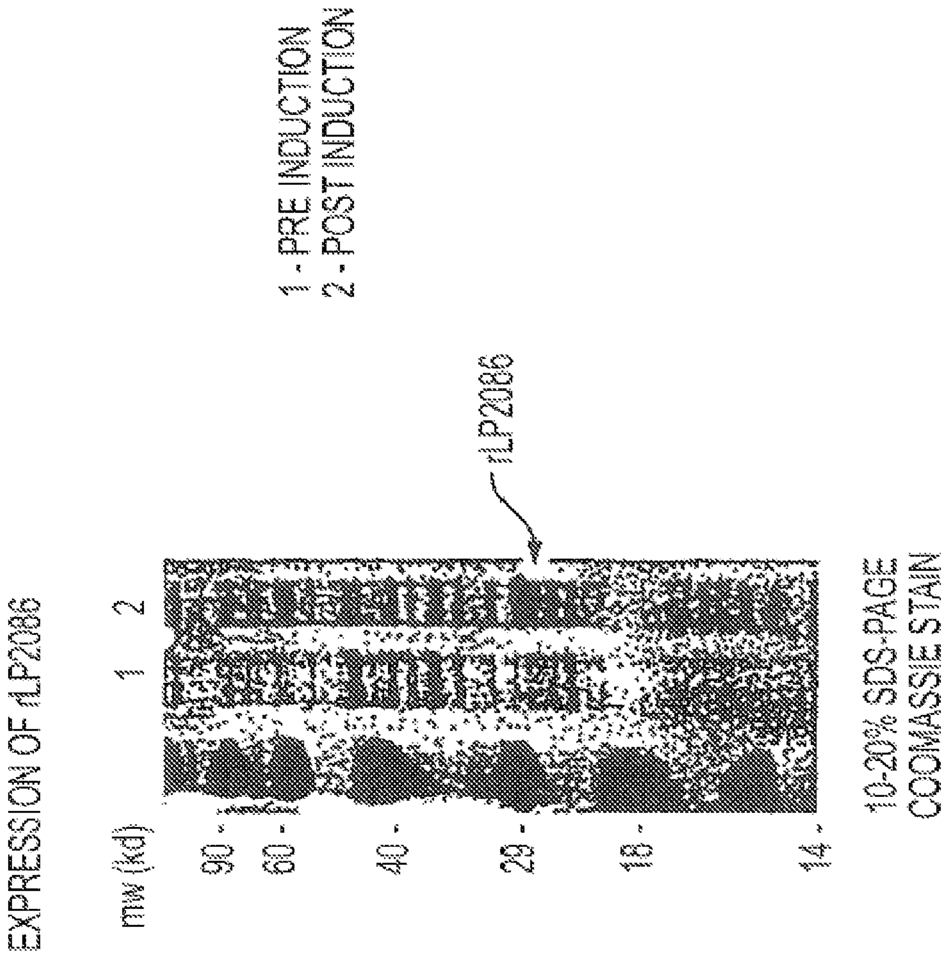
FIG. 4 is an SDS-PAGE gel from the recombinant expression of 2086 protein.
Figure 5:
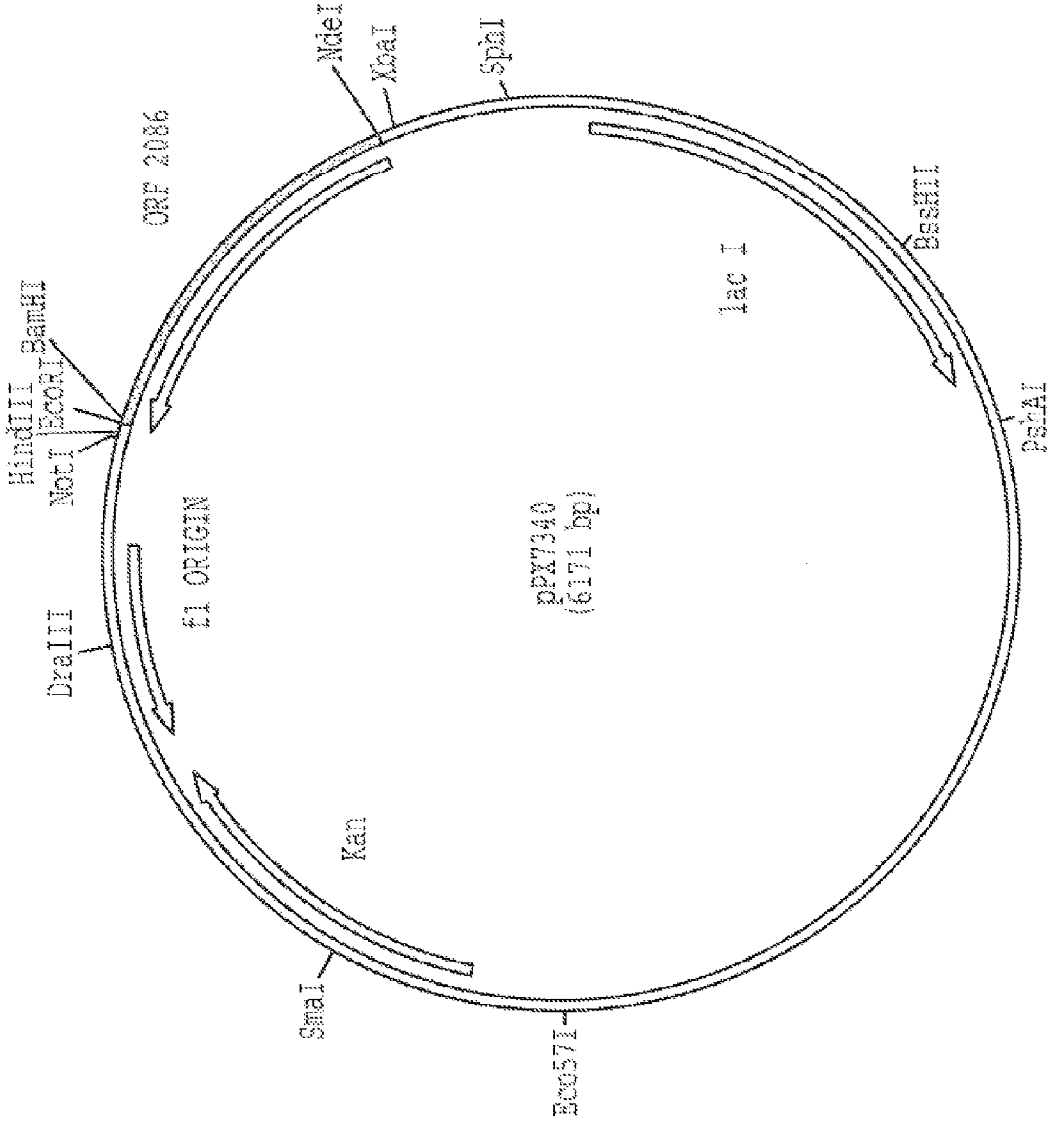
FIG. 5 is a schematic diagram of plasmid pPX7340, as described in the examples herein.

| PRIMERS | | | |
|---|---|---|---|
| SEQ ID NO. (Compound No.) | Primer | Sequence | Restriction sites |
| 315 (6473) | Forward | GCGGATCCAGCGGAGGCGGCGGTGTCGCC | BamHI |
| 316 (6474) | Forward | GAGATCTCATATGAGCAGCGGAGGCGGCG GAAGC | BglII and NdeI |
| 317 (6495) | Forward | GACAGCCTGATAAACC | |
| 318 (6496) | Reverse | GATGCCGATTTCGTGAACC | |
| 319 (6543) | Reverse | GCGCATGCCTACTGTTTGCCGGCGATG | SphI |
| 320 (6605) | Reverse | GAGATCTCACTCACTCACTACTGTTTGCC GGCGATGCCGATTTC | BglII |
| 321 (6721) | Forward | GCGCAGATCTCATATGAGCAGCGGAGGCG GCGGAAGCGGAGGCGGCGGTGTCACCGCC GACATAGGCACG | BglII and NdeI |

rLP2086 Lipoprotein Expression Utilizing Native Leader Sequence:

Referring to FIG. 5, plasmid pPX7340 was transformed/transfected or infected into BLR(DE3) pLysS host cells (Life Sciences). One transformant was selected and inoculated into 50 mL of Terrific Broth containing 2% glucose, kanamycin (30 μg/mL), chloramphenicol (30 μg/mL), and tetracycline (12 μg/mL). The OD600 for the overnight culture was 6.0. The overnight culture was diluted out in 1 liter of Terrific Broth with 1% glycerol and the same antibiotics. The starting OD600 was 0.4. After 2 hours the OD600 was 1.6 and a pre-induced sample was taken. Cells equivalent to an OD600=1 were centrifuged and the supernatant was removed. The whole cell pellet was resuspended in 150 μL, Tris-EDTA buffer and 150 μL of 2×SDS-PAGE sample buffer. IPTG was added to a final concentration of 1 mM. After 3.5 hours a post-induced sample was taken as described and analyzed on SDS-PAGE (See FIG. 4).

Purification of rLP2086:

The rLP2086 was solubilized from *E. coli* following differential detergent extraction. Unlike the P2086 in its native environment, the rLP2086 was not significantly solubilized by TRITON X-100 or ZWITTERGENT 3-12. The bulk of the rLP2086 was solubilized with sarcosyl, indicating that it interacts with the outer membrane components of *E. coli* differently than it does in *N. meningitidis*. Once solubilized the rLP2086 was purified similarly to the native protein in that many of the contaminating *E. coli* proteins could be removed by adsorbtion to an anion exchange resin at pH 8. Despite being greater than one half a pH unit above its theoretical pI, the rLP2086 remained unadsorbed at pH 8. Further purification was achieved by adsorbtion of the rLP2086 to a cation exchange resin at pH 4.5.

Figure 2:
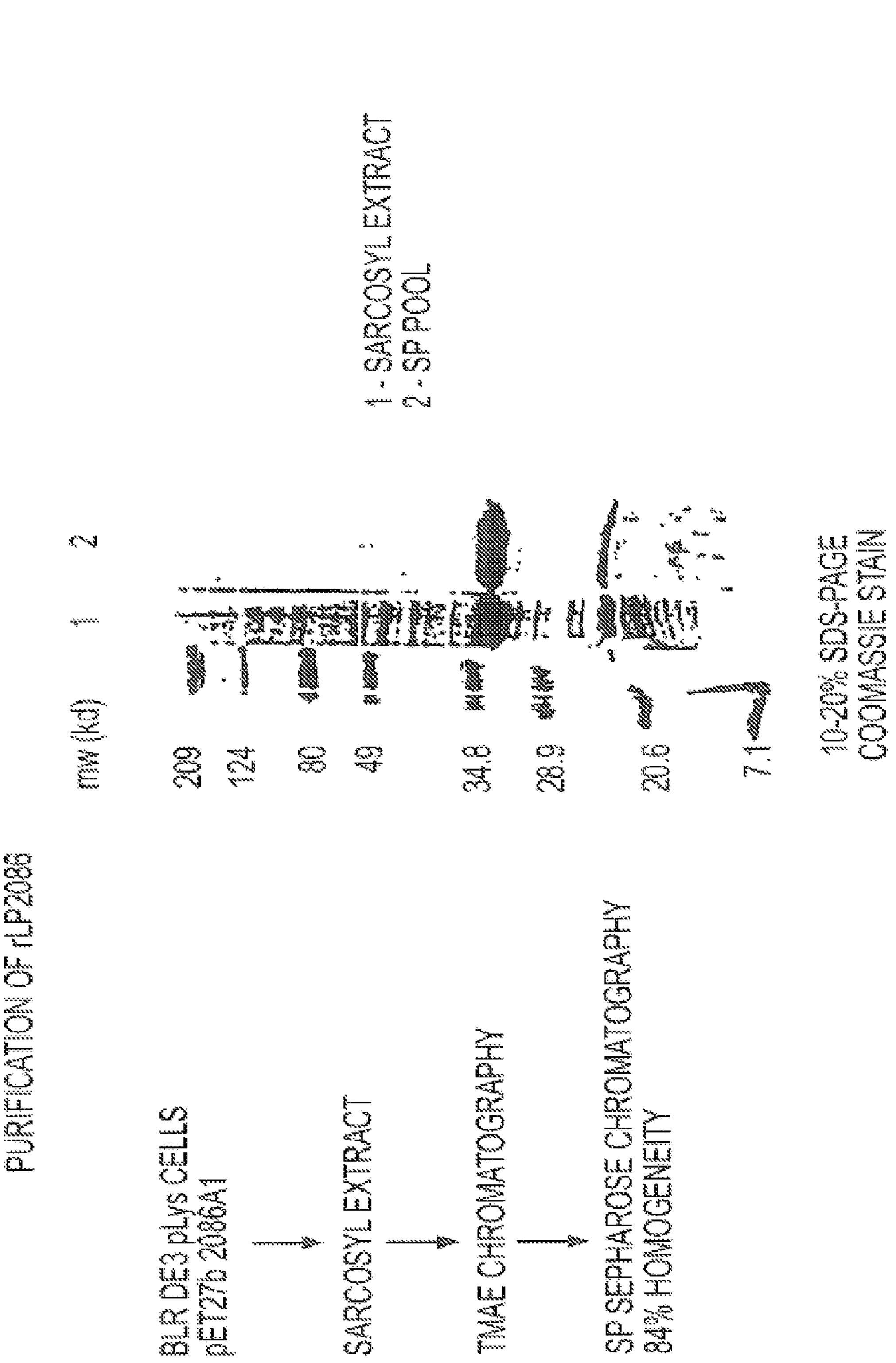
FIG. 2 depicts the purification scheme and homogeneity as determined by SDS-PAGE of rLP2086.

The homogeneity of the rLP2086 is shown in FIG. 2 following SDS-PAGE. The mass of rLP2086 was determined by MALDI-TOF mass spectral analysis to be 27,836. This mass differs from the theoretical mass of 27,100 by 736, which approximates the mass of the N-terminal lipid modification common to bacterial lipoproteins. Both native and rLP2086 appear to be outer membrane lipoproteins. Attempts with N-terminal sequencing were blocked and this is consistent with the terminal modification.

Purification Methods:

Frozen pellets of BLR DE3 pLysS cells expressing P2086 were resuspended in 10 mM HEPES-NaOH/1 mM EDTA/1 μg/mL Pefabloc SC protease inhibitor (Roche) pH 7.4 (HEP) at 20 mL/g wet cell weight and lysed by microfluidizer (Microfluidics Corporation Model 110Y). The cell lysate was centrifuged at 150,000×g for one hour. The pellet was washed twice with HEP and centrifuged twice, and the resulting membrane pellet was frozen overnight. The pellet was solubilized with 10 mM HEPES-NaOH/1 mM MgCl2/1% TX-100 pH 7.4 for 30 minutes, followed by centrifugation at 150,000×g for 30 minutes. This was repeated three times. The membrane pellet was washed as above twice with 50 mM Tris-HCl/5 mM EDTA/1% ZWITTERGENT 3-12 pH 8, followed by two washes each of 50 mM Tris-HCl/5 mM EDTA/1% ZWITTERGENT 3-14 pH 8 and 50 mM Tris-HCl/5 mM EDTA/1% ZWITTERGENT 3-14/0.5M NaCl pH 8.

The rLP2086 was then solubilized with 50 mM Tris-HCl/5 mM EDTA/1% sarcosyl pH 8. This sarcosyl extract was adjusted to 1% ZWITTERGENT 3-14 (Z3-14) and dialyzed twice against a 30 fold excess of 50 mM Tris-HCl/5 mM EDTA/1% Z3-14. The dialyzed rLP2086 extract was precipitated with 90% ethanol to remove remaining sarcosyl, and solubilized with 50 mM Tris-HCl/5 mM EDTA/1% Z3-14 pH 8 (TEZ). Insoluble material was removed by centrifugation, the supernatant was passed over an anion exchange chromatography column, and rLP2086 was collected in the unbound fraction. The unbound material was then dialyzed twice against a 30 fold excess of 25 mM NaAc/1% Z3-14 pH 4.5, and passed over a cation exchange chromatography column. The rLP2086 was eluted with a 0-0.3M NaCl gradient and analyzed by SDS-PAGE (COOMASSIE stain). The rLP2086 pool was determined to be 84% pure by laser densitometry.

Surface Reactivity and Bactericidal Activity of Antisera to rLP2086 Subfamily B.

Referring to Table VII, antisera to purified rLP2086 from the Subfamily B strain 8529, demonstrated surface reactivity to all ten 2086 Subfamily B strains tested by whole cell ELISA. Bactericidal activity was detected against nine of ten 2086 Subfamily B strains expressing heterologous serosubtype antigens, PorAs. These strains are representative of strains causing serogroup B meningococcal disease throughout western Europe, the Americas, Australia, and New Zealand. The only strain which was not killed in the bactericidal assay, 870227, reacted strongly with the anti-rLP2086 (Subfamily B) sera by whole cell ELISA, indicating that this strain expresses a protein with epitopes in common to P2086.

The 2086 Subfamily A strains listed in Table VII, were also tested for surface reactivity by whole cell ELISA. Two out of three of these strains appeared to have a very low level of reactivity, indicating that some 2086 Subfamily A strains may not be cross-reactive with antibodies raised to rLP2086 Subfamily B. The PCR amplification procedure used to identify the 2086 Subfamily B gene from strain 8529 was also performed on strains 870446, NMB and 6557. No 2086 Subfamily B PCR amplified product was detected.

Immunogenicity Methods:

Preparation of Antisera:

Vaccines were formulated as described previously in Example 1. However, a 10 μg dose was used.

Whole Cell Enzyme-Linked Immunosorbant Assay (ELISA):

*N. meningitidis* whole cell suspensions were diluted to an optical density of 0.1 at 620 nm in sterile 0.01M phosphate, 0.137M NaCl, 0.002M KCl (PBS). From this suspension, 0.1 mL were added to each well of NUNC BACT 96 well plates (Cat#2-69620). Cells were dried on the plates at room temperature for three days, then were covered, inverted and stored at 4° C. Plates were washed three times with wash buffer (0.01M Tris-HCl, 0.139M NaCl/KCl, 0.1% dodecylpoly(oxyethylereneglycolether)$_n$ n=23 (BRIJ-35®, available from ICI Americas, Inc., Wilmington, Del.), pH 7.0-7.4). Dilutions of antisera were prepared in PBS, 0.05% TWEEN-20/Azide and 0.1 mL was transferred to the coated plates. Plates were incubated for two hours at 37° C. Plates were washed three times in wash buffer. Goat-anti-mouse IgG AP (Southern Biotech) was diluted at 1:1500 in PBS/0.05% TWEEN-20, 0.1 mL was added to each well, and plates were incubated at 37° C. for two hours. Plates were washed (as above). Substrate solution was prepared by diluting p-nitrophenyl phosphate (Sigma) in 1M diethanolamine/0.5 mM $MgCl_2$ to 1 mg/mL. Substrate was added to the plate at 0.1 mL per well and incubated at room temperature for one hour. The reaction was stopped with 50 μL/well of 3N NaOH and plates were read at 405 nm with 690 nm reference.

B.) P4 Leader Sequence:

PCR Amplification and Cloning Strategy:

In order to optimize rLP2086 expression, the 2086 gene was cloned behind the P4 signal sequence of nontypable *Haemophilus influenzae* (Green et al., 1991). Primers utilized for lipoprotein cloning are listed in Table IV and are identified by compound numbers: 5658, 5660, 6473, 6543 and 6385. ORF 2086 was amplified from *N. meningitidis* B strain 8529 using primers with the following compound numbers 5658 and 5660. ORF 2086 was amplified from *N. meningitidis* serogroup B strain CDC1573 using primers with the following compound numbers 6385 and 5660. ORF 2086 was amplified from *N. meningitidis* serogroup B strain 2996 using primers with the following compound numbers 6473 and 6543. The N-terminal (5') primers were designed to be homologous to the mature region of the 2086 gene (starting at the serine residue at amino acid position 3 just downstream of the cysteine). The restriction site BamHI (GGATTC) was incorporated into the 5' end of each N-terminal primer and resulted in the insertion of a glycine residue in the mature protein at amino acid position 2. The C-terminal (3') primers were designed to be homologous to the C-terminal end of the 2086 gene and included the Stop codon as well as an SphI site for cloning purposes. The amplified fragment from each *N. meningitidis* B strain was cloned into an intermediate vector and screened by sequence analysis.

Plasmid DNA from correct clones was digested with BamHI and SphI restriction enzymes (New England Biolabs, (NEB)). A vector designated pLP339 (supplied by applicants' assignee) was chosen as the expression vector. This vector utilizes the pBAD18-Cm backbone (Beckwith et al., 1995) and contains the P4 lipoprotein signal sequence and P4 gene of nontypable *Haemophilus influenzae* (Green et al., 1991). The pLP339 vector was partially digested with the restriction enzyme BamHI and then subjected to SphI digestion. The amplified 2086 fragments (BamHI/SphI) were each ligated separately into the pLP339 vector (partial BamHI/SphI). This cloning strategy places the mature 2086 gene behind the P4 lipoprotein signal sequence. The BamHI site remains in the cloning junction between the P4 signal sequence and the 2086 gene (See the plasmid construct shown in FIG. 7). The following is an example of the sequence at the BamHI cloning junction:

[P4 signal sequence]-TGT GGA TCC-[remaining 2086 mature nucleic acid sequence]

[P4 signal sequence]-Cys Gly Ser-[remaining 2086 mature amino acid sequence]

Figure 7:
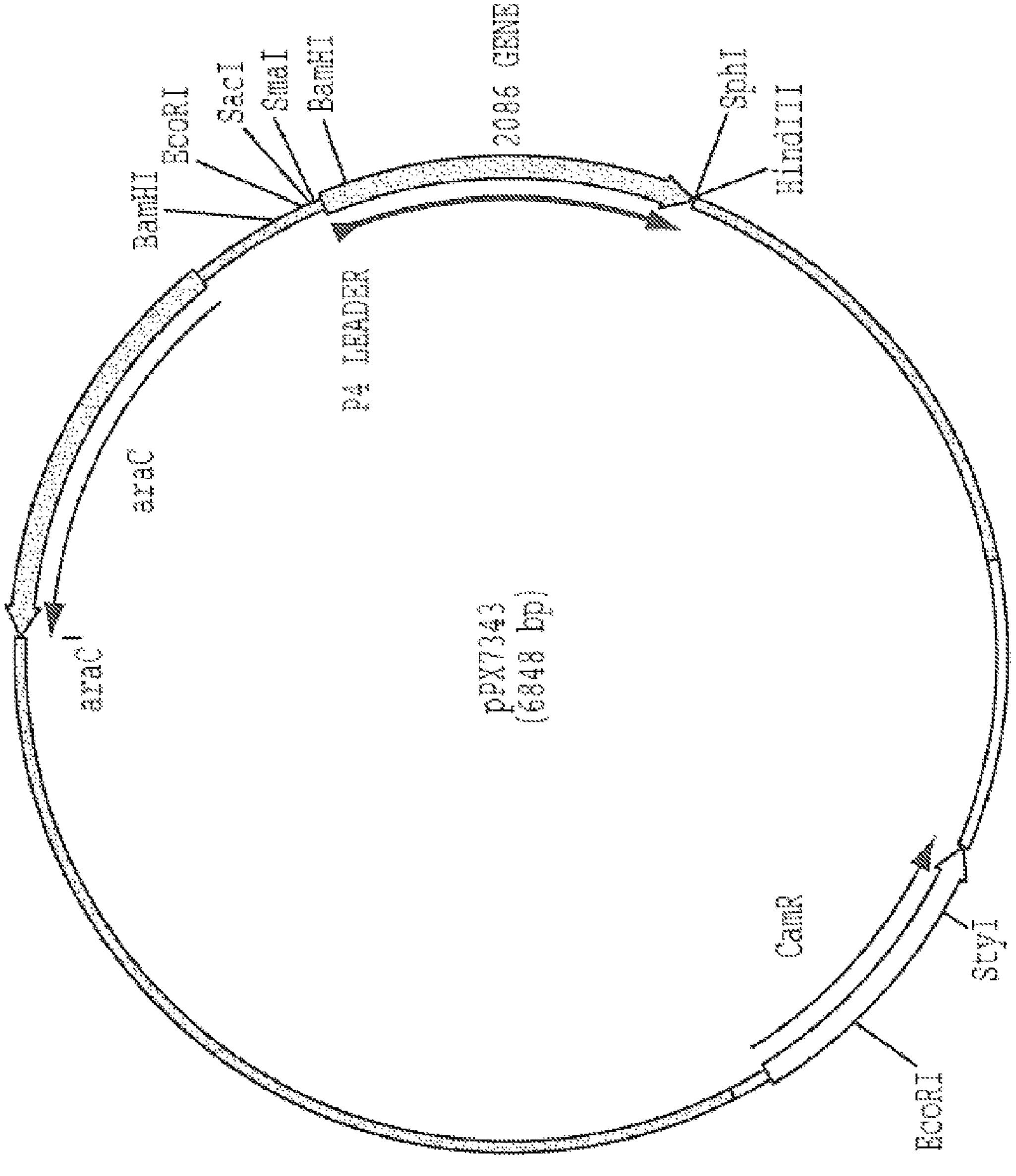
FIG. 7 is a schematic diagram of plasmid pPX7343 as described in the examples herein.
Figure 9B:
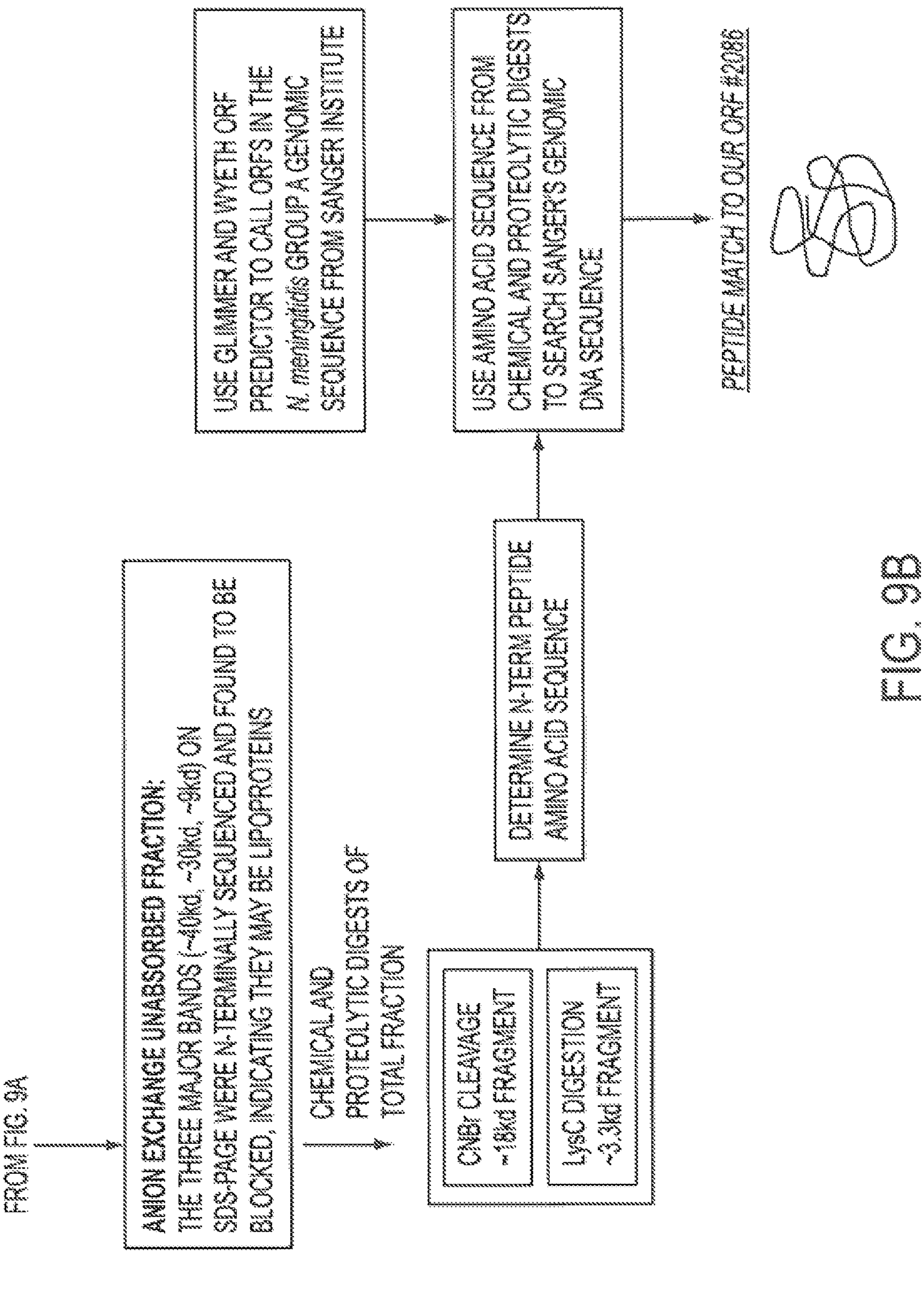
FIG. 9B is a flow chart showing the final steps in the identification of an immunogenic component in a nesserial strain.

Referring to FIG. 7, each amplified fragment was cloned into a modified pBAD18-Cm vector containing the P4 leader sequence. Fermentation was performed on recombinant *E. coli* BLR pPX7343 which expresses rP4LP2086 (recombinant P4 lipidated 2086) to try to increase the cell density by adding additional glucose. The fermentor was filled with 10 L complete M9 Minimal medium, according to Sambrook, supplemented with 1% glucose.

The initial concentration of glucose in the fermentor was 45 g/L. The fermentor was inoculated to initial OD of ~0.25. At ~OD 25, additional 20 g/L glucose was added. The culture was induced with 1% arabinose at glucose depletion at OD 63.4. The fermentation continued until 3 hours after induction. Samples were saved at t=0, 1, 2, 3 post induction and protein quantified using BSA. At t=3, protein yield is ~0.35 g/L, and 7% total cellular protein. A total of 895 grams of wet cell paste was harvested from ~10 L of culture.

Purification of the rP4LP2086 was performed using the same methods as described above in Example 2, section A.

Example 3

Development Genetics for Non-Lipidated Mature 2086 Protein

To further evaluate the immunogenicity of the 2086 protein, cloning and expression of the non-lipidated form of P2086 were performed.

PCR Gene Amplification of the ORF 2086:

Oligonucleotides used for PCR amplification of the non-lipidated 2086 gene are listed in the primer table, Table IV. The 2086 gene from strain 8529 can be amplified with primers identified by compound numbers 5135 and 6406 (SEQ ID NOS. 308 and 312, respectively), as indicated in the table. The 2086 gene from strain CDC1573 can be amplified with primers identified by compound numbers 5135 and 6474 (SEQ ID NOS. 308 and 316, respectively). The 2086 gene from strain 2996 can be amplified with primers identified by compound numbers 6406 and 6605 (SEQ ID NOS. 312 and 320, respectively).

Features of these primers include, a synthetic BglII restriction site in each primer, a synthetic NdeI restriction site in compound numbers 6406 and 6474 and termination codons in all three reading frames are present in compound numbers 5135 and 6605. Primer numbers 6406 and 6474 amplify the 2086 gene with an ATG (Met) fused to the second amino terminal codon (ACG) representing a single amino acid substitution (replaces TGC Cys) of the mature 2086 polypeptide.

The PCR cloning vector was TOPO-PCR2.1, Invitrogen, Valencia, Calif.

The vector used to express non-lipidated 2086 protein was pET9a from Novagen, Madison, Wis.

The *E. coli* cloning strain was Top10, Invitrogen, Carlsbad, Calif.

The *E. coli* expression strain was BLR(DE3)pLysS, Novagen, Madison, Wis.

The culture media for cloning purposes was Terrific Broth liquid or agar, according to Sambrook et al., with 1% sterile glucose substituted for glycerol, and the appropriate antibiotic (ampicillin or kanamycin).

Plasmid purification was with Qiagen Spin Miniprep Kit (Valencia, Calif.).

Preparation of the Production Strain or Cell Line for Non-Lipidated 2086 Expression:

The 2086 gene was amplified by polymerase chain reaction (PCR) [AmpliTaq and ABI 2400 thermal cycler, Applied Biosystems, Foster City, Calif.] from chromosomal DNA derived from meningococcal strain 8529. The PCR amplification of the 2086 gene utilized two oligonucleotide primers in each reaction identified by compound numbers 6474 and 5135 (SEQ ID NOS. 316 and 308, respectively). The amplified 2086 PCR product was cloned directly into the TOPO-PCR2.1 cloning vector and selected on Terrific Broth agar supplemented with 100 μg/ml ampicillin and 20 μg/ml X-Gal. White colonies were selected and grown. Plasmid DNA was prepared using a Qiagen miniprep kit and the plasmids were screened for the PCR fragment insert. PCR insert plasmids were subjected to DNA sequencing (Big Dye chemistry on an ABI377 sequencer, Applied Biosystems, Foster City, Calif.).

Plasmids exhibiting the correct DNA sequence were digested with BglII restriction enzyme and the BglII fragment was gel purified using a GeneClean II purification kit (Bio101, Carlsbad, Calif.). The purified BglII fragment was cloned into the BamHI site of the expression vector pET9a. The pET9a/2086 clones were selected on Terrific Broth plates supplemented with 30 μg/ml kanamycin. Kanamycin resistant clones were grown and miniprep plasmid DNA was prepared. The plasmids were screened for the appropriate orientation of the 2086 gene in the BamHI site. Correctly oriented plasmids represent a fusion of the T7-antigen to the amino terminus of 2086 gene (rP2086T7). These rP2086T7 gene fusions were transformed into BLR(DE3)pLysS, selected on Terrific Broth/Kan plates, grown in Terrific Broth and induced to express the rP2086T7 fusion protein with 1 mM IPTG (isopropyl β-D-thiogalactopyranoside). The rP2086T7 fusion protein expressed at high levels.

Figure 6:
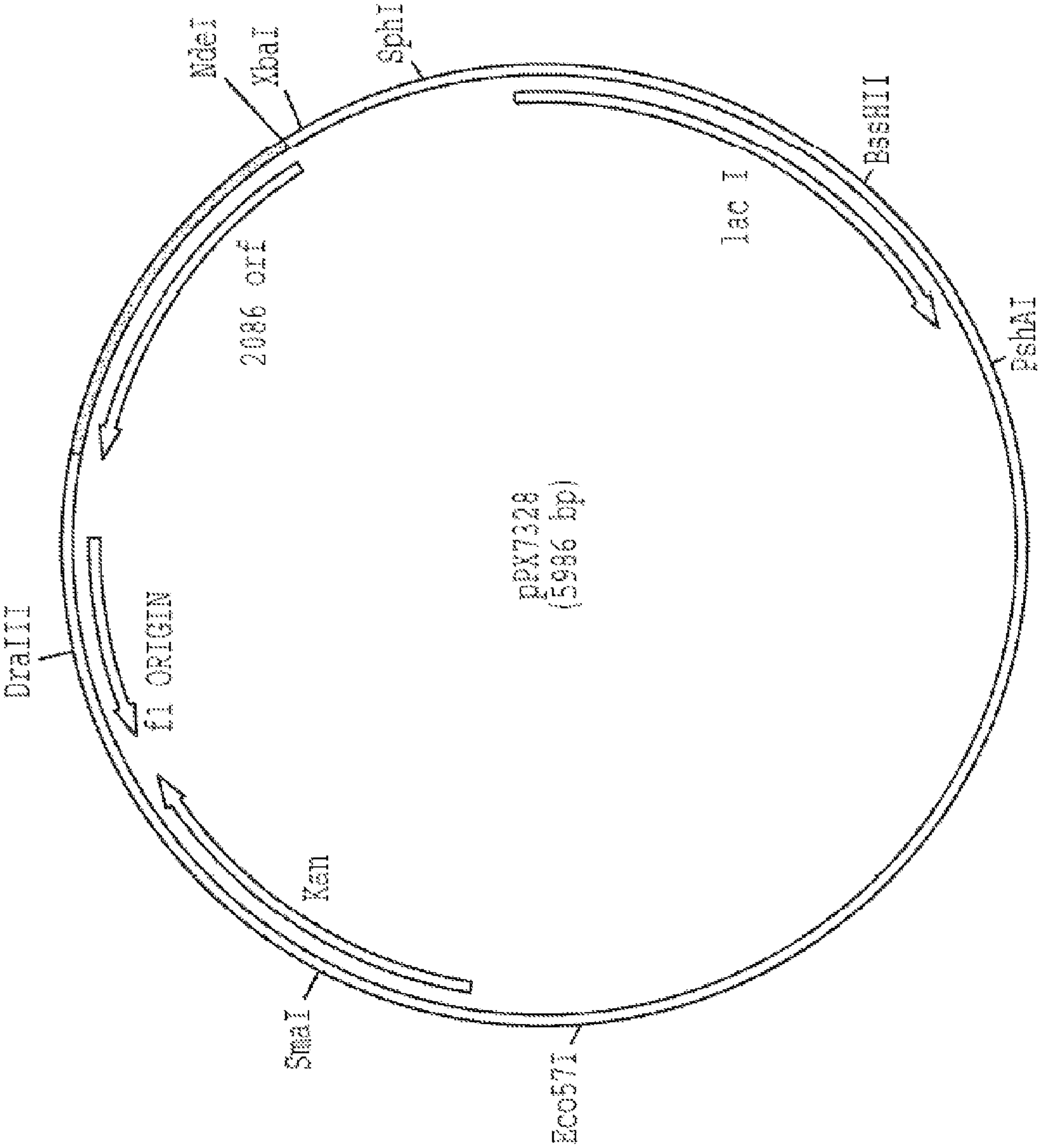
FIG. 6 is a schematic diagram of plasmid pPX7328 as described in the examples herein.

These fusion plasmids were then subjected to a NdeI restriction digest, which deletes the T7-antigen and links the mature 2086 gene directly to the ATG start provided by the vector. These NdeI deleted plasmids were transformed into Top10 cells and selected on Terrific Broth/Kan plates. Candidate clones were grown and miniprep plasmid DNA was prepared. The plasmid DNA was subjected to DNA sequencing to confirm the deletion and the integrity of the 2086 gene sequence. These plasmids are represented by the plasmid map designated pPX7328 (FIG. 6). Plasmids representing the correct DNA sequence were transformed into BLR(DE3)pLysS, selected on Terrific Broth/Kan plates, grown in Terrific Broth and induced to express the 2086 protein with IPTG. The pET9a vector failed to express the mature 2086 protein, in strain BLR(DE3)pLysS, when the T7-Tag was removed.

Production of Non-Lipidated 2086 Protein:

Purified plasmid DNA was used to transform the expression strain BLR(DE3)pLysS. BLR(DE3)pLysS cells carrying the plasmids are resistant to kanamycin and can be induced to express high levels of PorA protein by the addition of 1 mM IPTG. The rP2086T7 fusion protein can be expressed as insoluble inclusion bodies in the *E. coli* cell line BLR(DE3) pLysS at ~40% of total protein. This purified fusion protein was used to immunize mice and generated significant levels of bactericidal antibodies against a heterologous meningococcal strain. (See Table V)

2086 Non-Lipidated Gene Mutagenesis:

PCR primer mutagenesis was performed on the 5' end of the 2086 gene. Expression studies are under way to determine if the T7-Tag can be removed while exhibiting the high expression levels of mature rP2086T7.

Purification of Non-Lipidated rP2086T7:

*E. coli* BLR(DE3)pLysS cells expressing non-lipidated rP2086T7 were lysed by microfluidizer in 10 mM Hepes-NaOH/5 mM EDTA/1 mM Pefabloc SC pH 7.4. The cell lysate was then centrifuged at 18,000×g for 30 minutes. The inclusion body pellet was washed three times with 50 mM Tris-HCl/5 mM EDTA/1% TRITONX-100 pH 8 followed by centrifugation each time at 24,000×g for 30 min. The inclusion body pellet was then washed twice with 50 mM Tris-HCl/5 mM EDTA/1% ZWITTERGENT 3-14 pH 8 followed by centrifugation each time at 24,000×g for 15 min. The inclusion body pellet was then solubilized with 50 mM Tris-HCl/5 mM EDTA/4M Urea pH 8 for two hours followed by centrifugation to remove insoluble material. The supernatant (solubilized rP2086T7) was split into four equal samples. One sample was adjusted to 50 mM Tris-HCl/5 mM EDTA/250 mM NaCl/2M Urea pH8 (no detergent), one was adjusted to 50 mM Tris-HCl/5 mM EDTA/250 mM NaCl/2M Urea/1% hydrogenated TRITON X-100 pH8 (TX-100), one was adjusted to 50 mM Tris-HCl/5 mM EDTA/250 mM NaCl/2M Urea/1% ZWITTERGENT 3-12 pH8 (Z3-12), and one was adjusted to 50 mM Tris-HCl/5 mM EDTA/250 mM NaCl/2M Urea/1% ZWITTERGENT 3-14 pH8 (Z3-14) using stock solutions. To remove the urea, samples were dialyzed to completion against the respective buffer containing no urea. The samples were then dialyzed to completion against the respective buffer containing no urea and 60 mM NaCl to reduce the NaCl concentration. Insoluble material was removed by centrifugation at 2,000×g for 15 minutes, and the resulting supernatant (refolded rP2086T7) was used for further experiments. Homogeneity of rP2086T7 was found to be 91-95% as determined using COOMASSIE stained SDS-PAGE and laser densitometry.

Immunogenicity Procedure—as Described in Example 2

This purified fusion protein was used to immunize mice and generated significant levels of bactericidal antibodies against a heterologous meningococcal strain. (See Table V below):

TABLE V

Bactericidal titers of mouse antibody raised to rP2086T7

| MOUSE SERUM | DESCRIPTION | HETEROLOGOUS STRAIN/H44/76 |
|---|---|---|
| AF780 week 6 | r2086T7, 10 ug | 3200 |
| Week 0 pool | Pre-immune serum | 10 |
| AE203 week 6 | rLP2086, 10 ug (positive control)* | 6400 |

(*positive control sera generated by immunization of mice with rLP2086)

Example 4

Development of Chimeric Clones of ORF 2086

The N-terminal region of the 2086 gene from strain CDC-1573 contains a repeated segment not present in the 2086 gene from strains 8529 and 2996 (see FIG. 8). It appears that this repeated segment is responsible for increased levels of recombinant 2086 protein expression from two *E. coli* based expression systems (pET and pBAD). The recombinant protein expression level from the CDC-1573 2086 gene was significantly better in the pET and pBAD expression systems as compared to the recombinant expression levels from the 2086 gene with strains 8529 and 2996 using the same systems. The N-terminal region of the 2086 gene from all three strains is relatively homologous, except for this repeated segment. Therefore, it is reasonable to assume that by fusing the CDC-1573 N-terminus to the 2086 genes from strains 8529 and 2996, that the recombinant 2086 protein levels expressed from these genes will increase when using the pET and pBAD systems.

Materials and Methods:

Chromosomal DNA from strains 8529 and 2996 was purified and used as a template for PCR amplification of the chimeric 2086 gene. PCR primers with the compound numbers 6721 and 5135 (SEQ ID NOS. 321 and 308, respectively) were used to amplify the chimeric 2086 gene from strain 8529 and PCR primers with the compound numbers 6721 and 6605 (SEQ ID NOS. 321 and 320, respectively) were used to amplify the chimeric 2086 gene from strain 2996. The PCR products were cloned directly into the PCR2.1 TOPO vector from Invitrogen and then screened by DNA sequence analysis to identify an intact chimeric 2086 gene. That gene was then cleaved from the PCR2.1 vector with BglII and the BglII fragment was inserted into the BamHI site of the pET9a plasmid. Plasmid inserts were screened for the appropriate orientation and then subjected to a NdeI digestion. The linear NdeI fragments were self-ligated to achieve the deletion of a small NdeI fragment containing the T7-tag sequence contributed by the pET9a vector. This deletion directly links the T7 promoter to the 5' end of the chimeric 2086 gene. The NdeI deleted plasmid was transformed into *E. coli* strain BL21 (DE3) and kanamycin resistant colonies were screened for chimeric 2086 protein expression with IPTG induction.

Initial studies indicate that the chimeric 2086 gene from strain 2996 expresses about twice as much recombinant protein as compared to the native 2996/2086 gene when expressed in the pET9a system. The pBAD system has not been tested yet.

Although only one experiment has been performed, the data indicate that there is an enhanced utility from the chimeric 2086 gene. The generation of CDC-1573 N-terminal fusions to the 2086 genes from strains 8529 and 2996 provides enhanced recombinant 2086 protein expression.

Example 5

2086 PCR Screening of *N. meningitidis* Strains

In order to determine the conservation of the 2086 gene among clinical isolates, PCR amplification was performed on 88 *N. meningitidis* strains.

Initial PCR identification of ORF 2086 utilized primers listed in Table IV (see Example 2 above) identified by compound numbers: 4623, 4624 and 4625 (SEQ ID NOS. 303, 304 and 305, respectively). These primers were designed based on Sanger's *N. meningitidis* serogroup A sequence. To facilitate screening a large number of strains, internal primers were designed for the 2086 gene. A total of 88 *N. meningitidis* strains were screened by PCR with the newly designed internal 2086 primers identified by compound numbers 5005 and 5007 (SEQ ID NOS. 306 and 307). With these primers the applicants were able to identify the 2086 gene from 63 of the 88 (~70%) *N. meningitidis* strains, (see Table VI-A).

Expanded regions surrounding the 2086 gene in Sanger's *N. meningitidis* serogroup A sequence and TIGR's *N. meningitidis* serogroup B sequence were examined and aligned. Primers were designed to correspond to regions upstream and downstream of the 2086 gene. The purpose was to utilize these primers to amplify greater than full length 2086 genes from a variety of *N. meningitidis* strains for sequence comparison. PCR amplification of one strain (6557), using Compound Nos. 6470 and 6472 (SEQ ID NOS: 313 and 314, respectively), resulted in a low yield of product. The strain 6557 amplified product was cloned and plasmid DNA was submitted for sequence analysis. Results indicated a new type of 2086 gene with greater sequence variability than had previously been seen. The 2086 gene from strain 6557 was ~75% identical at the amino acid level to the other strains sequenced. Interestingly, strain 6557 was one of the 30% of strains that had previously tested negative by 2086 PCR screening described above.

Internal primers specific to the C-terminal variable regions within strain 6557 were designed. These primers were used to screen for the more variable 2086 gene in the ~30% of strains that had previously tested negative by 2086 PCR screening. All available *N. meningitidis* strains (n=88) were screened by PCR with these newly identified internal 2086 primers (identified by compound numbers 6495 and 6496; SEQ ID NOS. 159 and 160, respectively). Only the ~30% of *N. meningitidis* strains that had previously tested negative by PCR for 2086 were PCR positive in this screen. The set of genes amplified from the previously PCR negative (~30%) strains should represent a new type of 2086 gene or a second family of 2086 genes and herein are designated 2086 Subfamily A. The set of 2086 genes amplified from the ~70% of strains with the 8529 derived primers are herein designated Subfamily B.

Subfamily A of 2086 genes is exemplified by the odd numbered SEQ ID NOS:1-173 without limitation. Subfamily B of 2086 genes is exemplified, without limitation, by the odd numbered SEQ ID NOS: 175-251

*N. meningitidis* strains used for PCR amplification studies were selected from the following tables, Table VI-A and Table VI-B. The strains listed in the tables are provided as examples of *N. meningitidis* strains, without limitation. The strains listed in Table VI-A are classified in 2086 protein Subfamily A and the strains listed in Table VI-B are classified in 2086 protein Subfamily B. The strains listed in each table are grouped by serosubtype. The strains are available from the following four sources as indicated in the table: MPHL-Manchester Public Health Laboratory, Manchester, UK; RIVM, Bilthoven, The Netherlands; University of Iowa, College of Medicine, Department of Microbiology, Iowa City, Iowa; and Walter Reed Army Institute of Research, Washington, D.C.

TABLE VI-A

| Strain | Serosubtype | Source |
|---|---|---|
| M97 251854 | B:4z, PI:4 | MPHL |
| M98 250622 | B:2b, PI:10 | MPHL |
| M98 250572 | B:2b, PI:10 | MPHL |
| M98 250771 | B:4z, PI.22, 14 | MPHL |

TABLE VI-A-continued

| Strain | Serosubtype | Source |
|---|---|---|
| M98 250732 | B:4z, PI.22, 14a | MPHL |
| M98 250809 | B:15, PI:7, 16 | MPHL |
| M97 252697 | B:1, PI:6, P1.18, 25 | MPHL |
| M97 252988 | B:4, PI:6, P1.18, 25, 6 | MPHL |
| M97 252976 | B:4, PI:6, P1.18, 25 | MPHL |
| M97 252153 | B:4, PI:6, P1.18, 25 | MPHL |
| M97 253248 | B:15, PI:7, NT, 16 | MPHL |
| CDC1610 | P1:NT 4(15), P1.18-7, 16-14 | CDC |
| CDC1521 | P1.6, 3 2b(4) | CDC |
| CDC1034 | P1.7 4(15) | CDC |
| L8 | P1.7, 1 15(4) | Walter Reed |
| CDC1492 | P1.7, 1 4(15) | CDC |
| 870446 | P1.12a, 13 | RIVM |
| CDC2369 | P1.(9), 14 | CDC |
| 6557 | P1.(9), 14, P1.22a, 14a | RIVM |
| 2996 | P1.5, 2, P1.5a, 2c | RIVM |
| NmB | P1.5, 2, P1.5a, 2c | UIOWA |
| L3 | P1.5, 2 | Walter Reed |
| B16B6 | P1.5, 2 | RIVM |
| CDC1135 | | CDC |
| L5 | P1.NT, P1.21-6, 1 | Walter Reed |
| L4 | P1.21, 16 | Walter Reed |
| W135 | | Walter Reed |
| C11 | C:16, P1.7, 1 | CDC |
| Y | | Walter Reed |

TABLE VI-B

| Strain | Serosubtype | Source |
|---|---|---|
| M98 250670 | B:1, PI:4 | MPHL |
| M98 250024 | B:1, PI:4 | MPHL |
| M97 253524 | B:1, PI:4 | MPHL |
| M97 252060 | B:1, PI:4 | MPHL |
| M97 251870 | B:4z, PI:4 | MPHL |
| M97 251836 | B:4z, PI:4 | MPHL |
| M97 251830 | B:4z, PI:4 | MPHL |
| M97 251905 | B:4z, PI:4 | MPHL |
| M97 251898 | B:4z, PI:4 | MPHL |
| M97 251885 | B:4z, PI:4 | MPHL |
| M97 251876 | B:4z, PI:4 | MPHL |
| M97 251994 | B:4z, PI:4 | MPHL |
| M97 251985 | B:4z, PI:4 | MPHL |
| M97 251957 | B:4z, PI:4 | MPHL |
| M97 251926 | B:4z, PI:4 | MPHL |
| M97 252045 | B:4z, PI:4 | MPHL |
| M97 252038 | B:4z, PI:4 | MPHL |
| M97 252026 | B:4z, PI:4 | MPHL |
| M97 252010 | B:4z, PI:4 | MPHL |
| M97 252098 | B:4z, PI:4 | MPHL |
| M97 252083 | B:4z, PI:4 | MPHL |
| M97 252078 | B:4z, PI:4 | MPHL |
| M98 250735 | B:4z, PI:15 | MPHL |
| M98 250797 | B:4z, PI:15 | MPHL |
| M98 250768 | B:4z, PI:15 | MPHL |
| M98 250716 | B:2b, PI:10 | MPHL |
| M98 250699 | B:4z, PI:10 | MPHL |
| M98 250393 | B:4z, PI:10 | MPHL |
| M98 250173 | B:4z, PI:10 | MPHL |
| M97 253462 | B:4z, PI:14 | MPHL |
| M98 250762 | B:15, PI:7, 16 | MPHL |
| M98 250610 | B:15, PI:7, 16 | MPHL |
| M98 250626 | B:15, PI:7, 16 | MPHL |
| M97 250571 | B:15, PI:16 | MPHL |
| M97 252097 | B:15, PI:16, P1.7b, 16 | MPHL |
| M97 253092 | B:1, PI:6 | MPHL |
| M97 252029 | B:15, PI:7, NT | MPHL |
| M97 251875 | B:15, PI:7, NT | MPHL |
| CDC1127 | PI.7, 16 4(15) | CDC |
| CDC982 | PI.7, 16 4(15) | CDC |
| CDC1359 | PI.7, 16 4(15) | CDC |
| CDC798 | PI.7, 16 15(4) | CDC |
| CDC1078 | PI.7, 16 15(4) | CDC |
| CDC1614 | PI.7, 16 15(4) | CDC |
| CDC1658 | PI.7, 16 15(4) | CDC |

TABLE VI-B-continued

| Strain | Serosubtype | Source |
|---|---|---|
| H44/76 | PI.7, 16 15(4) | RIVM |
| CDC1985 | P1.7, 13 4(15) | CDC |
| L6 | P1.7, 1 ?(4) | Walter Reed |
| CDC1573 | P1.7, 1 4(15) | CDC |
| L7 | P1.7, (9), 1 | Walter Reed |
| CDC937 | P1.7, 3, P1.7b, 3 | CDC |
| 8529 | P1.7, 3, P1.7b, 3 | RIVM |
| 880049 | P1.7b, 4 | RIVM |
| CDC2367 | P1.15 4(15) | CDC |
| H355 | P1.19, 15 | RIVM |
| CDC1343 | P1.14 4(15) | CDC |
| M982 | P1.22, 9 | RIVM |
| 870227 | P1.5c, 10 | RIVM |
| B40 | P1.5c, 10 | RIVM |
| 5315 | P1.5c, 10 | RIVM |
| CDC983 | P1.5, 2 | CDC |
| CDC852 | P1.5, 2 | CDC |
| 6940 | P1.18, 25 (6) | RIVM |
| A4 | | |

Other strains are readily available as isolates from infected individuals.

Example 6

Reactivity of rLP2086 Antisera Against Meningococcal Strains

The following table, Table VII, shows the cross-reactive and cross protection capacity of the rLP2086 as described above. As indicated in the table, the rLP2086 was processed and analyzed using a variety of techniques including whole cell ELISA (WCE) titers, bactericidal assay (BCA) and Infant Rat (IR) assays to determine the bacterial cell surface reactivity of a polyclonal antibody raised against the 2086 protein.

TABLE VII

| Reactivity of rLP2086-8529 antisera against multiple meningococcal strains | | | | |
|---|---|---|---|---|
| Strain | Serosubtype | WCE | BC | IR |
| 2086 Subfamily A | | | | |
| 870446 | P1.12a, 13 | 808,615 | >800 | |
| NmB | P1.5a, 2c | 47,954 | <100 | |
| 6557 | P1.22a, 14a | 169,479 | <25 | − |
| 2086 Subfamily B | | | | |
| 880049 | P1.7b, 4 | 1,402,767 | 100 | + |
| H44/76 | P1.7, 16 | 8,009,507 | >6400 | |
| H355 | P1.19, 15 | 10,258,475 | 3,200 | + |
| 6940 | P1.18, 25(6) | 5,625,410 | 800 | |
| 870227 | P1.5c, 10 | 4,213,324 | <25 | + |
| 252097 | P1.7b, 16 | 10,354,512 | >800 | |
| 539/8529 | P1.7b, 3 | 11,635,737 | 3,200 | |
| M982 | P1.22, 9 | 1,896,800 | 800 | |
| CDC-1573 | P1.7a, 1 | 208,259 | 25 | |
| CDC-937 | P1.7b, (3) | 9,151,863 | >800 | |

+ greater than 10 fold reduction in bacteremia
− less than 10 fold reduction in bacteremia

Example 7

Various constructs for expressing ORF2086 protein were prepared. The following table, Table VIII, is an r2086 construct table which is provided for the purpose of showing examples and illustrating an implementation of the present invention, without limitation thereto.

TABLE VIII

| r2086 Construct Summary | | | | | | |
|---|---|---|---|---|---|---|
| Construct | Promoter | Leader | Expression | Extraction | Vector | % total Protein |
| pPX7340 | T7 | native | COOMASSIE | sarcosyl soluble | pET27b | 2.5% processed lipoprotein |
| pPX7341 | T7 | P4 | COOMASSIE | sarcosyl soluble | pET27b | 5% processed lipoprotein |
| pPX7343 | Arabinose | P4 | COOMASSIE | sarcosyl soluble | pBAD18 cm | 7-10% processed lipoprotein |
| pPX7325 | T7 | T7-tag fusion/ mature | COOMASSIE | inclusion bodies | pET9a | 40-50% mature protein |
| pPX7328 | T7 | mature | COOMASSIE | soluble | pET9a | 10% mature protein |

Example 8

Further studies with LOS depleted outer membrane proteins identified additional strains producing outer membrane protein(s) other than PorA which were capable of eliciting bactericidal antibodies to strains expressing heterologous serosubtypes. The following describes further studies to identify additional proteins according to one embodiment of the present invention, and specifically outer membrane lipoproteins, which can reduce the number of proteins required in a meningococcal immunogenic composition. These further studies supplement the studies described in the previous examples.

Figure 12:
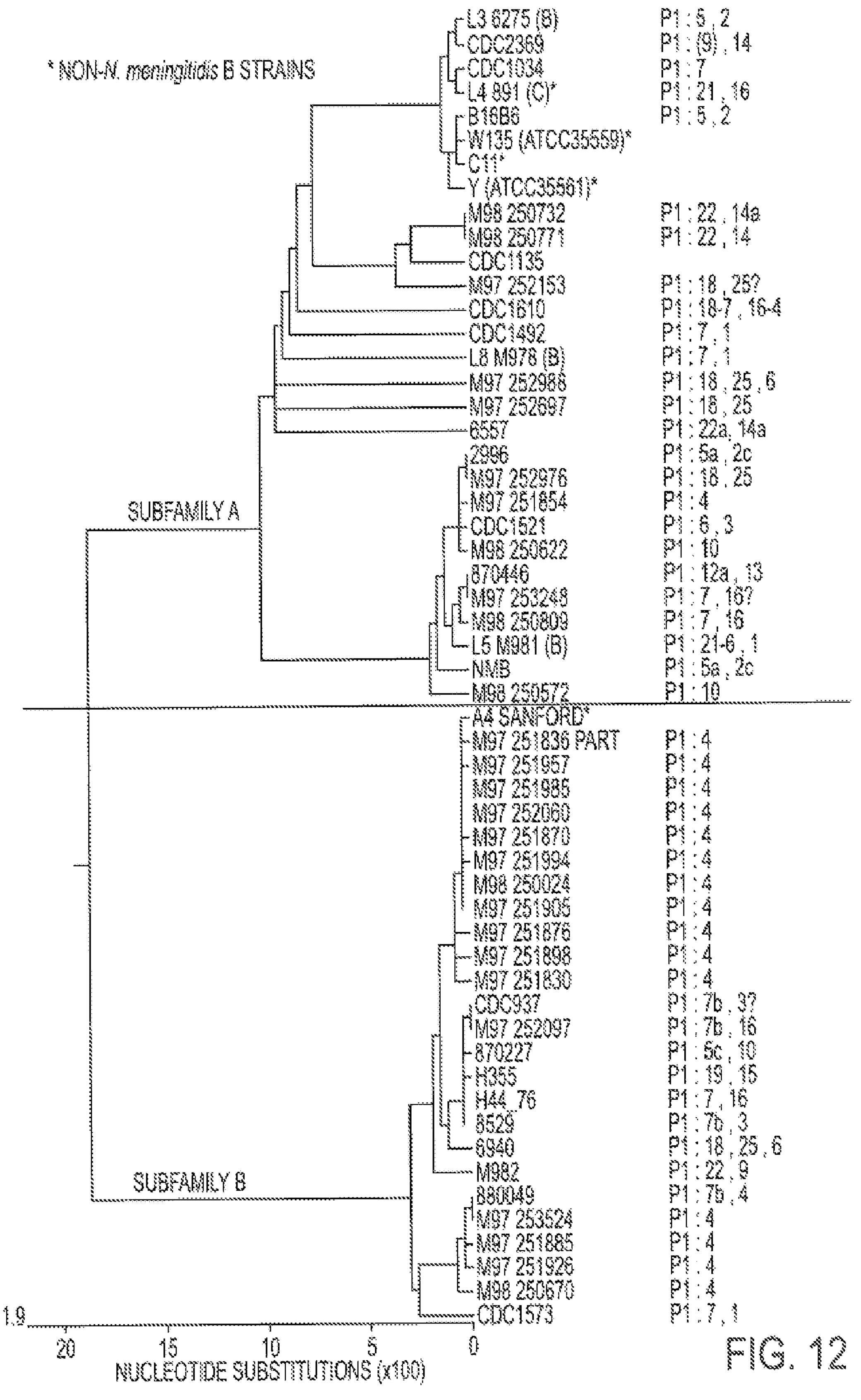
FIG. 12 is a phylogenetic tree showing the organization of the subfamilies and groups of ORF2086 proteins.
Figure 13:
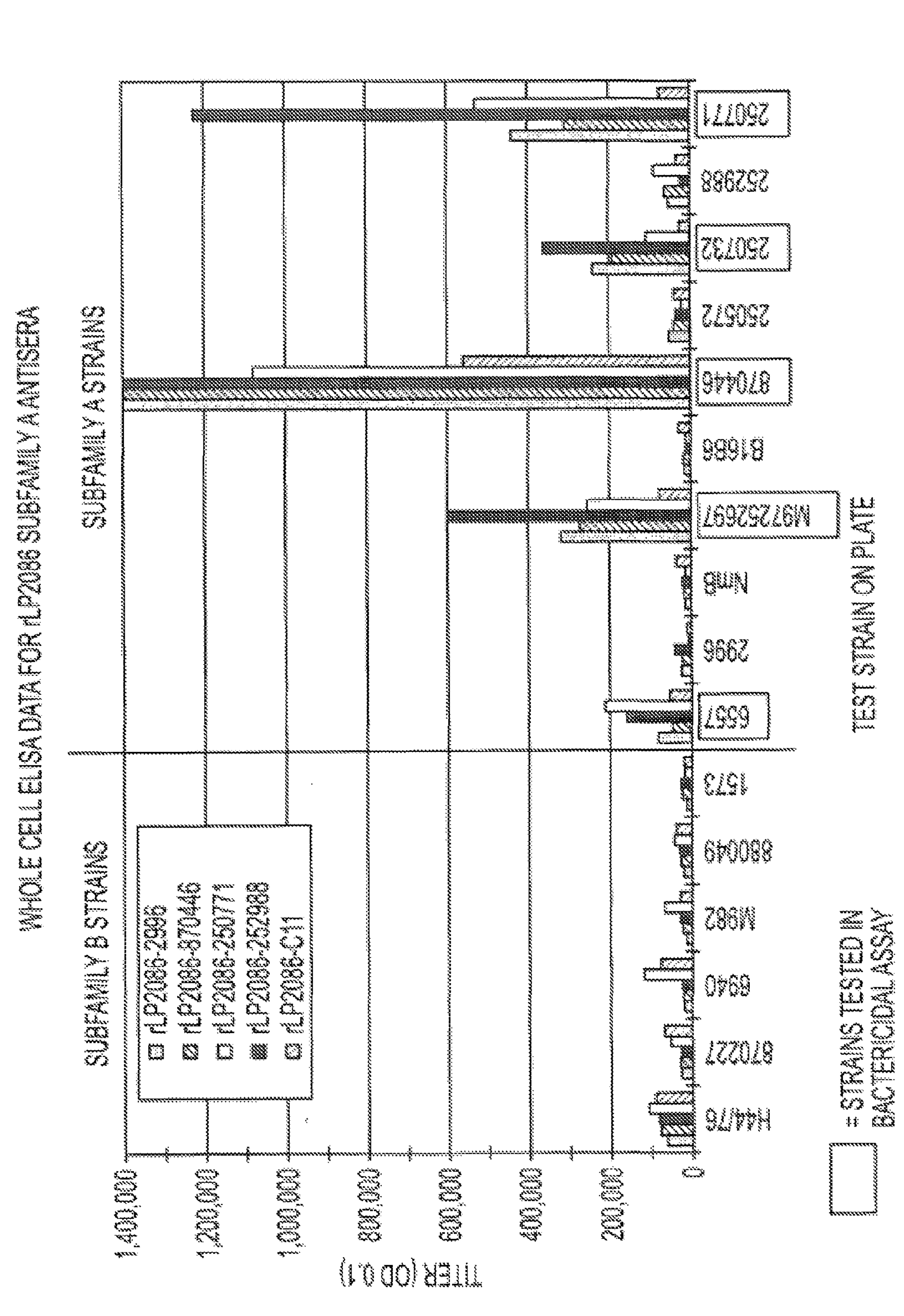
FIG. 13 is a graphical illustration of whole cell ELISA data for the rLP2086 Subfamily A antisera.
Figure 14:
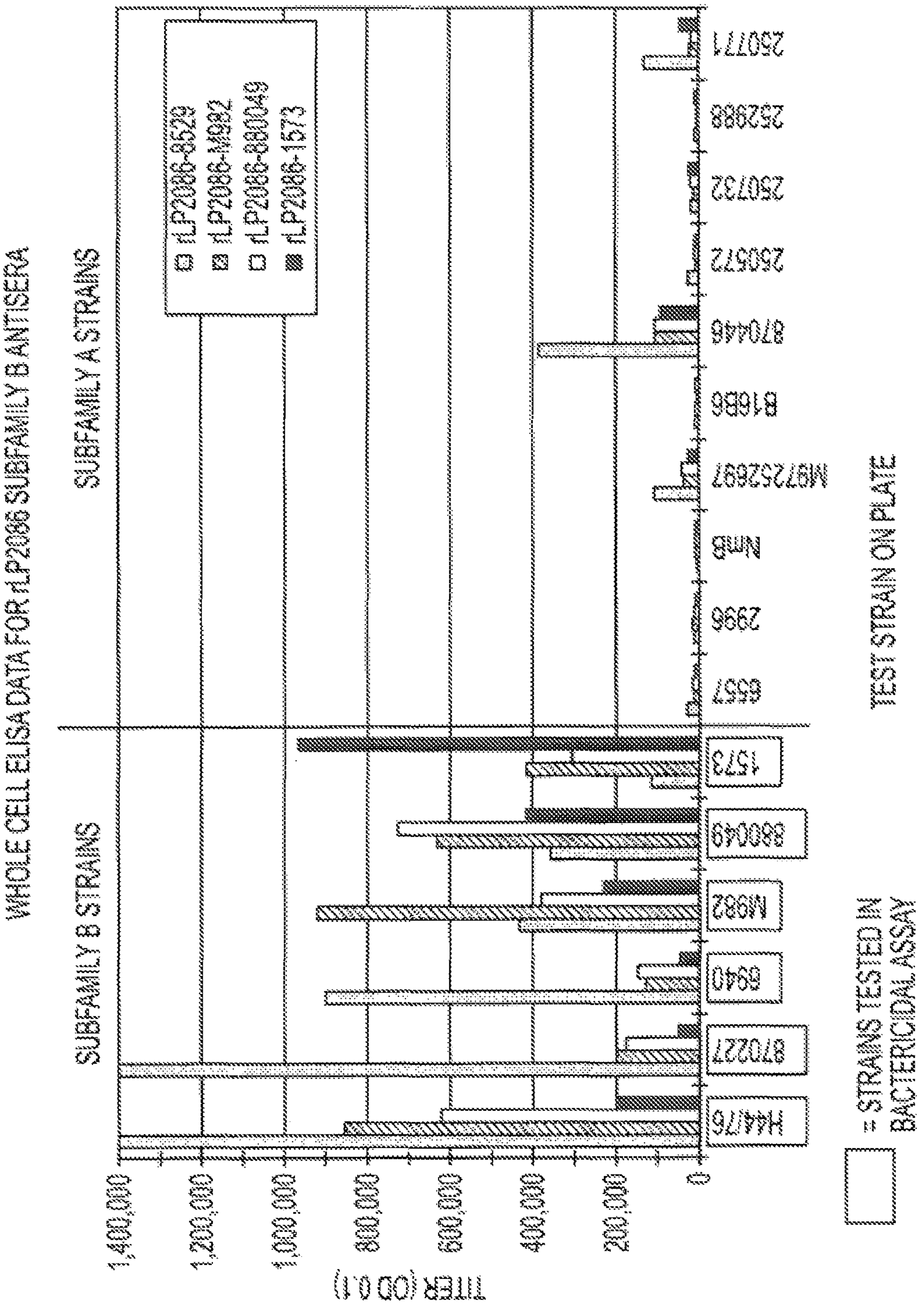
FIG. 14 is a graphical illustration of whole cell ELISA data for the rLP2086 Subfamily B antisera.
Figure 15:
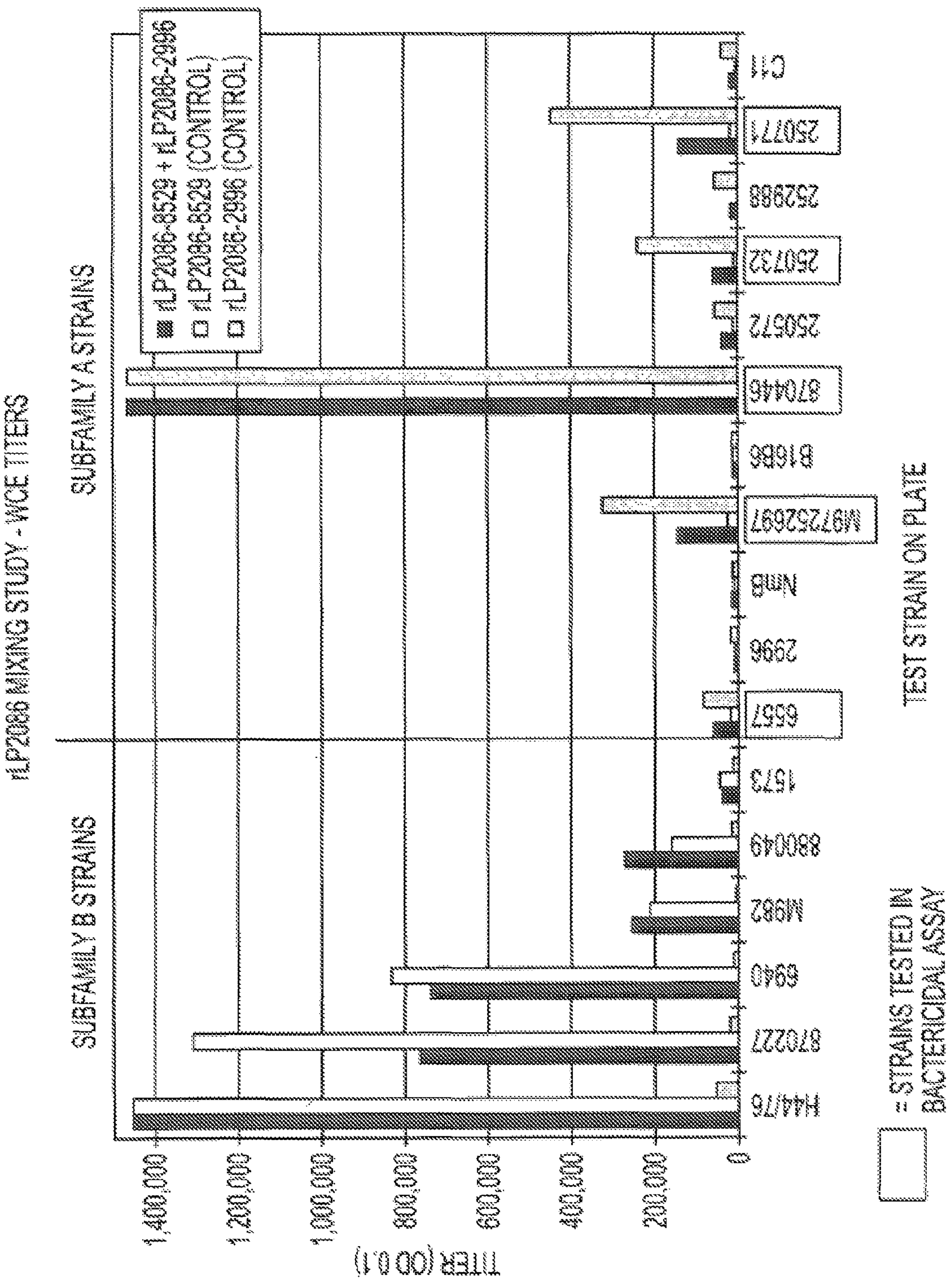
FIG. 15 is a graphical illustration of the results of the rLP2086 mixing study—WCE Titers.
Figure 16:
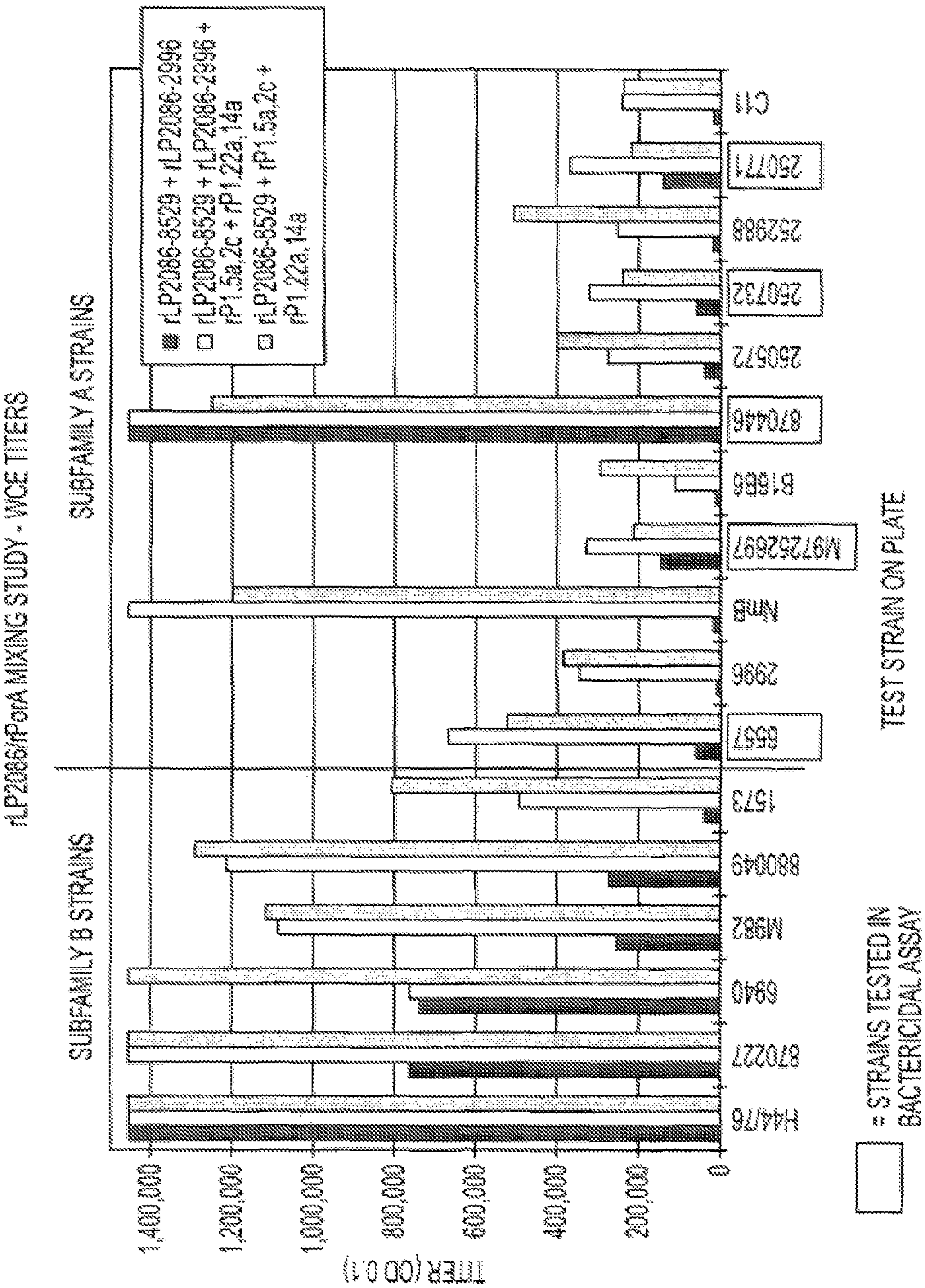
FIG. 16 is a graphical illustration of the results of the rLP2086/rPorA mixing study—WCE Titers.

Subcellular fractionation, differential detergent extraction, isoelectric focusing, and ion exchange chromatography were used in conjunction with immunization and bactericidal assays against multiple strains to identify small groups of proteins of interest. Direct sequencing of the main components indicated that the N-termini were blocked. Internal protein sequences were obtained by direct sequencing of polypeptides derived from chemical and proteolytic digests. The genomic sequence of a group A meningococcal strain was downloaded from the Sanger Center and analyzed by our Bioinformatics group using existing and proprietary algorithms to create a searchable database. The peptide sequence data indicated that ORF2086 was of interest. Primers based on this orf were used to PCR the P2086 gene from strain 8529. Analysis of the gene sequence, the fact that the N-terminus was blocked, and its subcellular location indicated that P2086 is a lipidated outer membrane protein (LP2086). rLP2086-8529 and variants from other meningococcal strains were recombinantly expressed as lipoproteins in *E. coli* using the *H. influenzae* P4 signal sequence. These recombinant proteins were isolated from *E. coli* membranes by differential detergent extraction, purified using ion exchange chromatography, and used to immunize mice. Mouse anti-LP2086 sera were able to facilitate bactericidal activity against several different serosubtype strains of *N. meningitidis*. Further analysis of the P2086 genes from many *N. meningitidis* strains showed that these sequences fell into two groups designated Subfamily A and Subfamily B. (See FIG. 12) The antisera raised against the Subfamily B proteins were bactericidal against nine strains expressing Subfamily B proteins, and one strain expressing a Subfamily A protein. Subfamily A antisera were bactericidal against Subfamily A strains. A mixture of one rPorA and one rLP2086 elicited complementary antibodies extending vaccine coverage beyond that induced by either protein alone.

These observations lead to the following conclusions. rLP2086 antigens are capable of eliciting bactericidal antibodies against meningococcal strains expressing heterologous PorAs and heterologous P2086 proteins. The P2086 family of antigens may be a useful vaccine or immunogenic either alone or in combination with other neisserial antigens.

The following describes the foregoing study in detail. A complex mixture of soluble outer membrane proteins (sOMPs) was found to elicit PorA independent bactericidal antibody against strains expressing heterologous PorA proteins. A process of differential detergent extraction, isoelectric focusing and ion exchange chromatography followed by mouse immunization was used to follow the immunologically active components.

At each step, sera was assayed for surface reactivity and bactericidal activity against several strains containing serosubtype antigens that are representative of the worldwide epidemiology of meningococcal disease.

This process of separation and immunization was used to identify a novel cross-reactive immunogenic candidate for Group B *N. meningitidis*.

Generation of PorA deficient strains—The porA chromosomal locus was cloned into plasmid pPX7016 from strain 2996. Within the plasmid the porA promoter, the S/D box and the first 38 N-terminal codons have been deleted and replaced with a self contained KanR expressing cassette. The plasmids were linearized with restriction enzymes and naturally transformed into the serosubtype strains PI:5,2; PI:9; PI:7,16; PI:15; PI:4; PI:3 & PI:10. Kanamycin resistant transformants were selected and screened for the loss of PorA by serosubtype specific monoclonals in an ELISA.

Bactericidal Assay: See Mountzourous, K. T. and Howell, A. P. Detection of Complement-Mediated Antibody-Dependent Bactericidal Activity in a Flourescence-Based Serum Bactericidal Assay for Group B *Neisseria meningitidis*. J Clin Microbiol. 2000; 38:2878-2884.

Whole Cell Enzyme Linked Immonosorbant Assay (ELISA): *N. meningitidis* whole cell suspensions were diluted to an optical density of 0.1 at 620 nm in sterile 0.01M phosphate, 0.137M NaCl, 0.002M KCl (PBS). From this suspension, 0.1 mL were added to each well of NUNC BACT 96 well plates (Cat#2-69620). Cells were dried on the plates at 37° C. overnight, then were covered, inverted and stored at 4° C. Plates were washed three times with wash buffer (0.01M Tris-HCl, 0.139M NaCl/KCl, 0.1% BRIJ-35, pH 7.0-7.4). Dilutions of antisera were prepared in PBS, 0.05% TWEEN-20/Azide and 0.1 mL was transferred to the coated plates and incubated for two hours at 37° C. Plates were washed three times in wash buffer. Goat-anti-mouse IgG AP (Southern Biotech) was diluted at 1:1500 in PBS/0.05% TWEEN-20, 0.1 mL was added to each well, and plates were incubated at 37° C. for two hours. Plates were washed (as above). Substrate solution was prepared by diluting p-nitrophenyl phosphate (Sigma) in diethanolamine at 1 mg/ml. Substrate was added to the plate at 0.1 mL per well and incubated at room temperature for one hour. The reaction was stopped with 50 ul/well of 3N NaOH and plates were read at 405 nm with 690 nm reference.

Recombinant PorA Induction: The BLR(DE3)/pET9a strains were grown overnight at 37° C. in HYSOY Broth (Sheffield Products) supplemented with Kan-30 and 2% glucose. In the morning the O/N cultures were diluted 1/20 in HYSOY Broth Kan-30 and 1% glycerol and grown at 37° C. for 1 hour. These cultures were induced by the addition of IPTG to a final concentration of 1 mM. The cultures were grown for an additional 2-3 hours and then harvested.

Recombinant PorA Purification: The rPorA was solubilized from *E. coli* inclusion bodies with 8M Urea, and refolded by dialysis against buffer containing no urea. The refolded rPorA was then concentrated by diafiltration and buffer exchanged by G25 column into NaPO4 pH6. The dialyzed rPorA was then run on a cation exchange column (S FRACTOGEL) and eluted with 1M NaCl.

The sOMPs from strain 8529 (P1.7-2,3) elicit PorA independent bactericidal activity in mice against strains expressing heterologous serosubtypes. The following table, Table IX, shows the bactericidal activity in the studied strains.

TABLE IX

| Test Strain | Serosubtype | $BC_{50}$Titer[1] |
|---|---|---|
| 539 | P1.7-2, 3 | 1280 |
| 539 PorA- | NST[2] | 1080 |
| H44/76 | P1.7, 16 | 3285 |
| H44/76 PorA- | NST | 2620 |
| H355 | P1.19, 15 | >1350 |
| H355 PorA- | NST | >1350 |
| 880049 | P1.7-2, 4 | 290 |
| 880049 PorA- | NST | 85 |
| M982 | P1.22, 9 | 85 |
| M982 PorA- | NST | <50 |

Preparation of sOMPs: *N. meningitidis* membranes were extracted with TX-100, ZWITTERGENT 3-14, and ZWITTERGENT 3-14+0.5M NaCl. The sOMPs referred to above were solubilized in the ZWITTERGENT 3-14/0.5M NaCl extract. The extraction is performed using techniques well known to persons skilled in the art, for example, see U.S. Pat. No. 6,355,253 which is hereby incorporated by reference.

Immunogencity: Female Swiss-Webster mice were immunized with 25 ug total protein adjuvanted with 20 ug QS-21 at week 0 and 4. An exsanguination bleed and data analysis were done at week 6.

1 Bactericidal ($BC_{50}$) titers represented as the reciprocal of the dilution of anti-sera which reduces viable cell count by 50%. Week 0 normal mouse sera had $BC_{50}$ titers of <25

2 NST=Non Serosubtypable

The following table, Table X, shows the purification and characterization summary for recombinant lipidated P2086 (rLP2086) for both Subfamily A and Subfamily B.

Subfamily A rLP2086 Purification

TABLE X

| rLP2086 Variant | A.A. Homology (%)[1] | Theoretical pI | Purity (%)[2] |
|---|---|---|---|
| 870446 | 75 | 6.1 | 80 |
| 2996 | 71 | 5.9 | 95 |
| M97 252988 | 71 | 6.3 | 96 |
| C11 | 68 | 6.4 | 82 |
| M98 250771 | 62 | 6.1 | 83 |

Subfamily B rLP2086 Purification

TABLE XI

| rLP2086 Variant | A.A. Homology (%)[1] | Theoretical pI | Purity (%)[2] |
|---|---|---|---|
| 8529 | 100 | 7.5 | 96 |
| M982 | 94 | 6.3 | 96 |
| 88049 | 92 | 6.2 | 90 |
| CDC1573 | 87 | 5.6 | 93 |

Purification Method: All variants were solubilized from *E. coli* membranes with TX-100 (exception rLP2086-8529 which was solubilized with Sarcosyl or Urea). Further purification was achieved with a combination of anion exchange (TMAE), size exclusion and/or cation exchange (S FRACTOGEL) chromatography in a Tris-HCl or NaPO4 buffer.

1 Amino acid homology as compared to P2086 from strain 8529

2 Purity as determined by SDS-PAGE and laser densitometry of colloidal COOMASSIE stained band (SIMPLY BLUE stain)

Immunogenicity of a Subfamily B member, rLP2086-8529, tested against homologous and heterologous strains Table XII below shows immunogenicity of a Subfamily B member, rLP2086-8529, tested against homologous and heterologous strains

TABLE XII

| Target Strain | P2086 Subfamily | Target Strain Serosubtype | A.A. Homology[a] | Whole Cell ELISA[b] Titer | $BC_{50}$ Titer[C] |
|---|---|---|---|---|---|
| 539 | B | P1.7-2, 3 | 100 | >1,458,000 | 3,200 |
| H44/76 | B | P1.7, 16 | 100 | >1,458,000 | 3,200 |
| H355 | B | P1.19, 15 | 100 | >1,458,000 | 3,200 |
| CDC937 | B | P1.7-2, 3-4 | 100 | >1,458,000 | >800 |
| M97 252097 | B | P1.7-2, 16 | 100 | >1,458,000 | >800 |
| 870227 | B | P1.5-2, 10 | 100 | >1,458,000 | <25 |
| 6940 | B | P1.18, 25, 6 | 97 | 900,162 | >800 |
| M982 | B | P1.22, 9 | 94 | 435,909 | 200 |
| 880049 | B | P1.7-2, 4 | 92 | 349,912 | 400 |
| CDC1573 | B | P1.7-1, 1 | 87 | 102,508 | 25 |
| 870446 | A | P1.12-1, 13 | 71 | 389,829 | 800 |
| M98 250771 | A | P1.22, 14 | 62 | 139,397 | <25 |
| NmB | A | P1.5-1, 2-2 | 71 | <2,000 | <25 |

Vaccination Procedure:

6-8 week old female Swiss-Webster mice were immunized with 10 ug rLP2086-8529 + 20 ug QS-21 at week 0 and week 4. Data analysis was performed on the week 6 exsanguination bleed.

[a]Amino acid homology of P2086 as compared to rLP2086-8529

[b]Endpoint titers expressed as the reciprocal of the dilution at absorbance = 0.1

[C]BC50 titers represented as the reciprocal of the dilution of anti-sera which reduces viable cell count by 50%. Week 0 normal mouse sera had BC50 titers of <10

Table XIII shows immunogenicity of a Subfamily B member, rLP2086-2996, tested against homologous and heterologous strains.

TABLE XIII

| Target Strain | P2086 Subfamily | Target Strain Serosubtype | A.A. Homology[a] | Whole Cell ELISA[b] Titer | $BC_{50}$ Titer[C] |
|---|---|---|---|---|---|
| NmB | A | P1.5-1, 2-2 | 99.6 | 8,979 | <25 |
| 870446 | A | P1.12-1, 13 | 99 | <1,458,000 | >800 |
| M97 252697 | A | P1.18, 25, 6 | 98 | 320,732 | >800 |
| 6557 | A | P1.22-1, 14-1 | 98 | 17,319 | <25 |
| M98 250732 | A | P1.22, 14-1 | 89 | 241,510 | >800 |

TABLE XIII-continued

| Target Strain | P2086 Subfamily | Target Strain Serosubtype | A.A. Homology[a] | Whole Cell ELISA[b] Titer | $BC_{50}$ Titer[C] |
|---|---|---|---|---|---|
| M98 250771 | A | P1.22, 14 | 89 | 447,867 | 800 |
| H44/76 | B | P1.7, 16 | 72 | 56,386 | <25 |

Vaccination Procedure:

6-8 week old female Swiss-Webster mice were immunized with 10 ug rLP2086-2996 + 20 ug QS-21 at week 0 and week 4. Data analysis was performed on the week 6 exsanguination bleed.

[a]Amino acid homology of P2086 as compared to rLP2086-2996

[b]Endpoint titers expressed as the reciprocal of the dilution at absorbance = 0.1

[C]Bactericidal (BC50) titers represented as the reciprocal of the dilution of anti-sera which reduces viable cell count by 50%. Week 0 normal mouse sera had BC50 titers of <10.

Table XIV below shows that antisera to rLP2086 and rPorA are complimentary when mixed and assayed for bactericidal activity.

TABLE XIV

| Antisera | H44/76 (P1.7, 16) | NMB (P1.5-1, 2-2) | 880049 (P1.7-2, 4) | H355 (P1.19, 15) | 870227 (P1.5-2, 10) | 6557 (P1.22-1, 14-1) |
|---|---|---|---|---|---|---|
| Anti-rLP2086 + three rPorA antisera | >3,200 | >800 | 200 | >800 | 200 | 200 |
| Controls | | | | | | |
| anti-rLP2086 | 6,400 | <25 | 100 | 3,200 | <25 | <25 |
| Corresponding monovalent rPorA antisera | — | 1,600 | — | — | 200 | 400 |

Vaccination Procedure: 6-8 week old female Swiss-Webster mice were immunized with either 10 ug rLP2086-8529/20 ug QS-21, or 15 ug rPorA/100 ug MPL at week 0 and week 4. Data analysis was performed on the week 6 exsanguination bleed.
a Bactericidal (BC50) titers represented as the reciprocal of the dilution of anti-sera which reduces viable cell count by 50%. Week 0 normal mouse sera had BC50 titers of <10.

The following table, Table XV, shows that mixtures of rLP2086 Subfamilies and two rPorAs elicit bactericidal antibody in mice.

TABLE XV

| | H44/76 SfB[b] P1.7, 16 | 6940 SfB P1.18 25, 6 | 880049 SfB P1.7-2, 4 | M982 SfB P1.22, 9 | M98 250771 SfA[b] P1.22, 14 | M98 250732 SfA P1.22, 14-1 | M97 252697 SfA P1.18, 25, 6 | 870446 SfA P1.12-1, 13 | NmB SfA P1.5-1, 2-2 | 6557 SfA P1.22-1, 14-1 |
|---|---|---|---|---|---|---|---|---|---|---|
| Antigen | | | | | | | | | | |
| rLP2086-8529 + rLP2086-2996 | >800 | >800 | 200 | 400 | 800 | >800 | >800 | >800 | — | <25 |
| rLP2086-8529 + rLP2086-2996 + rP1.5-1, 2-2 + rP1.22-1, 14-1 | >800 | 800 | 100 | 200 | 400 | 400 | >800 | >800 | >800 | 200 |
| Monovalent Controls[c] | >800 | >800 | 200 | 400 | 800 | >800 | >800 | >800 | >800 | 800 |

Vaccination Procedure: 6-8 week old female Swiss-Webster mice were immunized with 10 ug of each protein + 20 ug QS-21 at week 0 and week 4. Data analysis was performed on the week 6 exsanguination bleed.

[a]Bactericidal (BC50) titers represented as the reciprocal of the dilution of anti-sera which reduces viable cell count by 50%. Week 0 normal mouse sera had BC50 titers of <10.

[b]SfA—Subfamily A, SfB—Subfamily B

[c]Relevant monovalent control: rLP2086-8529, rLP2086-2996, rP1.5-1, 2-2 or rP1.22-1, 14-1 antisera The following summarizes the results of the above described studies. Anti-rLP2086 antisera is bactericidal against 13/16 test strains. Eleven strains expressing different serosubtypes are killed by anti-P2086 sera. Bactericidal activity of anti-rLP2086 sera is complimentary to anti-rPorA sera. Mixtures of P2086 and PorA elicit complimentary bactericidal antibodies in mice. Differential detergent extraction, purification and immunization in conjunction with a functional antibody assay against many strains can be used to identify new vaccine candidates. P2086 has been identified as a vaccine candidate which elicits bactericidal antibody against strains heterologous in both P2086 and rPorA. Thus, the 2086 family of proteins may be a useful vaccine either alone or in combination with other neisserial antigens.

Example 9

In accordance with the previous examples, additional meningococcal strains, of varying serogroups, were screened by PCR for the presence of the ORF 2086 gene. Ultimately, one hundred meningococcal strains were screened. The following describes the study and its overall results. These results supplement the data from the previous examples.

Two sets of internal PCR primers specific to the C-terminal variable regions were utilized to discriminate between Subfamily A and B gene sequences. The presence of a PCR amplified product of approximately 350 bp indicated that the 2086 gene sequence was present on the chromosome. All strains yielded a single PCR product of the expected size. The nucleotide sequences of fifty-five full-length ORF 2086 genes were determined, aligned (DNAStar MegAlign) and used to generate a phylogenetic tree. (See FIG. 12).

Nine of these 2086 genes were recombinantly expressed as a rLP2086 lipoprotein in a pBAD arabinose inducible promoter system and three of these genes were recombinantly expressed as a rP2086 non-lipidated protein in an IPTG inducible pET system. These recombinant proteins were expressed in *E. coli* B. The purified recombinant protein was used to immunize mice and the mouse antisera was assayed for its serum IgG titers and its bactericidal activity against a variety of heterologous meningococcal strains.

ORF 2086 was amplified by PCR from one of the following, whole meningococcal cells, purified chromosomal DNA or plasmid DNA templates.

Figure 10A:
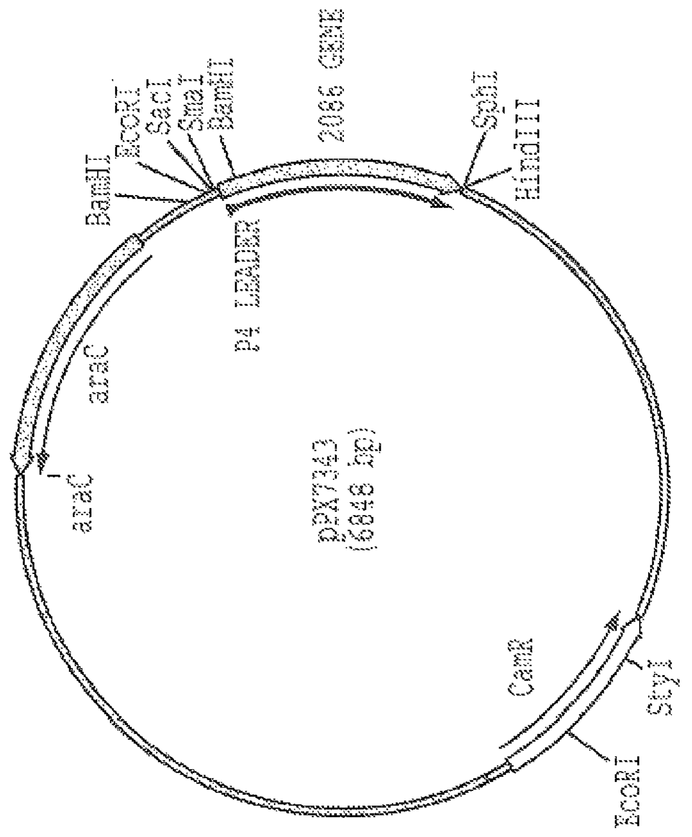
FIG. 10A is a schematic diagram of the pBAD arabinose inducible promoter which drives the expression of the P4 signal/ORF2086 fusion protein to express a lipidated form of rP2086 as described in the examples herein.
Figure 10B:
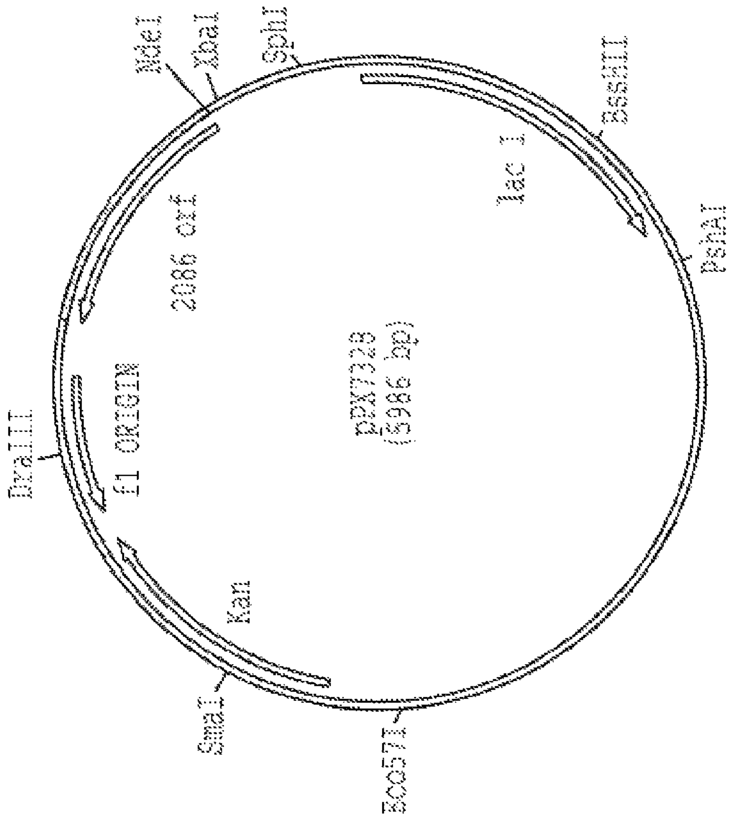
FIG. 10B is a schematic diagram of the pET9a-T7 vector for recombinant expression of nonlipidated form of ORF2086.

Nine ORF 2086 genes were cloned into the vector pLP339, which fuses the *Haemophilus* P4 leader sequence to the 5' end of the ORF 2086 genes. *E. coli* strain BLR was used as the host strain for recombinant expression of the lipidated form of rP2086 from the pBAD/ORF 2086 clones. (See FIG. 10A) The pBAD arabinose inducible promoter drives the expression the P4 signal/ORF 2086 fusion protein to express a lipidated form of rP2086. Three P2086 genes, lacking a signal sequence, were cloned into a pET9a vector behind the highly active T7 phage promoter. *E. coli* strain BL21(DE3) was used as the host strain for recombinant expression of a non-lipidated form of ORF 2086 from the pET9a/ORF 2086 clones. (See FIG. 10B) The DE3 lysogen in *E. coli* strain BL21 can be induced to express the T7 RNA polymerase under the control of the lacUV5 promoter by addition of IPTG. See, WCE; FEMS Micro. Lett., 48 (1987) 367-371 and BCA; J. Clin. Microbiol., 38 (2000) 2878-2884.

The gene, ORF2086, was cloned and sequenced from fifty-five different *N. meningitidis* strains. The nucleotide sequences were aligned (DNAStar MegAlign) and used to generate a phylogenetic tree. (See FIG. 12). This tree reveals two distinct subfamilies of the ORF 2086 gene nucleotide sequence. The two subfamilies of genes are similar at their 5' ends, but contain considerable variation near their 3' ends. Although there appears to be significant variability, certain key regions of the gene are highly homologous amongst the different strains. These conserved regions may provide functional continuity for the protein and may be indicative of cross-protective epitopes to be exploited as vaccine targets.

Figure 11A:
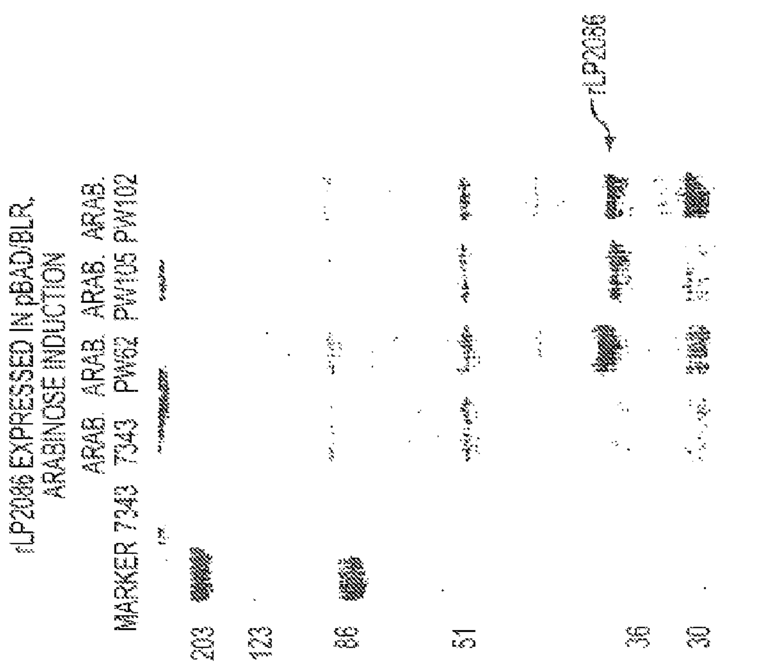
FIG. 11A is a photograph representing whole cell lysates of *E. coli* B expressing the rLP2086 protein.
Figure 11B:
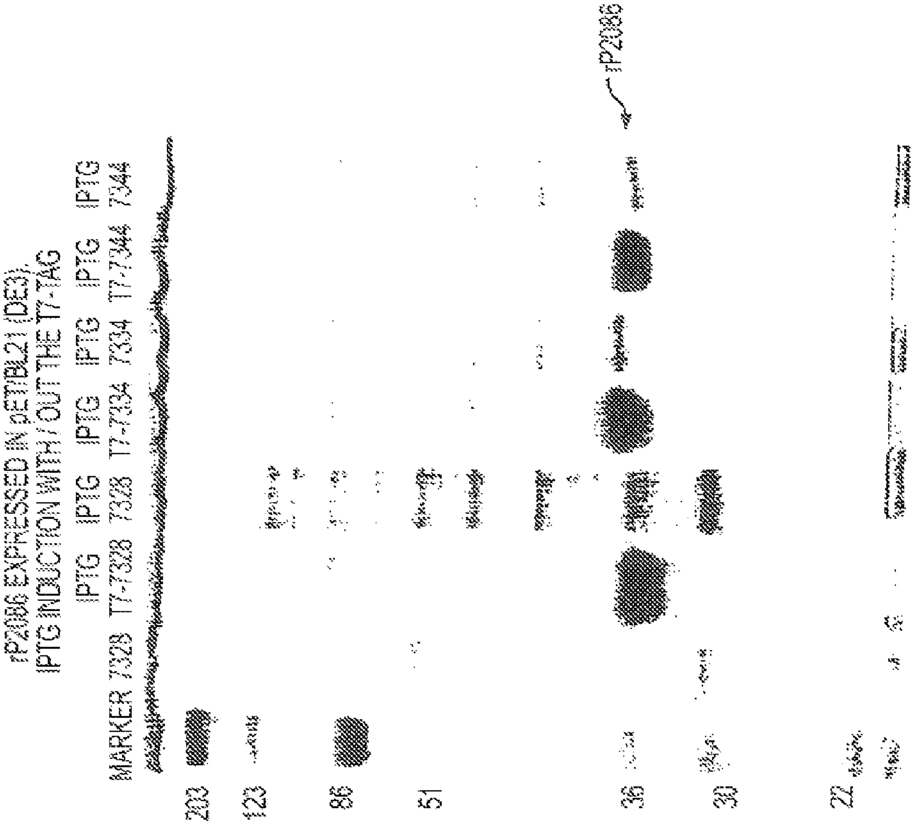
FIG. 11B is a photograph representing whole cell lysates of *E. coli* B expressing the rP2086 protein.

The 2086 gene was cloned from several serogroup B meningococcal strains and expressed with and without the lipidation signal sequence. Referring to FIGS. 11A and 11B, gel photographs show the whole cell lysates of *E. coli* B expressing the r2086 protein. The non-lipidated form fused to the T7-Tag expressed at the highest level. The T7-Tag sequence may provide stability to the mRNA and significantly enhances the level of polypeptide translated. This fusion protein appears to deposit in inclusion bodies and can be purified and refolded readily with known protocols. The lipidated and non-lipidated forms of P2086 are expressed at approximately 5 to 8% of total cellular protein, with the exception of the T7-Tag fusions, which express rP2086 as approximately 50% of total protein. The non-lipidated form of the protein appears to be soluble and localized in the cytoplasm. The lipidated form of the protein appears to be associated with the membrane fractions and is solubilized with detergent.

The recombinant lipidated 2086 protein from *N. meningitidis* B strain 8529 consistently elicits greater serum IgG titers than the non-lipidated form (see Table XVI below), which correlates well with the enhanced level of bactericidal activity against both homologous and heterologous meningococcal strains (see Table XVII below). The protein in its native lipidated form may have superior tertiary structure for antigen presentation and/or the attached lipid may act as an adjuvant stimulating a greater immunogenic response.

TABLE XVI

Immune Response Elicited at Week 6 by WCE using 8529 rP2086 (non-lipidated) vs. 8529 rLP2086 (lipidated)

| Mouse Sera | | | | | | |
|---|---|---|---|---|---|---|
| Antigen | Adjuvant | Meningococcal Strains | | | | |
| (10 ug) | (20 ug) | H44/76 | H355 | 870227 | 880049 | 870446 |
| rP2088 | QS-21 | 273,238 | 212,947 | 102,694 | 69,124 | 21,466 |
| rLP2086 | QS-21 | 5,384,306 | 4,819,061 | 2,930,946 | 1,307,091 | 886,056 |

TABLE XVII 8529 rP2086 Elicits Weaker Bactericidal Activity than 8529 rLP2086

| Mouse Sera | | | | | |
|---|---|---|---|---|---|
| Antigen | Adjuvant | Meningococcal Strains | | | |
| (10 ug) | (20 ug) | H44/76 | H355 | 880049 | NMB |
| rP2086 | QS-21 | 200 | 100 | <25 | <25 |
| rLP2086 | QS-21 | 6,400 | 3,200 | 100 | <25 |
| Pre-Immune | — | <10 | <10 | <10 | <10 |
| Positive Control | — | 1,600 | 100 | 200 | 1,600 |

The following is a summary of the results of the study. All *N. meningitidis* B strains tested appear to have one 2086-like gene. At least two families of the 2086 gene are represented: Subfamily A—about 30% of strains and Subfamily B—about 70% of strains. The 2086 gene has been cloned and sequenced from 55 *N. meningitidis* strains. Sequences within Subfamily A are ~86-100% identical at the DNA level. Sequence within Subfamily B are ~89.5-100% identical at the DNA level. Sequences within Subfamily A vs. Subfamily B ~60.9%-74% identical at the DNA level. 2086 homologs have been identified by PCR screening in the following:

*N. meningitidis* A, B, C, W135, Y

*N. lactamica*

*N. gonorrhoeae* FA1090

Several ORF 2086 genes have been cloned and recombinantly expressed

Lipidated versions of P2086 were expressed from nine meningococcal strains.

These recombinant proteins have been purified and used to vaccinate mice.

The resulting antisera is bactericidal.

Non-lipidated versions of P2086 were expressed from three of the above nine strains. rLP2086 consistently elicits a greater immune response than rP2086. rLP2086 also exhibits enhanced bactericidal activity against both homologous and heterologous meningococcal strains.

Example 10

The following tables, Tables XVIII and XIX, show the characterization of variants of members of the two subfamilies.

TABLE XVIII

| Subfamily A rLP2086 Variants - Characterization | | | | | | |
|---|---|---|---|---|---|---|
| | | rLP2086-252988 | rLP2086-250771 | rLP2086-870446 | rLP2086-2996 | rLP2086-C11 |
| Growth Media | | HYSOY | HYSOY | HYSOY | HYSOY | HYSOY |
| Solubility | | rTX-100⇒ Z3-12 | TX-100 | TX-100 | rTX-100⇒ Z3-12 | rTX-100⇒ Z3-12 |
| Purification Steps | | TMAE S FRACTO GEL SEC | HQ Poros SEC | HQ Poros SEC | TMAE SEC | TMAE S FRACTO GEL |
| Purity (%) | | 96 | 83 | 80 | 95 | 82 |
| Yield (mg/g cell pellet) | | 0.2 | 0.7 | 0.8 | 0.5 (fermentor) | 0.1 |
| Size | SEC (Z3-12) | 134,000 | 155,000 | 132,000 | 163,000 | 126,000 |
| | MS | 27,897 (712 lipid) | — | — | 27,878 (750 lipid) | 28,139 (682 lipid) |
| Thermal Denaturation Transition Midpoint ($T_M$) ° C. | | 66° C. | — | NT | 65° C. | 63° C. |
| Protein Available (mg) | | 2.7 mg | 1 mg (Z3-12) | 5.0 mg | 44 mg | 1.1 mg |
| 8529 Sequence Homology (%) | | 71 | 62 | 71 | 72 | 68 |

TABLE XIX

| Subfamily B rLP2086 Variants - Characterization | | | | | |
|---|---|---|---|---|---|
| | | rLP2086-8529 | rLP2086-M982 | rLP2086-880049 | rLP2086-CDC1573 |
| Growth Media | | Apollon (Sanford) | Apollon | HYSOY | HYSOY |
| Solubility | | 4M Urea⇒ Z3-12 | rTX-100⇒ Z3-12 | rTX-100⇒ Z3-12 | rTX-100 |
| Purification Steps | | TMAE S FRACTOGEL | TMAE S FRACTOGEL | TMAE S FRACTOGEL | TMAE SEC |
| Purity (%) | | 96 | 96 | 90 | 93 |
| Yield (mg/g cell pellet) | | 0.2 (fermentor) | 1.6 (fermentor) | 0.4 | 1.0 |
| Size | SEC (Z3-12) | 95,000 | 110,000 150,000 | 100,000 | 120,000 |
| | MS | 27,785 (822 lipid) | 27,719 (711 lipid) | 28,044 (819 lipid) | 28,385 (823 lipid) |
| Thermal Denaturation Transition Midpoint ($T_M$) ° C. | | 70° C. | 75° C. | 62° C. | NT |
| Protein Available (mg) | | Urea - 34 mg Sarc - 36 mg | Pool 1 - 47 mg Pool 2 - 17 mg | 3.6 mg | 4.9 mg |
| 8529 Sequence Homology (%) | | 100 | 94 | 92 | 87 |

Table XX below provides the results of fluorescent serum bactericidal assays for the 2086 Subfamily A.

TABLE XX

| Description | 250771 | 870446 | 6557 | NMB | M98 250732 | M97 252697 |
|---|---|---|---|---|---|---|
| rLP2086-252988, 10 μg | >800 (99%) * | >800 (99%) * | <25 | — | >800 (99%) * | >800 (93%) * |
| rLP2086-C11, 10 μg | 200 | >880 (91%) * | <25 | — | 200 | 400 |
| rLP2086-250771, 10 μg | >800 (92%) * | >800 (99%) * | <25 | — | >800 (96%) * | >800 (84%) * |
| rLP2086-870446, 10 μg | 400 | >800 (99%) * | <25 | — | 400 | 400 |
| rLP2086-2996, 10 μg | 800 | >800 (99%) * | <25 | — | >800 (93%) * | >800 (72%) * |
| rLP2086-8529 + rLP2086-2996, 10 μg | 800 | >800 (99%) * | <25 | — | >800 (80%) * | >800 (72%) * |
| rLP2086-8529 + rP1.22a, 14a + rP1.5a, 2c, 10 μg | — | 800 | 200 | >800 (98%) * | — | — |
| rLP2086-8529 + rLP2086-2996 + rP1.22a, 14a + rP1.5a, 2c, 10 μg | 400 | >800 (99%) * | 200 | >800 (99%) * | 400 | >800 (88%) * |
| NMB/rLP2086-8529 vesicles, 20 μg | — | 100 | — | 400 | — | — |
| rP1.22a, 14a, 10 μg | 25 | — | 800 | — | 100 | — |
| rP1.5a, 2c, 10 μg | — | — | — | >800 (99%) * | — | — |
| rLP2086-8529, 10 μg | — | 800 | — | — | — | — |
| rP1.22a, 14a, 25 μg | 200 | — | — | — | 800 | — |
| rP1.18, 25.6, 5 μg | — | — | — | — | — | — |
| nP1.22, 9 (M982), 25 μg | — | — | 100 | — | — | — |
| pre-immune mouse serum (negative control) | <10 | <10 | <10 | <10 | <10 | <10 |
| | 800 | 400 | 800 | 1600 | ** | ** |

Notes:

* Percentage indicates the % BC activity at the 1:800 dilution.

** Positive control not available.

— serum not tested

Example 11

The following further demonstrates that P2086 is expressed in neisserial strains and provides additional specific examples of P2086 expression in several strains.

Cell lysates were prepared with cells from plate cultures resuspended in SDS sample buffer and heated at 98° C. for four minutes. Samples were loaded at ~30-50 ug total protein per well on 10-20% pre-cast gels (ICN) and run at 175V. The gels were transferred to a nitrocellulose membrane, which was then blocked for 30 min. with 5% powdered milk in Tris-buffered saline (BLOTTO). The primary antibody used was a pool of polyclonal antisera raised against individual rLP2086 variants in mice.

Figure 17:
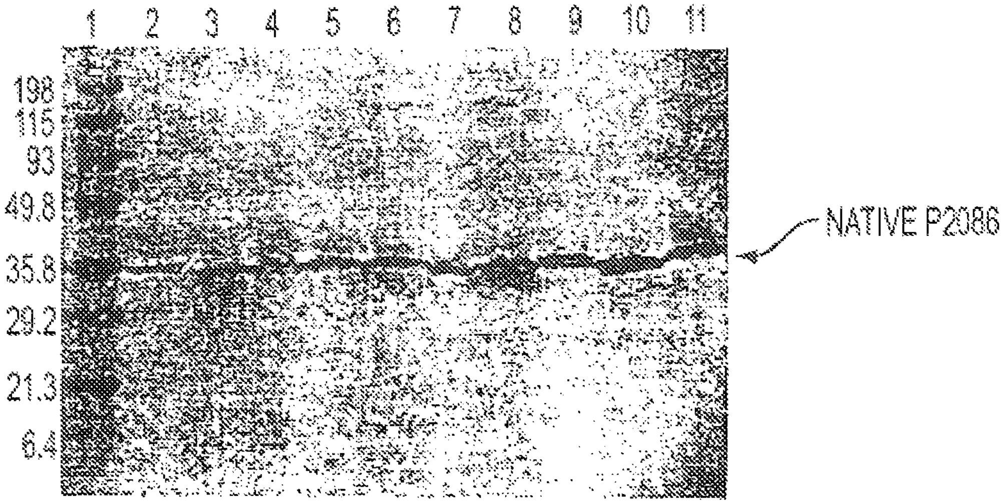
FIG. 17 is a Western Blot showing reactivity of rLP2086 mouse antisera to P2086 Subfamily B *N. meningitidis* whole cell lysates.
Figure 18:
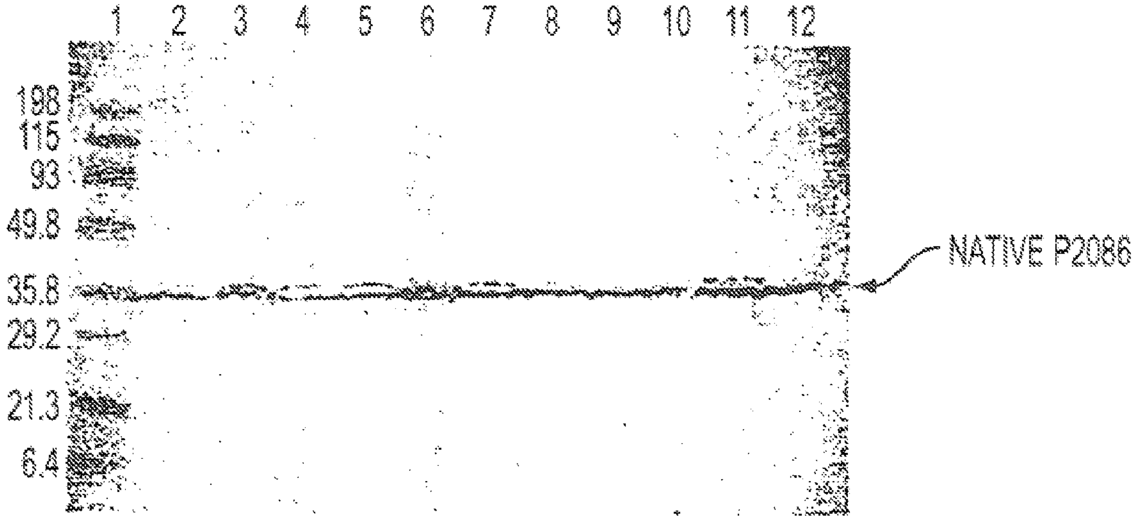
FIG. 18 is a Western Blot showing reactivity of rLP2086 mouse antisera to P2086 Subfamily A *N. meningitidis* and *N. lactamica* whole cell lysates.

Referring to FIGS. 17 and 18, a Western Blot shows the reactivity of rLP2086 mouse antisera to P2086 Subfamily A and B whole cell lysates. For the Subfamily A cell lysate blot, the antisera used were raised against rLP2086-2996, -870446 and -250771 with rLP2086-250771 diluted at 1/500 in BLOTTO and the others diluted at 1/1000 in BLOTTO. For the Subfamily B cell lysate blot, the antisera used were raised against rLP2086-8529 (diluted 1/1000 in BLOTTO), -CDC1573. -M982 and -880049 (these three diluted 1/500 in BLOTTO). The primary antisera and blot were incubated at 4° C. overnight. The blot was washed, a goat-anti-mouseAP secondary was added at 1/500 in BLOTTO, and the blot was incubated for 30 min. at room temperature. After washing, the blot was developed using the BCIP/NBT Membrane Phosphatase Substrate System (KPL).

BIBLIOGRAPHY

References referred to herein above are noted below and are incorporated herein by reference in their entirety:

1. 1997. Case definitions for Infectious Conditions Under Public Health Surveillance. CDC.
2. 1995 Sambrook, J. and D. W. Russell. 1995. Current Protocols in Molecular Biology. John Wiley & Sons, Inc., New York.
3. 1994. Griffin, A. M. and Griffin, H. G., ed., Computer Analysis of Sequence Data, Part I. Humana Press, New Jersey.
4. 1993. Smith, D. W. ed., Biocomputing: Informatics and Genome Projects. Academic Press, New York
5. 1991. Gribskov, M. and Devereux, J., ed. Sequence Analysis Primer. Stockton Press, New York.
6. 1988. Lesk, A. M., ed. Computational Molecular Biology. Oxford University Press, New York.

7. Abdillahi, H., and J. T. Poolman. 1988. *Neisseria meningitidis* group B serosubtyping using monoclonal antibodies in whole-cell ELISA. *Microbial Pathogenesis* 4(1):27-32.

8. Achtman, M. 1995. Epidemic spread and antigenic variability of *Neisseria meningitidis. Trends in Microbiology* 3(5):186-92.

9. Alm, R. A., L. S. Ling, D. T. Moir, B. L. King, E. D. Brown, P. C. Doig, D. R. Smith, B. Noonan, B. C. Guild, B. L. deJonge, G. Carmel, P. J. Tummino, A. Caruso, M. Uria-Nickelsen, D. M. Mills, C. Ives, R. Gibson, D. Merberg, S. D. Mills, Q. Jiang, D. E. Taylor, G. F. Vovis, and T. J. Trust. 1999. Genomic-sequence comparison of two unrelated isolates of the human gastric pathogen *Helicobacter pylori* [published erratum appears in Nature 1999 February 25; 397(6721):719*]. Nature.* 397:176-80.

10. Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. *Nucleic Acids Res.* 25:3389-402.

11. Anderson, T. F. 1951. Techniques for the preservation of three-dimensional structure in preparing specimens for the electron microscope. Trans N Y Acad Sci. 13:130-134.

12. Ambrosch, F., G. Wiedermann, P. Crooy, and A. M. George. 1983. Immunogenicity and side-effects of a new tetravalent meningococcal polysaccharide vaccine. *Bulletin of the World Health Organization* 61(2):317-23.

13. Benson, G. 1999. Tandem repeats finder: a program to analyze DNA sequences. Nucleic Acids Res. 27:573-80.

14. Carillo, H., D. Lipman, and J. Siam. 1988. *Applied Math* 48:1073.

15. Chen, C. C., and P. P. Cleary. 1989. Cloning and expression of the streptococcal C5a peptidase gene in *Escherichia coli*: linkage to the type 12 M protein gene. *Infect. Immun.* 57:1740-1745.

16. Chmouryguina, I., A. Suvorov, P. Ferrieri, and P. P. Cleary. 1996. Conservation of the C5a peptidase genes in group A and B streptococci. *Infect. Immun.* 64:2387-2390.

17. Cockerill, F. R., 3rd, R. L. Thompson, J. M. Musser, P. M. Schlievert, J. Talbot, K. E. Holley, W. S. Harmsen, D. M. Ilstrup, P. C. Kohner, M. H. Kim, B. Frankfort, J. M. Manahan, J. M. Steckelberg, F. Roberson, and W. R. Wilson. 1998. Molecular, serological, and clinical features of 16 consecutive cases of invasive streptococcal disease. Southeastern Minnesota Streptococcal Working Group. *Clin Infect Dis.* 26:1448-58.

18. Courtney, H. S., Y. Li, J. B. Dale, and D. L. Hasty. 1994. Cloning, sequencing, and expression of a fibronectin/fibrinogen-binding protein from group A streptococci. *Infect Immun.* 62:3937-46.

19. Cserzo, M., E. Wallin, I. Simon, G. von Heijne, and A. Elofsson. 1997. Prediction of transmembrane alpha-helices in prokaryotic membrane proteins: the dense alignment surface method. *Protein Engineering.* 10:673-6.

20. Cunningham, M. W., and A. Quinn. 1997. Immunological crossreactivity between the class I epitope of streptococcal M protein and myosin. *Adv Exp Med Biol.* 418:887-92.

21. Dale, J. B., R. W. Baird, H. S. Courtney, D. L. Hasty, and M. S. Bronze. 1994. Passive protection of mice against group A streptococcal pharyngeal infection by lipoteichoic acid. *J Infect Dis.* 169:319-23.

22. Dale, J. B., M. Simmons, E. C. Chiang, and E. Y. Chiang. 1996. Recombinant, octavalent group A streptococcal M protein vaccine. *Vaccine.* 14:944-8.

23. Dale, J. B., R. G. Washburn, M. B. Marques, and M. R. Wessels. 1996. Hyaluronate capsule and surface M protein in resistance to opsonization of group A streptococci. *Infect Immun.* 64:1495-501.

24. Eddy, S. R. 1996. Hidden Markov models. *Cur Opin Struct Bio.* 6:361-5.

25. Ellen, R. P., and R. J. Gibbons. 1972. M protein-associated adherence of *Streptococcus pyogenes* to epithelial surfaces: prerequisite for virulence. *Infect Immun.* 5:826-830.

26. Eng, J. K., A. L. McCormack, and J. R. Yates, 3rd. 1994. An approach to correlate tandem mass-spectral data of peptides with amino-acid-sequences in a protein database. *Am Soc Mass Spectrometry.* 5:976-89.

27. Fischetti, V. A., V. Pancholi, and O. Schneewind. 1990. Conservation of a hexapeptide sequence in the anchor region of surface proteins from gram-positive cocci. *Mol Microbiol.* 4:1603-5.

28. Fogg, G. C., and M. G. Caparon. 1997. Constitutive expression of fibronectin binding in *Streptococcus pyogenes* as a result of anaerobic activation of rofA. *J Bacteriol.* 179:6172-80.

29. Foster, T. J., and M. Hook. 1998. Surface protein adhesins of *Staphylococcus aureus. Trends Microbiol.* 6:484-8.

30. Fraser, C. M., S. Casjens, W. M. Huang, G. G. Sutton, R. Clayton, R. Lathigra, O. White, K. A. Ketchum, R. Dodson, E. K. Hickey, M. Gwinn, B. Dougherty, J. F. Tomb, R. D. Fleischmann, D. Richardson, J. Peterson, A. R. Kerlavage, J. Quackenbush, S. Salzberg, M. Hanson, R. van Vugt, N. Palmer, M. D. Adams, J. 31. Gocayne, J. C. Venter, and et al. 1997. Genomic sequence of a Lyme disease spirochaete, *Borrelia burgdorferi* [see comments]. *Nature.* 390:580-6.

32. Goldschneider, I., E. C. Gotschlich, and M. S. Artenstein. 1969. Human immunity to the meningococcus. I. The role of humoral antibodies. *Journal of Experimental Medicine* 129(6): 1307-26.

33. Goldschneider, I., E. C. Gotschlich, and M. S. Artenstein. 1969. Human immunity to the meningococcus. II. Development of natural immunity. *Journal of Experimental Medicine* 129(6):1327-48.

34. Gotschlich, E. C., I. Goldschneider, and M. S. Artenstein. 1969. Human immunity to the meningococcus. IV. Immunogenicity of group A and group C meningococcal polysaccharides in human volunteers. *Journal of Experimental Medicine* 129(6):1367-84.

35. Gotschlich, E. C., I. Goldschneider, and M. S. Artenstein. 1969. Human immunity to the meningococcus. V. The effect of immunization with meningococcal group C polysaccharide on the carrier state. *Journal of Experimental Medicine* 129(6):1385-95.

36. Hacker, J., G. Blum-Oehler, I. Muhldorfer, and H. Tschape. 1997. Pathogenicity islands of virulent bacteria: structure, function and impact on microbial evolution. *Mol Microbiol.* 23:1089-97.

37. Hanski, E., and M. Caparon. 1992. Protein F, a fibronectin-binding protein, is an adhesion of the group A *streptococcus Streptococcus pyogenes. Proc Natl Acad Sci., USA.* 89:6172-76.

38. Hanski, E., P. A. Horwitz, and M. G. Caparon. 1992. Expression of protein F, the fibronectin-binding protein of *Streptococcus pyogenes* JRS4, in heterologous streptococcal and enterococcal strains promotes their adherence to respiratory epithelial cells. *Infect Immun.* 60:5119-5125.

39. Hernandez-Sanchez, J., J. G. Valadez, J. V. Herrera, C. Ontiveros, and G. Guarneros. 1998. lambda bar minigene-mediated inhibition of protein synthesis involves accumulation of peptidyl-tRNA and starvation for tRNA. *EMBO Journal*. 17:3758-65.

40. Huang, T. T., H. Malke, and J. J. Ferretti. 1989. The streptokinase gene of group A streptococci: cloning, expression in *Escherichia coli*, and sequence analysis. *Mol Microbiol*. 3:197-205.
41. Hynes, W. L., A. R. Dixon, S. L. Walton, and L. J. Aridgides. 2000. The extracellular hyaluronidase gene (hylA) of *Streptococcus pyogenes*. *FEMS Microbiol Lett*. 184:109-12.
42. Hynes, W. L., L. Hancock, and J. J. Ferretti. 1995. Analysis of a second bacteriophage hyaluronidase gene from *Streptococcus pyogenes*: evidence for a third hyaluronidase involved in extracellular enzymatic activity. *Infect Immun*. 63:3015-20.
43. Isberg, R. R., and G. Tran Van Nhieu. 1994. Binding and internalization of microorganisms by integrin receptors. *Trends Microbio*. 2:10-4.
44. Jones, K. F., and V. A. Fischetti. 1988. The importance of the location of antibody binding on the M6 protein for opsonization and phagocytosis of group A M6 streptococci. *J Exp Med*. 167:1114-23.
45. Kihlberg, B. M., M. Collin, A. Olsen, and L. Bjorck. 1999. Protein H, an antiphagocytic surface protein in *Streptococcus pyogenes*. *Infect Immun*. 67:1708-14.
46. Koebnik, R. 1995. Proposal for a peptidoglycan-associating alpha-helical motif in the C-terminal regions of some bacterial cell-surface proteins [letter; comment]. *Molecular Microbiology*. 16:1269-70.
47. Kuipers, O. P., H. J. Boot, and W. M. de Vos. 1991. Improved site-directed mutagenesis method using PCR. *Nucleic Acids Res*. 19:4558.
48. Kyte, J., and R. F. Doolittle. 1982. A simple method for displaying the hydropathic character of a protein. *Journal of Molecular Biology* 157:105-132.
49. Landt, O., H. P. Grunert, and U. Hahn. 1990. A general method for rapid site-directed mutagenesis using the polymerase chain reaction. *Gene* 96:125-128.
50. Loessner, M. J., S. Gaeng, and S. Scherer. 1999. Evidence for a holin-like protein gene fully embedded out of frame in the endolysin gene of *Staphylococcus aureus* bacteriophage 187. *J Bacteriol*. 181:4452-60.
51. Lukashin, A. V., and M. Borodovsky. 1998. GeneMark.hmm: new solutions for gene finding. *Nucleic Acids Res*. 26:1107-15.
52. Lukomski, S., C. A. Montgomery, J. Rurangirwa, R. S. Geske, J. P. Barrish, G. J. Adams, and J. M. Musser. 1999. Extracellular cysteine protease produced by *Streptococcus pyogenes* participates in the pathogenesis of invasive skin infection and dissemination in mice. *Infect Immun*. 67:1779-88.
53. Madore, D. V. 1998. Characterization of immune response as an indicator of *Haemophilus influenzae* type b vaccine efficacy. *Pediatr Infect Dis J*. 17:S207-10.
54. Matsuka, Y. V., S. Pillai, S. Gubba, J. M. Musser, and S. B. Olmsted. 1999. Fibrinogen cleavage by the *Streptococcus pyogenes* extracellular cysteine protease and generation of antibodies that inhibit enzyme proteolytic activity. *Infect Immun*. 67:4326-33.
55. Mazmanian, S. K., G. Liu, H. Ton-That, and O. Schneewind. 1999. *Staphylococcus aureus* sortase, an enzyme that anchors surface proteins to the cell wall. *Science*. 285:760-3.
56. McAtee, C. P., K. E. Fry, and D. E. Berg. 1998. Identification of potential diagnostic and vaccine candidates of *Helicobacter pylori* by "proteome" technologies. *Helicobacter*. 3:163-9.
57. McAtee, C. P., M. Y. Lim, K. Fung, M. Velligan, K. Fry, T. Chow, and D. E. Berg. 1998. Identification of potential diagnostic and vaccine candidates of *Helicobacter pylori* by two-dimensional gel electrophoresis, sequence analysis, and serum profiling. *Clin Diagn Lab Immunol*. 5:537-42.
58. McAtee, C. P., M. Y. Lim, K. Fung, M. Velligan, K. Fry, T. P. Chow, and D. E. Berg. 1998. Characterization of a *Helicobacter pylori* vaccine candidate by proteome techniques. *J Chromatogr B Biomed Sci Appl*. 714:325-33.
59. Mejlhede, N., J. F. Atkins, and J. Neuhard. 1999. Ribosomal-1 frameshifting during decoding of *Bacillus subtilis* cdd occurs at the sequence CGA AAG. *J. Bacteriol*. 181:2930-7.
60. Molinari, G., S. R. Talay, P. Valentin-Weigand, M. Rohde, and G. S. Chhatwal. 1997. The fibronectin-binding protein of *Streptococcus pyogenes*, SfbI, is involved in the internalization of group A streptococci by epithelial cells. *Infect Immun*. 65:1357-63.
61. Mountzouros, K. T., and A. P. Howell. 2000. Detection of complement-mediated antibody-dependent bactericidal activity in a fluorescence-based serum bactericidal assay for group B *Neisseria meningitidis*. *J. Clin. Microbiol*. 38(8):2878-2884.
62. Nakai, K., and M. Kanehisa. 1991. Expert system for predicting protein localization sites in gram-negative bacteria. *Proteins*. 11:95-110.
63. Navarre, W. W., and O. Schneewind. 1999. Surface proteins of gram-positive bacteria and mechanisms of their targeting to the cell wall envelope. *Microbiol Mol Biol Rev*. 63:174-229.
64. Nielsen, H., J. Engelbrecht, S. Brunak, and G. von Heijne. 1997. Identification of prokaryotic and eukaryotic signal peptides and prediction of their cleavage sites. *Protein Engineering*. 10:1-6.
65. Nizet, V., B. Beall, D. J. Bast, V. Datta, L. Kilburn, D. E. Low, and J. C. De Azavedo. 2000. Genetic locus for streptolysin S production by group A *streptococcus*. *Infect Immun*. 68:4245-54.
66. Nordstrand, A., W. M. McShan, J. J. Ferretti, S. E. Holm, and M. Norgren. 2000. Allele substitution of the streptokinase gene reduces the nephritogenic capacity of group A streptococcal strain NZ131. *Infect Immun*. 68:1019-25.
67. Olmsted, S. B., S. L. Erlandsen, G. M. Dunny, and C. L. Wells. 1993. High-resolution visualization by field emission scanning electron microscopy of *Enterococcus faecalis* surface proteins encoded by the pheromone-inducible conjugative plasmid pCF10. *J Bacteriol*. 175:6229-37.
68. Park, J., and S. A. Teichmann. 1998. DIVCLUS: an automatic method in the GEANFAMMER package that finds homologous domains in single- and multi-domain proteins. *Bioinformatics*. 14:144-50.
69. Parkhill, J., M. Achtman, K. D. James, S. D. Bentley, C. Churcher, S. R. Klee, G. Morelli, D. Basham, D. Brown, T. Chillingworth, R. M. Davies, P. Davis, K. Devlin, T. Feltwell, N. Hamlin, S. Holroyd, K. Jagels, S. Leather, S. Moule, K. Mungall, M. A. Quail, M. A. Rajandream, K. M. Rutherford, M. Simmonds, J. Skelton, S. Whitehead, B. G. Spratt, and B. G. Barrell. 2000. Complete DNA sequence of a serogroup A strain of *Neisseria meningitidis* Z2491 [see comments]. *Nature*. 404:502-6.

70. Pierschbacher, M. D., and E. Ruoslahti. 1987. Influence of stereochemistry of the sequence Arg-Gly-Asp-Xaa on binding specificity in cell adhesion. *J Biol Chem.* 262: 17294-8.
71. Pizza, M., V. Scarlato, V. Masignani, M. M. Giuliani, B. Arico, M. Comanducci, G. T. Jennings, L. Baldi, E. Bartolini, B. Capecchi, C. L. Galeotti, E. Luzzi, R. Manetti, E. Marchetti, M. Mora, S. Nuti, G. Ratti, L. Santini, S. Savino, M. Scarselli, E. Storni, P. Zuo, M. Broeker, E. Hundt, B. Knapp, E. Blair, T. Mason, H. Tettelin, D. W. Hood, A. C. Jeffries, N. J. Saunders, D. M. Granoff, J. C. Venter, E. R. Moxon, G. Grandi, and R. Rappuoli. 2000. Identification of vaccine candidates against serogroup B meningococcus by whole-genome sequencing. *Science* 287(5459):1816-20.
72. Podbielski, A., A. Flosdorff, and J. Weber-Heynemann. 1995. The group A streptococcal virR49 gene controls expression of four structural vir regulon genes. *Infect Immun.* 63:9-20.
73. Poolman, J. T. 1996. Bacterial outer membrane protein vaccines. The meningococcal example. *Advances in Experimental Medicine* & *Biology* 397:73-7.
74. Proft, T., S. Louise Moffatt, C. J. Berkahn, and J. D. Fraser. 1999. Identification and Characterization of Novel Superantigens from *Streptococcus pyogenes. J Exp Med.* 189:89-102.
75. Pugsley, A. P. 1993. The complete general secretory pathway in gram-negative bacteria. *Microbiol Rev.* 57:50-108.
76. Quinn, A., K. Ward, V. A. Fischetti, M. Hemric, and M. W. Cunningham. 1998. Immunological relationship between the class I epitope of streptococcal M protein and myosin. *Infect Immun.* 66:4418-24.
77. Reda, K. B., V. Kapur, D. Goela, J. G. Lamphear, J. M. Musser, and R. R. Rich. 1996. Phylogenetic distribution of streptococcal superantigen SSA allelic variants provides evidence for horizontal transfer of ssa within *Streptococcus pyogenes. Infect Immun.* 64:1161-5.
78. Sambrook, J., and D. W. Russell. 2001. *Molecular cloning a laboratory manual*, Third ed, vol. 3. Cold Spring Harbor Laboratory Press, Cold Spring Harbor, N.Y.
79. Salzberg, S. L., A. L. Delcher, S. Kasif, and O. White. 1998. Microbial gene identification using interpolated Markov models. Nucleic Acids Res. 26:544-8.
80. Saukkonen, K., H. Abdillahi, J. T. Poolman, and M. Leinonen. 1987. Protective efficacy of monoclonal antibodies to class 1 and class 3 outer membrane proteins of *Neisseria meningitidis* B:15:P1.16 in infant rat infection model: new prospects for vaccine development. *Microbial Pathogenesis* 3(4):261-7.
81. Sedegah et al. 1994. *Immunology.* 91, 9866-9870.
82. Sonnenberg, M. G., and J. T. Belisle. 1997. Definition of *Mycobacterium tuberculosis* culture filtrate proteins by two-dimensional polyacrylamide gel electrophoresis, N-terminal amino acid sequencing, and electrospray mass spectrometry. *Infect Immun.* 65:4515-24.
83. Sonnhammer, E. L., S. R. Eddy, and R. Durbin. 1997. Pfam: a comprehensive database of protein domain families based on seed alignments. *Proteins.* 28:405-20.
84. Stevens, D. L. 1995. Streptococcal toxic-shock syndrome: spectrum of disease, pathogenesis, and new concepts in treatment. *Emerg Infect Dis.* 1:69-78.
85. Stockbauer, K. E., L. Magoun, M. Liu, E. H. Burns, Jr., S. Gubba, S. Renish, X. Pan, S. C. Bodary, E. Baker, J. Coburn, J. M. Leong, and J. M. Musser. 1999. A natural variant of the cysteine protease virulence factor of group A *streptococcus* with an arginine-glycine-aspartic acid (RGD) motif preferentially binds human integrins alphavbeta3 and alphaIIbbeta3 *Proc Natl Acad Sci., USA.* 96:242-7.
86. Tettelin, H., N. J. Saunders, J. Heidelberg, A. C. Jeffries, K. E. Nelson, J. A. Eisen, K. A. Ketchum, D. W. Hood, J. F. Peden, R. J. Dodson, W. C. Nelson, M. L. Gwinn, R. DeBoy, J. D. Peterson, E. K. Hickey, D. H. Haft, S. L. Salzberg, O. White, R. D. Fleischmann, B. A. Dougherty, T. Mason, A. Ciecko, D. S. Parksey, E. Blair, H. Cittone, E. B. Clark, M. D. Cotton, T. R. Utterback, H. Khouri, H. Qin, J. Vamathevan, J. Gill, V. Scarlato, V. Masignani, M. Pizza, G. Grandi, L. Sun, H. O. Smith, C. M. Fraser, E. R. Moxon, R. Rappuoli, and J. C. Venter. 2000. Complete genome sequence of *Neisseria meningitidis* serogroup B strain MC58. *Science* 287(5459):1809-15.
87. Ton-That, H., G. Liu, S. K. Mazmanian, K. F. Faull, and O. Schneewind. 1999. Purification and characterization of sortase, the transpeptidase that cleaves surface proteins of *Staphylococcus aureus* at the LPXTG motif. *Proc Natl Acad Sci USA.* 96:12424-12429.
88. von Heinje, G. 1987. Sequence Analysis in Molecular Biology. Academic Press, New York.
89. Weldingh, K., I. Rosenkrands, S. Jacobsen, P. B. Rasmussen, M. J. Elhay, and P. Andersen. 1998. Two-dimensional electrophoresis for analysis of *Mycobacterium tuberculosis* culture filtrate and purification and characterization of six novel proteins. *Infect Immun.* 66:3492-500.
90. Wolff et al. 1990. *Science.* 247, 1465-1468.
91. Yutsudo, T., K. Okumura, M. Iwasaki, A. Hara, S. Kamitani, W. Minamide, H. Igarashi, and Y. Hinuma. 1994. The gene encoding a new mitogenic factor in a *Streptococcus pyogenes* strain is distributed only in group A streptococci. *Infection and Immunity.* 62:4000-4004.
92. Zagursky, R. J. and D. Russell. 2001. Bioinformatics: Use in Bacterial Vaccine Discovery. *Bio Techniques.* 31:636-659.

The invention now being fully described, it will be apparent to one of ordinary skill in the art that many changes and modifications can be made thereto without departing from the spirit or scope of the invention as set forth herein. The foregoing describes the preferred embodiments of the present invention along with a number of possible alternatives. These embodiments, however, are merely for example and the invention is not restricted thereto.

What is claimed is:

1. A composition comprising (a) at least one isolated *Neisseria meningitidis* serogroup B ORF2086 protein belonging to subfamily A having the amino acid sequence of SEQ ID NO: 301, wherein x is any amino acid; wherein the region from amino acid position 5 to amino acid position 8 is any of 0 to 4 amino acids; wherein the region from amino acid position 66 to amino acid position 68 is any of 0 to 3 amino acids; wherein the ORF2086 protein belonging to the subfamily A comprises the amino acid sequence of SEQ ID NO: 278; and (b) at least one isolated *Neisseria meningitidis* serogroup B ORF2086 protein belonging to subfamily B having the amino acid sequence of SEQ ID NO: 302, wherein x is any amino acid; and wherein the region from amino acid position 8 to amino acid position 12 is any of 0 to 5 amino acids; and wherein the ORF2086 protein belonging to the subfamily B comprises the amino acid sequence of SEQ ID NO: 279; wherein the composition further comprises an immunostimulatory amount of aluminum hydroxide or aluminum phosphate.

2. The composition of claim 1, wherein the at least one *Neisseria meningitidis* serogroup B ORF2086 protein has a molecular weight of 26-30 kDa as measured by mass spectroscopy.

3. The composition of claim 1, wherein the at least one *Neisseria meningitidis* serogroup B ORF2086 protein has a molecular weight of 28-35 kDa as measured on a 10%-20% SDS polyacrylamide gel.

4. The composition of claim 1, wherein the at least one *Neisseria meningitidis* serogroup B ORF2086 protein is non-lipidated.

5. The composition of claim 1, wherein the at least one *Neisseria meningitidis* serogroup B ORF2086 protein is lipidated.

6. The composition of claim 1, wherein the at least one *Neisseria meningitidis* serogroup B ORF2086 protein is a recombinant protein.

7. The composition of claim 1, wherein the at least one *Neisseria meningitidis* serogroup B ORF2086 protein is a fusion protein.

8. The composition of claim 1, wherein the at least one *Neisseria meningitidis* serogroup B ORF2086 protein is conjugated to a carrier.

9. The composition of claim 1, wherein said composition additionally comprises a pharmaceutically acceptable buffer, diluent, adjuvant or carrier.

10. The composition of claim 1, further comprising at least one PorA, PorB, transferrin binding protein, opacity protein (Opc) or an additional surface antigen of *Neisseria* species, said additional surface antigen being a non-ORF2086 protein.

11. The composition of claim 1, wherein said composition additionally comprises a polysaccharide.

12. The composition of claim 11, wherein the polysaccharide is a meningococcus serogroup A, C, Y or W 135 polysaccharide or a conjugate thereof.

13. The composition of claim 1, wherein the at least one *Neisseria meningitidis* serogroup B ORF2086 protein elicits bactericidal antibodies to multiple strains of *N. meningitidis*.

14. A method of inducing an immune response in a mammal comprising administering to the mammal an immunogenically effective amount of the composition of claim 1.

* * * * *

SEQUENCE LISTING

```
<160> NUMBER OF SEQ ID NOS: 329

<210> SEQ ID NO 1
<211> LENGTH: 765
<212> TYPE: DNA
<213> ORGANISM: Neisseria meningitidis

<400> SEQUENCE: 1
```

-continued

```
tgcagcagcg gaggcggcgg tgtcgccgcc gacatcggcg cggggcttgc cgatgcacta      60

accacaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacggaca aaccatcacg ctggcaagcg gcgaatttca aatatacaaa     300

cagaaccact ccgccgtcgt tgccctacag attgaaaaaa tcaacaaccc cgacaaaatc     360

gacagcctga taaaccaacg ctccttcctt gtcagcggtt tgggcggaga acataccgcc     420

ttcaaccaac tgcctgacgg caaagccgag tatcacggca aagcattcag ctccgacgac     480

ccgaacggca ggctgcacta ctccattgat tttaccaaaa aacagggtta cggcagaatc     540

gaacacctga aaacgcccga gcagaatgtc gagcttgcct ccgccgaact caaagcagat     600

gaaaaatcac acgccgtcat tttgggcgac acgcgctacg gcggcgaaga aaaaggcact     660

taccacctcg ccctttttcgg cgaccgcgcc caagaaatcg ccggctcggc aaccgtgaag     720

ataagggaaa aggttcacga aatcggcatc gccggcaaac agtag                     765
```

<210> SEQ ID NO 2
<211> LENGTH: 254
<212> TYPE: PRT
<213> ORGANISM: Neisseria meningitidis

<400> SEQUENCE: 2

```
Cys Ser Ser Gly Gly Gly Gly Val Ala Ala Asp Ile Gly Ala Gly Leu
1               5                   10                  15

Ala Asp Ala Leu Thr Thr Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240
```

-continued

```
Ile Arg Glu Lys Val His Glu Ile Gly Ile Ala Gly Lys Gln
                245                 250


<210> SEQ ID NO 3
<211> LENGTH: 768
<212> TYPE: DNA
<213> ORGANISM: Neisseria meningitidis

<400> SEQUENCE: 3

tgcggatcca gcggaggcgg cggtgtcgcc gccgacatcg gcgcggggct tgccgatgca      60

ctaaccacac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc tcaatacggg caaattgaag aacgacaagg tcagccgctt cgactttatc     240

cgtcaaatcg aagtggacgg acaaaccatc acgctggcaa gcggcgaatt tcaaatatac     300

aaacagaacc actccgccgt cgttgcccta cagattgaaa aaatcaacaa ccccgacaaa     360

atcgacagcc tgataaacca acgctccttc cttgtcagcg gtttgggcgg agaacatacc     420

gccttcaacc aactgcctga cggcaaagcc gagtatcacg gcaaagcatt cagctccgac     480

gacccgaacg gcaggctgca ctactccatt gattttacca aaaaacaggg ttacggcaga     540

atcgaacacc tgaaaacgcc cgagcagaat gtcgagcttg cctccgccga actcaaagca     600

gatgaaaaat cacacgccgt cattttgggc gacacgcgct acggcggcga agaaaaaggc     660

acttaccacc tcgccctttt cggcgaccgc gcccaagaaa tcgccggctc ggcaaccgtg     720

aagataaggg aaaaggttca cgaaatcggc atcgccggca aacagtag                  768


<210> SEQ ID NO 4
<211> LENGTH: 255
<212> TYPE: PRT
<213> ORGANISM: Neisseria meningitidis

<400> SEQUENCE: 4

Cys Gly Ser Ser Gly Gly Gly Gly Val Ala Ala Asp Ile Gly Ala Gly
1               5                   10                  15

Leu Ala Asp Ala Leu Thr Thr Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Thr Ile Thr Leu Ala Ser Gly Glu
                85                  90                  95

Phe Gln Ile Tyr Lys Gln Asn His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Pro Asn Gly Arg Leu His Tyr Ser Ile Asp Phe Thr Lys Lys Gln
                165                 170                 175
```

```
Gly Tyr Gly Arg Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255


<210> SEQ ID NO 5
<211> LENGTH: 765
<212> TYPE: DNA
<213> ORGANISM: Neisseria meningitidis

<400> SEQUENCE: 5

atgagcagcg gaggcggcgg tgtcgccgcc gacatcggcg cggggcttgc cgatgcacta      60

accacaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacggaca aaccatcacg ctggcaagcg gcgaatttca aatatacaaa     300

cagaaccact ccgccgtcgt tgccctacag attgaaaaaa tcaacaaccc cgacaaaatc     360

gacagcctga taaaccaacg ctccttcctt gtcagcggtt tgggcggaga acataccgcc     420

ttcaaccaac tgcctgacgg caaagccgag tatcacggca aagcattcag ctccgacgac     480

ccgaacggca ggctgcacta ctccattgat tttaccaaaa aacagggtta cggcagaatc     540

gaacacctga aaacgcccga gcagaatgtc gagcttgcct ccgccgaact caaagcagat     600

gaaaaatcac acgccgtcat tttgggcgac acgcgctacg gcggcgaaga aaaaggcact     660

taccacctcg ccctttttcgg cgaccgcgcc caagaaatcg ccggctcggc aaccgtgaag     720

ataagggaaa aggttcacga aatcggcatc gccggcaaac agtag                     765


<210> SEQ ID NO 6
<211> LENGTH: 254
<212> TYPE: PRT
<213> ORGANISM: Neisseria meningitidis

<400> SEQUENCE: 6

Met Ser Ser Gly Gly Gly Gly Val Ala Ala Asp Ile Gly Ala Gly Leu
1               5                   10                  15

Ala Asp Ala Leu Thr Thr Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
```

-continued

```
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250


<210> SEQ ID NO 7
<211> LENGTH: 765
<212> TYPE: DNA
<213> ORGANISM: Neisseria meningitidis

<400> SEQUENCE: 7

tgcagcagcg gaggcggcgg tgtcgccgcc gacatcggcg cggggcttgc cgatgcacta      60

accacaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacggaca aaccatcacg ctggcaagcg gcgaatttca aatatacaaa     300

cagaaccact ccgccgtcgt tgccctacag attgaaaaaa tcaacaaccc cgacaaaatc     360

gacagcctga taaaccaacg ctccttcctt gtcagcggtt tgggcggaga acataccgcc     420

ttcaaccaac tgcctgacgg caaagccgag tatcacggca aagcattcag ctccgacgac     480

ccgaacggca ggctgcacta ctccattgat tttaccaaaa aacagggtta cggcagaatc     540

gaacacctga aaacgcccga gcagaatgtc gagcttgcct ccgccgaact caaagcagat     600

gaaaaatcac acgccgtcat tttgggcgac acgcgctacg gcggcgaaga aaaaggcact     660

taccacctcg cccttttcgg cgaccgcgcc caagaaatcg ccggcccggc aaccgtgaag     720

ataagggaaa aggttcacga aatcggcatc gccagcaaac agtag                     765


<210> SEQ ID NO 8
<211> LENGTH: 254
<212> TYPE: PRT
<213> ORGANISM: Neisseria meningitidis

<400> SEQUENCE: 8

Cys Ser Ser Gly Gly Gly Gly Val Ala Ala Asp Ile Gly Ala Gly Leu
1               5                   10                  15

Ala Asp Ala Leu Thr Thr Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60
```

-continued

```
Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Pro Ala Thr Val Lys
225                 230                 235                 240

Ile Arg Glu Lys Val His Glu Ile Gly Ile Ala Ser Lys Gln
                245                 250
```

<210> SEQ ID NO 9
<211> LENGTH: 768
<212> TYPE: DNA
<213> ORGANISM: Neisseria meningitidis

<400> SEQUENCE: 9

```
tgcggatcca gcggaggcgg cggtgtcgcc gccgacatcg gcgcggggct tgccgatgca      60

ctaaccacac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc tcaatacggg caaattgaag aacgacaagg tcagccgctt cgactttatc     240

cgtcaaatcg aagtggacgg acaaaccatc acgctggcaa gcggcgaatt tcaaatatac     300

aaacagaacc actccgccgt cgttgcccta cagattgaaa aaatcaacaa ccccgacaaa     360

atcgacagcc tgataaacca acgctccttc cttgtcagcg gtttgggcgg agaacatacc     420

gccttcaacc aactgcctga cggcaaagcc gagtatcacg gcaaagcatt cagctccgac     480

gacccgaacg gcaggctgca ctactccatt gattttacca aaaaacaggg ttacggcaga     540

atcgaacacc tgaaaacgcc cgagcagaat gtcgagcttg cctccgccga actcaaagca     600

gatgaaaaat cacacgccgt cattttgggc gacacgcgct acggcggcga agaaaaaggc     660

acttaccacc tcgccctttt cggcgaccgc gcccaagaaa tcgccggccc ggcaaccgtg     720

aagataaggg aaaaggttca cgaaatcggc atcgccagca aacagtag                  768
```

<210> SEQ ID NO 10
<211> LENGTH: 255
<212> TYPE: PRT
<213> ORGANISM: Neisseria meningitidis

<400> SEQUENCE: 10

-continued

```
Cys Gly Ser Ser Gly Gly Gly Gly Val Ala Ala Asp Ile Gly Ala Gly
1               5                   10                  15

Leu Ala Asp Ala Leu Thr Thr Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Thr Ile Thr Leu Ala Ser Gly Glu
                85                  90                  95

Phe Gln Ile Tyr Lys Gln Asn His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Pro Asn Gly Arg Leu His Tyr Ser Ile Asp Phe Thr Lys Lys Gln
                165                 170                 175

Gly Tyr Gly Arg Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Pro Ala Thr Val
225                 230                 235                 240

Lys Ile Arg Glu Lys Val His Glu Ile Gly Ile Ala Ser Lys Gln
                245                 250                 255
```

<210> SEQ ID NO 11
<211> LENGTH: 765
<212> TYPE: DNA
<213> ORGANISM: Neisseria meningitidis

<400> SEQUENCE: 11

```
atgagcagcg gaggcggcgg tgtcgccgcc gacatcggcg cggggcttgc cgatgcacta     60

accacaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacggaca aaccatcacg ctggcaagcg gcgaatttca aatatacaaa    300

cagaaccact ccgccgtcgt tgccctacag attgaaaaaa tcaacaaccc cgacaaaatc    360

gacagcctga taaaccaacg ctccttcctt gtcagcggtt tgggcggaga acataccgcc    420

ttcaaccaac tgcctgacgg caaagccgag tatcacggca aagcattcag ctccgacgac    480

ccgaacggca ggctgcacta ctccattgat tttaccaaaa aacagggtta cggcagaatc    540

gaacacctga aaacgcccga gcagaatgtc gagcttgcct ccgccgaact caaagcagat    600

gaaaaatcac acgccgtcat tttgggcgac acgcgctacg gcggcgaaga aaaaggcact    660

taccacctcg ccctttttcgg cgaccgcgcc caagaaatcg ccggcccggc aaccgtgaag    720
```

ataagggaaa aggttcacga aatcggcatc gccagcaaac agtag 765

<210> SEQ ID NO 12
<211> LENGTH: 254
<212> TYPE: PRT
<213> ORGANISM: Neisseria meningitidis

<400> SEQUENCE: 12

Met Ser Ser Gly Gly Gly Gly Val Ala Ala Asp Ile Gly Ala Gly Leu
1 5 10 15

Ala Asp Ala Leu Thr Thr Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Thr Ile Thr Leu Ala Ser Gly Glu Phe
85 90 95

Gln Ile Tyr Lys Gln Asn His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Asp Gly Lys Ala Glu Tyr His Gly Lys Ala Phe Ser Ser Asp Asp
145 150 155 160

Pro Asn Gly Arg Leu His Tyr Ser Ile Asp Phe Thr Lys Lys Gln Gly
165 170 175

Tyr Gly Arg Ile Glu His Leu Lys Thr Pro Glu Gln Asn Val Glu Leu
180 185 190

Ala Ser Ala Glu Leu Lys Ala Asp Glu Lys Ser His Ala Val Ile Leu
195 200 205

Gly Asp Thr Arg Tyr Gly Gly Glu Glu Lys Gly Thr Tyr His Leu Ala
210 215 220

Leu Phe Gly Asp Arg Ala Gln Glu Ile Ala Gly Pro Ala Thr Val Lys
225 230 235 240

Ile Arg Glu Lys Val His Glu Ile Gly Ile Ala Ser Lys Gln
245 250

<210> SEQ ID NO 13
<211> LENGTH: 765
<212> TYPE: DNA
<213> ORGANISM: Neisseria meningitidis

<400> SEQUENCE: 13
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcggag tggacggaca aaccatcacg ctggcaagcg gcgaatttca aatatacaaa 300
cagaaccact ccgccgtcgt tgccctacag attgaaaaaa tcaacaaccc cgacaaaatc 360

-continued

```
gacagcctga taaaccaacg ctccttcctt gtcagcggtt tgggcggaga acataccgcc     420

ttcaaccaac tgcctgacgg caaagccgag tatcacggca aagcattcag ctccgacgac     480

ccgaacggca ggctgcacta ctccattgat tttaccaaaa aacagggtta cggcagaatc     540

gaacacctga aaacgcccga gcagaatgtc gagcttgcct ccgccgaact caaagcagat     600

gaaaaatcac acgccgtcat tttgggcgac acgcgctacg gcggcgaaga aaaaggcact     660

taccacctcg cccttttcgg cgaccgcgcc caagaaatcg ccggctcggc aaccgtgaag     720

ataagggaaa aggttcacga aatcggcatc gccggcaaac agtag                     765
```

<210> SEQ ID NO 14
<211> LENGTH: 254
<212> TYPE: PRT
<213> ORGANISM: Neisseria meningitidis

<400> SEQUENCE: 14

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Gly Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 15
<211> LENGTH: 768
<212> TYPE: DNA
<213> ORGANISM: Neisseria meningitidis

<400> SEQUENCE: 15

```
tgcggatcca gcggaggcgg cggtgtcgcc gccgacatcg gcgcggggct tgccgatgca      60
```

```
ctaaccgcac cgctcgacca taaagacaaa agtttgcagt ctttgacgct ggatcagtcc    120

gtcaggaaaa acgagaaact gaagctggcg gcacaaggtg cggaaaaaac ttatggaaac    180

ggcgacagcc tcaatacggg caaattgaag aacgacaagg tcagccgctt cgactttatc    240

cgtcaaatcg gagtggacgg acaaaccatc acgctggcaa gcggcgaatt tcaaatatac    300

aaacagaacc actccgccgt cgttgcccta cagattgaaa aatcaacaa ccccgacaaa    360

atcgacagcc tgataaacca acgctccttc cttgtcagcg gtttgggcgg agaacatacc    420

gccttcaacc aactgcctga cggcaaagcc gagtatcacg gcaaagcatt cagctccgac    480

gacccgaacg gcaggctgca ctactccatt gattttacca aaaaacaggg ttacggcaga    540

atcgaacacc tgaaaacgcc cgagcagaat gtcgagcttg cctccgccga actcaaagca    600

gatgaaaaat cacacgccgt cattttgggc gacacgcgct acggcggcga agaaaaaggc    660

acttaccacc tcgccctttt cggcgaccgc gcccaagaaa tcgccggctc ggcaaccgtg    720

aagataaggg aaaaggttca cgaaatcggc atcgccggca aacagtag                 768


<210> SEQ ID NO 16
<211> LENGTH: 255
<212> TYPE: PRT
<213> ORGANISM: Neisseria meningitidis

<400> SEQUENCE: 16

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Gly Val Asp Gly Gln Thr Ile Thr Leu Ala Ser Gly Glu
                85                  90                  95

Phe Gln Ile Tyr Lys Gln Asn His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Pro Asn Gly Arg Leu His Tyr Ser Ile Asp Phe Thr Lys Lys Gln
                165                 170                 175

Gly Tyr Gly Arg Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
```

-continued 245 250 255

<210> SEQ ID NO 17
<211> LENGTH: 765
<212> TYPE: DNA
<213> ORGANISM: Neisseria meningitidis

<400> SEQUENCE: 17
atgagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcggag tggacggaca aaccatcacg ctggcaagcg gcgaatttca aatatacaaa 300
cagaaccact ccgccgtcgt tgccctacag attgaaaaaa tcaacaaccc cgacaaaatc 360
gacagcctga taaaccaacg ctccttcctt gtcagcggtt tgggcggaga acataccgcc 420
ttcaaccaac tgcctgacgg caaagccgag tatcacggca aagcattcag ctccgacgac 480
ccgaacggca ggctgcacta ctccattgat tttaccaaaa aacagggtta cggcagaatc 540
gaacacctga aaacgcccga gcagaatgtc gagcttgcct ccgccgaact caaagcagat 600
gaaaaatcac acgccgtcat tttgggcgac acgcgctacg gcggcgaaga aaaaggcact 660
taccacctcg cccttttcgg cgaccgcgcc caagaaatcg ccggctcggc aaccgtgaag 720
ataagggaaa aggttcacga aatcggcatc gccggcaaac agtag 765

<210> SEQ ID NO 18
<211> LENGTH: 254
<212> TYPE: PRT
<213> ORGANISM: Neisseria meningitidis

<400> SEQUENCE: 18

Met Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Gly Val Asp Gly Gln Thr Ile Thr Leu Ala Ser Gly Glu Phe
85 90 95

Gln Ile Tyr Lys Gln Asn His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Asp Gly Lys Ala Glu Tyr His Gly Lys Ala Phe Ser Ser Asp Asp
145 150 155 160

Pro Asn Gly Arg Leu His Tyr Ser Ile Asp Phe Thr Lys Lys Gln Gly
165 170 175

Tyr Gly Arg Ile Glu His Leu Lys Thr Pro Glu Gln Asn Val Glu Leu
180 185 190

Ala Ser Ala Glu Leu Lys Ala Asp Glu Lys Ser His Ala Val Ile Leu
195 200 205

Gly Asp Thr Arg Tyr Gly Gly Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Arg Glu Lys Val His Glu Ile Gly Ile Ala Gly Lys Gln
245 250

<210> SEQ ID NO 19
<211> LENGTH: 765
<212> TYPE: DNA
<213> ORGANISM: Neisseria meningitidis

<400> SEQUENCE: 19
tgcagcagca gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacggaca aaccatcacg ctggcaagcg gcgaatttca aatatacaaa 300
cagaaccact ccgccgtcgt tgccctacag attgaaaaaa tcaacaaccc cgacaaaatc 360
gacagcctga taaaccaacg ctccttcctt gtcagcggtt tgggcggaga acataccgcc 420
ttcaaccaac tgcctgacgg caaagccgag tatcacggca aagcattcag ctccgacgac 480
ccgaacggca ggctgcacta ctccattgat tttaccaaaa aacagggtta cggcagaatc 540
gaacacctga aaacgcccga gcagaatgtc gagcttgcct ccgccgaact caaagcagat 600
gaaaaatcac acgccgtcat tttgggcgac acgcgctacg gcggcgaaga aaaaggcact 660
taccacctcg cccttttcgg cgaccgcgcc caagaaatcg ccggctcggc aaccgtgaag 720
ataagggaaa aggttcacga aatcggcatc gccggcaaac agtag 765

<210> SEQ ID NO 20
<211> LENGTH: 254
<212> TYPE: PRT
<213> ORGANISM: Neisseria meningitidis

<400> SEQUENCE: 20

Cys Ser Ser Arg Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Thr Ile Thr Leu Ala Ser Gly Glu Phe
85 90 95

Gln Ile Tyr Lys Gln Asn His Ser Ala Val Val Ala Leu Gln Ile Glu
100 105 110

Lys Ile Asn Asn Pro Asp Lys Ile Asp Ser Leu Ile Asn Gln Arg Ser
115 120 125

```
Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250


<210> SEQ ID NO 21
<211> LENGTH: 768
<212> TYPE: DNA
<213> ORGANISM: Neisseria meningitidis

<400> SEQUENCE: 21

tgcggatcca gcagaggcgg cggtgtcgcc gccgacatcg gcgcggggct tgccgatgca      60

ctaaccgcac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc tcaatacggg caaattgaag aacgacaagg tcagccgctt cgactttatc     240

cgtcaaatcg aagtggacgg acaaaccatc acgctggcaa gcggcgaatt tcaaatatac     300

aaacagaacc actccgccgt cgttgcccta cagattgaaa aatcaacaa ccccgacaaa     360

atcgacagcc tgataaacca acgctccttc cttgtcagcg gtttgggcgg agaacatacc     420

gccttcaacc aactgcctga cggcaaagcc gagtatcacg gcaaagcatt cagctccgac     480

gacccgaacg gcaggctgca ctactccatt gattttacca aaaaacaggg ttacggcaga     540

atcgaacacc tgaaaacgcc cgagcagaat gtcgagcttg cctccgccga actcaaagca     600

gatgaaaaat cacacgccgt cattttgggc gacacgcgct acggcggcga agaaaaaggc     660

acttaccacc tcgccctttt cggcgaccgc gcccaagaaa tcgccggctc ggcaaccgtg     720

aagataaggg aaaaggttca cgaaatcggc atcgccggca aacagtag                  768


<210> SEQ ID NO 22
<211> LENGTH: 255
<212> TYPE: PRT
<213> ORGANISM: Neisseria meningitidis

<400> SEQUENCE: 22

Cys Gly Ser Ser Arg Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
```

```
65                  70                  75                  80

Arg Gln Ile Glu Val Asp Gly Gln Thr Ile Thr Leu Ala Ser Gly Glu
                85                  90                  95

Phe Gln Ile Tyr Lys Gln Asn His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Pro Asn Gly Arg Leu His Tyr Ser Ile Asp Phe Thr Lys Lys Gln
                165                 170                 175

Gly Tyr Gly Arg Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255
```

<210> SEQ ID NO 23
<211> LENGTH: 765
<212> TYPE: DNA
<213> ORGANISM: Neisseria meningitidis

<400> SEQUENCE: 23

```
atgagcagca gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacggaca aaccatcacg ctggcaagcg gcgaatttca aatatacaaa    300

cagaaccact ccgccgtcgt tgccctacag attgaaaaaa tcaacaaccc cgacaaaatc    360

gacagcctga taaaccaacg ctccttcctt gtcagcggtt tgggcggaga acataccgcc    420

ttcaaccaac tgcctgacgg caaagccgag tatcacggca aagcattcag ctccgacgac    480

ccgaacggca ggctgcacta ctccattgat tttaccaaaa aacagggtta cggcagaatc    540

gaacacctga aaacgcccga gcagaatgtc gagcttgcct ccgccgaact caaagcagat    600

gaaaaatcac acgccgtcat tttgggcgac acgcgctacg gcggcgaaga aaaaggcact    660

taccacctcg ccctttttcgg cgaccgcgcc caagaaatcg ccggctcggc aaccgtgaag    720

ataagggaaa aggttcacga aatcggcatc gccggcaaac agtag                    765
```

<210> SEQ ID NO 24
<211> LENGTH: 254
<212> TYPE: PRT
<213> ORGANISM: Neisseria meningitidis

<400> SEQUENCE: 24

```
Met Ser Ser Arg Gly Gly Gly Val Ala Ala Asp Ile Gly Ala Gly Leu
1               5                   10                  15
```

```
Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Thr Ile Thr Leu Ala Ser Gly Glu Phe
                85                  90                  95

Gln Ile Tyr Lys Gln Asn His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

```
<210> SEQ ID NO 25
<211> LENGTH: 765
<212> TYPE: DNA
<213> ORGANISM: Neisseria meningitidis

<400> SEQUENCE: 25

tgcagcagcg gaggcggcgg tgtcgccgcc gacatcggcg cggggcttgc cgatgcacta     60

accgcaccgt tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgac    480

ccgaacggca ggctgcacta ctccattgat tttaccaaaa aacagggtta cggcagaatc    540

gaacacctga aaacgcccga gcagaatgtc gagcttgcct ccgccgaact caaagcagat    600

gaaaaatcac acgccgtcat tttgggcgac acgcgctacg gcggcgaaga aaaaggcact    660

taccacctcg ccctttttcgg cgaccgcgcc caagaaatcg ccggctcggc aaccgtgaag    720

ataagggaaa aggttcacga aatcggcatc gccggcaaac agtag                    765
```

<210> SEQ ID NO 26
<211> LENGTH: 254
<212> TYPE: PRT
<213> ORGANISM: Neisseria meningitidis

<400> SEQUENCE: 26

```
Cys Ser Ser Gly Gly Gly Gly Val Ala Ala Asp Ile Gly Ala Gly Leu
1               5                   10                  15

Ala Asp Ala Leu Thr Ala Pro Phe Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 27
<211> LENGTH: 768
<212> TYPE: DNA
<213> ORGANISM: Neisseria meningitidis

<400> SEQUENCE: 27

```
tgcggatcca gcggaggcgg cggtgtcgcc gccgacatcg gcgcggggct tgccgatgca      60

ctaaccgcac cgttcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc tcaatacggg caaattgaag aacgacaagg tcagccgctt cgactttatc     240

cgtcaaatcg aagtggacgg gcagctcatt accttggaga gcggagagtt ccaaatatac     300

aaacaggacc actccgccgt cgttgcccta cagattgaaa aatcaacaa ccccgacaaa     360

atcgacagcc tgataaacca acgctccttc cttgtcagcg gtttgggtgg agaacatacc     420
```

gccttcaacc aactgcccag cggcaaagcc gagtatcacg gcaaagcatt cagctccgac 480
gacccgaacg gcaggctgca ctactccatt gattttacca aaaaacaggg ttacggcaga 540
atcgaacacc tgaaaacgcc cgagcagaat gtcgagcttg cctccgccga actcaaagca 600
gatgaaaaat cacacgccgt cattttgggc gacacgcgct acggcggcga agaaaaaggc 660
acttaccacc tcgccctttt cggcgaccgc gcccaagaaa tcgccggctc ggcaaccgtg 720
aagataaggg aaaaggttca cgaaatcggc atcgccggca aacagtag 768

<210> SEQ ID NO 28
<211> LENGTH: 255
<212> TYPE: PRT
<213> ORGANISM: Neisseria meningitidis

<400> SEQUENCE: 28

Cys Gly Ser Ser Gly Gly Gly Gly Val Ala Ala Asp Ile Gly Ala Gly
1 5 10 15

Leu Ala Asp Ala Leu Thr Ala Pro Phe Asp His Lys Asp Lys Ser Leu
20 25 30

Gln Ser Leu Thr Leu Asp Gln Ser Val Arg Lys Asn Glu Lys Leu Lys
35 40 45

Leu Ala Ala Gln Gly Ala Glu Lys Thr Tyr Gly Asn Gly Asp Ser Leu
50 55 60

Asn Thr Gly Lys Leu Lys Asn Asp Lys Val Ser Arg Phe Asp Phe Ile
65 70 75 80

Arg Gln Ile Glu Val Asp Gly Gln Leu Ile Thr Leu Glu Ser Gly Glu
85 90 95

Phe Gln Ile Tyr Lys Gln Asp His Ser Ala Val Val Ala Leu Gln Ile
100 105 110

Glu Lys Ile Asn Asn Pro Asp Lys Ile Asp Ser Leu Ile Asn Gln Arg
115 120 125

Ser Phe Leu Val Ser Gly Leu Gly Gly Glu His Thr Ala Phe Asn Gln
130 135 140

Leu Pro Ser Gly Lys Ala Glu Tyr His Gly Lys Ala Phe Ser Ser Asp
145 150 155 160

Asp Pro Asn Gly Arg Leu His Tyr Ser Ile Asp Phe Thr Lys Lys Gln
165 170 175

Gly Tyr Gly Arg Ile Glu His Leu Lys Thr Pro Glu Gln Asn Val Glu
180 185 190

Leu Ala Ser Ala Glu Leu Lys Ala Asp Glu Lys Ser His Ala Val Ile
195 200 205

Leu Gly Asp Thr Arg Tyr Gly Gly Glu Glu Lys Gly Thr Tyr His Leu
210 215 220

Ala Leu Phe Gly Asp Arg Ala Gln Glu Ile Ala Gly Ser Ala Thr Val
225 230 235 240

Lys Ile Arg Glu Lys Val His Glu Ile Gly Ile Ala Gly Lys Gln
245 250 255

<210> SEQ ID NO 29
<211> LENGTH: 765
<212> TYPE: DNA
<213> ORGANISM: Neisseria meningitidis

<400> SEQUENCE: 29
atgagcagcg gaggcggcgg tgtcgccgcc gacatcggcg cggggcttgc cgatgcacta 60
accgcaccgt tcgaccataa agacaaaagt ttgcagtctt tgacgctgga tcagtccgtc 120

```
aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgac    480

ccgaacggca ggctgcacta ctccattgat tttaccaaaa aacagggtta cggcagaatc    540

gaacacctga aaacgcccga gcagaatgtc gagcttgcct ccgccgaact caaagcagat    600

gaaaaatcac acgccgtcat tttgggcgac acgcgctacg gcggcgaaga aaaaggcact    660

taccacctcg ccctttttcgg cgaccgcgcc caagaaatcg ccggctcggc aaccgtgaag    720

ataagggaaa aggttcacga aatcggcatc gccggcaaac agtag                    765
```

<210> SEQ ID NO 30
<211> LENGTH: 254
<212> TYPE: PRT
<213> ORGANISM: Neisseria meningitidis

<400> SEQUENCE: 30

```
Met Ser Ser Gly Gly Gly Gly Val Ala Ala Asp Ile Gly Ala Gly Leu
1               5                   10                  15

Ala Asp Ala Leu Thr Ala Pro Phe Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 31
<211> LENGTH: 765
<212> TYPE: DNA
<213> ORGANISM: Neisseria meningitidis

<400> SEQUENCE: 31
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgac 480
ccgaacggca ggctgcacta ctccattgat tttaccaaaa aacagggtta cggcagaatc 540
gaacacctga aaacgcccga gcagaatgtc gagcttgcct ccgccgaact caaagcagat 600
gaaaaatcac acgccgtcat tttgggcgac acgcgctacg gcggcgaaga aaaaggcact 660
taccacctcg cccttttcgg cgaccgcgcc caagaaatcg ccggctcggc aaccgtgaag 720
ataagggaaa aggttcacga aatcggcatc gccggcaaac agtag 765

<210> SEQ ID NO 32
<211> LENGTH: 254
<212> TYPE: PRT
<213> ORGANISM: Neisseria meningitidis

<400> SEQUENCE: 32

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Ser Gly Lys Ala Glu Tyr His Gly Lys Ala Phe Ser Ser Asp Asp
145 150 155 160

Pro Asn Gly Arg Leu His Tyr Ser Ile Asp Phe Thr Lys Lys Gln Gly
165 170 175

Tyr Gly Arg Ile Glu His Leu Lys Thr Pro Glu Gln Asn Val Glu Leu
180 185 190

Ala Ser Ala Glu Leu Lys Ala Asp Glu Lys Ser His Ala Val Ile Leu

```
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 33
<211> LENGTH: 768
<212> TYPE: DNA
<213> ORGANISM: Neisseria meningitidis

<400> SEQUENCE: 33

```
tgcggatcca gcggaggcgg cggtgtcgcc gccgacatcg gcgcggggct tgccgatgca      60

ctaaccgcac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc tcaatacggg caaattgaag aacgacaagg tcagccgctt cgactttatc     240

cgtcaaatcg aagtggacgg gcagctcatt accttggaga gcggagagtt ccaaatatac     300

aaacaggacc actccgccgt cgttgcccta cagattgaaa aatcaacaa ccccgacaaa     360

atcgacagcc tgataaacca acgctccttc cttgtcagcg gtttgggtgg agaacatacc     420

gccttcaacc aactgcccag cggcaaagcc gagtatcacg gcaaagcatt cagctccgac     480

gacccgaacg gcaggctgca ctactccatt gattttacca aaaaacaggg ttacggcaga     540

atcgaacacc tgaaaacgcc cgagcagaat gtcgagcttg cctccgccga actcaaagca     600

gatgaaaaat cacacgccgt cattttgggc gacacgcgct acggcggcga agaaaaaggc     660

acttaccacc tcgccctttt cggcgaccgc gcccaagaaa tcgccggctc ggcaaccgtg     720

aagataaggg aaaaggttca cgaaatcggc atcgccggca aacagtag                  768
```

<210> SEQ ID NO 34
<211> LENGTH: 255
<212> TYPE: PRT
<213> ORGANISM: Neisseria meningitidis

<400> SEQUENCE: 34

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140
```

Leu Pro Ser Gly Lys Ala Glu Tyr His Gly Lys Ala Phe Ser Ser Asp
145 150 155 160

Asp Pro Asn Gly Arg Leu His Tyr Ser Ile Asp Phe Thr Lys Lys Gln
165 170 175

Gly Tyr Gly Arg Ile Glu His Leu Lys Thr Pro Glu Gln Asn Val Glu
180 185 190

Leu Ala Ser Ala Glu Leu Lys Ala Asp Glu Lys Ser His Ala Val Ile
195 200 205

Leu Gly Asp Thr Arg Tyr Gly Gly Glu Glu Lys Gly Thr Tyr His Leu
210 215 220

Ala Leu Phe Gly Asp Arg Ala Gln Glu Ile Ala Gly Ser Ala Thr Val
225 230 235 240

Lys Ile Arg Glu Lys Val His Glu Ile Gly Ile Ala Gly Lys Gln
245 250 255

<210> SEQ ID NO 35
<211> LENGTH: 765
<212> TYPE: DNA
<213> ORGANISM: Neisseria meningitidis

<400> SEQUENCE: 35
atgagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgac 480
ccgaacggca ggctgcacta ctccattgat tttaccaaaa aacagggtta cggcagaatc 540
gaacacctga aaacgcccga gcagaatgtc gagcttgcct ccgccgaact caaagcagat 600
gaaaaatcac acgccgtcat tttgggcgac acgcgctacg gcggcgaaga aaaaggcact 660
taccacctcg cccttttcgg cgaccgcgcc caagaaatcg ccggctcggc aaccgtgaag 720
ataagggaaa aggttcacga aatcggcatc gccggcaaac agtag 765

<210> SEQ ID NO 36
<211> LENGTH: 254
<212> TYPE: PRT
<213> ORGANISM: Neisseria meningitidis

<400> SEQUENCE: 36

Met Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Ser Gly Lys Ala Glu Tyr His Gly Lys Ala Phe Ser Ser Asp Asp
145 150 155 160

Pro Asn Gly Arg Leu His Tyr Ser Ile Asp Phe Thr Lys Lys Gln Gly
165 170 175

Tyr Gly Arg Ile Glu His Leu Lys Thr Pro Glu Gln Asn Val Glu Leu
180 185 190

Ala Ser Ala Glu Leu Lys Ala Asp Glu Lys Ser His Ala Val Ile Leu
195 200 205

Gly Asp Thr Arg Tyr Gly Gly Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Arg Glu Lys Val His Glu Ile Gly Ile Ala Gly Lys Gln
245 250

<210> SEQ ID NO 37
<211> LENGTH: 765
<212> TYPE: DNA
<213> ORGANISM: Neisseria meningitidis

<400> SEQUENCE: 37
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgac 480
ccgaacggca ggctgcacta ctccattgat tttaccaaaa aacagggtta cggcagaatc 540
gaacacctga aaacgcccga gcagaatgtc gagcttgcct ccgccgaact caaagcagat 600
gaaaaatcac acgccgtcat tttgggcgac acgcgctacg gcggcgaaga aaaaggcact 660
taccacctcg cccttttcgg cgaccgcgcc caagaaatcg ccggctcggc aaccgtgaag 720
ataagggaaa aggttcacga aatcggcatc gccggcaaac agtag 765

<210> SEQ ID NO 38
<211> LENGTH: 254
<212> TYPE: PRT
<213> ORGANISM: Neisseria meningitidis

<400> SEQUENCE: 38

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln

```
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 39
<211> LENGTH: 768
<212> TYPE: DNA
<213> ORGANISM: Neisseria meningitidis

<400> SEQUENCE: 39

```
tgcggatcca gcggaggcgg cggtgtcgcc gccgacatcg gcgcggggct tgccgatgca     60

ctaaccgcac cgctcgacca taaagacaaa agtttgcagt ctttgacgct ggatcagtcc    120

gtcaggaaaa acgagaaact gaagctggcg gcacaaggtg cggaaaaaac ttatggaaac    180

ggcgacagcc tcaatacggg caaattgaag aacgacaagg tcagccgctt cgactttatc    240

cgtcaaatcg aagtggacgg gcagctcatt accttggaga gcggagagtt ccaaatatac    300

aaacaggacc actccgccgt cgttgcccta cagattgaaa aaatcaacaa ccccgacaaa    360

atcgacagcc tgataaacca acgctccttc cttgtcagcg gtttgggtgg agaacatacc    420

gccttcaacc aactgcccag cggcaaagcc gagtatcacg gcaaagcatt cagctccgac    480

gacccgaacg gcaggctgca ctactccatt gattttacca aaaaacaggg ttacggcaga    540

atcgaacacc tgaaaacgcc cgagcagaat gtcgagcttg cctccgccga actcaaagca    600

gatgaaaaat cacacgccgt cattttgggc gacacgcgct acggcggcga agaaaaaggc    660

acttaccacc tcgccctttt cggcgaccgc gcccaagaaa tcgccggctc ggcaaccgtg    720

aagataaggg aaaaggttca cgaaatcggc atcgccggca aacagtag                 768
```

-continued

<210> SEQ ID NO 40
<211> LENGTH: 255
<212> TYPE: PRT
<213> ORGANISM: Neisseria meningitidis

<400> SEQUENCE: 40

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Ser Gly Lys Ala Glu Tyr His Gly Lys Ala Phe Ser Ser Asp
145                 150                 155                 160

Asp Pro Asn Gly Arg Leu His Tyr Ser Ile Asp Phe Thr Lys Lys Gln
                165                 170                 175

Gly Tyr Gly Arg Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255
```

<210> SEQ ID NO 41
<211> LENGTH: 765
<212> TYPE: DNA
<213> ORGANISM: Neisseria meningitidis

<400> SEQUENCE: 41

```
atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggtggaga acataccgcc     420

ttcaaccaac tgcccagcgg caaagccgag tatcacggca aagcattcag ctccgacgac     480
```

-continued

```
ccgaacggca ggctgcacta ctccattgat tttaccaaaa aacagggtta cggcagaatc    540

gaacacctga aaacgcccga gcagaatgtc gagcttgcct ccgccgaact caaagcagat    600

gaaaaatcac acgccgtcat tttgggcgac acgcgctacg gcggcgaaga aaaaggcact    660

taccacctcg cccttttcgg cgaccgcgcc caagaaatcg ccggctcggc aaccgtgaag    720

ataagggaaa aggttcacga aatcggcatc gccggcaaac agtag                    765


<210> SEQ ID NO 42
<211> LENGTH: 254
<212> TYPE: PRT
<213> ORGANISM: Neisseria meningitidis

<400> SEQUENCE: 42

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250


<210> SEQ ID NO 43
<211> LENGTH: 765
<212> TYPE: DNA
<213> ORGANISM: Neisseria meningitidis

<400> SEQUENCE: 43

tgcagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180
```

-continued

```
gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgac    480

ccgaacggca ggctgcacta ctccattgat tttaccaaaa aacagggtta cggcagaatc    540

gaacacctga aaacgcccga gcagaatgtc gagcttgcct ccgccgaact caaagcagat    600

gaaaaatcac acgccgtcat tttgggcgac acgcgctacg gcggcgaaga aaaaggcact    660

taccacctcg cccttttcgg cgaccgcgcc caagaaatcg ccggctcggc aaccgtgaag    720

ataagggaaa aggttcacga aatcggcatc gccggcaaac agtag                    765
```

<210> SEQ ID NO 44
<211> LENGTH: 254
<212> TYPE: PRT
<213> ORGANISM: Neisseria meningitidis

<400> SEQUENCE: 44

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Pro Asn Gly Arg Leu His Tyr Ser Ile Asp Phe Thr Lys Lys Gln Gly
                165                 170                 175

Tyr Gly Arg Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 45

<211> LENGTH: 768
<212> TYPE: DNA
<213> ORGANISM: Neisseria meningitidis

<400> SEQUENCE: 45

```
tgcggatcca gcggaggcgg cggtgtcgcc gccgacatcg gcgcggggct tgccgatgca     60

ctaaccgcac cgctcgacca taaagacaaa agtttgcagt ctttgacgct ggatcagtcc    120

gtcaggaaaa acgagaaact gaagctggcg gcacaaggtg cggaaaaaac ttatggaaac    180

ggcgacagcc tcaatacggg caaattgaag aacgacaagg tcagccgctt cgactttatc    240

cgtcaaatcg aagtggacgg gcagctcatt accttggaga gcggagagtt ccaaatatac    300

aaacaggacc actccgccgt cgttgcccta cagattgaaa aaatcaacaa ccccgacaaa    360

atcgacagcc tgataaacca acgctccttc cttgtcagcg gtttgggtgg agaacatacc    420

gccttcaacc aactgcccag cggcaaagcc gagtatcacg gcaaagcatt cagctccgac    480

gacccgaacg gcaggctgca ctactccatt gattttacca aaaaacaggg ttacggcaga    540

atcgaacacc tgaaaacgcc cgagcagaat gtcgagcttg cctccgccga actcaaagca    600

gatgaaaaat cacacgccgt cattttgggc gacacgcgct acggcggcga agaaaaaggc    660

acttaccacc tcgccctttt cggcgaccgc gcccaagaaa tcgccggctc ggcaaccgtg    720

aagataaggg aaaaggttca cgaaatcggc atcgccggca aacagtag                 768
```

<210> SEQ ID NO 46
<211> LENGTH: 255
<212> TYPE: PRT
<213> ORGANISM: Neisseria meningitidis

<400> SEQUENCE: 46

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Ser Gly Lys Ala Glu Tyr His Gly Lys Ala Phe Ser Ser Asp
145                 150                 155                 160

Asp Pro Asn Gly Arg Leu His Tyr Ser Ile Asp Phe Thr Lys Lys Gln
                165                 170                 175

Gly Tyr Gly Arg Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205
```

```
Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255


<210> SEQ ID NO 47
<211> LENGTH: 765
<212> TYPE: DNA
<213> ORGANISM: Neisseria meningitidis

<400> SEQUENCE: 47

atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggtggaga acataccgcc     420

ttcaaccaac tgcccagcgg caaagccgag tatcacggca aagcattcag ctccgacgac     480

ccgaacggca ggctgcacta ctccattgat tttaccaaaa aacagggtta cggcagaatc     540

gaacacctga aaacgcccga gcagaatgtc gagcttgcct ccgccgaact caaagcagat     600

gaaaaatcac acgccgtcat tttgggcgac acgcgctacg gcggcgaaga aaaaggcact     660

taccacctcg cccttttcgg cgaccgcgcc caagaaatcg ccggctcggc aaccgtgaag     720

ataagggaaa aggttcacga aatcggcatc gccggcaaac agtag                     765


<210> SEQ ID NO 48
<211> LENGTH: 254
<212> TYPE: PRT
<213> ORGANISM: Neisseria meningitidis

<400> SEQUENCE: 48

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
```

-continued 145 150 155 160

Pro Asn Gly Arg Leu His Tyr Ser Ile Asp Phe Thr Lys Lys Gln Gly
165 170 175

Tyr Gly Arg Ile Glu His Leu Lys Thr Pro Glu Gln Asn Val Glu Leu
180 185 190

Ala Ser Ala Glu Leu Lys Ala Asp Glu Lys Ser His Ala Val Ile Leu
195 200 205

Gly Asp Thr Arg Tyr Gly Gly Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Arg Glu Lys Val His Glu Ile Gly Ile Ala Gly Lys Gln
245 250

<210> SEQ ID NO 49
<211> LENGTH: 786
<212> TYPE: DNA
<213> ORGANISM: Neisseria meningitidis

<400> SEQUENCE: 49
tgcagcagcg gaagcggaag cggaggcggc ggtgtcgccg ccgacatcgg cacagggctt 60
gccgatgcac taactgcgcc gctcgaccat aaagacaaag gtttgaaatc cctgacattg 120
gaagactcca tttcccaaaa cggaacactg accctgtcgg cacaaggtgc ggaaaaaact 180
ttcaaagtcg gcgacaaaga caacagtctc aatacaggca aattgaagaa cgacaaaatc 240
agccgcttcg actttgtgca aaaaatcgaa gtggacggac aaaccatcac gctggcaagc 300
ggcgaatttc aaatatacaa acaggaccac tccgccgtcg ttgccctaca gattgaaaaa 360
atcaacaacc ccgacaaaat cgacagcctg ataaaccaac gctccttcct tgtcagcggt 420
ttgggcggag aacataccgc cttcaaccaa ctgcccagcg gcaaagccga gtatcacggc 480
aaagcattca gctccgacga tgccggcgga aaactgacct ataccataga ttttgccgcc 540
aaacagggac acggcaaaat cgaacacctg aaaacacccg agcagaatgt cgagcttgcc 600
tccgccgaac tcaaagcaga tgaaaaatca cacgccgtca ttttgggcga cacgcgctac 660
ggcagcgaag aaaaaggcac ttaccacctc gctcttttcg gcgaccgagc ccaagaaatc 720
gccggctcgg caaccgtgaa gataagggaa aaggttcacg aaatcggcat cgccggcaaa 780
cagtag 786

<210> SEQ ID NO 50
<211> LENGTH: 261
<212> TYPE: PRT
<213> ORGANISM: Neisseria meningitidis

<400> SEQUENCE: 50

Cys Ser Ser Gly Ser Gly Ser Gly Gly Gly Gly Val Ala Ala Asp Ile
1 5 10 15

Gly Thr Gly Leu Ala Asp Ala Leu Thr Ala Pro Leu Asp His Lys Asp
20 25 30

Lys Gly Leu Lys Ser Leu Thr Leu Glu Asp Ser Ile Ser Gln Asn Gly
35 40 45

Thr Leu Thr Leu Ser Ala Gln Gly Ala Glu Lys Thr Phe Lys Val Gly
50 55 60

Asp Lys Asp Asn Ser Leu Asn Thr Gly Lys Leu Lys Asn Asp Lys Ile
65 70 75 80

-continued

```
Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260
```

<210> SEQ ID NO 51
<211> LENGTH: 789
<212> TYPE: DNA
<213> ORGANISM: Neisseria meningitidis

<400> SEQUENCE: 51

```
tgcggatcca gcggaagcgg aagcggaggc ggcggtgtcg ccgccgacat cggcacaggg     60

cttgccgatg cactaactgc gccgctcgac cataaagaca aaggtttgaa atccctgaca    120

ttggaagact ccatttccca aaacggaaca ctgaccctgt cggcacaagg tgcggaaaaa    180

actttcaaag tcggcgacaa agacaacagt ctcaatacag gcaaattgaa gaacgacaaa    240

atcagccgct tcgactttgt gcaaaaaatc gaagtggacg gacaaaccat cacgctggca    300

agcggcgaat ttcaaatata caaacaggac cactccgccg tcgttgccct acagattgaa    360

aaaatcaaca accccgacaa aatcgacagc ctgataaacc aacgctcctt ccttgtcagc    420

ggtttgggcg gagaacatac cgccttcaac caactgccca gcggcaaagc cgagtatcac    480

ggcaaagcat tcagctccga cgatgccggc ggaaaactga cctataccat agattttgcc    540

gccaaacagg gacacggcaa aatcgaacac ctgaaaacac ccgagcagaa tgtcgagctt    600

gcctccgccg aactcaaagc agatgaaaaa tcacacgccg tcattttggg cgacacgcgc    660

tacggcagcg aagaaaaagg cacttaccac ctcgctcttt tcggcgaccg agcccaagaa    720

atcgccggct cggcaaccgt gaagataagg gaaaaggttc acgaaatcgg catcgccggc    780

aaacagtag                                                            789
```

<210> SEQ ID NO 52
<211> LENGTH: 262
<212> TYPE: PRT
<213> ORGANISM: Neisseria meningitidis

<400> SEQUENCE: 52

```
Cys Gly Ser Ser Gly Ser Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Lys Thr Phe Lys Val
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Ser Gly Lys Ala Glu Tyr His
145                 150                 155                 160

Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Arg Glu Lys Val His Glu Ile
                245                 250                 255

Gly Ile Ala Gly Lys Gln
            260
```

<210> SEQ ID NO 53
<211> LENGTH: 786
<212> TYPE: DNA
<213> ORGANISM: Neisseria meningitidis

<400> SEQUENCE: 53

```
atgagcagcg gaagcggaag cggaggcggc ggtgtcgccg ccgacatcgg cacagggctt      60

gccgatgcac taactgcgcc gctcgaccat aaagacaaag gtttgaaatc cctgacattg     120

gaagactcca tttcccaaaa cggaacactg accctgtcgg cacaaggtgc ggaaaaaact     180

ttcaaagtcg gcgacaaaga caacagtctc aatacaggca aattgaagaa cgacaaaatc     240

agccgcttcg actttgtgca aaaaatcgaa gtggacggac aaaccatcac gctggcaagc     300

ggcgaatttc aaatatacaa acaggaccac tccgccgtcg ttgccctaca gattgaaaaa     360

atcaacaacc ccgacaaaat cgacagcctg ataaaccaac gctccttcct tgtcagcggt     420

ttgggcggag aacataccgc cttcaaccaa ctgcccagcg gcaaagccga gtatcacggc     480

aaagcattca gctccgacga tgccggcgga aaactgacct ataccataga ttttgccgcc     540

aaacagggac acggcaaaat cgaacacctg aaaacacccg agcagaatgt cgagcttgcc     600
```

```
tccgccgaac tcaaagcaga tgaaaaatca cacgccgtca ttttgggcga cacgcgctac    660

ggcagcgaag aaaaaggcac ttaccacctc gctcttttcg gcgaccgagc ccaagaaatc    720

gccggctcgg caaccgtgaa gataagggaa aaggttcacg aaatcggcat cgccggcaaa    780

cagtag                                                               786
```

```
<210> SEQ ID NO 54
<211> LENGTH: 261
<212> TYPE: PRT
<213> ORGANISM: Neisseria meningitidis

<400> SEQUENCE: 54

Met Ser Ser Gly Ser Gly Ser Gly Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
                245                 250                 255

Ile Ala Gly Lys Gln
            260
```

```
<210> SEQ ID NO 55
<211> LENGTH: 786
<212> TYPE: DNA
<213> ORGANISM: Neisseria meningitidis

<400> SEQUENCE: 55

tgcagcagcg gaagcggaag cggaggcggc ggtgtcgccg ccgacatcgg cacagggctt     60

gccgatgcac taactgcgcc gctcgaccat aaagacaaag gtttgaaatc cctgacattg    120
```

```
gaagactcca tttcccaaaa cggaacactg accctgtcgg cacaaggtgc ggaaaaaact    180

ttcaaagtcg gcgacaaaga caacagtctc aatacaggca aattgaagaa cgacaaaatc    240

agccgcttcg actttgtgca aaaaatcgaa gtggacggac aaaccatcac gctggcaagc    300

ggcgaatttc aaatatacaa acaggaccac tccgccgtcg ttgccctaca gattgaaaaa    360

atcaacaacc ccgacaaaat cgacagcctg ataaaccaac gctccttcct tgtcagcggt    420

ttgggcggag aacataccgc cttcaaccaa ctgcccagcg gcaaagccga gtatcacggc    480

aaagcattca gctccgacga tgccggcgga aaactgacct ataccataga ttttgccgcc    540

aaacagggac acggcaaaat cgaacacctg aaaacacccg agcagaatgt cgagcttgcc    600

tccgccgaac tcaaagcaga tgaaaaatca cacgccgtca ttttgggcga cacgcgctac    660

ggcagcgaag aaaaaggcac ttaccacctc gctcttttcg gcgaccgagc ccaagaaatc    720

gccggctcgg caaccgtgaa gataagggaa aaggttcacg aaatcggcat cgccggcaaa    780

cagtag                                                                786
```

<210> SEQ ID NO 56
<211> LENGTH: 261
<212> TYPE: PRT
<213> ORGANISM: Neisseria meningitidis

<400> SEQUENCE: 56

```
Cys Ser Ser Gly Ser Gly Ser Gly Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
65                  70                  75                  80

Ser Arg Phe Asp Phe Val Gln Lys Ile Glu Val Asp Gly Gln Thr Ile
                85                  90                  95

Thr Leu Ala Ser Gly Glu Phe Gln Ile Tyr Lys Gln Asp His Ser Ala
            100                 105                 110

Val Val Ala Leu Gln Ile Glu Lys Ile Asn Asn Pro Asp Lys Ile Asp
        115                 120                 125

Ser Leu Ile Asn Gln Arg Ser Phe Leu Val Ser Gly Leu Gly Gly Glu
    130                 135                 140

His Thr Ala Phe Asn Gln Leu Pro Ser Gly Lys Ala Glu Tyr His Gly
145                 150                 155                 160

Lys Ala Phe Ser Ser Asp Asp Ala Gly Gly Lys Leu Thr Tyr Thr Ile
                165                 170                 175

Asp Phe Ala Ala Lys Gln Gly His Gly Lys Ile Glu His Leu Lys Thr
            180                 185                 190

Pro Glu Gln Asn Val Glu Leu Ala Ser Ala Glu Leu Lys Ala Asp Glu
        195                 200                 205

Lys Ser His Ala Val Ile Leu Gly Asp Thr Arg Tyr Gly Ser Glu Glu
    210                 215                 220

Lys Gly Thr Tyr His Leu Ala Leu Phe Gly Asp Arg Ala Gln Glu Ile
225                 230                 235                 240

Ala Gly Ser Ala Thr Val Lys Ile Arg Glu Lys Val His Glu Ile Gly
```

245 250 255

Ile Ala Gly Lys Gln
260

<210> SEQ ID NO 57
<211> LENGTH: 789
<212> TYPE: DNA
<213> ORGANISM: Neisseria meningitidis

<400> SEQUENCE: 57
tgcggatcca gcggaagcgg aagcggaggc ggcggtgtcg ccgccgacat cggcacaggg 60
cttgccgatg cactaactgc gccgctcgac cataaagaca aaggtttgaa atccctgaca 120
ttggaagact ccatttccca aaacggaaca ctgaccctgt cggcacaagg tgcggaaaaa 180
actttcaaag tcggcgacaa agacaacagt ctcaatacag gcaaattgaa gaacgacaaa 240
atcagccgct tcgactttgt gcaaaaaatc gaagtggacg gacaaaccat cacgctggca 300
agcggcgaat ttcaaatata caaacaggac cactccgccg tcgttgccct acagattgaa 360
aaaatcaaca accccgacaa aatcgacagc ctgataaacc aacgctcctt ccttgtcagc 420
ggtttgggcg gagaacatac cgccttcaac caactgccca gcggcaaagc cgagtatcac 480
ggcaaagcat tcagctccga cgatgccggc ggaaaactga cctataccat agattttgcc 540
gccaaacagg gacacggcaa aatcgaacac ctgaaaacac ccgagcagaa tgtcgagctt 600
gcctccgccg aactcaaagc agatgaaaaa tcacacgccg tcattttggg cgacacgcgc 660
tacggcagcg aagaaaaagg cacttaccac ctcgctcttt tcggcgaccg agcccaagaa 720
atcgccggct cggcaaccgt gaagataagg gaaaaggttc acgaaatcgg catcgccggc 780
aaacagtag 789

<210> SEQ ID NO 58
<211> LENGTH: 262
<212> TYPE: PRT
<213> ORGANISM: Neisseria meningitidis

<400> SEQUENCE: 58

Cys Gly Ser Ser Gly Ser Gly Ser Gly Gly Gly Gly Val Ala Ala Asp
1 5 10 15

Ile Gly Thr Gly Leu Ala Asp Ala Leu Thr Ala Pro Leu Asp His Lys
20 25 30

Asp Lys Gly Leu Lys Ser Leu Thr Leu Glu Asp Ser Ile Ser Gln Asn
35 40 45

Gly Thr Leu Thr Leu Ser Ala Gln Gly Ala Glu Lys Thr Phe Lys Val
50 55 60

Gly Asp Lys Asp Asn Ser Leu Asn Thr Gly Lys Leu Lys Asn Asp Lys
65 70 75 80

Ile Ser Arg Phe Asp Phe Val Gln Lys Ile Glu Val Asp Gly Gln Thr
85 90 95

Ile Thr Leu Ala Ser Gly Glu Phe Gln Ile Tyr Lys Gln Asp His Ser
100 105 110

Ala Val Val Ala Leu Gln Ile Glu Lys Ile Asn Asn Pro Asp Lys Ile
115 120 125

Asp Ser Leu Ile Asn Gln Arg Ser Phe Leu Val Ser Gly Leu Gly Gly
130 135 140

Glu His Thr Ala Phe Asn Gln Leu Pro Ser Gly Lys Ala Glu Tyr His
145 150 155 160

```
Gly Lys Ala Phe Ser Ser Asp Asp Ala Gly Gly Lys Leu Thr Tyr Thr
                165                 170                 175

Ile Asp Phe Ala Ala Lys Gln Gly His Gly Lys Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Arg Glu Lys Val His Glu Ile
                245                 250                 255

Gly Ile Ala Gly Lys Gln
            260


<210> SEQ ID NO 59
<211> LENGTH: 786
<212> TYPE: DNA
<213> ORGANISM: Neisseria meningitidis

<400> SEQUENCE: 59

atgagcagcg gaagcggaag cggaggcggc ggtgtcgccg ccgacatcgg cacagggctt      60

gccgatgcac taactgcgcc gctcgaccat aaagacaaag gtttgaaatc cctgacattg     120

gaagactcca tttcccaaaa cggaacactg accctgtcgg cacaaggtgc ggaaaaaact     180

ttcaaagtcg gcgacaaaga caacagtctc aatacaggca aattgaagaa cgacaaaatc     240

agccgcttcg actttgtgca aaaaatcgaa gtggacggac aaaccatcac gctggcaagc     300

ggcgaatttc aaatatacaa acaggaccac tccgccgtcg ttgccctaca gattgaaaaa     360

atcaacaacc ccgacaaaat cgacagcctg ataaaccaac gctccttcct tgtcagcggt     420

ttgggcggag aacataccgc cttcaaccaa ctgcccagcg gcaaagccga gtatcacggc     480

aaagcattca gctccgacga tgccggcgga aaactgacct ataccataga ttttgccgcc     540

aaacagggac acggcaaaat cgaacacctg aaaacacccg agcagaatgt cgagcttgcc     600

tccgccgaac tcaaagcaga tgaaaaatca cacgccgtca ttttgggcga cacgcgctac     660

ggcagcgaag aaaaaggcac ttaccacctc gctcttttcg gcgaccgagc ccaagaaatc     720

gccggctcgg caaccgtgaa gataagggaa aaggttcacg aaatcggcat cgccggcaaa     780

cagtag                                                                786


<210> SEQ ID NO 60
<211> LENGTH: 261
<212> TYPE: PRT
<213> ORGANISM: Neisseria meningitidis

<400> SEQUENCE: 60

Met Ser Ser Gly Ser Gly Ser Gly Gly Gly Gly Val Ala Ala Asp Ile
1               5                   10                  15

Gly Thr Gly Leu Ala Asp Ala Leu Thr Ala Pro Leu Asp His Lys Asp
            20                  25                  30

Lys Gly Leu Lys Ser Leu Thr Leu Glu Asp Ser Ile Ser Gln Asn Gly
        35                  40                  45

Thr Leu Thr Leu Ser Ala Gln Gly Ala Glu Lys Thr Phe Lys Val Gly
    50                  55                  60

Asp Lys Asp Asn Ser Leu Asn Thr Gly Lys Leu Lys Asn Asp Lys Ile
65                  70                  75                  80
```

-continued

Ser Arg Phe Asp Phe Val Gln Lys Ile Glu Val Asp Gly Gln Thr Ile
85 90 95

Thr Leu Ala Ser Gly Glu Phe Gln Ile Tyr Lys Gln Asp His Ser Ala
100 105 110

Val Val Ala Leu Gln Ile Glu Lys Ile Asn Asn Pro Asp Lys Ile Asp
115 120 125

Ser Leu Ile Asn Gln Arg Ser Phe Leu Val Ser Gly Leu Gly Gly Glu
130 135 140

His Thr Ala Phe Asn Gln Leu Pro Ser Gly Lys Ala Glu Tyr His Gly
145 150 155 160

Lys Ala Phe Ser Ser Asp Asp Ala Gly Gly Lys Leu Thr Tyr Thr Ile
165 170 175

Asp Phe Ala Ala Lys Gln Gly His Gly Lys Ile Glu His Leu Lys Thr
180 185 190

Pro Glu Gln Asn Val Glu Leu Ala Ser Ala Glu Leu Lys Ala Asp Glu
195 200 205

Lys Ser His Ala Val Ile Leu Gly Asp Thr Arg Tyr Gly Ser Glu Glu
210 215 220

Lys Gly Thr Tyr His Leu Ala Leu Phe Gly Asp Arg Ala Gln Glu Ile
225 230 235 240

Ala Gly Ser Ala Thr Val Lys Ile Arg Glu Lys Val His Glu Ile Gly
245 250 255

Ile Ala Gly Lys Gln
260

<210> SEQ ID NO 61
<211> LENGTH: 789
<212> TYPE: DNA
<213> ORGANISM: Neisseria meningitidis

<400> SEQUENCE: 61
tgcagcagcg gaggcggcgg aagcggaggc ggcggtgtcg ccgccgacat cggcacgggg 60
cttgccgatg cactaactgc gccgctcgac cataaagaca aaggtttgaa atccctgaca 120
ttggaagact ctattcccca aaacggaaca ctaaccctgt cggcacaagg tgcggaaaaa 180
actttcaaag ccggcgacaa agacaacagc ctcaacacgg gcaaactgaa gaacgacaaa 240
atcagccgct tcgactttgt gcaaaaaatc gaagtggacg gacaaaccat cacgctggca 300
agcggcgaat ttcaaatata caaacaggac cactccgccg tcgttgccct acagattgaa 360
aaaatcaaca accccgacaa aatcgacagc ctgataaacc aacgctcctt ccttgtcagc 420
ggtttgggcg gagaacatac cgccttcaac caactgcccg gcggcaaagc cgagtatcac 480
ggcaaagcat tcagctccga cgacccgaac ggcaggctgc actactccat tgattttacc 540
aaaaaacagg gttacggcgg aatcgaacac ctgaaaacac ccgagcaaaa tgtcgagctt 600
gcctccgccg aactcaaagc agatgaaaaa tcacacgccg tcattttggg cgacacgcgc 660
tacggcagcg aagaaaaagg cacttaccac ctcgcccttt tcggcgaccg cgcccaagaa 720
atcgccggct cggcaaccgt gaagataggg gaaaaggttc acgaaatcgg catcgccggc 780
aaacagtag 789

<210> SEQ ID NO 62
<211> LENGTH: 262
<212> TYPE: PRT
<213> ORGANISM: Neisseria meningitidis

<400> SEQUENCE: 62

Cys Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Gly Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240

Ile Ala Gly Ser Ala Thr Val Lys Ile Gly Glu Lys Val His Glu Ile
                245                 250                 255

Gly Ile Ala Gly Lys Gln
            260

<210> SEQ ID NO 63
<211> LENGTH: 792
<212> TYPE: DNA
<213> ORGANISM: Neisseria meningitidis

<400> SEQUENCE: 63
tgcggatcca gcggaggcgg cggaagcgga ggcggcggtg tcgccgccga catcggcacg 60
gggcttgccg atgcactaac tgcgccgctc gaccataaag acaaaggttt gaaatccctg 120
acattggaag actctattcc ccaaaacgga acactaaccc tgtcggcaca aggtgcggaa 180
aaaactttca aagccggcga caaagacaac agcctcaaca cgggcaaact gaagaacgac 240
aaaatcagcc gcttcgactt tgtgcaaaaa atcgaagtgg acggacaaac catcacgctg 300
gcaagcggcg aatttcaaat atacaaacag gaccactccg ccgtcgttgc cctacagatt 360
gaaaaaatca acaaccccga caaaatcgac agcctgataa accaacgctc cttccttgtc 420
agcggtttgg gcggagaaca taccgccttc aaccaactgc ccggcggcaa agccgagtat 480
cacggcaaag cattcagctc cgacgacccg aacggcaggc tgcactactc cattgatttt 540

```
accaaaaaac agggttacgg cggaatcgaa cacctgaaaa cacccgagca aaatgtcgag    600

cttgcctccg ccgaactcaa agcagatgaa aaatcacacg ccgtcatttt gggcgacacg    660

cgctacggca gcgaagaaaa aggcacttac cacctcgccc ttttcggcga ccgcgcccaa    720

gaaatcgccg gctcggcaac cgtgaagata ggggaaaagg ttcacgaaat cggcatcgcc    780

ggcaaacagt ag                                                        792


<210> SEQ ID NO 64
<211> LENGTH: 263
<212> TYPE: PRT
<213> ORGANISM: Neisseria meningitidis

<400> SEQUENCE: 64

Cys Gly Ser Ser Gly Gly Gly Gly Ser Gly Gly Gly Gly Val Ala Ala
1               5                   10                  15

Asp Ile Gly Thr Gly Leu Ala Asp Ala Leu Thr Ala Pro Leu Asp His
            20                  25                  30

Lys Asp Lys Gly Leu Lys Ser Leu Thr Leu Glu Asp Ser Ile Pro Gln
        35                  40                  45

Asn Gly Thr Leu Thr Leu Ser Ala Gln Gly Ala Glu Lys Thr Phe Lys
    50                  55                  60

Ala Gly Asp Lys Asp Asn Ser Leu Asn Thr Gly Lys Leu Lys Asn Asp
65                  70                  75                  80

Lys Ile Ser Arg Phe Asp Phe Val Gln Lys Ile Glu Val Asp Gly Gln
                85                  90                  95

Thr Ile Thr Leu Ala Ser Gly Glu Phe Gln Ile Tyr Lys Gln Asp His
            100                 105                 110

Ser Ala Val Val Ala Leu Gln Ile Glu Lys Ile Asn Asn Pro Asp Lys
        115                 120                 125

Ile Asp Ser Leu Ile Asn Gln Arg Ser Phe Leu Val Ser Gly Leu Gly
    130                 135                 140

Gly Glu His Thr Ala Phe Asn Gln Leu Pro Gly Gly Lys Ala Glu Tyr
145                 150                 155                 160

His Gly Lys Ala Phe Ser Ser Asp Asp Pro Asn Gly Arg Leu His Tyr
                165                 170                 175

Ser Ile Asp Phe Thr Lys Lys Gln Gly Tyr Gly Gly Ile Glu His Leu
            180                 185                 190

Lys Thr Pro Glu Gln Asn Val Glu Leu Ala Ser Ala Glu Leu Lys Ala
        195                 200                 205

Asp Glu Lys Ser His Ala Val Ile Leu Gly Asp Thr Arg Tyr Gly Ser
    210                 215                 220

Glu Glu Lys Gly Thr Tyr His Leu Ala Leu Phe Gly Asp Arg Ala Gln
225                 230                 235                 240

Glu Ile Ala Gly Ser Ala Thr Val Lys Ile Gly Glu Lys Val His Glu
                245                 250                 255

Ile Gly Ile Ala Gly Lys Gln
            260


<210> SEQ ID NO 65
<211> LENGTH: 789
<212> TYPE: DNA
<213> ORGANISM: Neisseria meningitidis

<400> SEQUENCE: 65

atgagcagcg gaggcggcgg aagcggaggc ggcggtgtcg ccgccgacat cggcacgggg     60
```

-continued

```
cttgccgatg cactaactgc gccgctcgac cataaagaca aaggtttgaa atccctgaca    120

ttggaagact ctattcccca aaacggaaca ctaaccctgt cggcacaagg tgcggaaaaa    180

actttcaaag ccggcgacaa agacaacagc ctcaacacgg gcaaactgaa gaacgacaaa    240

atcagccgct tcgactttgt gcaaaaaatc gaagtggacg gacaaaccat cacgctggca    300

agcggcgaat ttcaaatata caaacaggac cactccgccg tcgttgccct acagattgaa    360

aaaatcaaca accccgacaa aatcgacagc ctgataaacc aacgctcctt ccttgtcagc    420

ggtttgggcg gagaacatac cgccttcaac caactgcccg gcggcaaagc cgagtatcac    480

ggcaaagcat tcagctccga cgacccgaac ggcaggctgc actactccat tgattttacc    540

aaaaaacagg gttacggcgg aatcgaacac ctgaaaacac ccgagcaaaa tgtcgagctt    600

gcctccgccg aactcaaagc agatgaaaaa tcacacgccg tcattttggg cgacacgcgc    660

tacggcagcg aagaaaaagg cacttaccac ctcgcccttt tcggcgaccg cgcccaagaa    720

atcgccggct cggcaaccgt gaagataggg gaaaaggttc acgaaatcgg catcgccggc    780

aaacagtag                                                            789
```

<210> SEQ ID NO 66
<211> LENGTH: 262
<212> TYPE: PRT
<213> ORGANISM: Neisseria meningitidis

<400> SEQUENCE: 66

```
Met Ser Ser Gly Gly Gly Gly Ser Gly Gly Gly Gly Val Ala Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Pro Gln Asn
        35                  40                  45

Gly Thr Leu Thr Leu Ser Ala Gln Gly Ala Glu Lys Thr Phe Lys Ala
    50                  55                  60

Gly Asp Lys Asp Asn Ser Leu Asn Thr Gly Lys Leu Lys Asn Asp Lys
65                  70                  75                  80

Ile Ser Arg Phe Asp Phe Val Gln Lys Ile Glu Val Asp Gly Gln Thr
                85                  90                  95

Ile Thr Leu Ala Ser Gly Glu Phe Gln Ile Tyr Lys Gln Asp His Ser
            100                 105                 110

Ala Val Val Ala Leu Gln Ile Glu Lys Ile Asn Asn Pro Asp Lys Ile
        115                 120                 125

Asp Ser Leu Ile Asn Gln Arg Ser Phe Leu Val Ser Gly Leu Gly Gly
    130                 135                 140

Glu His Thr Ala Phe Asn Gln Leu Pro Gly Gly Lys Ala Glu Tyr His
145                 150                 155                 160

Gly Lys Ala Phe Ser Ser Asp Asp Pro Asn Gly Arg Leu His Tyr Ser
                165                 170                 175

Ile Asp Phe Thr Lys Lys Gln Gly Tyr Gly Gly Ile Glu His Leu Lys
            180                 185                 190

Thr Pro Glu Gln Asn Val Glu Leu Ala Ser Ala Glu Leu Lys Ala Asp
        195                 200                 205

Glu Lys Ser His Ala Val Ile Leu Gly Asp Thr Arg Tyr Gly Ser Glu
    210                 215                 220

Glu Lys Gly Thr Tyr His Leu Ala Leu Phe Gly Asp Arg Ala Gln Glu
225                 230                 235                 240
```

-continued

Ile Ala Gly Ser Ala Thr Val Lys Ile Gly Glu Lys Val His Glu Ile
245 250 255

Gly Ile Ala Gly Lys Gln
260

<210> SEQ ID NO 67
<211> LENGTH: 774
<212> TYPE: DNA
<213> ORGANISM: Neisseria meningitidis

<400> SEQUENCE: 67
tgcagcagcg gaggcggcgg tgtcgccgcc gacatcggcg cggggcttgc cgatgcacta 60
accgcaccgc tcgaccataa agacaaaggt ttgaaatccc tgacattgga agactccatt 120
tcccaaaacg gaacactgac cctgtcggca caaggtgcgg aaaaaacttt caaagtcggc 180
gacaaagaca acagtctcaa tacaggcaaa ttgaagaacg acaaaatcag ccgcttcgac 240
tttgtgcaaa aaatcgaagt ggacggacaa accatcacgc tggcaagcgg cgaatttcaa 300
atatacaaac agaaccactc cgccgtcgtt gccctacaga ttgaaaaaat caacaacccc 360
gacaaaatcg acagcctgat aaaccaacgc tccttccttg tcagcggttt gggcggagaa 420
cataccgcct tcaaccaact gcccggcggc aaagccgagt atcacggcaa agcattcagc 480
tccgacgatg ccggcggaaa actgacctat accatagatt ttgccgccaa acagggacac 540
ggcaaaatcg aacacctgaa aacacccgag caaaatgtcg agcttgccgc cgccgaactc 600
aaagcagatg aaaaatcaca cgccgtcatt ttgggcgaca cgcgctacgg cagcgaagaa 660
aaaggcactt accacctcgc ccttttcggc gaccgcgctc aagaaatcgc cggctcggca 720
accgtgaaga taggagaaaa ggttcacgaa atcagcatcg ccggcaaaca gtag 774

<210> SEQ ID NO 68
<211> LENGTH: 257
<212> TYPE: PRT
<213> ORGANISM: Neisseria meningitidis

<400> SEQUENCE: 68

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Gly Leu Lys
20 25 30

Ser Leu Thr Leu Glu Asp Ser Ile Ser Gln Asn Gly Thr Leu Thr Leu
35 40 45

Ser Ala Gln Gly Ala Glu Lys Thr Phe Lys Val Gly Asp Lys Asp Asn
50 55 60

Ser Leu Asn Thr Gly Lys Leu Lys Asn Asp Lys Ile Ser Arg Phe Asp
65 70 75 80

Phe Val Gln Lys Ile Glu Val Asp Gly Gln Thr Ile Thr Leu Ala Ser
85 90 95

Gly Glu Phe Gln Ile Tyr Lys Gln Asn His Ser Ala Val Val Ala Leu
100 105 110

Gln Ile Glu Lys Ile Asn Asn Pro Asp Lys Ile Asp Ser Leu Ile Asn
115 120 125

Gln Arg Ser Phe Leu Val Ser Gly Leu Gly Gly Glu His Thr Ala Phe
130 135 140

Asn Gln Leu Pro Gly Gly Lys Ala Glu Tyr His Gly Lys Ala Phe Ser
145 150 155 160

Ser Asp Asp Ala Gly Gly Lys Leu Thr Tyr Thr Ile Asp Phe Ala Ala

-continued

```
                165                 170                 175

Lys Gln Gly His Gly Lys Ile Glu His Leu Lys Thr Pro Glu Gln Asn
            180                 185                 190

Val Glu Leu Ala Ala Ala Glu Leu Lys Ala Asp Glu Lys Ser His Ala
        195                 200                 205

Val Ile Leu Gly Asp Thr Arg Tyr Gly Ser Glu Glu Lys Gly Thr Tyr
    210                 215                 220

His Leu Ala Leu Phe Gly Asp Arg Ala Gln Glu Ile Ala Gly Ser Ala
225                 230                 235                 240

Thr Val Lys Ile Gly Glu Lys Val His Glu Ile Ser Ile Ala Gly Lys
                245                 250                 255

Gln


<210> SEQ ID NO 69
<211> LENGTH: 777
<212> TYPE: DNA
<213> ORGANISM: Neisseria meningitidis

<400> SEQUENCE: 69

tgcggatcca gcggaggcgg cggtgtcgcc gccgacatcg gcgcggggct tgccgatgca      60

ctaaccgcac cgctcgacca taaagacaaa ggtttgaaat ccctgacatt ggaagactcc     120

atttcccaaa acggaacact gaccctgtcg gcacaaggtg cggaaaaaac tttcaaagtc     180

ggcgacaaag acaacagtct caatacaggc aaattgaaga acgacaaaat cagccgcttc     240

gactttgtgc aaaaaatcga agtggacgga caaaccatca cgctggcaag cggcgaattt     300

caaatataca aacagaacca ctccgccgtc gttgccctac agattgaaaa aatcaacaac     360

cccgacaaaa tcgacagcct gataaaccaa cgctccttcc ttgtcagcgg tttgggcgga     420

gaacataccg ccttcaacca actgcccggc ggcaaagccg agtatcacgg caaagcattc     480

agctccgacg atgccggcgg aaaactgacc tataccatag attttgccgc caaacaggga     540

cacggcaaaa tcgaacacct gaaaacaccc gagcaaaatg tcgagcttgc cgccgccgaa     600

ctcaaagcag atgaaaaatc acacgccgtc attttgggcg acacgcgcta cggcagcgaa     660

gaaaaaggca cttaccacct cgcccttttc ggcgaccgcg ctcaagaaat cgccggctcg     720

gcaaccgtga agataggaga aaaggttcac gaaatcagca tcgccggcaa acagtag        777


<210> SEQ ID NO 70
<211> LENGTH: 258
<212> TYPE: PRT
<213> ORGANISM: Neisseria meningitidis

<400> SEQUENCE: 70

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Gly Leu
            20                  25                  30

Lys Ser Leu Thr Leu Glu Asp Ser Ile Ser Gln Asn Gly Thr Leu Thr
        35                  40                  45

Leu Ser Ala Gln Gly Ala Glu Lys Thr Phe Lys Val Gly Asp Lys Asp
    50                  55                  60

Asn Ser Leu Asn Thr Gly Lys Leu Lys Asn Asp Lys Ile Ser Arg Phe
65                  70                  75                  80

Asp Phe Val Gln Lys Ile Glu Val Asp Gly Gln Thr Ile Thr Leu Ala
                85                  90                  95
```

```
Ser Gly Glu Phe Gln Ile Tyr Lys Gln Asn His Ser Ala Val Val Ala
            100                 105                 110

Leu Gln Ile Glu Lys Ile Asn Asn Pro Asp Lys Ile Asp Ser Leu Ile
        115                 120                 125

Asn Gln Arg Ser Phe Leu Val Ser Gly Leu Gly Gly Glu His Thr Ala
    130                 135                 140

Phe Asn Gln Leu Pro Gly Gly Lys Ala Glu Tyr His Gly Lys Ala Phe
145                 150                 155                 160

Ser Ser Asp Asp Ala Gly Gly Lys Leu Thr Tyr Thr Ile Asp Phe Ala
                165                 170                 175

Ala Lys Gln Gly His Gly Lys Ile Glu His Leu Lys Thr Pro Glu Gln
            180                 185                 190

Asn Val Glu Leu Ala Ala Ala Glu Leu Lys Ala Asp Glu Lys Ser His
        195                 200                 205

Ala Val Ile Leu Gly Asp Thr Arg Tyr Gly Ser Glu Glu Lys Gly Thr
    210                 215                 220

Tyr His Leu Ala Leu Phe Gly Asp Arg Ala Gln Glu Ile Ala Gly Ser
225                 230                 235                 240

Ala Thr Val Lys Ile Gly Glu Lys Val His Glu Ile Ser Ile Ala Gly
                245                 250                 255

Lys Gln
```

<210> SEQ ID NO 71
<211> LENGTH: 774
<212> TYPE: DNA
<213> ORGANISM: Neisseria meningitidis

<400> SEQUENCE: 71

```
atgagcagcg gaggcggcgg tgtcgccgcc gacatcggcg cggggcttgc cgatgcacta      60

accgcaccgc tcgaccataa agacaaaggt ttgaaatccc tgacattgga agactccatt     120

tcccaaaacg gaacactgac cctgtcggca caaggtgcgg aaaaaacttt caaagtcggc     180

gacaaagaca acagtctcaa tacaggcaaa ttgaagaacg acaaaatcag ccgcttcgac     240

tttgtgcaaa aaatcgaagt ggacggacaa accatcacgc tggcaagcgg cgaatttcaa     300

atatacaaac agaaccactc cgccgtcgtt gccctacaga ttgaaaaaat caacaacccc     360

gacaaaatcg acagcctgat aaaccaacgc tccttccttg tcagcggttt gggcggagaa     420

cataccgcct tcaaccaact gcccggcggc aaagccgagt atcacggcaa agcattcagc     480

tccgacgatg ccggcggaaa actgacctat accatagatt ttgccgccaa acagggacac     540

ggcaaaatcg aacacctgaa aacacccgag caaaatgtcg agcttgccgc cgccgaactc     600

aaagcagatg aaaaatcaca cgccgtcatt ttgggcgaca cgcgctacgg cagcgaagaa     660

aaaggcactt accacctcgc ccttttcggc gaccgcgctc aagaaatcgc cggctcggca     720

accgtgaaga taggagaaaa ggttcacgaa atcagcatcg ccggcaaaca gtag           774
```

<210> SEQ ID NO 72
<211> LENGTH: 257
<212> TYPE: PRT
<213> ORGANISM: Neisseria meningitidis

<400> SEQUENCE: 72

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Lys
            20                  25                  30
```

Ser Leu Thr Leu Glu Asp Ser Ile Ser Gln Asn Gly Thr Leu Thr Leu
35 40 45

Ser Ala Gln Gly Ala Glu Lys Thr Phe Lys Val Gly Asp Lys Asp Asn
50 55 60

Ser Leu Asn Thr Gly Lys Leu Lys Asn Asp Lys Ile Ser Arg Phe Asp
65 70 75 80

Phe Val Gln Lys Ile Glu Val Asp Gly Gln Thr Ile Thr Leu Ala Ser
85 90 95

Gly Glu Phe Gln Ile Tyr Lys Gln Asn His Ser Ala Val Val Ala Leu
100 105 110

Gln Ile Glu Lys Ile Asn Asn Pro Asp Lys Ile Asp Ser Leu Ile Asn
115 120 125

Gln Arg Ser Phe Leu Val Ser Gly Leu Gly Gly Glu His Thr Ala Phe
130 135 140

Asn Gln Leu Pro Gly Gly Lys Ala Glu Tyr His Gly Lys Ala Phe Ser
145 150 155 160

Ser Asp Asp Ala Gly Gly Lys Leu Thr Tyr Thr Ile Asp Phe Ala Ala
165 170 175

Lys Gln Gly His Gly Lys Ile Glu His Leu Lys Thr Pro Glu Gln Asn
180 185 190

Val Glu Leu Ala Ala Ala Glu Leu Lys Ala Asp Glu Lys Ser His Ala
195 200 205

Val Ile Leu Gly Asp Thr Arg Tyr Gly Ser Glu Glu Lys Gly Thr Tyr
210 215 220

His Leu Ala Leu Phe Gly Asp Arg Ala Gln Glu Ile Ala Gly Ser Ala
225 230 235 240

Thr Val Lys Ile Gly Glu Lys Val His Glu Ile Ser Ile Ala Gly Lys
245 250 255

Gln

<210> SEQ ID NO 73
<211> LENGTH: 765
<212> TYPE: DNA
<213> ORGANISM: Neisseria meningitidis

<400> SEQUENCE: 73
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgat 480
gctggcggaa aactgaccta taccatagat ttcgccgcca aacagggaca cggcaaaatc 540
gaacacttga aaacacccga gcaaaatgtc gagcttgcct ccgccgaact caaagcagat 600
gaaaaatcac acgccgtcat tttgggcgac acgcgctacg gcggcgaaga aaaaggcact 660
taccacctcg cccttctcgg cgaccgcgcc caagaaatcg ccggctcggc aaccgtgaag 720
ataagggaaa aggttcacga aatcggcatt gccggcaaac agtag 765

<210> SEQ ID NO 74
<211> LENGTH: 254
<212> TYPE: PRT
<213> ORGANISM: Neisseria meningitidis

<400> SEQUENCE: 74

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Leu Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 75
<211> LENGTH: 768
<212> TYPE: DNA
<213> ORGANISM: Neisseria meningitidis

<400> SEQUENCE: 75

```
tgcggatcca gcggaggcgg cggtgtcgcc gccgacatcg gcgcggggct tgccgatgca     60

ctaaccgcac cgctcgacca taaagacaaa agtttgcagt ctttgacgct ggatcagtcc    120

gtcaggaaaa acgagaaact gaagctggcg gcacaaggtg cggaaaaaac ttatggaaac    180

ggcgacagcc tcaatacggg caaattgaag aacgacaagg tcagccgctt cgactttatc    240

cgtcaaatcg aagtggacgg gcagctcatt accttggaga gcggagagtt ccaaatatac    300

aaacaggacc actccgccgt cgttgcccta cagattgaaa aaatcaacaa ccccgacaaa    360

atcgacagcc tgataaacca acgctccttc cttgtcagcg gtttgggtgg agaacatacc    420

gccttcaacc aactgcccag cggcaaagcc gagtatcacg gcaaagcatt cagctccgac    480
```

```
gatgctggcg gaaaactgac ctataccata gatttcgccg ccaaacaggg acacggcaaa    540

atcgaacact tgaaaacacc cgagcaaaat gtcgagcttg cctccgccga actcaaagca    600

gatgaaaaat cacacgccgt cattttgggc gacacgcgct acggcggcga agaaaaaggc    660

acttaccacc tcgcccttct cggcgaccgc gcccaagaaa tcgccggctc ggcaaccgtg    720

aagataaggg aaaaggttca cgaaatcggc attgccggca aacagtag                 768


<210> SEQ ID NO 76
<211> LENGTH: 255
<212> TYPE: PRT
<213> ORGANISM: Neisseria meningitidis

<400> SEQUENCE: 76

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Ser Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Leu Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255


<210> SEQ ID NO 77
<211> LENGTH: 765
<212> TYPE: DNA
<213> ORGANISM: Neisseria meningitidis

<400> SEQUENCE: 77

atgagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120
```

```
aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgat    480

gctggcggaa aactgaccta taccatagat ttcgccgcca aacagggaca cggcaaaatc    540

gaacacttga aaacacccga gcaaaatgtc gagcttgcct ccgccgaact caaagcagat    600

gaaaaatcac acgccgtcat tttgggcgac acgcgctacg gcggcgaaga aaaaggcact    660

taccacctcg cccttctcgg cgaccgcgcc caagaaatcg ccggctcggc aaccgtgaag    720

ataagggaaa aggttcacga aatcggcatt gccggcaaac agtag                     765


<210> SEQ ID NO 78
<211> LENGTH: 254
<212> TYPE: PRT
<213> ORGANISM: Neisseria meningitidis

<400> SEQUENCE: 78

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Leu Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 79
<211> LENGTH: 765
<212> TYPE: DNA
<213> ORGANISM: Neisseria meningitidis

<400> SEQUENCE: 79

```
tgcagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgat    480

gctggcggaa aactgaccta taccatagat ttcgccgcca aacagggaca cggcaaaatc    540

gaacacttga aaacacccga gcaaaatgtc gagcttgcct ccgccgaact caaagcagat    600

gaaaaatcac acgccgtcat tttgggcgac acgcgctacg gcggcgaaga aaaaggcact    660

taccacctcg cccttttcgg cgaccgcgcc caagaaatcg ccggctcggc aaccgtgaag    720

ataagggaaa aggttcacga aatcggcatc gccggcaaac agtag                    765
```

<210> SEQ ID NO 80
<211> LENGTH: 254
<212> TYPE: PRT
<213> ORGANISM: Neisseria meningitidis

<400> SEQUENCE: 80

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205
```

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 81
<211> LENGTH: 768
<212> TYPE: DNA
<213> ORGANISM: Neisseria meningitidis

<400> SEQUENCE: 81
tgcggatcca gcggaggcgg cggtgtcgcc gccgacatcg gcgcggggct tgccgatgca 60
ctaaccgcac cgctcgacca taaagacaaa agtttgcagt ctttgacgct ggatcagtcc 120
gtcaggaaaa acgagaaact gaagctggcg gcacaaggtg cggaaaaaac ttatggaaac 180
ggcgacagcc tcaatacggg caaattgaag aacgacaagg tcagccgctt cgactttatc 240
cgtcaaatcg aagtggacgg gcagctcatt accttggaga gcggagagtt ccaaatatac 300
aaacaggacc actccgccgt cgttgcccta cagattgaaa aaatcaacaa ccccgacaaa 360
atcgacagcc tgataaacca acgctccttc cttgtcagcg gtttgggtgg agaacatacc 420
gccttcaacc aactgcccag cggcaaagcc gagtatcacg gcaaagcatt cagctccgac 480
gatgctggcg gaaaactgac ctataccata gatttcgccg ccaaacaggg acacggcaaa 540
atcgaacact tgaaaacacc cgagcaaaat gtcgagcttg cctccgccga actcaaagca 600
gatgaaaaat cacacgccgt cattttgggc gacacgcgct acggcggcga agaaaaaggc 660
acttaccacc tcgccctttt cggcgaccgc gcccaagaaa tcgccggctc ggcaaccgtg 720
aagataaggg aaaaggttca cgaaatcggc atcgccggca aacagtag 768

<210> SEQ ID NO 82
<211> LENGTH: 255
<212> TYPE: PRT
<213> ORGANISM: Neisseria meningitidis

<400> SEQUENCE: 82

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

```
Leu Pro Ser Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255


<210> SEQ ID NO 83
<211> LENGTH: 765
<212> TYPE: DNA
<213> ORGANISM: Neisseria meningitidis

<400> SEQUENCE: 83

atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggtggaga acataccgcc     420

ttcaaccaac tgcccagcgg caaagccgag tatcacggca aagcattcag ctccgacgat     480

gctggcggaa aactgaccta taccatagat ttcgccgcca aacagggaca cggcaaaatc     540

gaacacttga aaacacccga gcaaaatgtc gagcttgcct ccgccgaact caaagcagat     600

gaaaaatcac acgccgtcat tttgggcgac acgcgctacg gcggcgaaga aaaaggcact     660

taccacctcg ccctttttcgg cgaccgcgcc caagaaatcg ccggctcggc aaccgtgaag     720

ataagggaaa aggttcacga aatcggcatc gccggcaaac agtag                     765


<210> SEQ ID NO 84
<211> LENGTH: 254
<212> TYPE: PRT
<213> ORGANISM: Neisseria meningitidis

<400> SEQUENCE: 84

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
```

```
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 85
<211> LENGTH: 765
<212> TYPE: DNA
<213> ORGANISM: Neisseria meningitidis

<400> SEQUENCE: 85

```
tgcagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggtggaga acataccgcc     420

ttcaaccaac tgcccagcgg caaagccgag tatcacggca aagcattcag ctccgacgat     480

gctggcggaa aactgaccta taccatagat ttcgccgcca aacagggaca cggcaaaatc     540

gaacacttga aaacacccga gcaaaatgtc gagcttgcct ccgccgaact caaagcagat     600

gaaaaatcac acgccgtcat tttgggcgac acgcgctacg gcggcgaaga aaaaggcact     660

taccacctcg cccttttcgg cgaccgcgcc caagaaatcg ccggctcggc aaccgtgaag     720

ataagggaaa aggttcacga aatcggcatc gccggcaaac agtag                     765
```

<210> SEQ ID NO 86
<211> LENGTH: 254
<212> TYPE: PRT
<213> ORGANISM: Neisseria meningitidis

<400> SEQUENCE: 86

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30
```

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Ser Gly Lys Ala Glu Tyr His Gly Lys Ala Phe Ser Ser Asp Asp
145 150 155 160

Ala Gly Gly Lys Leu Thr Tyr Thr Ile Asp Phe Ala Ala Lys Gln Gly
165 170 175

His Gly Lys Ile Glu His Leu Lys Thr Pro Glu Gln Asn Val Glu Leu
180 185 190

Ala Ser Ala Glu Leu Lys Ala Asp Glu Lys Ser His Ala Val Ile Leu
195 200 205

Gly Asp Thr Arg Tyr Gly Gly Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Arg Glu Lys Val His Glu Ile Gly Ile Ala Gly Lys Gln
245 250

<210> SEQ ID NO 87
<211> LENGTH: 768
<212> TYPE: DNA
<213> ORGANISM: Neisseria meningitidis

<400> SEQUENCE: 87
tgcggatcca gcggaggcgg cggtgtcgcc gccgacatcg gcgcggggct tgccgatgca 60
ctaaccgcac cgctcgacca taaagacaaa agtttgcagt ctttgacgct ggatcagtcc 120
gtcaggaaaa acgagaaact gaagctggcg gcacaaggtg cggaaaaaac ttatggaaac 180
ggcgacagcc tcaatacggg caaattgaag aacgacaagg tcagccgctt cgactttatc 240
cgtcaaatcg aagtggacgg gcagctcatt accttggaga gcggagagtt ccaaatatac 300
aaacaggacc actccgccgt cgttgcccta cagattgaaa aaatcaacaa ccccgacaaa 360
atcgacagcc tgataaacca acgctccttc cttgtcagcg gtttgggtgg agaacatacc 420
gccttcaacc aactgcccag cggcaaagcc gagtatcacg gcaaagcatt cagctccgac 480
gatgctggcg gaaaactgac ctataccata gatttcgccg ccaaacaggg acacggcaaa 540
atcgaacact tgaaaacacc cgagcaaaat gtcgagcttg cctccgccga actcaaagca 600
gatgaaaaat cacacgccgt cattttgggc gacacgcgct acggcggcga agaaaaaggc 660
acttaccacc tcgccctttt cggcgaccgc gcccaagaaa tcgccggctc ggcaaccgtg 720
aagataaggg aaaaggttca cgaaatcggc atcgccggca aacagtag 768

<210> SEQ ID NO 88

<211> LENGTH: 255
<212> TYPE: PRT
<213> ORGANISM: Neisseria meningitidis

<400> SEQUENCE: 88

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Ser Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255
```

<210> SEQ ID NO 89
<211> LENGTH: 765
<212> TYPE: DNA
<213> ORGANISM: Neisseria meningitidis

<400> SEQUENCE: 89

```
atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggtggaga acataccgcc     420

ttcaaccaac tgcccagcgg caaagccgag tatcacggca aagcattcag ctccgacgat     480

gctggcggaa aactgaccta taccatagat ttcgccgcca aacagggaca cggcaaaatc     540
```

-continued

```
gaacacttga aaacacccga gcaaaatgtc gagcttgcct ccgccgaact caaagcagat    600

gaaaaatcac acgccgtcat tttgggcgac acgcgctacg gcggcgaaga aaaaggcact    660

taccacctcg cccttttcgg cgaccgcgcc caagaaatcg ccggctcggc aaccgtgaag    720

ataagggaaa aggttcacga aatcggcatc gccggcaaac agtag                    765
```

<210> SEQ ID NO 90
<211> LENGTH: 254
<212> TYPE: PRT
<213> ORGANISM: Neisseria meningitidis

<400> SEQUENCE: 90

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 91
<211> LENGTH: 765
<212> TYPE: DNA
<213> ORGANISM: Neisseria meningitidis

<400> SEQUENCE: 91

```
tgcagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180
```

-continued gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgat 480
gctggcggaa aactgaccta taccatagat ttcgccgcca aacagggaca cggcaaaatc 540
gaacacttga aaacacccga gcaaaatgtc gagcttgcct ccgccgaact caaagcagat 600
gaaaaatcac acgccgtcat tttgggcgac acgcgctacg gcggcgaaga aaaaggcact 660
taccacctcg ccctttcgg cgaccgcgcc caagaaatcg ccggctcggc aaccgtgaag 720
ataagggaaa aggttcacga aatcggcatc gccggcaaac agtag 765

<210> SEQ ID NO 92
<211> LENGTH: 254
<212> TYPE: PRT
<213> ORGANISM: Neisseria meningitidis

<400> SEQUENCE: 92

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Ser Gly Lys Ala Glu Tyr His Gly Lys Ala Phe Ser Ser Asp Asp
145 150 155 160

Ala Gly Gly Lys Leu Thr Tyr Thr Ile Asp Phe Ala Ala Lys Gln Gly
165 170 175

His Gly Lys Ile Glu His Leu Lys Thr Pro Glu Gln Asn Val Glu Leu
180 185 190

Ala Ser Ala Glu Leu Lys Ala Asp Glu Lys Ser His Ala Val Ile Leu
195 200 205

Gly Asp Thr Arg Tyr Gly Gly Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Arg Glu Lys Val His Glu Ile Gly Ile Ala Gly Lys Gln
245 250

<210> SEQ ID NO 93
<211> LENGTH: 768

<212> TYPE: DNA
<213> ORGANISM: Neisseria meningitidis

<400> SEQUENCE: 93
tgcggatcca gcggaggcgg cggtgtcgcc gccgacatcg gcgcggggct tgccgatgca 60
ctaaccgcac cgctcgacca taaagacaaa agtttgcagt ctttgacgct ggatcagtcc 120
gtcaggaaaa acgagaaact gaagctggcg gcacaaggtg cggaaaaaac ttatggaaac 180
ggcgacagcc tcaatacggg caaattgaag aacgacaagg tcagccgctt cgactttatc 240
cgtcaaatcg aagtggacgg gcagctcatt accttggaga gcggagagtt ccaaatatac 300
aaacaggacc actccgccgt cgttgcccta cagattgaaa aaatcaacaa ccccgacaaa 360
atcgacagcc tgataaacca acgctccttc cttgtcagcg gtttgggtgg agaacatacc 420
gccttcaacc aactgcccag cggcaaagcc gagtatcacg gcaaagcatt cagctccgac 480
gatgctggcg gaaaactgac ctataccata gatttcgccg ccaaacaggg acacggcaaa 540
atcgaacact tgaaaacacc cgagcaaaat gtcgagcttg cctccgccga actcaaagca 600
gatgaaaaat cacacgccgt cattttgggc gacacgcgct acggcggcga agaaaaaggc 660
acttaccacc tcgccctttt cggcgaccgc gcccaagaaa tcgccggctc ggcaaccgtg 720
aagataaggg aaaaggttca cgaaatcggc atcgccggca aacagtag 768

<210> SEQ ID NO 94
<211> LENGTH: 255
<212> TYPE: PRT
<213> ORGANISM: Neisseria meningitidis

<400> SEQUENCE: 94

Cys Gly Ser Ser Gly Gly Gly Gly Val Ala Ala Asp Ile Gly Ala Gly
1 5 10 15

Leu Ala Asp Ala Leu Thr Ala Pro Leu Asp His Lys Asp Lys Ser Leu
20 25 30

Gln Ser Leu Thr Leu Asp Gln Ser Val Arg Lys Asn Glu Lys Leu Lys
35 40 45

Leu Ala Ala Gln Gly Ala Glu Lys Thr Tyr Gly Asn Gly Asp Ser Leu
50 55 60

Asn Thr Gly Lys Leu Lys Asn Asp Lys Val Ser Arg Phe Asp Phe Ile
65 70 75 80

Arg Gln Ile Glu Val Asp Gly Gln Leu Ile Thr Leu Glu Ser Gly Glu
85 90 95

Phe Gln Ile Tyr Lys Gln Asp His Ser Ala Val Val Ala Leu Gln Ile
100 105 110

Glu Lys Ile Asn Asn Pro Asp Lys Ile Asp Ser Leu Ile Asn Gln Arg
115 120 125

Ser Phe Leu Val Ser Gly Leu Gly Gly Glu His Thr Ala Phe Asn Gln
130 135 140

Leu Pro Ser Gly Lys Ala Glu Tyr His Gly Lys Ala Phe Ser Ser Asp
145 150 155 160

Asp Ala Gly Gly Lys Leu Thr Tyr Thr Ile Asp Phe Ala Ala Lys Gln
165 170 175

Gly His Gly Lys Ile Glu His Leu Lys Thr Pro Glu Gln Asn Val Glu
180 185 190

Leu Ala Ser Ala Glu Leu Lys Ala Asp Glu Lys Ser His Ala Val Ile
195 200 205

Leu Gly Asp Thr Arg Tyr Gly Gly Glu Glu Lys Gly Thr Tyr His Leu

-continued

```
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255
```

<210> SEQ ID NO 95
<211> LENGTH: 765
<212> TYPE: DNA
<213> ORGANISM: Neisseria meningitidis

<400> SEQUENCE: 95

```
atgagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgat    480

gctggcggaa aactgaccta taccatagat ttcgccgcca aacagggaca cggcaaaatc    540

gaacacttga aaacacccga gcaaaatgtc gagcttgcct ccgccgaact caaagcagat    600

gaaaaatcac acgccgtcat tttgggcgac acgcgctacg gcggcgaaga aaaaggcact    660

taccacctcg ccctttttcgg cgaccgcgcc caagaaatcg ccggctcggc aaccgtgaag    720

ataagggaaa aggttcacga aatcggcatc gccggcaaac agtag                    765
```

<210> SEQ ID NO 96
<211> LENGTH: 254
<212> TYPE: PRT
<213> ORGANISM: Neisseria meningitidis

<400> SEQUENCE: 96

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160
```

```
Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250


<210> SEQ ID NO 97
<211> LENGTH: 765
<212> TYPE: DNA
<213> ORGANISM: Neisseria meningitidis

<400> SEQUENCE: 97

tgcagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgat    480

gctggcggaa aactgaccta taccatagat ttcgccgcca aacagggaca cggcaaaatc    540

gaacacttga aaacacccga gcaaaatgtc gagcttgcct ccgccgaact caaagcagat    600

gaaaaatcac acgccgtcat tttgggcgac acgcgctacg gcggcgaaga aaaaggcact    660

taccacctcg cccttttcgg cgaccgcgcc caagaaatcg ccggctcggc aaccgtgaag    720

ataagggaaa aggttcacga aatcggcatc gccggcaaac agtaa                    765


<210> SEQ ID NO 98
<211> LENGTH: 254
<212> TYPE: PRT
<213> ORGANISM: Neisseria meningitidis

<400> SEQUENCE: 98

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95
```

-continued

```
Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250
```

<210> SEQ ID NO 99
<211> LENGTH: 768
<212> TYPE: DNA
<213> ORGANISM: Neisseria meningitidis

<400> SEQUENCE: 99

```
tgcggatcca gcggaggcgg cggtgtcgcc gccgacatcg gcgcggggct tgccgatgca      60

ctaaccgcac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc tcaatacggg caaattgaag aacgacaagg tcagccgctt cgactttatc     240

cgtcaaatcg aagtggacgg gcagctcatt accttggaga gcggagagtt ccaaatatac     300

aaacaggacc actccgccgt cgttgcccta cagattgaaa aaatcaacaa ccccgacaaa     360

atcgacagcc tgataaacca acgctccttc cttgtcagcg gtttgggtgg agaacatacc     420

gccttcaacc aactgcccag cggcaaagcc gagtatcacg gcaaagcatt cagctccgac     480

gatgctggcg gaaaactgac ctataccata gatttcgccg ccaaacaggg acacggcaaa     540

atcgaacact tgaaaacacc cgagcaaaat gtcgagcttg cctccgccga actcaaagca     600

gatgaaaaat cacacgccgt cattttgggc gacacgcgct acggcggcga agaaaaaggc     660

acttaccacc tcgccctttt cggcgaccgc gcccaagaaa tcgccggctc ggcaaccgtg     720

aagataaggg aaaaggttca cgaaatcggc atcgccggca aacagtaa                  768
```

<210> SEQ ID NO 100
<211> LENGTH: 255
<212> TYPE: PRT
<213> ORGANISM: Neisseria meningitidis

<400> SEQUENCE: 100

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
```

```
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Ser Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ser Ala Glu Leu Lys Ala Asp Glu Lys Ser His Ala Val Ile
        195                 200                 205

Leu Gly Asp Thr Arg Tyr Gly Gly Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Arg Glu Lys Val His Glu Ile Gly Ile Ala Gly Lys Gln
                245                 250                 255
```

<210> SEQ ID NO 101
<211> LENGTH: 765
<212> TYPE: DNA
<213> ORGANISM: Neisseria meningitidis

<400> SEQUENCE: 101

```
atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggtggaga acataccgcc     420

ttcaaccaac tgcccagcgg caaagccgag tatcacggca aagcattcag ctccgacgat     480

gctggcggaa aactgaccta taccatagat ttcgccgcca aacagggaca cggcaaaatc     540

gaacacttga aaacacccga gcaaaatgtc gagcttgcct ccgccgaact caaagcagat     600

gaaaaatcac acgccgtcat tttgggcgac acgcgctacg gcggcgaaga aaaaggcact     660

taccacctcg ccctttcgg cgaccgcgcc caagaaatcg ccggctcggc aaccgtgaag     720

ataaggggaaa aggttcacga aatcggcatc gccggcaaac agtaa                  765
```

<210> SEQ ID NO 102
<211> LENGTH: 254
<212> TYPE: PRT

<213> ORGANISM: Neisseria meningitidis

<400> SEQUENCE: 102

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Arg Glu Lys Val His Glu Ile Gly Ile Ala Gly Lys Gln
                245                 250

<210> SEQ ID NO 103
<211> LENGTH: 765
<212> TYPE: DNA
<213> ORGANISM: Neisseria meningitidis

<400> SEQUENCE: 103
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctta atacgggcaa attgaagaac gacaaggtca gccgtttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgat 480
gctggcggaa aactgaccta taccatagat ttcgccgcca aacagggaca cggcaaaatc 540
gaacacttga aaacacccga gcaaaatgtc gagcttgcct ccgccgaact caaagcagat 600
gaaaaatcac acgccgtcat tttgggcgac acgcgctacg gcggcgaaga aaaaggcact 660
taccacctcg cccttttcgg cgaccgcgcc caagaaatcg ccggctcggc aaccgtgaag 720
ataagggaaa aggttcacga aatcggcatc gccggcaaac agtag 765

<210> SEQ ID NO 104
<211> LENGTH: 254
<212> TYPE: PRT
<213> ORGANISM: Neisseria meningitidis

<400> SEQUENCE: 104

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Ser Gly Lys Ala Glu Tyr His Gly Lys Ala Phe Ser Ser Asp Asp
145 150 155 160

Ala Gly Gly Lys Leu Thr Tyr Thr Ile Asp Phe Ala Ala Lys Gln Gly
165 170 175

His Gly Lys Ile Glu His Leu Lys Thr Pro Glu Gln Asn Val Glu Leu
180 185 190

Ala Ser Ala Glu Leu Lys Ala Asp Glu Lys Ser His Ala Val Ile Leu
195 200 205

Gly Asp Thr Arg Tyr Gly Gly Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Arg Glu Lys Val His Glu Ile Gly Ile Ala Gly Lys Gln
245 250

<210> SEQ ID NO 105
<211> LENGTH: 768
<212> TYPE: DNA
<213> ORGANISM: Neisseria meningitidis

<400> SEQUENCE: 105
tgcggatcca gcggaggcgg cggtgtcgcc gccgacatcg gcgcggggct tgccgatgca 60
ctaaccgcac cgctcgacca taaagacaaa agtttgcagt ctttgacgct ggatcagtcc 120
gtcaggaaaa acgagaaact gaagctggcg gcacaaggtg cggaaaaaac ttatggaaac 180
ggcgacagcc ttaatacggg caaattgaag aacgacaagg tcagccgttt cgactttatc 240
cgtcaaatcg aagtggacgg gcagctcatt accttggaga gcggagagtt ccaaatatac 300
aaacaggacc actccgccgt cgttgcccta cagattgaaa aaatcaacaa ccccgacaaa 360
atcgacagcc tgataaacca acgctccttc cttgtcagcg gtttgggtgg agaacatacc 420
gccttcaacc aactgcccag cggcaaagcc gagtatcacg gcaaagcatt cagctccgac 480
gatgctggcg gaaaactgac ctataccata gatttcgccg ccaaacaggg acacggcaaa 540
atcgaacact tgaaaacacc cgagcaaaat gtcgagcttg cctccgccga actcaaagca 600
gatgaaaaat cacacgccgt cattttgggc gacacgcgct acggcggcga agaaaaaggc 660
acttaccacc tcgccctttt cggcgaccgc gcccaagaaa tcgccggctc ggcaaccgtg 720
aagataaggg aaaaggttca cgaaatcggc atcgccggca aacagtag 768

<210> SEQ ID NO 106
<211> LENGTH: 255
<212> TYPE: PRT
<213> ORGANISM: Neisseria meningitidis

<400> SEQUENCE: 106

Cys Gly Ser Ser Gly Gly Gly Gly Val Ala Ala Asp Ile Gly Ala Gly
1 5 10 15

Leu Ala Asp Ala Leu Thr Ala Pro Leu Asp His Lys Asp Lys Ser Leu
20 25 30

Gln Ser Leu Thr Leu Asp Gln Ser Val Arg Lys Asn Glu Lys Leu Lys
35 40 45

Leu Ala Ala Gln Gly Ala Glu Lys Thr Tyr Gly Asn Gly Asp Ser Leu
50 55 60

Asn Thr Gly Lys Leu Lys Asn Asp Lys Val Ser Arg Phe Asp Phe Ile
65 70 75 80

Arg Gln Ile Glu Val Asp Gly Gln Leu Ile Thr Leu Glu Ser Gly Glu
85 90 95

Phe Gln Ile Tyr Lys Gln Asp His Ser Ala Val Val Ala Leu Gln Ile
100 105 110

Glu Lys Ile Asn Asn Pro Asp Lys Ile Asp Ser Leu Ile Asn Gln Arg
115 120 125

Ser Phe Leu Val Ser Gly Leu Gly Gly Glu His Thr Ala Phe Asn Gln
130 135 140

Leu Pro Ser Gly Lys Ala Glu Tyr His Gly Lys Ala Phe Ser Ser Asp
145 150 155 160

Asp Ala Gly Gly Lys Leu Thr Tyr Thr Ile Asp Phe Ala Ala Lys Gln
165 170 175

Gly His Gly Lys Ile Glu His Leu Lys Thr Pro Glu Gln Asn Val Glu
180 185 190

Leu Ala Ser Ala Glu Leu Lys Ala Asp Glu Lys Ser His Ala Val Ile
195 200 205

Leu Gly Asp Thr Arg Tyr Gly Gly Glu Glu Lys Gly Thr Tyr His Leu
210 215 220

Ala Leu Phe Gly Asp Arg Ala Gln Glu Ile Ala Gly Ser Ala Thr Val
225 230 235 240

Lys Ile Arg Glu Lys Val His Glu Ile Gly Ile Ala Gly Lys Gln
245 250 255

<210> SEQ ID NO 107
<211> LENGTH: 765
<212> TYPE: DNA
<213> ORGANISM: Neisseria meningitidis

<400> SEQUENCE: 107

```
atgagcagcg gaggcggcgg tgtcgccgcc gacatcggcg cggggcttgc cgatgcacta      60
accgcaccgc tcgaccataa agacaaaagt ttgcagtctt tgacgctgga tcagtccgtc     120
aggaaaaacg agaaactgaa gctggcggca caaggtgcgg aaaaaactta tggaaacggc     180
gacagcctta atacgggcaa attgaagaac gacaaggtca gccgtttcga ctttatccgt     240
caaatcgaag tggacgggca gctcattacc ttggagagcg gagagttcca aatatacaaa     300
caggaccact ccgccgtcgt tgccctacag attgaaaaaa tcaacaaccc cgacaaaatc     360
gacagcctga taaaccaacg ctccttcctt gtcagcggtt tgggtggaga acataccgcc     420
ttcaaccaac tgcccagcgg caaagccgag tatcacggca aagcattcag ctccgacgat     480
gctggcggaa aactgaccta taccatagat ttcgccgcca aacagggaca cggcaaaatc     540
gaacacttga aaacacccga gcaaaatgtc gagcttgcct ccgccgaact caaagcagat     600
gaaaaatcac acgccgtcat tttgggcgac acgcgctacg gcggcgaaga aaaaggcact     660
taccacctcg cccttttcgg cgaccgcgcc caagaaatcg ccggctcggc aaccgtgaag     720
ataagggaaa aggttcacga aatcggcatc gccggcaaac agtag                     765
```

<210> SEQ ID NO 108
<211> LENGTH: 254
<212> TYPE: PRT
<213> ORGANISM: Neisseria meningitidis

<400> SEQUENCE: 108

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ser Ala Glu Leu Lys Ala Asp Glu Lys Ser His Ala Val Ile Leu
        195                 200                 205

Gly Asp Thr Arg Tyr Gly Gly Glu Glu Lys Gly Thr Tyr His Leu Ala
    210                 215                 220
```

Leu Phe Gly Asp Arg Ala Gln Glu Ile Ala Gly Ser Ala Thr Val Lys
225 230 235 240

Ile Arg Glu Lys Val His Glu Ile Gly Ile Ala Gly Lys Gln
245 250

<210> SEQ ID NO 109
<211> LENGTH: 765
<212> TYPE: DNA
<213> ORGANISM: Neisseria meningitidis

<400> SEQUENCE: 109
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg agaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggcggaga acataccgcc 420
ttcaaccaac tgcctgacgg caaagccgag tatcacggca aagcattcag ctccgacgat 480
gctggcggaa aactgaccta taccatagat ttcgccgcca aacagggaca cggcaaaatc 540
gaacacctga aaacacccga gcaaaatgtc gagcttgccg ccgccgaact caaagcagat 600
gaaaaatcac acgccgtcat tttgggcgac acgcgctacg gcagcgaaga aaaaggcact 660
taccacctcg cccttttcgg cgaccgcgcc caagaaatcg ccggctcggc aaccgtgaag 720 atagggggaaa aggttcacga aatcggcatc gccggcaaac agtag 765

<210> SEQ ID NO 110
<211> LENGTH: 254
<212> TYPE: PRT
<213> ORGANISM: Neisseria meningitidis

<400> SEQUENCE: 110

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Asp Gly Lys Ala Glu Tyr His Gly Lys Ala Phe Ser Ser Asp Asp
145 150 155 160

Ala Gly Gly Lys Leu Thr Tyr Thr Ile Asp Phe Ala Ala Lys Gln Gly

-continued

```
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250


<210> SEQ ID NO 111
<211> LENGTH: 768
<212> TYPE: DNA
<213> ORGANISM: Neisseria meningitidis

<400> SEQUENCE: 111

tgcggatcca gcggaggcgg cggtgtcgcc gccgacatcg gcgcggggct tgccgatgca      60

ctaaccgcac cgctcgacca taaagacaaa agtttgcagt ctttgacgct ggatcagtcc     120

gtcaggaaaa acgagaaact gaagctggcg gcacaaggtg cggagaaaac ttatggaaac     180

ggcgacagcc tcaatacggg caaattgaag aacgacaagg tcagccgctt cgactttatc     240

cgtcaaatcg aagtggacgg gcagctcatt accttggaga gcggagagtt ccaaatatac     300

aaacaggacc actccgccgt cgttgcccta cagattgaaa aaatcaacaa ccccgacaaa     360

atcgacagcc tgataaacca acgctccttc cttgtcagcg gtttgggcgg agaacatacc     420

gccttcaacc aactgcctga cggcaaagcc gagtatcacg gcaaagcatt cagctccgac     480

gatgctggcg gaaaactgac ctataccata gatttcgccg ccaaacaggg acacggcaaa     540

atcgaacacc tgaaaacacc cgagcaaaat gtcgagcttg ccgccgccga actcaaagca     600

gatgaaaaat cacacgccgt cattttgggc gacacgcgct acggcagcga agaaaaaggc     660

acttaccacc tcgccctttt cggcgaccgc gcccaagaaa tcgccggctc ggcaaccgtg     720

aagatagggg aaaaggttca cgaaatcggc atcgccggca aacagtag                  768


<210> SEQ ID NO 112
<211> LENGTH: 255
<212> TYPE: PRT
<213> ORGANISM: Neisseria meningitidis

<400> SEQUENCE: 112

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110
```

```
Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205

Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Gly Glu Lys Val His Glu Ile Gly Ile Ala Gly Lys Gln
                245                 250                 255


<210> SEQ ID NO 113
<211> LENGTH: 765
<212> TYPE: DNA
<213> ORGANISM: Neisseria meningitidis

<400> SEQUENCE: 113

atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg agaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggcggaga acataccgcc     420

ttcaaccaac tgcctgacgg caaagccgag tatcacggca aagcattcag ctccgacgat     480

gctggcggaa aactgaccta taccatagat ttcgccgcca aacagggaca cggcaaaatc     540

gaacacctga aaacacccga gcaaaatgtc gagcttgccg ccgccgaact caaagcagat     600

gaaaaatcac acgccgtcat tttgggcgac acgcgctacg gcagcgaaga aaaaggcact     660

taccacctcg cccttttcgg cgaccgcgcc caagaaatcg ccggctcggc aaccgtgaag     720

ataggggaaa aggttcacga aatcggcatc gccggcaaac agtag                     765


<210> SEQ ID NO 114
<211> LENGTH: 254
<212> TYPE: PRT
<213> ORGANISM: Neisseria meningitidis

<400> SEQUENCE: 114

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45
```

-continued

```
Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 115
<211> LENGTH: 765
<212> TYPE: DNA
<213> ORGANISM: Neisseria meningitidis

<400> SEQUENCE: 115

```
tgcagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggcggaga acataccgcc     420

ttcaaccaac tgcctgacgg caaagccgag tatcacggca aagcattcag ctccgacgat     480

gctggcggaa aactgaccta taccatagat ttcgccgcca aacagggaca cggcaaaatc     540

gaacacctga aaacacccga gcaaaatgtc gagcttgccg ccgccgaact caaagcagat     600

gaaaaatcac acgccgtcat tttgggcgac acgcgctacg gcagcgaaga aaaaggcact     660

taccacctcg ccctttttcgg cgaccgcgcc caagaaatcg ccggctcggc aaccgtgaag     720

ataggggaaa aggttcacga aatcggcatc gccggcaaac agtag                     765
```

<210> SEQ ID NO 116
<211> LENGTH: 254
<212> TYPE: PRT
<213> ORGANISM: Neisseria meningitidis

<400> SEQUENCE: 116

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 117
<211> LENGTH: 768
<212> TYPE: DNA
<213> ORGANISM: Neisseria meningitidis

<400> SEQUENCE: 117
tgcggatcca gcggaggcgg cggtgtcgcc gccgacatcg gcgcggggct tgccgatgca 60
ctaaccgcac cgctcgacca taaagacaaa agtttgcagt ctttgacgct ggatcagtcc 120
gtcaggaaaa acgagaaact gaagctggcg gcacaaggtg cggaaaaaac ttatggaaac 180
ggcgacagcc tcaatacggg caaattgaag aacgacaagg tcagccgctt cgactttatc 240
cgtcaaatcg aagtggacgg gcagctcatt accttggaga gcggagagtt ccaaatatac 300
aaacaggacc actccgccgt cgttgcccta cagattgaaa aaatcaacaa ccccgacaaa 360
atcgacagcc tgataaacca acgctccttc cttgtcagcg gtttgggcgg agaacatacc 420
gccttcaacc aactgcctga cggcaaagcc gagtatcacg gcaaagcatt cagctccgac 480
gatgctggcg gaaaactgac ctataccata gatttcgccg ccaaacaggg acacggcaaa 540
atcgaacacc tgaaaacacc cgagcaaaat gtcgagcttg ccgccgccga actcaaagca 600
gatgaaaaat cacacgccgt cattttgggc gacacgcgct acggcagcga agaaaaaggc 660
acttaccacc tcgccctttt cggcgaccgc gcccaagaaa tcgccggctc ggcaaccgtg 720
aagatagggg aaaaggttca cgaaatcggc atcgccggca aacagtag 768

<210> SEQ ID NO 118
<211> LENGTH: 255
<212> TYPE: PRT
<213> ORGANISM: Neisseria meningitidis

<400> SEQUENCE: 118

Cys Gly Ser Ser Gly Gly Gly Gly Val Ala Ala Asp Ile Gly Ala Gly
1 5 10 15

Leu Ala Asp Ala Leu Thr Ala Pro Leu Asp His Lys Asp Lys Ser Leu
20 25 30

Gln Ser Leu Thr Leu Asp Gln Ser Val Arg Lys Asn Glu Lys Leu Lys
35 40 45

Leu Ala Ala Gln Gly Ala Glu Lys Thr Tyr Gly Asn Gly Asp Ser Leu
50 55 60

Asn Thr Gly Lys Leu Lys Asn Asp Lys Val Ser Arg Phe Asp Phe Ile
65 70 75 80

Arg Gln Ile Glu Val Asp Gly Gln Leu Ile Thr Leu Glu Ser Gly Glu
85 90 95

Phe Gln Ile Tyr Lys Gln Asp His Ser Ala Val Val Ala Leu Gln Ile
100 105 110

Glu Lys Ile Asn Asn Pro Asp Lys Ile Asp Ser Leu Ile Asn Gln Arg
115 120 125

Ser Phe Leu Val Ser Gly Leu Gly Gly Glu His Thr Ala Phe Asn Gln
130 135 140

Leu Pro Asp Gly Lys Ala Glu Tyr His Gly Lys Ala Phe Ser Ser Asp
145 150 155 160

Asp Ala Gly Gly Lys Leu Thr Tyr Thr Ile Asp Phe Ala Ala Lys Gln
165 170 175

Gly His Gly Lys Ile Glu His Leu Lys Thr Pro Glu Gln Asn Val Glu
180 185 190

Leu Ala Ala Ala Glu Leu Lys Ala Asp Glu Lys Ser His Ala Val Ile
195 200 205

Leu Gly Asp Thr Arg Tyr Gly Ser Glu Glu Lys Gly Thr Tyr His Leu
210 215 220

Ala Leu Phe Gly Asp Arg Ala Gln Glu Ile Ala Gly Ser Ala Thr Val
225 230 235 240

Lys Ile Gly Glu Lys Val His Glu Ile Gly Ile Ala Gly Lys Gln
245 250 255

<210> SEQ ID NO 119
<211> LENGTH: 765
<212> TYPE: DNA
<213> ORGANISM: Neisseria meningitidis

<400> SEQUENCE: 119
atgagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300

-continued

```
caggaccact ccgccgtcgt tgccctacag attgaaaaaa tcaacaaccc cgacaaaatc    360

gacagcctga taaaccaacg ctccttcctt gtcagcggtt tgggcggaga acataccgcc    420

ttcaaccaac tgcctgacgg caaagccgag tatcacggca aagcattcag ctccgacgat    480

gctggcggaa aactgaccta taccatagat ttcgccgcca aacagggaca cggcaaaatc    540

gaacacctga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg cccttttcgg cgaccgcgcc caagaaatcg ccggctcggc aaccgtgaag    720

atagggggaaa aggttcacga aatcggcatc gccggcaaac agtag                   765
```

<210> SEQ ID NO 120
<211> LENGTH: 254
<212> TYPE: PRT
<213> ORGANISM: Neisseria meningitidis

<400> SEQUENCE: 120

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 121
<211> LENGTH: 765
<212> TYPE: DNA
<213> ORGANISM: Neisseria meningitidis

<400> SEQUENCE: 121
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggcggaga acataccgcc 420
ttcaaccaac tgcctgacgg caaagccgag tatcacggca aagcattcag ctccgacgat 480
gctggcggaa aactgaccta taccatagat ttcgccgcca aacagggaca cggcaaaatc 540
gaacacctga aaacacccga gcaaaatgtc gagcttgccg ccgccgaact caaagcagat 600
gaaaaatcac acgccgtcat tttgggcgac acgcgctacg gcagcgaaga aaaaggcact 660
taccacctcg ccctttttcgg cgaccgcgcc caagaaatcg ccggctcggc aaccgtgaag 720
ataggggaaa aggttcacga aatcggcatc gccggcaaac agtag 765

<210> SEQ ID NO 122
<211> LENGTH: 254
<212> TYPE: PRT
<213> ORGANISM: Neisseria meningitidis

<400> SEQUENCE: 122

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Asp Gly Lys Ala Glu Tyr His Gly Lys Ala Phe Ser Ser Asp Asp
145 150 155 160

Ala Gly Gly Lys Leu Thr Tyr Thr Ile Asp Phe Ala Ala Lys Gln Gly
165 170 175

His Gly Lys Ile Glu His Leu Lys Thr Pro Glu Gln Asn Val Glu Leu
180 185 190

Ala Ala Ala Glu Leu Lys Ala Asp Glu Lys Ser His Ala Val Ile Leu
195 200 205

Gly Asp Thr Arg Tyr Gly Ser Glu Glu Lys Gly Thr Tyr His Leu Ala
210 215 220

Leu Phe Gly Asp Arg Ala Gln Glu Ile Ala Gly Ser Ala Thr Val Lys
225 230 235 240

```
Ile Gly Glu Lys Val His Glu Ile Gly Ile Ala Gly Lys Gln
                245                 250

<210> SEQ ID NO 123
<211> LENGTH: 768
<212> TYPE: DNA
<213> ORGANISM: Neisseria meningitidis

<400> SEQUENCE: 123

tgcggatcca gcggaggcgg cggtgtcgcc gccgacatcg gcgcggggct tgccgatgca      60

ctaaccgcac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc tcaatacggg caaattgaag aacgacaagg tcagccgctt cgactttatc     240

cgtcaaatcg aagtggacgg gcagctcatt accttggaga gcggagagtt ccaaatatac     300

aaacaggacc actccgccgt cgttgcccta cagattgaaa aaatcaacaa ccccgacaaa     360

atcgacagcc tgataaacca acgctccttc cttgtcagcg gtttgggcgg agaacatacc     420

gccttcaacc aactgcctga cggcaaagcc gagtatcacg gcaaagcatt cagctccgac     480

gatgctggcg gaaaactgac ctataccata gatttcgccg ccaaacaggg acacggcaaa     540

atcgaacacc tgaaaacacc cgagcaaaat gtcgagcttg ccgccgccga actcaaagca     600

gatgaaaaat cacacgccgt cattttgggc gacacgcgct acggcagcga agaaaaaggc     660

acttaccacc tcgccctttt cggcgaccgc gcccaagaaa tcgccggctc ggcaaccgtg     720

aagatagggg aaaaggttca cgaaatcggc atcgccggca aacagtag                  768

<210> SEQ ID NO 124
<211> LENGTH: 255
<212> TYPE: PRT
<213> ORGANISM: Neisseria meningitidis

<400> SEQUENCE: 124

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175
```

```
Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205

Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Gly Glu Lys Val His Glu Ile Gly Ile Ala Gly Lys Gln
                245                 250                 255


<210> SEQ ID NO 125
<211> LENGTH: 765
<212> TYPE: DNA
<213> ORGANISM: Neisseria meningitidis

<400> SEQUENCE: 125

atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggcggaga acataccgcc     420

ttcaaccaac tgcctgacgg caaagccgag tatcacggca aagcattcag ctccgacgat     480

gctggcggaa aactgaccta taccatagat ttcgccgcca aacagggaca cggcaaaatc     540

gaacacctga aaacacccga gcaaaatgtc gagcttgccg ccgccgaact caaagcagat     600

gaaaaatcac acgccgtcat tttgggcgac acgcgctacg gcagcgaaga aaaaggcact     660

taccacctcg ccctttttcgg cgaccgcgcc caagaaatcg ccggctcggc aaccgtgaag     720

ataggggaaa aggttcacga aatcggcatc gccggcaaac agtag                     765


<210> SEQ ID NO 126
<211> LENGTH: 254
<212> TYPE: PRT
<213> ORGANISM: Neisseria meningitidis

<400> SEQUENCE: 126

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
```

-continued

```
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 127
<211> LENGTH: 765
<212> TYPE: DNA
<213> ORGANISM: Neisseria meningitidis

<400> SEQUENCE: 127

```
tgcagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggcggaga acataccgcc     420

ttcaaccaac tgcctgacgg caaagccgag tatcacggca aagcattcag ctccgacgat     480

gctggcggaa aactgaccta taccatagat ttcgccgcca aacagggaca cggcaaaatc     540

gaacacctga aaacacccga gcaaaatgtc gagcttgccg ccgccgaact caaagcagat     600

gaaaaatcac acgccgtcat tttgggcgac acgcgctacg gcagcgaaga aaaaggcact     660

taccacctcg ccctttttcgg cgaccgcgcc caagaaatcg ccggctcggc aaccgtgaag     720

ataggggaaa aggttcacga aatcggcatc gccggcaaac agtag                     765
```

<210> SEQ ID NO 128
<211> LENGTH: 254
<212> TYPE: PRT
<213> ORGANISM: Neisseria meningitidis

<400> SEQUENCE: 128

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60
```

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Asp Gly Lys Ala Glu Tyr His Gly Lys Ala Phe Ser Ser Asp Asp
145 150 155 160

Ala Gly Gly Lys Leu Thr Tyr Thr Ile Asp Phe Ala Ala Lys Gln Gly
165 170 175

His Gly Lys Ile Glu His Leu Lys Thr Pro Glu Gln Asn Val Glu Leu
180 185 190

Ala Ala Ala Glu Leu Lys Ala Asp Glu Lys Ser His Ala Val Ile Leu
195 200 205

Gly Asp Thr Arg Tyr Gly Ser Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Gly Glu Lys Val His Glu Ile Gly Ile Ala Gly Lys Gln
245 250

<210> SEQ ID NO 129
<211> LENGTH: 768
<212> TYPE: DNA
<213> ORGANISM: Neisseria meningitidis

<400> SEQUENCE: 129
tgcggatcca gcggaggcgg cggtgtcgcc gccgacatcg gcgcggggct tgccgatgca 60
ctaaccgcac cgctcgacca taaagacaaa agtttgcagt ctttgacgct ggatcagtcc 120
gtcaggaaaa acgagaaact gaagctggcg gcacaaggtg cggaaaaaac ttatggaaac 180
ggcgacagcc tcaatacggg caaattgaag aacgacaagg tcagccgctt cgactttatc 240
cgtcaaatcg aagtggacgg gcagctcatt accttggaga gcggagagtt ccaaatatac 300
aaacaggacc actccgccgt cgttgcccta cagattgaaa aaatcaacaa ccccgacaaa 360
atcgacagcc tgataaacca acgctccttc cttgtcagcg gtttgggcgg agaacatacc 420
gccttcaacc aactgcctga cggcaaagcc gagtatcacg gcaaagcatt cagctccgac 480
gatgctggcg gaaaactgac ctataccata gatttcgccg ccaaacaggg acacggcaaa 540
atcgaacacc tgaaaacacc cgagcaaaat gtcgagcttg ccgccgccga actcaaagca 600
gatgaaaaat cacacgccgt cattttgggc gacacgcgct acggcagcga agaaaaaggc 660
acttaccacc tcgccctttt cggcgaccgc gcccaagaaa tcgccggctc ggcaaccgtg 720
aagatagggg aaaaggttca cgaaatcggc atcgccggca aacagtag 768

<210> SEQ ID NO 130
<211> LENGTH: 255
<212> TYPE: PRT
<213> ORGANISM: Neisseria meningitidis

<400> SEQUENCE: 130

-continued

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205

Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Gly Glu Lys Val His Glu Ile Gly Ile Ala Gly Lys Gln
                245                 250                 255
```

<210> SEQ ID NO 131
<211> LENGTH: 765
<212> TYPE: DNA
<213> ORGANISM: Neisseria meningitidis

<400> SEQUENCE: 131

```
atgagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggcggaga acataccgcc    420

ttcaaccaac tgcctgacgg caaagccgag tatcacggca aagcattcag ctccgacgat    480

gctggcggaa aactgaccta taccatagat ttcgccgcca aacagggaca cggcaaaatc    540

gaacacctga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg ccctttttcgg cgaccgcgcc caagaaatcg ccggctcggc aaccgtgaag    720
```

atagggg aaa aggttcacga aatcggcatc gccggcaaac agtag 765

<210> SEQ ID NO 132
<211> LENGTH: 254
<212> TYPE: PRT
<213> ORGANISM: Neisseria meningitidis

<400> SEQUENCE: 132

Met Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Asp Gly Lys Ala Glu Tyr His Gly Lys Ala Phe Ser Ser Asp Asp
145 150 155 160

Ala Gly Gly Lys Leu Thr Tyr Thr Ile Asp Phe Ala Ala Lys Gln Gly
165 170 175

His Gly Lys Ile Glu His Leu Lys Thr Pro Glu Gln Asn Val Glu Leu
180 185 190

Ala Ala Ala Glu Leu Lys Ala Asp Glu Lys Ser His Ala Val Ile Leu
195 200 205

Gly Asp Thr Arg Tyr Gly Ser Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Gly Glu Lys Val His Glu Ile Gly Ile Ala Gly Lys Gln
245 250

<210> SEQ ID NO 133
<211> LENGTH: 765
<212> TYPE: DNA
<213> ORGANISM: Neisseria meningitidis

<400> SEQUENCE: 133
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360

```
gacagcctga taaaccaacg ctccttcctt gtcagcggtt tgggcggaga acataccgcc    420

ttcaaccaac tgcctgacgg caaagccgag tatcacggca aagcattcag ctccgacgat    480

gctggcggaa aactgaccta taccatagat ttcgccgcca aacagggaca cggcaaaatc    540

gaacacctga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg cccttttcgg cgaccgcgcc caagaaatcg ccggctcggc aaccgtgaag    720

ataggggaaa aggttcacga aatcggcatc gccggcaaac agtaa                    765
```

<210> SEQ ID NO 134
<211> LENGTH: 254
<212> TYPE: PRT
<213> ORGANISM: Neisseria meningitidis

<400> SEQUENCE: 134

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 135
<211> LENGTH: 768
<212> TYPE: DNA
<213> ORGANISM: Neisseria meningitidis

<400> SEQUENCE: 135

```
tgcggatcca gcggaggcgg cggtgtcgcc gccgacatcg gcgcggggct tgccgatgca     60
```

```
ctaaccgcac cgctcgacca taaagacaaa agtttgcagt ctttgacgct ggatcagtcc    120

gtcaggaaaa acgagaaact gaagctggcg gcacaaggtg cggaaaaaac ttatggaaac    180

ggcgacagcc tcaatacggg caaattgaag aacgacaagg tcagccgctt cgactttatc    240

cgtcaaatcg aagtggacgg gcagctcatt accttggaga gcggagagtt ccaaatatac    300

aaacaggacc actccgccgt cgttgcccta cagattgaaa aatcaacaa ccccgacaaa    360

atcgacagcc tgataaacca acgctccttc cttgtcagcg gtttgggcgg agaacatacc    420

gccttcaacc aactgcctga cggcaaagcc gagtatcacg gcaaagcatt cagctccgac    480

gatgctggcg gaaaactgac ctataccata gatttcgccg ccaaacaggg acacggcaaa    540

atcgaacacc tgaaaacacc cgagcaaaat gtcgagcttg ccgccgccga actcaaagca    600

gatgaaaaat cacacgccgt cattttgggc gacacgcgct acggcagcga agaaaaaggc    660

acttaccacc tcgccctttt cggcgaccgc gcccaagaaa tcgccggctc ggcaaccgtg    720

aagatagggg aaaaggttca cgaaatcggc atcgccggca aacagtaa                768
```

```
<210> SEQ ID NO 136
<211> LENGTH: 255
<212> TYPE: PRT
<213> ORGANISM: Neisseria meningitidis

<400> SEQUENCE: 136

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205

Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Gly Glu Lys Val His Glu Ile Gly Ile Ala Gly Lys Gln
```

-continued 245 250 255

<210> SEQ ID NO 137
<211> LENGTH: 765
<212> TYPE: DNA
<213> ORGANISM: Neisseria meningitidis

<400> SEQUENCE: 137
atgagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggcggaga acataccgcc 420
ttcaaccaac tgcctgacgg caaagccgag tatcacggca aagcattcag ctccgacgat 480
gctggcggaa aactgaccta taccatagat ttcgccgcca aacagggaca cggcaaaatc 540
gaacacctga aaacacccga gcaaaatgtc gagcttgccg ccgccgaact caaagcagat 600
gaaaaatcac acgccgtcat tttgggcgac acgcgctacg gcagcgaaga aaaaggcact 660
taccacctcg ccctttttcgg cgaccgcgcc caagaaatcg ccggctcggc aaccgtgaag 720
ataggggaaa aggttcacga aatcggcatc gccggcaaac agtaa 765

<210> SEQ ID NO 138
<211> LENGTH: 254
<212> TYPE: PRT
<213> ORGANISM: Neisseria meningitidis

<400> SEQUENCE: 138

Met Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Asp Gly Lys Ala Glu Tyr His Gly Lys Ala Phe Ser Ser Asp Asp
145 150 155 160

Ala Gly Gly Lys Leu Thr Tyr Thr Ile Asp Phe Ala Ala Lys Gln Gly
165 170 175

His Gly Lys Ile Glu His Leu Lys Thr Pro Glu Gln Asn Val Glu Leu
180 185 190

Ala Ala Ala Glu Leu Lys Ala Asp Glu Lys Ser His Ala Val Ile Leu
195 200 205

Gly Asp Thr Arg Tyr Gly Ser Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Gly Glu Lys Val His Glu Ile Gly Ile Ala Gly Lys Gln
245 250

<210> SEQ ID NO 139
<211> LENGTH: 765
<212> TYPE: DNA
<213> ORGANISM: Neisseria meningitidis

<400> SEQUENCE: 139
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctta atacgggcaa attgaagaac gacaaggtca gccgtttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgat 480
gctggcggaa aactgaccta taccatagat ttcgccacca aacagggaca cggcaaaatc 540
gaacacttga aaacacccga gcaaaatgtc gagcttgccg ccgccgaact caaagcagat 600
gaaaaatcac acgccgtcat tttgggcgac acgcgctacg gcagcgaaga aaaaggcact 660
taccacctcg cccttttcgg cgaccgcgcc caagaaatcg ccggctcggc aaccgtgaag 720
ataggggaaa aggttcacga aatcggcatc gccggcaaac agtag 765

<210> SEQ ID NO 140
<211> LENGTH: 254
<212> TYPE: PRT
<213> ORGANISM: Neisseria meningitidis

<400> SEQUENCE: 140

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Thr Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 141
<211> LENGTH: 768
<212> TYPE: DNA
<213> ORGANISM: Neisseria meningitidis

<400> SEQUENCE: 141
tgcggatcca gcggaggcgg cggtgtcgcc gccgacatcg gcgcggggct tgccgatgca 60
ctaaccgcac cgctcgacca taaagacaaa agtttgcagt ctttgacgct ggatcagtcc 120
gtcaggaaaa acgagaaact gaagctggcg gcacaaggtg cggaaaaaac ttatggaaac 180
ggcgacagcc ttaatacggg caaattgaag aacgacaagg tcagccgttt cgactttatc 240
cgtcaaatcg aagtggacgg gcagctcatt accttggaga gcggagagtt ccaaatatac 300
aaacaggacc actccgccgt cgttgcccta cagattgaaa aatcaacaa ccccgacaaa 360 atcgacagcc tgataaacca acgctccttc cttgtcagcg gtttgggtgg agaacatacc 420
gccttcaacc aactgcccag cggcaaagcc gagtatcacg gcaaagcatt cagctccgac 480
gatgctggcg gaaaactgac ctataccata gatttcgcca ccaaacaggg acacggcaaa 540
atcgaacact tgaaaacacc cgagcaaaat gtcgagcttg ccgccgccga actcaaagca 600
gatgaaaaat cacacgccgt cattttgggc gacacgcgct acggcagcga agaaaaaggc 660
acttaccacc tcgccctttt cggcgaccgc gcccaagaaa tcgccggctc ggcaaccgtg 720
aagatagggg aaaaggttca cgaaatcggc atcgccggca aacagtag 768

<210> SEQ ID NO 142
<211> LENGTH: 255
<212> TYPE: PRT
<213> ORGANISM: Neisseria meningitidis

<400> SEQUENCE: 142

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile

```
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Ser Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Thr Lys Gln
                165                 170                 175

Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205

Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Gly Glu Lys Val His Glu Ile Gly Ile Ala Gly Lys Gln
                245                 250                 255
```

<210> SEQ ID NO 143
<211> LENGTH: 765
<212> TYPE: DNA
<213> ORGANISM: Neisseria meningitidis

<400> SEQUENCE: 143

```
atgagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctta atacgggcaa attgaagaac gacaaggtca gccgtttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgat    480

gctggcggaa aactgaccta taccatagat ttcgccacca aacagggaca cggcaaaatc    540

gaacacttga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg cccttttcgg cgaccgcgcc caagaaatcg ccggctcggc aaccgtgaag    720

atagggggaaa aggttcacga aatcggcatc gccggcaaac agtag                   765
```

<210> SEQ ID NO 144
<211> LENGTH: 254
<212> TYPE: PRT
<213> ORGANISM: Neisseria meningitidis

<400> SEQUENCE: 144

```
Met Ser Ser Gly Gly Gly Gly Val Ala Ala Asp Ile Gly Ala Gly Leu
1               5                   10                  15
```

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Ser Gly Lys Ala Glu Tyr His Gly Lys Ala Phe Ser Ser Asp Asp
145 150 155 160

Ala Gly Gly Lys Leu Thr Tyr Thr Ile Asp Phe Ala Thr Lys Gln Gly
165 170 175

His Gly Lys Ile Glu His Leu Lys Thr Pro Glu Gln Asn Val Glu Leu
180 185 190

Ala Ala Ala Glu Leu Lys Ala Asp Glu Lys Ser His Ala Val Ile Leu
195 200 205

Gly Asp Thr Arg Tyr Gly Ser Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Gly Glu Lys Val His Glu Ile Gly Ile Ala Gly Lys Gln
245 250

<210> SEQ ID NO 145
<211> LENGTH: 765
<212> TYPE: DNA
<213> ORGANISM: Neisseria meningitidis

<400> SEQUENCE: 145
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctta atacgggcaa attgaagaac gacaaggtca gccgtttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgat 480
gctggcggaa aactgaccta taccatagat ttcgccacca aacagggaca cggcaaaatc 540
gaacacttga aaacacccga gcaaaatgtc gagcttgccg ccgccgaact caaagcagat 600
gaaaaatcac acgccgtcat tttgggcgac acgcgctacg gcagcgaaga aaaaggcact 660
taccacctcg ccctttttcgg cgaccgcgcc caagaaatcg ccggctcggc aaccgtgaag 720
ataggggaaa aggttcacga aatcggcatc gccggcaaac agtag 765

<210> SEQ ID NO 146
<211> LENGTH: 254
<212> TYPE: PRT
<213> ORGANISM: Neisseria meningitidis

<400> SEQUENCE: 146

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Ser Gly Lys Ala Glu Tyr His Gly Lys Ala Phe Ser Ser Asp Asp
145 150 155 160

Ala Gly Gly Lys Leu Thr Tyr Thr Ile Asp Phe Ala Thr Lys Gln Gly
165 170 175

His Gly Lys Ile Glu His Leu Lys Thr Pro Glu Gln Asn Val Glu Leu
180 185 190

Ala Ala Ala Glu Leu Lys Ala Asp Glu Lys Ser His Ala Val Ile Leu
195 200 205

Gly Asp Thr Arg Tyr Gly Ser Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Gly Glu Lys Val His Glu Ile Gly Ile Ala Gly Lys Gln
245 250

<210> SEQ ID NO 147
<211> LENGTH: 768
<212> TYPE: DNA
<213> ORGANISM: Neisseria meningitidis

<400> SEQUENCE: 147
tgcggatcca gcggaggcgg cggtgtcgcc gccgacatcg gcgcggggct tgccgatgca 60
ctaaccgcac cgctcgacca taaagacaaa agtttgcagt ctttgacgct ggatcagtcc 120
gtcaggaaaa acgagaaact gaagctggcg gcacaaggtg cggaaaaaac ttatggaaac 180
ggcgacagcc ttaatacggg caaattgaag aacgacaagg tcagccgttt cgactttatc 240
cgtcaaatcg aagtggacgg gcagctcatt accttggaga gcggagagtt ccaaatatac 300
aaacaggacc actccgccgt cgttgcccta cagattgaaa aaatcaacaa ccccgacaaa 360
atcgacagcc tgataaacca acgctccttc cttgtcagcg gtttgggtgg agaacatacc 420

-continued

```
gccttcaacc aactgcccag cggcaaagcc gagtatcacg gcaaagcatt cagctccgac    480

gatgctggcg gaaaactgac ctataccata gatttcgcca ccaaacaggg acacggcaaa    540

atcgaacact tgaaaacacc cgagcaaaat gtcgagcttg ccgccgccga actcaaagca    600

gatgaaaaat cacacgccgt cattttgggc gacacgcgct acggcagcga agaaaaaggc    660

acttaccacc tcgccctttt cggcgaccgc gcccaagaaa tcgccggctc ggcaaccgtg    720

aagatagggg aaaaggttca cgaaatcggc atcgccggca aacagtag                 768


<210> SEQ ID NO 148
<211> LENGTH: 255
<212> TYPE: PRT
<213> ORGANISM: Neisseria meningitidis

<400> SEQUENCE: 148

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Ser Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Thr Lys Gln
                165                 170                 175

Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205

Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Gly Glu Lys Val His Glu Ile Gly Ile Ala Gly Lys Gln
                245                 250                 255


<210> SEQ ID NO 149
<211> LENGTH: 765
<212> TYPE: DNA
<213> ORGANISM: Neisseria meningitidis

<400> SEQUENCE: 149

atgagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120
```

```
aggaaaaacg agaaactgaa gctggcggca caaggtgcgg aaaaaactta tggaaacggc    180

gacagcctta atacgggcaa attgaagaac gacaaggtca gccgtttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggtggaga acataccgcc    420

ttcaaccaac tgcccagcgg caaagccgag tatcacggca aagcattcag ctccgacgat    480

gctggcggaa aactgaccta taccatagat ttcgccacca aacagggaca cggcaaaatc    540

gaacacttga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg cccttttcgg cgaccgcgcc caagaaatcg ccggctcggc aaccgtgaag    720

ataggggaaa aggttcacga aatcggcatc gccggcaaac agtag                    765
```

```
<210> SEQ ID NO 150
<211> LENGTH: 254
<212> TYPE: PRT
<213> ORGANISM: Neisseria meningitidis

<400> SEQUENCE: 150

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Thr Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 151
<211> LENGTH: 765
<212> TYPE: DNA
<213> ORGANISM: Neisseria meningitidis

<400> SEQUENCE: 151
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctta atacgggcaa attgaagaac gacaaggtca gccgtttcga ctttatccgt 240
caaatcgaag tggacgggca gctcattacc ttggagagcg gagagttcca aatatacaaa 300
caggaccact ccgccgtcgt tgccctacag attgaaaaaa tcaacaaccc cgacaaaatc 360
gacagcctga taaaccaacg ctccttcctt gtcagcggtt tgggtggaga acataccgcc 420
ttcaaccaac tgcccagcgg caaagccgag tatcacggca aagcattcag ctccgacgat 480
gctggcggaa aactgaccta taccatagat ttcgccacca aacagggaca cggcaaaatc 540
gaacacttga aaacacccga gcaaaatgtc gagcttgccg ccgccgaact caaagcagat 600
gaaaaatcac acgccgtcat tttgggcgac acgcgctacg gcagcgaaga aaaaggcact 660
taccacctcg cccttttcgg cgaccgcgcc caagaaatcg ccggctcggc aaccgtgaag 720
ataggggaaa aggttcacga aatcggcatc gccggcaaac agtag 765

<210> SEQ ID NO 152
<211> LENGTH: 254
<212> TYPE: PRT
<213> ORGANISM: Neisseria meningitidis

<400> SEQUENCE: 152

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Ser Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Thr Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu

-continued

```
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250


<210> SEQ ID NO 153
<211> LENGTH: 768
<212> TYPE: DNA
<213> ORGANISM: Neisseria meningitidis

<400> SEQUENCE: 153

tgcggatcca gcggaggcgg cggtgtcgcc gccgacatcg gcgcggggct tgccgatgca      60

ctaaccgcac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc ttaatacggg caaattgaag aacgacaagg tcagccgttt cgactttatc     240

cgtcaaatcg aagtggacgg gcagctcatt accttggaga gcggagagtt ccaaatatac     300

aaacaggacc actccgccgt cgttgcccta cagattgaaa aatcaacaa ccccgacaaa      360

atcgacagcc tgataaacca acgctccttc cttgtcagcg gtttgggtgg agaacatacc     420

gccttcaacc aactgcccag cggcaaagcc gagtatcacg gcaaagcatt cagctccgac     480

gatgctggcg gaaaactgac ctataccata gatttcgcca ccaaacaggg acacggcaaa     540

atcgaacact tgaaaacacc cgagcaaaat gtcgagcttg ccgccgccga actcaaagca     600

gatgaaaaat cacacgccgt cattttgggc gacacgcgct acggcagcga agaaaaaggc     660

acttaccacc tcgccctttt cggcgaccgc gcccaagaaa tcgccggctc ggcaaccgtg     720

aagatagggg aaaaggttca cgaaatcggc atcgccggca aacagtag                  768


<210> SEQ ID NO 154
<211> LENGTH: 255
<212> TYPE: PRT
<213> ORGANISM: Neisseria meningitidis

<400> SEQUENCE: 154

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140
```

```
Leu Pro Ser Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Thr Lys Gln
                165                 170                 175

Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205

Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Gly Glu Lys Val His Glu Ile Gly Ile Ala Gly Lys Gln
                245                 250                 255


<210> SEQ ID NO 155
<211> LENGTH: 765
<212> TYPE: DNA
<213> ORGANISM: Neisseria meningitidis

<400> SEQUENCE: 155

atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctta atacgggcaa attgaagaac gacaaggtca gccgtttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggtggaga acataccgcc     420

ttcaaccaac tgcccagcgg caaagccgag tatcacggca aagcattcag ctccgacgat     480

gctggcggaa aactgaccta taccatagat ttcgccacca aacagggaca cggcaaaatc     540

gaacacttga aaacacccga gcaaaatgtc gagcttgccg ccgccgaact caaagcagat     600

gaaaaatcac acgccgtcat tttgggcgac acgcgctacg gcagcgaaga aaaaggcact     660

taccacctcg ccctttttcgg cgaccgcgcc caagaaatcg ccggctcggc aaccgtgaag     720

ataggggaaa aggttcacga aatcggcatc gccggcaaac agtag                     765


<210> SEQ ID NO 156
<211> LENGTH: 254
<212> TYPE: PRT
<213> ORGANISM: Neisseria meningitidis

<400> SEQUENCE: 156

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80
```

-continued

Gln Ile Glu Val Asp Gly Gln Leu Ile Thr Leu Glu Ser Gly Glu Phe
85 90 95

Gln Ile Tyr Lys Gln Asp His Ser Ala Val Val Ala Leu Gln Ile Glu
100 105 110

Lys Ile Asn Asn Pro Asp Lys Ile Asp Ser Leu Ile Asn Gln Arg Ser
115 120 125

Phe Leu Val Ser Gly Leu Gly Gly Glu His Thr Ala Phe Asn Gln Leu
130 135 140

Pro Ser Gly Lys Ala Glu Tyr His Gly Lys Ala Phe Ser Ser Asp Asp
145 150 155 160

Ala Gly Gly Lys Leu Thr Tyr Thr Ile Asp Phe Ala Thr Lys Gln Gly
165 170 175

His Gly Lys Ile Glu His Leu Lys Thr Pro Glu Gln Asn Val Glu Leu
180 185 190

Ala Ala Ala Glu Leu Lys Ala Asp Glu Lys Ser His Ala Val Ile Leu
195 200 205

Gly Asp Thr Arg Tyr Gly Ser Glu Glu Lys Gly Thr Tyr His Leu Ala
210 215 220

Leu Phe Gly Asp Arg Ala Gln Glu Ile Ala Gly Ser Ala Thr Val Lys
225 230 235 240

Ile Gly Glu Lys Val His Glu Ile Gly Ile Ala Gly Lys Gln
245 250

<210> SEQ ID NO 157
<211> LENGTH: 765
<212> TYPE: DNA
<213> ORGANISM: Neisseria meningitidis

<400> SEQUENCE: 157
tgcagcagcg gaggcggcgg tgtcgccgcc gacatcggcg cggggcttgc cgatgcacta 60
accgcaccgc tcgactataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca aatatacaaa 300
caggaccact ccgccgtcgt tgccctatag attgaaaaaa tcaacaaccc cgacaaaatc 360
gacagcctga taaaccaacg ctccttcctt gtcagcggtt tgggtggaga acataccgcc 420
ttcaaccaac tgcccggcgg caaagccgag tatcacggca aagcattcag ctccgacgat 480
gctggcggaa aactgaccta taccatagat ttcgccgcca aacagggaca cggcaaaatc 540
gaacacctga aaacacccga gcaaaatgtc gagcttgccg ccgccgaact caaagcagat 600
gaaaaatcac acgccgtcat tttgggcgac acgcgctacg gcagcgaaga aaaaggcact 660
taccacctcg cccttttcgg cgaccgcgct caagaaatcg ccggctcggc aaccgtgaag 720
ataggggaaa aggttcacga aatcggcatc gccggcaaac agtag 765

<210> SEQ ID NO 158
<211> LENGTH: 253
<212> TYPE: PRT
<213> ORGANISM: Neisseria meningitidis

<400> SEQUENCE: 158

Cys Ser Ser Gly Gly Gly Gly Val Ala Ala Asp Ile Gly Ala Gly Leu
1 5 10 15

Ala Asp Ala Leu Thr Ala Pro Leu Asp Tyr Lys Asp Lys Ser Leu Gln

-continued

```
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Ile Glu Lys
            100                 105                 110

Ile Asn Asn Pro Asp Lys Ile Asp Ser Leu Ile Asn Gln Arg Ser Phe
        115                 120                 125

Leu Val Ser Gly Leu Gly Gly Glu His Thr Ala Phe Asn Gln Leu Pro
    130                 135                 140

Gly Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
            180                 185                 190

Ala Ala Glu Leu Lys Ala Asp Glu Lys Ser His Ala Val Ile Leu Gly
        195                 200                 205

Asp Thr Arg Tyr Gly Ser Glu Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Gly Glu Lys Val His Glu Ile Gly Ile Ala Gly Lys Gln
                245                 250
```

<210> SEQ ID NO 159
<211> LENGTH: 768
<212> TYPE: DNA
<213> ORGANISM: Neisseria meningitidis

<400> SEQUENCE: 159

```
tgcggatcca gcggaggcgg cggtgtcgcc gccgacatcg gcgcggggct tgccgatgca     60

ctaaccgcac cgctcgacta taaagacaaa agtttgcagt ctttgacgct ggatcagtcc    120

gtcaggaaaa acgagaaact gaagctggcg gcacaaggtg cggaaaaaac ttatggaaac    180

ggcgacagcc tcaatacggg caaattgaag aacgacaagg tcagccgctt cgactttatc    240

cgtcaaatcg aagtggacgg gcagctcatt accttggaga gcggagagtt ccaaatatac    300

aaacaggacc actccgccgt cgttgcccta tagattgaaa aatcaacaa ccccgacaaa    360

atcgacagcc tgataaacca acgctccttc cttgtcagcg gtttgggtgg agaacatacc    420

gccttcaacc aactgcccgg cggcaaagcc gagtatcacg gcaaagcatt cagctccgac    480

gatgctggcg gaaaactgac ctataccata gatttcgccg ccaaacaggg acacggcaaa    540

atcgaacacc tgaaaacacc cgagcaaaat gtcgagcttg ccgccgccga actcaaagca    600

gatgaaaaat cacacgccgt cattttgggc gacacgcgct acggcagcga agaaaaaggc    660

acttaccacc tcgccctttt cggcgaccgc gctcaagaaa tcgccggctc ggcaaccgtg    720

aagatagggg aaaaggttca cgaaatcggc atcgccggca aacagtag                 768
```

-continued

<210> SEQ ID NO 160
<211> LENGTH: 254
<212> TYPE: PRT
<213> ORGANISM: Neisseria meningitidis

<400> SEQUENCE: 160

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp Tyr Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Gly Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250
```

<210> SEQ ID NO 161
<211> LENGTH: 765
<212> TYPE: DNA
<213> ORGANISM: Neisseria meningitidis

<400> SEQUENCE: 161

```
atgagcagcg gaggcggcgg tgtcgccgcc gacatcggcg cggggcttgc cgatgcacta     60

accgcaccgc tcgactataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctatag attgaaaaaa tcaacaaccc cgacaaaatc    360

gacagcctga taaaccaacg ctccttcctt gtcagcggtt tgggtggaga acataccgcc    420

ttcaaccaac tgcccggcgg caaagccgag tatcacggca aagcattcag ctccgacgat    480
```

```
gctggcggaa aactgaccta taccatagat ttcgccgcca aacagggaca cggcaaaatc    540

gaacacctga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg cccttttcgg cgaccgcgct caagaaatcg ccggctcggc aaccgtgaag    720

ataggggaaa aggttcacga aatcggcatc gccggcaaac agtag                    765
```

```
<210> SEQ ID NO 162
<211> LENGTH: 253
<212> TYPE: PRT
<213> ORGANISM: Neisseria meningitidis

<400> SEQUENCE: 162

Met Ser Ser Gly Gly Gly Gly Val Ala Ala Asp Ile Gly Ala Gly Leu
1               5                   10                  15

Ala Asp Ala Leu Thr Ala Pro Leu Asp Tyr Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Ile Glu Lys
            100                 105                 110

Ile Asn Asn Pro Asp Lys Ile Asp Ser Leu Ile Asn Gln Arg Ser Phe
        115                 120                 125

Leu Val Ser Gly Leu Gly Gly Glu His Thr Ala Phe Asn Gln Leu Pro
    130                 135                 140

Gly Gly Lys Ala Glu Tyr His Gly Lys Ala Phe Ser Ser Asp Asp Ala
145                 150                 155                 160

Gly Gly Lys Leu Thr Tyr Thr Ile Asp Phe Ala Ala Lys Gln Gly His
                165                 170                 175

Gly Lys Ile Glu His Leu Lys Thr Pro Glu Gln Asn Val Glu Leu Ala
            180                 185                 190

Ala Ala Glu Leu Lys Ala Asp Glu Lys Ser His Ala Val Ile Leu Gly
        195                 200                 205

Asp Thr Arg Tyr Gly Ser Glu Glu Lys Gly Thr Tyr His Leu Ala Leu
    210                 215                 220

Phe Gly Asp Arg Ala Gln Glu Ile Ala Gly Ser Ala Thr Val Lys Ile
225                 230                 235                 240

Gly Glu Lys Val His Glu Ile Gly Ile Ala Gly Lys Gln
                245                 250
```

```
<210> SEQ ID NO 163
<211> LENGTH: 765
<212> TYPE: DNA
<213> ORGANISM: Neisseria meningitidis

<400> SEQUENCE: 163

tgcagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180
```

-continued

```
gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccgacg ctccttcctt gtcagcggtt tgggcggaga acataccgcc    420

ttcaaccaac tgcctgacgg caaagccgag tatcacggca aagcattcag ctccgacgat    480

gctggcggaa aactgaccta taccatagat ttcgccgcca aacagggaca cggcaaaatc    540

gaacacctga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg cccttttcgg cgaccgcgcc caagaaatcg ccggctcggc aaccgtgaag    720

ataggggaaa aggttcacga aatcggcatc gccggcaaac agtag                    765
```

```
<210> SEQ ID NO 164
<211> LENGTH: 254
<212> TYPE: PRT
<213> ORGANISM: Neisseria meningitidis

<400> SEQUENCE: 164

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Arg Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250

<210> SEQ ID NO 165
```

<211> LENGTH: 768
<212> TYPE: DNA
<213> ORGANISM: Neisseria meningitidis

<400> SEQUENCE: 165

```
tgcggatcca gcggaggcgg cggtgtcgcc gccgacatcg gcgcggggct tgccgatgca     60

ctaaccgcac cgctcgacca taaagacaaa agtttgcagt ctttgacgct ggatcagtcc    120

gtcaggaaaa acgagaaact gaagctggcg gcacaaggtg cggaaaaaac ttatggaaac    180

ggcgacagcc tcaatacggg caaattgaag aacgacaagg tcagccgctt cgactttatc    240

cgtcaaatcg aagtggacgg gcagctcatt accttggaga gcggagagtt ccaaatatac    300

aaacaggacc actccgccgt cgttgcccta cagattgaaa aaatcaacaa ccccgacaaa    360

atcgacagcc tgataaaccg acgctccttc cttgtcagcg gtttgggcgg agaacatacc    420

gccttcaacc aactgcctga cggcaaagcc gagtatcacg gcaaagcatt cagctccgac    480

gatgctggcg gaaaactgac ctataccata gatttcgccg ccaaacaggg acacggcaaa    540

atcgaacacc tgaaaacacc cgagcaaaat gtcgagcttg ccgccgccga actcaaagca    600

gatgaaaaat cacacgccgt cattttgggc gacacgcgct acggcagcga agaaaaaggc    660

acttaccacc tcgccctttt cggcgaccgc gcccaagaaa tcgccggctc ggcaaccgtg    720

aagataggg aaaaggttca cgaaatcggc atcgccggca aacagtag                 768
```

<210> SEQ ID NO 166
<211> LENGTH: 255
<212> TYPE: PRT
<213> ORGANISM: Neisseria meningitidis

<400> SEQUENCE: 166

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Arg Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205
```

```
Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Lys Ile Gly Glu Lys Val His Glu Ile Gly Ile Ala Gly Lys Gln
                245                 250                 255
```

<210> SEQ ID NO 167
<211> LENGTH: 765
<212> TYPE: DNA
<213> ORGANISM: Neisseria meningitidis

<400> SEQUENCE: 167

```
atgagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccgacg ctccttcctt gtcagcggtt tgggcggaga acataccgcc    420

ttcaaccaac tgcctgacgg caaagccgag tatcacggca aagcattcag ctccgacgat    480

gctggcggaa aactgaccta taccatagat ttcgccgcca aacagggaca cggcaaaatc    540

gaacacctga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg cccttttcgg cgaccgcgcc caagaaatcg ccggctcggc aaccgtgaag    720

ataggggaaa aggttcacga aatcggcatc gccggcaaac agtag                    765
```

<210> SEQ ID NO 168
<211> LENGTH: 254
<212> TYPE: PRT
<213> ORGANISM: Neisseria meningitidis

<400> SEQUENCE: 168

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Arg Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
```

-continued

```
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Lys
225                 230                 235                 240

Ile Gly Glu Lys Val His Glu Ile Gly Ile Ala Gly Lys Gln
                245                 250


<210> SEQ ID NO 169
<211> LENGTH: 765
<212> TYPE: DNA
<213> ORGANISM: Neisseria meningitidis

<400> SEQUENCE: 169

tgcagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacgggca gctcattacc ttggagagcg gagagttcca aatatacaaa     300

caggaccact ccgccgtcgt tgccctacag attgaaaaaa tcaacaaccc cgacaaaatc     360

gacagcctga taaaccaacg ctccttcctt gtcagcggtt tgggcggaga acataccgcc     420

ttcaaccaac tgcctgacgg caaagccgag tatcacggca aagcattcag ctccgacgat     480

gctggcggaa aactgaccta taccatagat ttcgccgcca aacagggaca cggcaaaatc     540

gaacacctga aaacacccga gcaaaatgtc gagcttgccg ccgccgaact caaagcagat     600

gaaaaatcac acgccgtcat tttgggcgac acgcgctacg gcagcgaaga aaaaggcact     660

taccacctcg ccctttcgg cgaccgcgcc caagaaatcg ccggctcggc aaccgtggag      720

atagggaaa aggttcacga aatcggcatc gccggcaaac agtag                      765


<210> SEQ ID NO 170
<211> LENGTH: 254
<212> TYPE: PRT
<213> ORGANISM: Neisseria meningitidis

<400> SEQUENCE: 170

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95
```

```
Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Glu
225                 230                 235                 240

Ile Gly Glu Lys Val His Glu Ile Gly Ile Ala Gly Lys Gln
                245                 250


<210> SEQ ID NO 171
<211> LENGTH: 768
<212> TYPE: DNA
<213> ORGANISM: Neisseria meningitidis

<400> SEQUENCE: 171

tgcggatcca gcggaggcgg cggtgtcgcc gccgacatcg gcgcggggct tgccgatgca      60

ctaaccgcac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc tcaatacggg caaattgaag aacgacaagg tcagccgctt cgactttatc     240

cgtcaaatcg aagtggacgg gcagctcatt accttggaga gcggagagtt ccaaatatac     300

aaacaggacc actccgccgt cgttgcccta cagattgaaa aaatcaacaa ccccgacaaa     360

atcgacagcc tgataaacca acgctccttc cttgtcagcg gtttgggcgg agaacatacc     420

gccttcaacc aactgcctga cggcaaagcc gagtatcacg gcaaagcatt cagctccgac     480

gatgctggcg gaaaactgac ctataccata gatttcgccg ccaaacaggg acacggcaaa     540

atcgaacacc tgaaaacacc cgagcaaaat gtcgagcttg ccgccgccga actcaaagca     600

gatgaaaaat cacacgccgt cattttgggc gacacgcgct acggcagcga agaaaaaggc     660

acttaccacc tcgccctttt cggcgaccgc gcccaagaaa tcgccggctc ggcaaccgtg     720

gagataggggg aaaaggttca cgaaatcggc atcgccggca aacagtag                768


<210> SEQ ID NO 172
<211> LENGTH: 255
<212> TYPE: PRT
<213> ORGANISM: Neisseria meningitidis

<400> SEQUENCE: 172

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30
```

-continued

```
Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Ile Tyr Lys Gln Asp His Ser Ala Val Val Ala Leu Gln Ile
            100                 105                 110

Glu Lys Ile Asn Asn Pro Asp Lys Ile Asp Ser Leu Ile Asn Gln Arg
        115                 120                 125

Ser Phe Leu Val Ser Gly Leu Gly Gly Glu His Thr Ala Phe Asn Gln
    130                 135                 140

Leu Pro Asp Gly Lys Ala Glu Tyr His Gly Lys Ala Phe Ser Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Thr Pro Glu Gln Asn Val Glu
            180                 185                 190

Leu Ala Ala Ala Glu Leu Lys Ala Asp Glu Lys Ser His Ala Val Ile
        195                 200                 205

Leu Gly Asp Thr Arg Tyr Gly Ser Glu Glu Lys Gly Thr Tyr His Leu
    210                 215                 220

Ala Leu Phe Gly Asp Arg Ala Gln Glu Ile Ala Gly Ser Ala Thr Val
225                 230                 235                 240

Glu Ile Gly Glu Lys Val His Glu Ile Gly Ile Ala Gly Lys Gln
                245                 250                 255
```

<210> SEQ ID NO 173
<211> LENGTH: 765
<212> TYPE: DNA
<213> ORGANISM: Neisseria meningitidis

<400> SEQUENCE: 173

```
atgagcagcg gaggcggcgg tgtcgccgcc gacatcggcg cggggcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca aatatacaaa    300

caggaccact ccgccgtcgt tgccctacag attgaaaaaa tcaacaaccc cgacaaaatc    360

gacagcctga taaaccaacg ctccttcctt gtcagcggtt tgggcggaga acataccgcc    420

ttcaaccaac tgcctgacgg caaagccgag tatcacggca aagcattcag ctccgacgat    480

gctggcggaa aactgaccta taccatagat ttcgccgcca aacagggaca cggcaaaatc    540

gaacacctga aaacacccga gcaaaatgtc gagcttgccg ccgccgaact caaagcagat    600

gaaaaatcac acgccgtcat tttgggcgac acgcgctacg gcagcgaaga aaaaggcact    660

taccacctcg ccctttttcgg cgaccgcgcc caagaaatcg ccggctcggc aaccgtggag    720

atagggggaaa aggttcacga aatcggcatc gccggcaaac agtag                  765
```

<210> SEQ ID NO 174
<211> LENGTH: 254

<212> TYPE: PRT
<213> ORGANISM: Neisseria meningitidis

<400> SEQUENCE: 174

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Ile Tyr Lys Gln Asp His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Asp Gly Lys Ala Glu Tyr His Gly Lys Ala Phe Ser Ser Asp Asp
145                 150                 155                 160

Ala Gly Gly Lys Leu Thr Tyr Thr Ile Asp Phe Ala Ala Lys Gln Gly
                165                 170                 175

His Gly Lys Ile Glu His Leu Lys Thr Pro Glu Gln Asn Val Glu Leu
            180                 185                 190

Ala Ala Ala Glu Leu Lys Ala Asp Glu Lys Ser His Ala Val Ile Leu
        195                 200                 205

Gly Asp Thr Arg Tyr Gly Ser Glu Glu Lys Gly Thr Tyr His Leu Ala
    210                 215                 220

Leu Phe Gly Asp Arg Ala Gln Glu Ile Ala Gly Ser Ala Thr Val Glu
225                 230                 235                 240

Ile Gly Glu Lys Val His Glu Ile Gly Ile Ala Gly Lys Gln
                245                 250

<210> SEQ ID NO 175
<211> LENGTH: 768
<212> TYPE: DNA
<213> ORGANISM: Neisseria meningitidis

<400> SEQUENCE: 175
tgcagcagcg gaggcggcgg tgtcgccgcc gacatcggcg cggtgcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctca atacgggcaa attgaagaac gacaaggtca gccgcttcga ctttatccgt 240
caaatcgaag tggacgggca gctcattacc ttggagagcg gagagttcca agtgtacaaa 300
caaagccatt ccgccttaac cgcccttcag accgagcaag tacaagattc ggagcattca 360
gggaagatgg ttgcgaaacg ccagttcaga atcggcgata tagcgggtga acatacatct 420
tttgacaagc ttcccgaagg cggcagggcg acatatcgcg ggacggcatt cggttcagac 480
gatgccagtg gaaaactgac ctacaccata gatttcgccg ccaagcaggg acacggcaaa 540

```
atcgaacatt tgaaatcgcc agaactcaat gttgacctgg ccgcctccga tatcaagccg    600

gataaaaaac gccatgccgt catcagcggt tccgtccttt acaaccaagc cgagaaaggc    660

agttactctc taggcatctt tggcgggcaa gcccaggaag ttgccggcag cgcagaagtg    720

gaaaccgcaa acggcatacg ccatatcggt cttgccgcca agcagtaa                 768


<210> SEQ ID NO 176
<211> LENGTH: 255
<212> TYPE: PRT
<213> ORGANISM: Neisseria meningitidis

<400> SEQUENCE: 176

Cys Ser Ser Gly Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255


<210> SEQ ID NO 177
<211> LENGTH: 771
<212> TYPE: DNA
<213> ORGANISM: Neisseria meningitidis

<400> SEQUENCE: 177

tgcggatcca gcggaggcgg cggtgtcgcc gccgacatcg gcgcggtgct tgccgatgca     60

ctaaccgcac cgctcgacca taaagacaaa agtttgcagt ctttgacgct ggatcagtcc    120

gtcaggaaaa acgagaaact gaagctggcg gcacaaggtg cggaaaaaac ttatggaaac    180

ggcgacagcc tcaatacggg caaattgaag aacgacaagg tcagccgctt cgactttatc    240
```

```
cgtcaaatcg aagtggacgg gcagctcatt accttggaga gcggagagtt ccaagtgtac    300

aaacaaagcc attccgcctt aaccgccctt cagaccgagc aagtacaaga ttcggagcat    360

tcagggaaga tggttgcgaa acgccagttc agaatcggcg atatagcggg tgaacataca    420

tcttttgaca agcttcccga aggcggcagg gcgacatatc gcgggacggc attcggttca    480

gacgatgcca gtggaaaact gacctacacc atagatttcg ccgccaagca gggacacggc    540

aaaatcgaac atttgaaatc gccagaactc aatgttgacc tggccgcctc cgatatcaag    600

ccggataaaa aacgccatgc cgtcatcagc ggttccgtcc tttacaacca agccgagaaa    660

ggcagttact ctctaggcat ctttggcggg caagcccagg aagttgccgg cagcgcagaa    720

gtggaaaccg caaacggcat acgccatatc ggtcttgccg ccaagcagta a             771
```

<210> SEQ ID NO 178
<211> LENGTH: 256
<212> TYPE: PRT
<213> ORGANISM: Neisseria meningitidis

<400> SEQUENCE: 178

```
Cys Gly Ser Ser Gly Gly Gly Gly Val Ala Ala Asp Ile Gly Ala Val
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Val Tyr Lys Gln Ser His Ser Ala Leu Thr Ala Leu Gln Thr
            100                 105                 110

Glu Gln Val Gln Asp Ser Glu His Ser Gly Lys Met Val Ala Lys Arg
        115                 120                 125

Gln Phe Arg Ile Gly Asp Ile Ala Gly Glu His Thr Ser Phe Asp Lys
    130                 135                 140

Leu Pro Glu Gly Gly Arg Ala Thr Tyr Arg Gly Thr Ala Phe Gly Ser
145                 150                 155                 160

Asp Asp Ala Ser Gly Lys Leu Thr Tyr Thr Ile Asp Phe Ala Ala Lys
                165                 170                 175

Gln Gly His Gly Lys Ile Glu His Leu Lys Ser Pro Glu Leu Asn Val
            180                 185                 190

Asp Leu Ala Ala Ser Asp Ile Lys Pro Asp Lys Lys Arg His Ala Val
        195                 200                 205

Ile Ser Gly Ser Val Leu Tyr Asn Gln Ala Glu Lys Gly Ser Tyr Ser
    210                 215                 220

Leu Gly Ile Phe Gly Gly Gln Ala Gln Glu Val Ala Gly Ser Ala Glu
225                 230                 235                 240

Val Glu Thr Ala Asn Gly Ile Arg His Ile Gly Leu Ala Ala Lys Gln
                245                 250                 255
```

<210> SEQ ID NO 179
<211> LENGTH: 768
<212> TYPE: DNA

<213> ORGANISM: Neisseria meningitidis

<400> SEQUENCE: 179

```
atgagcagcg gaggcggcgg tgtcgccgcc gacatcggcg cggtgcttgc cgatgcacta     60

accgcaccgc tcgaccataa agacaaaagt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacgggca gctcattacc ttggagagcg gagagttcca agtgtacaaa    300

caaagccatt ccgccttaac cgcccttcag accgagcaag tacaagattc ggagcattca    360

gggaagatgg ttgcgaaacg ccagttcaga atcggcgata tagcgggtga acatacatct    420

tttgacaagc ttcccgaagg cggcagggcg acatatcgcg ggacggcatt cggttcagac    480

gatgccagtg gaaaactgac ctacaccata gatttcgccg ccaagcaggg acacggcaaa    540

atcgaacatt tgaaatcgcc agaactcaat gttgacctgg ccgcctccga tatcaagccg    600

gataaaaaac gccatgccgt catcagcggt tccgtccttt acaaccaagc cgagaaaggc    660

agttactctc taggcatctt tggcgggcaa gcccaggaag ttgccggcag cgcagaagtg    720

gaaaccgcaa acggcatacg ccatatcggt cttgccgcca agcagtaa                 768
```

<210> SEQ ID NO 180
<211> LENGTH: 255
<212> TYPE: PRT
<213> ORGANISM: Neisseria meningitidis

<400> SEQUENCE: 180

```
Met Ser Ser Gly Gly Gly Gly Val Ala Ala Asp Ile Gly Ala Val Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Ser Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ser Asp Ile Lys Pro Asp Lys Lys Arg His Ala Val Ile
        195                 200                 205

Ser Gly Ser Val Leu Tyr Asn Gln Ala Glu Lys Gly Ser Tyr Ser Leu
    210                 215                 220
```

```
Gly Ile Phe Gly Gly Gln Ala Gln Glu Val Ala Gly Ser Ala Glu Val
225                 230                 235                 240

Glu Thr Ala Asn Gly Ile Arg His Ile Gly Leu Ala Ala Lys Gln
                245                 250                 255


<210> SEQ ID NO 181
<211> LENGTH: 747
<212> TYPE: DNA
<213> ORGANISM: Neisseria meningitidis

<400> SEQUENCE: 181

tgcagcagcg gagggggtgg tgtcgccgcc gacatcggtg cggggcttgc cgatgcacta      60

accgcaccgc tcgaccataa agacaaaggt ttgcagtctt tgacgctgga tcagtccgtc     120

aggaaaaacg agaaactgaa gctggcggca caaggtgcgg aaaaaactta tggaaacggt     180

gacagcctca atacgggcaa attgaagaac gacaaggtca gccgtttcga ctttatccgc     240

caaatcgaag tggacgggca gctcattacc ttggagagtg gagagttcca agtatacaaa     300

caaagccatt ccgccttaac cgcctttcag accgagcaaa tacaagattc ggagcattcc     360

gggaagatgg ttgcgaaacg ccagttcaga atcggcgaca tagcgggcga acatacatct     420

tttgacaagc ttcccgaagg cggcagggcg acatatcgcg ggacggcgtt cggttcagac     480

gatgccggcg gaaaactgac ctacaccata gatttcgccg ccaagcaggg aaacggcaaa     540

atcgaacatt tgaaatcgcc agaactcaat gtcgacctgg ccgccgccga tatcaagccg     600

gatggaaaac gccatgccgt catcagcggt tccgtccttt acaaccaagc cgagaaaggc     660

agttactccc tcggtatctt tggcggaaaa gcccaggaag ttgccggcag cgcggaagtg     720

aaaaccgtaa acggcatacg ccatatc                                         747


<210> SEQ ID NO 182
<211> LENGTH: 249
<212> TYPE: PRT
<213> ORGANISM: Neisseria meningitidis

<400> SEQUENCE: 182

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160
```

-continued

Asp Ala Gly Gly Lys Leu Thr Tyr Thr Ile Asp Phe Ala Ala Lys Gln
165 170 175

Gly Asn Gly Lys Ile Glu His Leu Lys Ser Pro Glu Leu Asn Val Asp
180 185 190

Leu Ala Ala Ala Asp Ile Lys Pro Asp Gly Lys Arg His Ala Val Ile
195 200 205

Ser Gly Ser Val Leu Tyr Asn Gln Ala Glu Lys Gly Ser Tyr Ser Leu
210 215 220

Gly Ile Phe Gly Gly Lys Ala Gln Glu Val Ala Gly Ser Ala Glu Val
225 230 235 240

Lys Thr Val Asn Gly Ile Arg His Ile
245

<210> SEQ ID NO 183
<211> LENGTH: 750
<212> TYPE: DNA
<213> ORGANISM: Neisseria meningitidis

<400> SEQUENCE: 183
tgcggatcca gcggaggggg tggtgtcgcc gccgacatcg gtgcggggct tgccgatgca 60
ctaaccgcac cgctcgacca taaagacaaa ggtttgcagt ctttgacgct ggatcagtcc 120
gtcaggaaaa acgagaaact gaagctggcg gcacaaggtg cggaaaaaac ttatggaaac 180
ggtgacagcc tcaatacggg caaattgaag aacgacaagg tcagccgttt cgactttatc 240
cgccaaatcg aagtggacgg gcagctcatt accttggaga gtggagagtt ccaagtatac 300
aaacaaagcc attccgcctt aaccgccttt cagaccgagc aaatacaaga ttcggagcat 360
tccgggaaga tggttgcgaa acgccagttc agaatcggcg acatagcggg cgaacataca 420
tcttttgaca agcttcccga aggcggcagg gcgacatatc gcgggacggc gttcggttca 480
gacgatgccg gcggaaaact gacctacacc atagatttcg ccgccaagca gggaaacggc 540
aaaatcgaac atttgaaatc gccagaactc aatgtcgacc tggccgccgc cgatatcaag 600
ccggatggaa aacgccatgc cgtcatcagc ggttccgtcc tttacaacca agccgagaaa 660
ggcagttact ccctcggtat ctttggcgga aaagcccagg aagttgccgg cagcgcggaa 720
gtgaaaaccg taaacggcat acgccatatc 750

<210> SEQ ID NO 184
<211> LENGTH: 250
<212> TYPE: PRT
<213> ORGANISM: Neisseria meningitidis

<400> SEQUENCE: 184

Cys Gly Ser Ser Gly Gly Gly Gly Val Ala Ala Asp Ile Gly Ala Gly
1 5 10 15

Leu Ala Asp Ala Leu Thr Ala Pro Leu Asp His Lys Asp Lys Gly Leu
20 25 30

Gln Ser Leu Thr Leu Asp Gln Ser Val Arg Lys Asn Glu Lys Leu Lys
35 40 45

Leu Ala Ala Gln Gly Ala Glu Lys Thr Tyr Gly Asn Gly Asp Ser Leu
50 55 60

Asn Thr Gly Lys Leu Lys Asn Asp Lys Val Ser Arg Phe Asp Phe Ile
65 70 75 80

Arg Gln Ile Glu Val Asp Gly Gln Leu Ile Thr Leu Glu Ser Gly Glu
85 90 95

Phe Gln Val Tyr Lys Gln Ser His Ser Ala Leu Thr Ala Phe Gln Thr

```
            100                 105                 110

Glu Gln Ile Gln Asp Ser Glu His Ser Gly Lys Met Val Ala Lys Arg
        115                 120                 125

Gln Phe Arg Ile Gly Asp Ile Ala Gly Glu His Thr Ser Phe Asp Lys
    130                 135                 140

Leu Pro Glu Gly Gly Arg Ala Thr Tyr Arg Gly Thr Ala Phe Gly Ser
145                 150                 155                 160

Asp Asp Ala Gly Gly Lys Leu Thr Tyr Thr Ile Asp Phe Ala Ala Lys
                165                 170                 175

Gln Gly Asn Gly Lys Ile Glu His Leu Lys Ser Pro Glu Leu Asn Val
            180                 185                 190

Asp Leu Ala Ala Ala Asp Ile Lys Pro Asp Gly Lys Arg His Ala Val
        195                 200                 205

Ile Ser Gly Ser Val Leu Tyr Asn Gln Ala Glu Lys Gly Ser Tyr Ser
    210                 215                 220

Leu Gly Ile Phe Gly Gly Lys Ala Gln Glu Val Ala Gly Ser Ala Glu
225                 230                 235                 240

Val Lys Thr Val Asn Gly Ile Arg His Ile
                245                 250
```

<210> SEQ ID NO 185
<211> LENGTH: 747
<212> TYPE: DNA
<213> ORGANISM: Neisseria meningitidis

<400> SEQUENCE: 185

```
atgagcagcg gagggggtgg tgtcgccgcc gacatcggtg cggggcttgc cgatgcacta      60

accgcaccgc tcgaccataa agacaaaggt ttgcagtctt tgacgctgga tcagtccgtc     120

aggaaaaacg agaaactgaa gctggcggca caaggtgcgg aaaaaactta tggaaacggt     180

gacagcctca atacgggcaa attgaagaac gacaaggtca gccgtttcga ctttatccgc     240

caaatcgaag tggacgggca gctcattacc ttggagagtg gagagttcca agtatacaaa     300

caaagccatt ccgccttaac cgcctttcag accgagcaaa tacaagattc ggagcattcc     360

gggaagatgg ttgcgaaacg ccagttcaga atcggcgaca tagcgggcga acatacatct     420

tttgacaagc ttcccgaagg cggcagggcg acatatcgcg ggacggcgtt cggttcagac     480

gatgccggcg gaaaactgac ctacaccata gatttcgccg ccaagcaggg aaacggcaaa     540

atcgaacatt tgaaatcgcc agaactcaat gtcgacctgg ccgccgccga tatcaagccg     600

gatggaaaac gccatgccgt catcagcggt tccgtccttt acaaccaagc cgagaaaggc     660

agttactccc tcggtatctt tggcggaaaa gcccaggaag ttgccggcag cgcggaagtg     720

aaaaccgtaa acggcatacg ccatatc                                         747
```

<210> SEQ ID NO 186
<211> LENGTH: 249
<212> TYPE: PRT
<213> ORGANISM: Neisseria meningitidis

<400> SEQUENCE: 186

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45
```

```
Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile
                245
```

<210> SEQ ID NO 187
<211> LENGTH: 747
<212> TYPE: DNA
<213> ORGANISM: Neisseria meningitidis

<400> SEQUENCE: 187

```
tgcagcagcg gaggggggtgg tgtcgccgcc gacatcggtg cggggcttgc cgatgcacta     60

accgcaccgc tcgaccataa agacaaaggt ttgcagtctt tgacgctgga tcagtccgtc    120

aggaaaaacg agaaactgaa gctggcggca caaggtgcgg aaaaaactta tggaaacggt    180

gacagcctca atacgggcaa attgaagaac gacaaggtca gccgtttcga ctttatccgc    240

caaatcgaag tggacgggca gctcattacc ttggagagtg gagagttcca agtatacaaa    300

caaagccatt ccgccttaac cgcctttcag accgagcaaa tacaagattc ggagcattcc    360

gggaagatgg ttgcgaaacg ccagttcaga atcggcgaca tagcgggcga acatacatct    420

tttgacaagc ttcccgaagg cggcagggcg acatatcgcg ggacggcgtt cggttcagac    480

gatgccggcg gaaaactgac ctacaccata gatttcgccg ccaagcaggg aaacggcaaa    540

atcgaacatt tgaaatcgcc agaactcaat gtcgacctgg ccgccgccga tatcaagccg    600

gatggaaaac gccatgccgt catcagcggt tccgtccttt acaaccaagc cgagaaaggc    660

agttactccc tcggtatctt tggcggaaaa gcccaggaag ttgccggcag cgcggaagtg    720

aaaaccgtaa acggcatacg ccatatc                                         747
```

<210> SEQ ID NO 188
<211> LENGTH: 249
<212> TYPE: PRT
<213> ORGANISM: Neisseria meningitidis

<400> SEQUENCE: 188

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile
                245
```

<210> SEQ ID NO 189
<211> LENGTH: 750
<212> TYPE: DNA
<213> ORGANISM: Neisseria meningitidis

<400> SEQUENCE: 189

```
tgcggatcca gcggaggggg tggtgtcgcc gccgacatcg gtgcggggct tgccgatgca      60

ctaaccgcac cgctcgacca taaagacaaa ggtttgcagt ctttgacgct ggatcagtcc     120

gtcaggaaaa acgagaaact gaagctggcg gcacaaggtg cggaaaaaac ttatggaaac     180

ggtgacagcc tcaatacggg caaattgaag aacgacaagg tcagccgttt cgactttatc     240

cgccaaatcg aagtggacgg gcagctcatt accttggaga gtggagagtt ccaagtatac     300

aaacaaagcc attccgcctt aaccgccttt cagaccgagc aaatacaaga ttcggagcat     360

tccgggaaga tggttgcgaa acgccagttc agaatcggcg acatagcggg cgaacataca     420

tcttttgaca agcttcccga aggcggcagg gcgacatatc gcgggacggc gttcggttca     480

gacgatgccg gcggaaaact gacctacacc atagatttcg ccgccaagca gggaaacggc     540

aaaatcgaac atttgaaatc gccagaactc aatgtcgacc tggccgccgc cgatatcaag     600
```

ccggatggaa aacgccatgc cgtcatcagc ggttccgtcc tttacaacca agccgagaaa 660
ggcagttact ccctcggtat ctttggcgga aaagcccagg aagttgccgg cagcgcggaa 720
gtgaaaaccg taaacggcat acgccatatc 750

<210> SEQ ID NO 190
<211> LENGTH: 250
<212> TYPE: PRT
<213> ORGANISM: Neisseria meningitidis

<400> SEQUENCE: 190

Cys Gly Ser Ser Gly Gly Gly Gly Val Ala Ala Asp Ile Gly Ala Gly
1 5 10 15

Leu Ala Asp Ala Leu Thr Ala Pro Leu Asp His Lys Asp Lys Gly Leu
20 25 30

Gln Ser Leu Thr Leu Asp Gln Ser Val Arg Lys Asn Glu Lys Leu Lys
35 40 45

Leu Ala Ala Gln Gly Ala Glu Lys Thr Tyr Gly Asn Gly Asp Ser Leu
50 55 60

Asn Thr Gly Lys Leu Lys Asn Asp Lys Val Ser Arg Phe Asp Phe Ile
65 70 75 80

Arg Gln Ile Glu Val Asp Gly Gln Leu Ile Thr Leu Glu Ser Gly Glu
85 90 95

Phe Gln Val Tyr Lys Gln Ser His Ser Ala Leu Thr Ala Phe Gln Thr
100 105 110

Glu Gln Ile Gln Asp Ser Glu His Ser Gly Lys Met Val Ala Lys Arg
115 120 125

Gln Phe Arg Ile Gly Asp Ile Ala Gly Glu His Thr Ser Phe Asp Lys
130 135 140

Leu Pro Glu Gly Gly Arg Ala Thr Tyr Arg Gly Thr Ala Phe Gly Ser
145 150 155 160

Asp Asp Ala Gly Gly Lys Leu Thr Tyr Thr Ile Asp Phe Ala Ala Lys
165 170 175

Gln Gly Asn Gly Lys Ile Glu His Leu Lys Ser Pro Glu Leu Asn Val
180 185 190

Asp Leu Ala Ala Ala Asp Ile Lys Pro Asp Gly Lys Arg His Ala Val
195 200 205

Ile Ser Gly Ser Val Leu Tyr Asn Gln Ala Glu Lys Gly Ser Tyr Ser
210 215 220

Leu Gly Ile Phe Gly Gly Lys Ala Gln Glu Val Ala Gly Ser Ala Glu
225 230 235 240

Val Lys Thr Val Asn Gly Ile Arg His Ile
245 250

<210> SEQ ID NO 191
<211> LENGTH: 747
<212> TYPE: DNA
<213> ORGANISM: Neisseria meningitidis

<400> SEQUENCE: 191
atgagcagcg gagggggtgg tgtcgccgcc gacatcggtg cggggcttgc cgatgcacta 60
accgcaccgc tcgaccataa agacaaaggt ttgcagtctt tgacgctgga tcagtccgtc 120
aggaaaaacg agaaactgaa gctggcggca caaggtgcgg aaaaaactta tggaaacggt 180
gacagcctca atacgggcaa attgaagaac gacaaggtca gccgtttcga ctttatccgc 240
caaatcgaag tggacgggca gctcattacc ttggagagtg gagagttcca agtatacaaa 300

```
caaagccatt ccgccttaac cgcctttcag accgagcaaa tacaagattc ggagcattcc    360

gggaagatgg ttgcgaaacg ccagttcaga atcggcgaca tagcgggcga acatacatct    420

tttgacaagc ttcccgaagg cggcagggcg acatatcgcg ggacggcgtt cggttcagac    480

gatgccggcg gaaaactgac ctacaccata gatttcgccg ccaagcaggg aaacggcaaa    540

atcgaacatt tgaaatcgcc agaactcaat gtcgacctgg ccgccgccga tatcaagccg    600

gatggaaaac gccatgccgt catcagcggt tccgtccttt acaaccaagc cgagaaaggc    660

agttactccc tcggtatctt tggcggaaaa gcccaggaag ttgccggcag cgcggaagtg    720

aaaaccgtaa acggcatacg ccatatc                                        747
```

<210> SEQ ID NO 192
<211> LENGTH: 249
<212> TYPE: PRT
<213> ORGANISM: Neisseria meningitidis

<400> SEQUENCE: 192

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile
                245
```

<210> SEQ ID NO 193
<211> LENGTH: 768
<212> TYPE: DNA
<213> ORGANISM: Neisseria meningitidis

<400> SEQUENCE: 193

```
tgcagcagcg gagggggtgg tgtcgccgcc gacatcggtg cggggcttgc cgatgcacta     60
accgcaccgc tcgaccataa agacaaaggt ttgcagtctt tgacgctgga tcagtccgtc    120
aggaaaaacg agaaactgaa gctggcggca caaggtgcgg aaaaaactta tggaaacggt    180
gacagcctca atacgggcaa attgaagaac gacaaggtca gccgtttcga ctttatccgc    240
caaatcgaag tggacgggca gctcattacc ttggagagtg gagagttcca agtatacaaa    300
caaagccatt ccgccttaac cgcctttcag accgagcaaa tacaagattc ggagcattcc    360
gggaagatgg ttgcgaaacg ccagttcaga atcggcgaca tagcgggcga acatacatct    420
tttgacaagc ttcccgaagg cggcagggcg acatatcgcg ggacggcgtt cggttcagac    480
gatgccggcg gaaaactgac ctacaccata gatttcgccg ccaagcaggg aaacggcaaa    540
atcgaacatt tgaaatcgcc agaactcaat gtcgacctgg ccgccgccga tatcaagccg    600
gatggaaaac gccatgccgt catcagcggt tccgtccttt acaaccaagc cgagaaaggc    660
agttactccc tcggtatctt tggcggaaaa gcccaggaag ttgccggcag cgcggaagtg    720
aaaaccgtaa acggcatacg ccatatcggc cttgccgcca agcaataa                 768
```

<210> SEQ ID NO 194
<211> LENGTH: 255
<212> TYPE: PRT
<213> ORGANISM: Neisseria meningitidis

<400> SEQUENCE: 194

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
```

225 230 235 240

Lys Thr Val Asn Gly Ile Arg His Ile Gly Leu Ala Ala Lys Gln
245 250 255

<210> SEQ ID NO 195
<211> LENGTH: 771
<212> TYPE: DNA
<213> ORGANISM: Neisseria meningitidis

<400> SEQUENCE: 195
tgcggatcca gcggaggggg tggtgtcgcc gccgacatcg gtgcggggct tgccgatgca 60
ctaaccgcac cgctcgacca taaagacaaa ggtttgcagt ctttgacgct ggatcagtcc 120
gtcaggaaaa acgagaaact gaagctggcg gcacaaggtg cggaaaaaac ttatggaaac 180
ggtgacagcc tcaatacggg caaattgaag aacgacaagg tcagccgttt cgactttatc 240
cgccaaatcg aagtggacgg gcagctcatt accttggaga gtggagagtt ccaagtatac 300
aaacaaagcc attccgcctt aaccgccttt cagaccgagc aaatacaaga ttcggagcat 360
tccgggaaga tggttgcgaa acgccagttc agaatcggcg acatagcggg cgaacataca 420
tcttttgaca agcttcccga aggcggcagg gcgacatatc gcgggacggc gttcggttca 480
gacgatgccg gcggaaaact gacctacacc atagatttcg ccgccaagca gggaaacggc 540
aaaatcgaac atttgaaatc gccagaactc aatgtcgacc tggccgccgc cgatatcaag 600
ccggatggaa aacgccatgc cgtcatcagc ggttccgtcc tttacaacca agccgagaaa 660
ggcagttact ccctcggtat ctttggcgga aaagcccagg aagttgccgg cagcgcggaa 720
gtgaaaaccg taaacggcat acgccatatc ggccttgccg ccaagcaata a 771

<210> SEQ ID NO 196
<211> LENGTH: 256
<212> TYPE: PRT
<213> ORGANISM: Neisseria meningitidis

<400> SEQUENCE: 196

Cys Gly Ser Ser Gly Gly Gly Gly Val Ala Ala Asp Ile Gly Ala Gly
1 5 10 15

Leu Ala Asp Ala Leu Thr Ala Pro Leu Asp His Lys Asp Lys Gly Leu
20 25 30

Gln Ser Leu Thr Leu Asp Gln Ser Val Arg Lys Asn Glu Lys Leu Lys
35 40 45

Leu Ala Ala Gln Gly Ala Glu Lys Thr Tyr Gly Asn Gly Asp Ser Leu
50 55 60

Asn Thr Gly Lys Leu Lys Asn Asp Lys Val Ser Arg Phe Asp Phe Ile
65 70 75 80

Arg Gln Ile Glu Val Asp Gly Gln Leu Ile Thr Leu Glu Ser Gly Glu
85 90 95

Phe Gln Val Tyr Lys Gln Ser His Ser Ala Leu Thr Ala Phe Gln Thr
100 105 110

Glu Gln Ile Gln Asp Ser Glu His Ser Gly Lys Met Val Ala Lys Arg
115 120 125

Gln Phe Arg Ile Gly Asp Ile Ala Gly Glu His Thr Ser Phe Asp Lys
130 135 140

Leu Pro Glu Gly Gly Arg Ala Thr Tyr Arg Gly Thr Ala Phe Gly Ser
145 150 155 160

Asp Asp Ala Gly Gly Lys Leu Thr Tyr Thr Ile Asp Phe Ala Ala Lys
165 170 175

```
Gln Gly Asn Gly Lys Ile Glu His Leu Lys Ser Pro Glu Leu Asn Val
            180                 185                 190

Asp Leu Ala Ala Ala Asp Ile Lys Pro Asp Gly Lys Arg His Ala Val
        195                 200                 205

Ile Ser Gly Ser Val Leu Tyr Asn Gln Ala Glu Lys Gly Ser Tyr Ser
    210                 215                 220

Leu Gly Ile Phe Gly Gly Lys Ala Gln Glu Val Ala Gly Ser Ala Glu
225                 230                 235                 240

Val Lys Thr Val Asn Gly Ile Arg His Ile Gly Leu Ala Ala Lys Gln
                245                 250                 255
```

<210> SEQ ID NO 197
<211> LENGTH: 768
<212> TYPE: DNA
<213> ORGANISM: Neisseria meningitidis

<400> SEQUENCE: 197

```
atgagcagcg gagggggtgg tgtcgccgcc gacatcggtg cggggcttgc cgatgcacta     60

accgcaccgc tcgaccataa agacaaaggt ttgcagtctt tgacgctgga tcagtccgtc    120

aggaaaaacg agaaactgaa gctggcggca caaggtgcgg aaaaaactta tggaaacggt    180

gacagcctca atacgggcaa attgaagaac gacaaggtca gccgtttcga ctttatccgc    240

caaatcgaag tggacgggca gctcattacc ttggagagtg gagagttcca agtatacaaa    300

caaagccatt ccgccttaac cgcctttcag accgagcaaa tacaagattc ggagcattcc    360

gggaagatgg ttgcgaaacg ccagttcaga atcggcgaca tagcgggcga acatacatct    420

tttgacaagc ttcccgaagg cggcagggcg acatatcgcg ggacggcgtt cggttcagac    480

gatgccggcg gaaaactgac ctacaccata gatttcgccg ccaagcaggg aaacggcaaa    540

atcgaacatt tgaaatcgcc agaactcaat gtcgacctgg ccgccgccga tatcaagccg    600

gatggaaaac gccatgccgt catcagcggt tccgtccttt acaaccaagc cgagaaaggc    660

agttactccc tcggtatctt tggcggaaaa gcccaggaag ttgccggcag cgcggaagtg    720

aaaaccgtaa acggcatacg ccatatcggc cttgccgcca agcaataa                 768
```

<210> SEQ ID NO 198
<211> LENGTH: 255
<212> TYPE: PRT
<213> ORGANISM: Neisseria meningitidis

<400> SEQUENCE: 198

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110
```

```
Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

<210> SEQ ID NO 199
<211> LENGTH: 768
<212> TYPE: DNA
<213> ORGANISM: Neisseria meningitidis

<400> SEQUENCE: 199

```
tgcagcagcg gaggggggtgg tgtcgccgcc gacatcggtg cggggcttgc cgatgcacta     60

accgcaccgc tcgaccataa agacaaaggt ttgcagtctt tgacgctgga tcagtccgtc    120

aggaaaaacg agaaactgaa gctggcggca caaggtgcgg aaaaaactta tggaaacggt    180

gacagcctca atacgggcaa attgaagaac gacaaggtca gccgtttcga ctttatccgc    240

caaatcgaag tggacgggca gctcattacc ttggagagtg gagagttcca agtatacaaa    300

caaagccatt ccgccttaac cgcctttcag accgagcaaa tacaagattc ggagcattcc    360

gggaagatgg ttgcgaaacg ccagttcaga atcggcgaca tagcgggcga acatacatct    420

tttgacaagc ttcccgaagg cggcagggcg acatatcgcg ggacggcgtt cggttcagac    480

gatgccggcg gaaaactgac ctacaccata gatttcgccg ccaagcaggg aaacggcaaa    540

atcgaacatt tgaaatcgcc agaactcaat gtcgacctgg ccgccgccga tatcaagccg    600

gatggaaaac gccatgccgt catcagcggt tccgtccttt acaaccaagc cgagaaaggc    660

agttactccc tcggtatctt tggcggaaaa gcccaggaag ttgccggcag cgcggaagtg    720

aaaaccgtaa acggcatacg ccatatcggc cttgccgcca agcaataa                 768
```

<210> SEQ ID NO 200
<211> LENGTH: 255
<212> TYPE: PRT
<213> ORGANISM: Neisseria meningitidis

<400> SEQUENCE: 200

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
```

```
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255


<210> SEQ ID NO 201
<211> LENGTH: 771
<212> TYPE: DNA
<213> ORGANISM: Neisseria meningitidis

<400> SEQUENCE: 201

tgcggatcca gcggaggggg tggtgtcgcc gccgacatcg gtgcggggct tgccgatgca      60

ctaaccgcac cgctcgacca taaagacaaa ggtttgcagt ctttgacgct ggatcagtcc     120

gtcaggaaaa acgagaaact gaagctggcg gcacaaggtg cggaaaaaac ttatggaaac     180

ggtgacagcc tcaatacggg caaattgaag aacgacaagg tcagccgttt cgactttatc     240

cgccaaatcg aagtggacgg gcagctcatt accttggaga gtggagagtt ccaagtatac     300

aaacaaagcc attccgcctt aaccgccttt cagaccgagc aaatacaaga ttcggagcat     360

tccgggaaga tggttgcgaa acgccagttc agaatcggcg acatagcggg cgaacataca     420

tcttttgaca agcttcccga aggcggcagg gcgacatatc gcgggacggc gttcggttca     480

gacgatgccg gcggaaaact gacctacacc atagatttcg ccgccaagca gggaaacggc     540

aaaatcgaac atttgaaatc gccagaactc aatgtcgacc tggccgccgc cgatatcaag     600

ccggatggaa aacgccatgc cgtcatcagc ggttccgtcc tttacaacca agccgagaaa     660

ggcagttact ccctcggtat ctttggcgga aaagcccagg aagttgccgg cagcgcggaa     720

gtgaaaaccg taaacggcat acgccatatc ggccttgccg ccaagcaata a              771


<210> SEQ ID NO 202
<211> LENGTH: 256
<212> TYPE: PRT
<213> ORGANISM: Neisseria meningitidis

<400> SEQUENCE: 202
```

-continued

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Gly Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Val Tyr Lys Gln Ser His Ser Ala Leu Thr Ala Phe Gln Thr
            100                 105                 110

Glu Gln Ile Gln Asp Ser Glu His Ser Gly Lys Met Val Ala Lys Arg
        115                 120                 125

Gln Phe Arg Ile Gly Asp Ile Ala Gly Glu His Thr Ser Phe Asp Lys
    130                 135                 140

Leu Pro Glu Gly Gly Arg Ala Thr Tyr Arg Gly Thr Ala Phe Gly Ser
145                 150                 155                 160

Asp Asp Ala Gly Gly Lys Leu Thr Tyr Thr Ile Asp Phe Ala Ala Lys
                165                 170                 175

Gln Gly Asn Gly Lys Ile Glu His Leu Lys Ser Pro Glu Leu Asn Val
            180                 185                 190

Asp Leu Ala Ala Ala Asp Ile Lys Pro Asp Gly Lys Arg His Ala Val
        195                 200                 205

Ile Ser Gly Ser Val Leu Tyr Asn Gln Ala Glu Lys Gly Ser Tyr Ser
    210                 215                 220

Leu Gly Ile Phe Gly Gly Lys Ala Gln Glu Val Ala Gly Ser Ala Glu
225                 230                 235                 240

Val Lys Thr Val Asn Gly Ile Arg His Ile Gly Leu Ala Ala Lys Gln
                245                 250                 255
```

<210> SEQ ID NO 203
<211> LENGTH: 768
<212> TYPE: DNA
<213> ORGANISM: Neisseria meningitidis

<400> SEQUENCE: 203

```
atgagcagcg gagggggtgg tgtcgccgcc gacatcggtg cggggcttgc cgatgcacta     60

accgcaccgc tcgaccataa agacaaaggt ttgcagtctt tgacgctgga tcagtccgtc    120

aggaaaaacg agaaactgaa gctggcggca caaggtgcgg aaaaaactta tggaaacggt    180

gacagcctca atacgggcaa attgaagaac gacaaggtca gccgtttcga ctttatccgc    240

caaatcgaag tggacgggca gctcattacc ttggagagtg gagagttcca agtatacaaa    300

caaagccatt ccgccttaac cgcctttcag accgagcaaa tacaagattc ggagcattcc    360

gggaagatgg ttgcgaaacg ccagttcaga atcggcgaca tagcgggcga acatacatct    420

tttgacaagc ttcccgaagg cggcagggcg acatatcgcg ggacggcgtt cggttcagac    480

gatgccggcg gaaaactgac ctacaccata gatttcgccg ccaagcaggg aaacggcaaa    540

atcgaacatt tgaaatcgcc agaactcaat gtcgacctgg ccgccgccga tatcaagccg    600

gatggaaaac gccatgccgt catcagcggt tccgtccttt acaaccaagc cgagaaaggc    660
```

-continued

```
agttactccc tcggtatctt tggcggaaaa gcccaggaag ttgccggcag cgcggaagtg    720

aaaaccgtaa acggcatacg ccatatcggc cttgccgcca agcaataa                 768


<210> SEQ ID NO 204
<211> LENGTH: 255
<212> TYPE: PRT
<213> ORGANISM: Neisseria meningitidis

<400> SEQUENCE: 204

Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255


<210> SEQ ID NO 205
<211> LENGTH: 768
<212> TYPE: DNA
<213> ORGANISM: Neisseria meningitidis

<400> SEQUENCE: 205

tgcagcagcg gagggggtgg tgtcgccgcc gacatcggtg cggggcttgc cgatgcacta     60

accgcaccgc tcgaccataa agacaaaggt ttgcagtctt tgacgctgga tcagtccgtc    120

aggaaaaacg agaaactgaa gctggcggca caaggtgcgg aaaaaactta tggaaacggt    180

gacagcctca atacgggcaa attgaagaac gacaaggtca gccgtttcga ctttatccgc    240

caaatcgaag tggacgggca gctcattacc ttggagagtg gagagttcca agtatacaaa    300

caaagccatt ccgccttaac cgcctttcag accgagcaaa tacaagattc ggagcattcc    360
```

```
gggaagatgg ttgcgaaacg ccagttcaga atcggcgaca tagcgggcga acatacatct    420

tttgacaagc ttcccgaagg cggcagggcg acatatcgcg ggacggcgtt cggttcagac    480

gatgccggcg gaaaactgac ctacaccata gatttcgccg ccaagcaggg aaacggcaaa    540

atcgaacatt tgaaatcgcc agaactcaat gtcgacctgg ccgccgccga tatcaagccg    600

gatggaaaac gccatgccgt catcagcggt tccgtccttt acaaccaagc cgagaaaggc    660

agttactccc tcggtatctt tggcggaaaa gcccaggaag ttgccggcag cgcggaagtg    720

aaaaccgtaa acggcatacg ccatatcggc cttgccgcca agcaataa                 768
```

<210> SEQ ID NO 206
<211> LENGTH: 255
<212> TYPE: PRT
<213> ORGANISM: Neisseria meningitidis

<400> SEQUENCE: 206

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

<210> SEQ ID NO 207
<211> LENGTH: 771
<212> TYPE: DNA
<213> ORGANISM: Neisseria meningitidis

<400> SEQUENCE: 207

-continued

```
tgcggatcca gcggaggggg tggtgtcgcc gccgacatcg gtgcggggct tgccgatgca     60

ctaaccgcac cgctcgacca taaagacaaa ggtttgcagt ctttgacgct ggatcagtcc    120

gtcaggaaaa acgagaaact gaagctggcg gcacaaggtg cggaaaaaac ttatggaaac    180

ggtgacagcc tcaatacggg caaattgaag aacgacaagg tcagccgttt cgactttatc    240

cgccaaatcg aagtggacgg gcagctcatt accttggaga gtggagagtt ccaagtatac    300

aaacaaagcc attccgcctt aaccgccttt cagaccgagc aaatacaaga ttcggagcat    360

tccgggaaga tggttgcgaa acgccagttc agaatcggcg acatagcggg cgaacataca    420

tcttttgaca agcttcccga aggcggcagg gcgacatatc gcgggacggc gttcggttca    480

gacgatgccg gcggaaaact gacctacacc atagatttcg ccgccaagca gggaaacggc    540

aaaatcgaac atttgaaatc gccagaactc aatgtcgacc tggccgccgc cgatatcaag    600

ccggatggaa aacgccatgc cgtcatcagc ggttccgtcc tttacaacca agccgagaaa    660

ggcagttact ccctcggtat ctttggcgga aaagcccagg aagttgccgg cagcgcggaa    720

gtgaaaaccg taaacggcat acgccatatc ggccttgccg ccaagcaata a             771
```

<210> SEQ ID NO 208
<211> LENGTH: 256
<212> TYPE: PRT
<213> ORGANISM: Neisseria meningitidis

<400> SEQUENCE: 208

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Gly Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Val Tyr Lys Gln Ser His Ser Ala Leu Thr Ala Phe Gln Thr
            100                 105                 110

Glu Gln Ile Gln Asp Ser Glu His Ser Gly Lys Met Val Ala Lys Arg
        115                 120                 125

Gln Phe Arg Ile Gly Asp Ile Ala Gly Glu His Thr Ser Phe Asp Lys
    130                 135                 140

Leu Pro Glu Gly Gly Arg Ala Thr Tyr Arg Gly Thr Ala Phe Gly Ser
145                 150                 155                 160

Asp Asp Ala Gly Gly Lys Leu Thr Tyr Thr Ile Asp Phe Ala Ala Lys
                165                 170                 175

Gln Gly Asn Gly Lys Ile Glu His Leu Lys Ser Pro Glu Leu Asn Val
            180                 185                 190

Asp Leu Ala Ala Ala Asp Ile Lys Pro Asp Gly Lys Arg His Ala Val
        195                 200                 205

Ile Ser Gly Ser Val Leu Tyr Asn Gln Ala Glu Lys Gly Ser Tyr Ser
    210                 215                 220

Leu Gly Ile Phe Gly Gly Lys Ala Gln Glu Val Ala Gly Ser Ala Glu
225                 230                 235                 240
```

Val Lys Thr Val Asn Gly Ile Arg His Ile Gly Leu Ala Ala Lys Gln
245 250 255

<210> SEQ ID NO 209
<211> LENGTH: 768
<212> TYPE: DNA
<213> ORGANISM: Neisseria meningitidis

<400> SEQUENCE: 209
atgagcagcg gagggggtgg tgtcgccgcc gacatcggtg cggggcttgc cgatgcacta 60
accgcaccgc tcgaccataa agacaaaggt ttgcagtctt tgacgctgga tcagtccgtc 120
aggaaaaacg agaaactgaa gctggcggca caaggtgcgg aaaaaactta tggaaacggt 180
gacagcctca atacgggcaa attgaagaac gacaaggtca gccgtttcga ctttatccgc 240
caaatcgaag tggacgggca gctcattacc ttggagagtg gagagttcca agtatacaaa 300
caaagccatt ccgccttaac cgcctttcag accgagcaaa tacaagattc ggagcattcc 360
gggaagatgg ttgcgaaacg ccagttcaga atcggcgaca tagcgggcga acatacatct 420
tttgacaagc ttcccgaagg cggcagggcg acatatcgcg ggacggcgtt cggttcagac 480
gatgccggcg gaaaactgac ctacaccata gatttcgccg ccaagcaggg aaacggcaaa 540
atcgaacatt tgaaatcgcc agaactcaat gtcgacctgg ccgccgccga tatcaagccg 600
gatggaaaac gccatgccgt catcagcggt tccgtccttt acaaccaagc cgagaaaggc 660
agttactccc tcggtatctt tggcggaaaa gcccaggaag ttgccggcag cgcggaagtg 720
aaaaccgtaa acggcatacg ccatatcggc cttgccgcca agcaataa 768

<210> SEQ ID NO 210
<211> LENGTH: 255
<212> TYPE: PRT
<213> ORGANISM: Neisseria meningitidis

<400> SEQUENCE: 210

Met Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Gly Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Val Tyr Lys Gln Ser His Ser Ala Leu Thr Ala Phe Gln Thr Glu
100 105 110

Gln Ile Gln Asp Ser Glu His Ser Gly Lys Met Val Ala Lys Arg Gln
115 120 125

Phe Arg Ile Gly Asp Ile Ala Gly Glu His Thr Ser Phe Asp Lys Leu
130 135 140

Pro Glu Gly Gly Arg Ala Thr Tyr Arg Gly Thr Ala Phe Gly Ser Asp
145 150 155 160

Asp Ala Gly Gly Lys Leu Thr Tyr Thr Ile Asp Phe Ala Ala Lys Gln
165 170 175

Gly Asn Gly Lys Ile Glu His Leu Lys Ser Pro Glu Leu Asn Val Asp

-continued

```
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255


<210> SEQ ID NO 211
<211> LENGTH: 768
<212> TYPE: DNA
<213> ORGANISM: Neisseria meningitidis

<400> SEQUENCE: 211

tgcagcagcg gaggggggtgg tgtcgccgcc gacatcggtg cggggcttgc cgatgcacta      60

accgcaccgc tcgaccataa agacaaaggt ttgcagtctt tgacgctgga tcagtccgtc     120

aggaaaaacg agaaactgaa gctggcggca caaggtgcgg aaaaaactta tggaaacggt     180

gacagcctca atacgggcaa attgaagaac gacaaggtca gccgtttcga ctttatccgc     240

caaatcgaag tggacgggca gctcattacc ttggagagtg gagagttcca agtatacaaa     300

caaagccatt ccgccttaac cgcctttcag accgagcaaa tacaagattc ggagcattcc     360

gggaagatgg ttgcgaaacg ccagttcaga atcggcgaca tagcgggcga acatacatct     420

tttgacaagc ttcccgaagg cggcagggcg acatatcgcg ggacggcgtt cggttcagac     480

gatgccggcg gaaaactgac ctacaccata gatttcgccg ccaagcaggg aaacggcaaa     540

atcgaacatt tgaaatcgcc agaactcaat gtcgacctgg ccgccgccga tatcaagccg     600

gatggaaaac gccatgccgt catcagcggt tccgtccttt acaaccaagc cgagaaaggc     660

agttactccc tcggtatctt tggcggaaaa gcccaggaag ttgccggcag cgcggaagtg     720

aaaaccgtaa acggcatacg ccatatcggt cttgccgcca agcagtaa                  768


<210> SEQ ID NO 212
<211> LENGTH: 255
<212> TYPE: PRT
<213> ORGANISM: Neisseria meningitidis

<400> SEQUENCE: 212

Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125
```

```
Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

<210> SEQ ID NO 213
<211> LENGTH: 771
<212> TYPE: DNA
<213> ORGANISM: Neisseria meningitidis

<400> SEQUENCE: 213

```
tgcggatcca gcggaggggg tggtgtcgcc gccgacatcg gtgcggggct tgccgatgca      60

ctaaccgcac cgctcgacca taaagacaaa ggtttgcagt ctttgacgct ggatcagtcc     120

gtcaggaaaa acgagaaact gaagctggcg gcacaaggtg cggaaaaaac ttatggaaac     180

ggtgacagcc tcaatacggg caaattgaag aacgacaagg tcagccgttt cgactttatc     240

cgccaaatcg aagtggacgg gcagctcatt accttggaga gtggagagtt ccaagtatac     300

aaacaaagcc attccgcctt aaccgccttt cagaccgagc aaatacaaga ttcggagcat     360

tccgggaaga tggttgcgaa acgccagttc agaatcggcg acatagcggg cgaacataca     420

tcttttgaca agcttcccga aggcggcagg gcgacatatc gcgggacggc gttcggttca     480

gacgatgccg gcggaaaact gacctacacc atagatttcg ccgccaagca gggaaacggc     540

aaaatcgaac atttgaaatc gccagaactc aatgtcgacc tggccgccgc cgatatcaag     600

ccggatggaa aacgccatgc cgtcatcagc ggttccgtcc tttacaacca agccgagaaa     660

ggcagttact ccctcggtat ctttggcgga aaagcccagg aagttgccgg cagcgcggaa     720

gtgaaaaccg taaacggcat acgccatatc ggtcttgccg ccaagcagta a              771
```

<210> SEQ ID NO 214
<211> LENGTH: 256
<212> TYPE: PRT
<213> ORGANISM: Neisseria meningitidis

<400> SEQUENCE: 214

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Gly Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60
```

-continued

```
Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Val Tyr Lys Gln Ser His Ser Ala Leu Thr Ala Phe Gln Thr
            100                 105                 110

Glu Gln Ile Gln Asp Ser Glu His Ser Gly Lys Met Val Ala Lys Arg
        115                 120                 125

Gln Phe Arg Ile Gly Asp Ile Ala Gly Glu His Thr Ser Phe Asp Lys
    130                 135                 140

Leu Pro Glu Gly Gly Arg Ala Thr Tyr Arg Gly Thr Ala Phe Gly Ser
145                 150                 155                 160

Asp Asp Ala Gly Gly Lys Leu Thr Tyr Thr Ile Asp Phe Ala Ala Lys
                165                 170                 175

Gln Gly Asn Gly Lys Ile Glu His Leu Lys Ser Pro Glu Leu Asn Val
            180                 185                 190

Asp Leu Ala Ala Ala Asp Ile Lys Pro Asp Gly Lys Arg His Ala Val
        195                 200                 205

Ile Ser Gly Ser Val Leu Tyr Asn Gln Ala Glu Lys Gly Ser Tyr Ser
    210                 215                 220

Leu Gly Ile Phe Gly Gly Lys Ala Gln Glu Val Ala Gly Ser Ala Glu
225                 230                 235                 240

Val Lys Thr Val Asn Gly Ile Arg His Ile Gly Leu Ala Ala Lys Gln
                245                 250                 255
```

<210> SEQ ID NO 215
<211> LENGTH: 768
<212> TYPE: DNA
<213> ORGANISM: Neisseria meningitidis

<400> SEQUENCE: 215

```
atgagcagcg gagggggtgg tgtcgccgcc gacatcggtg cggggcttgc cgatgcacta     60

accgcaccgc tcgaccataa agacaaaggt ttgcagtctt tgacgctgga tcagtccgtc    120

aggaaaaacg agaaactgaa gctggcggca caaggtgcgg aaaaaactta tggaaacggt    180

gacagcctca atacgggcaa attgaagaac gacaaggtca gccgtttcga ctttatccgc    240

caaatcgaag tggacgggca gctcattacc ttggagagtg gagagttcca agtatacaaa    300

caaagccatt ccgccttaac cgcctttcag accgagcaaa tacaagattc ggagcattcc    360

gggaagatgg ttgcgaaacg ccagttcaga atcggcgaca tagcgggcga acatacatct    420

tttgacaagc ttcccgaagg cggcagggcg acatatcgcg ggacggcgtt cggttcagac    480

gatgccggcg gaaaactgac ctacaccata gatttcgccg ccaagcaggg aaacggcaaa    540

atcgaacatt tgaaatcgcc agaactcaat gtcgacctgg ccgccgccga tatcaagccg    600

gatggaaaac gccatgccgt catcagcggt tccgtccttt acaaccaagc cgagaaaggc    660

agttactccc tcggtatctt tggcggaaaa gcccaggaag ttgccggcag cgcggaagtg    720

aaaaccgtaa acggcatacg ccatatcggt cttgccgcca agcagtaa                 768
```

<210> SEQ ID NO 216
<211> LENGTH: 255
<212> TYPE: PRT
<213> ORGANISM: Neisseria meningitidis

<400> SEQUENCE: 216

```
Met Ser Ser Gly Gly Gly Gly Val Ala Ala Asp Ile Gly Ala Gly Leu
```

-continued

```
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

<210> SEQ ID NO 217
<211> LENGTH: 768
<212> TYPE: DNA
<213> ORGANISM: Neisseria meningitidis

<400> SEQUENCE: 217

```
tgcagcagcg gagggggcgg tgtcgccgcc gacatcggtg cggggcttgc cgatgcacta      60

accgcaccgc tcgaccataa agacaaaggt ttgcagtctt tgacgctgga tcagtccgtc     120

aggaaaaacg agaaactgaa gctggcggca caaggtgcgg aaaaaactta tggaaacggc     180

gacagcctca atacgggcaa attgaagaac gacaaggtca gccgcttcga ctttatccgt     240

caaatcgaag tggacaggca gctcattacc ttggagagcg gagagttcca agtgtacaaa     300

caaagccatt ccgccttaac cgcccttcag accgagcaag tacaagactc ggagcattcc     360

gggaagatgg ttgcgaaacg tcagttcaga atcggcgaca tagcgggtga acatacatct     420

tttgacaagc ttcccgaagg cggcagggcg acatatcgcg ggacggcgtt cggttcagac     480

gatgccggcg gaaaactgat ttacaccata gatttcgccg ctaagcaggg acacggtaaa     540

atcgaacatt tgaaatcgcc agaactcaat gtcgacctgg ccgccgccga tatcaagccg     600

gatgaaaaac accatgccgt catcagcggt tccgtccttt acaaccaagc cgagaaaggc     660

agttactccc tcggtatctt tggcggaaaa gcccaggaag ttgccggcag cgcggaagtg     720
```

aaaaccgtaa acggtatacg ccatatcggc cttgccgcca agcaataa 768

<210> SEQ ID NO 218
<211> LENGTH: 255
<212> TYPE: PRT
<213> ORGANISM: Neisseria meningitidis

<400> SEQUENCE: 218

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Gly Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Arg Gln Leu Ile Thr Leu Glu Ser Gly Glu Phe
85 90 95

Gln Val Tyr Lys Gln Ser His Ser Ala Leu Thr Ala Leu Gln Thr Glu
100 105 110

Gln Val Gln Asp Ser Glu His Ser Gly Lys Met Val Ala Lys Arg Gln
115 120 125

Phe Arg Ile Gly Asp Ile Ala Gly Glu His Thr Ser Phe Asp Lys Leu
130 135 140

Pro Glu Gly Gly Arg Ala Thr Tyr Arg Gly Thr Ala Phe Gly Ser Asp
145 150 155 160

Asp Ala Gly Gly Lys Leu Ile Tyr Thr Ile Asp Phe Ala Ala Lys Gln
165 170 175

Gly His Gly Lys Ile Glu His Leu Lys Ser Pro Glu Leu Asn Val Asp
180 185 190

Leu Ala Ala Ala Asp Ile Lys Pro Asp Glu Lys His His Ala Val Ile
195 200 205

Ser Gly Ser Val Leu Tyr Asn Gln Ala Glu Lys Gly Ser Tyr Ser Leu
210 215 220

Gly Ile Phe Gly Gly Lys Ala Gln Glu Val Ala Gly Ser Ala Glu Val
225 230 235 240

Lys Thr Val Asn Gly Ile Arg His Ile Gly Leu Ala Ala Lys Gln
245 250 255

<210> SEQ ID NO 219
<211> LENGTH: 771
<212> TYPE: DNA
<213> ORGANISM: Neisseria meningitidis

<400> SEQUENCE: 219
tgcggatcca gcggaggggg cggtgtcgcc gccgacatcg gtgcggggct tgccgatgca 60
ctaaccgcac cgctcgacca taaagacaaa ggtttgcagt ctttgacgct ggatcagtcc 120
gtcaggaaaa acgagaaact gaagctggcg gcacaaggtg cggaaaaaac ttatggaaac 180
ggcgacagcc tcaatacggg caaattgaag aacgacaagg tcagccgctt cgactttatc 240
cgtcaaatcg aagtggacag gcagctcatt accttggaga gcggagagtt ccaagtgtac 300
aaacaaagcc attccgcctt aaccgccctt cagaccgagc aagtacaaga ctcggagcat 360
tccgggaaga tggttgcgaa acgtcagttc agaatcggcg acatagcggg tgaacataca 420

```
tcttttgaca agcttcccga aggcggcagg gcgacatatc gcgggacggc gttcggttca    480

gacgatgccg gcggaaaact gatttacacc atagatttcg ccgctaagca gggacacggt    540

aaaatcgaac atttgaaatc gccagaactc aatgtcgacc tggccgccgc cgatatcaag    600

ccggatgaaa aacaccatgc cgtcatcagc ggttccgtcc tttacaacca agccgagaaa    660

ggcagttact ccctcggtat ctttggcgga aaagcccagg aagttgccgg cagcgcggaa    720

gtgaaaaccg taaacggtat acgccatatc ggccttgccg ccaagcaata a             771


<210> SEQ ID NO 220
<211> LENGTH: 256
<212> TYPE: PRT
<213> ORGANISM: Neisseria meningitidis

<400> SEQUENCE: 220

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Gly Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Arg Gln Leu Ile Thr Leu Glu Ser Gly Glu
                85                  90                  95

Phe Gln Val Tyr Lys Gln Ser His Ser Ala Leu Thr Ala Leu Gln Thr
            100                 105                 110

Glu Gln Val Gln Asp Ser Glu His Ser Gly Lys Met Val Ala Lys Arg
        115                 120                 125

Gln Phe Arg Ile Gly Asp Ile Ala Gly Glu His Thr Ser Phe Asp Lys
    130                 135                 140

Leu Pro Glu Gly Gly Arg Ala Thr Tyr Arg Gly Thr Ala Phe Gly Ser
145                 150                 155                 160

Asp Asp Ala Gly Gly Lys Leu Ile Tyr Thr Ile Asp Phe Ala Ala Lys
                165                 170                 175

Gln Gly His Gly Lys Ile Glu His Leu Lys Ser Pro Glu Leu Asn Val
            180                 185                 190

Asp Leu Ala Ala Ala Asp Ile Lys Pro Asp Glu Lys His His Ala Val
        195                 200                 205

Ile Ser Gly Ser Val Leu Tyr Asn Gln Ala Glu Lys Gly Ser Tyr Ser
    210                 215                 220

Leu Gly Ile Phe Gly Gly Lys Ala Gln Glu Val Ala Gly Ser Ala Glu
225                 230                 235                 240

Val Lys Thr Val Asn Gly Ile Arg His Ile Gly Leu Ala Ala Lys Gln
                245                 250                 255


<210> SEQ ID NO 221
<211> LENGTH: 768
<212> TYPE: DNA
<213> ORGANISM: Neisseria meningitidis

<400> SEQUENCE: 221

atgagcagcg gagggggcgg tgtcgccgcc gacatcggtg cggggcttgc cgatgcacta     60
```

```
accgcaccgc tcgaccataa agacaaaggt ttgcagtctt tgacgctgga tcagtccgtc    120

aggaaaaacg agaaactgaa gctggcggca caaggtgcgg aaaaaactta tggaaacggc    180

gacagcctca atacgggcaa attgaagaac gacaaggtca gccgcttcga ctttatccgt    240

caaatcgaag tggacaggca gctcattacc ttggagagcg gagagttcca agtgtacaaa    300

caaagccatt ccgccttaac cgcccttcag accgagcaag tacaagactc ggagcattcc    360

gggaagatgg ttgcgaaacg tcagttcaga atcggcgaca tagcgggtga acatacatct    420

tttgacaagc ttcccgaagg cggcagggcg acatatcgcg ggacggcgtt cggttcagac    480

gatgccggcg gaaaactgat ttacaccata gatttcgccg ctaagcaggg acacggtaaa    540

atcgaacatt tgaaatcgcc agaactcaat gtcgacctgg ccgccgccga tatcaagccg    600

gatgaaaaac accatgccgt catcagcggt tccgtccttt acaaccaagc cgagaaaggc    660

agttactccc tcggtatctt tggcggaaaa gcccaggaag ttgccggcag cgcggaagtg    720

aaaaccgtaa acggtatacg ccatatcggc cttgccgcca agcaataa                 768
```

<210> SEQ ID NO 222
<211> LENGTH: 255
<212> TYPE: PRT
<213> ORGANISM: Neisseria meningitidis

<400> SEQUENCE: 222

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Arg Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Glu Gly Gly Arg Ala Thr Tyr Arg Gly Thr Ala Phe Gly Ser Asp
145                 150                 155                 160

Asp Ala Gly Gly Lys Leu Ile Tyr Thr Ile Asp Phe Ala Ala Lys Gln
                165                 170                 175

Gly His Gly Lys Ile Glu His Leu Lys Ser Pro Glu Leu Asn Val Asp
            180                 185                 190

Leu Ala Ala Ala Asp Ile Lys Pro Asp Glu Lys His His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

<210> SEQ ID NO 223
<211> LENGTH: 768
<212> TYPE: DNA
<213> ORGANISM: Neisseria meningitidis

<400> SEQUENCE: 223

```
tgcagcagcg gagggggcgg tgtcgccgcc gacatcggtg cggggcttgc cgatgcacta     60

accgcaccgc tcgaccataa agacaaaggt ttgcagtctt taacgctgga tcagtccgtc    120

aggaaaaacg agaaactgaa gctggcggca caaggtgcgg aaaaaactta tggaaacggc    180

gacagcctta atacgggcaa attgaagaac gacaaggtca gccgcttcga ctttatccgt    240

caaatcgaag tggacgggaa gctcattacc ttggagagcg gagagttcca agtgtacaaa    300

caaagccatt ccgccttaac cgcccttcag accgagcaag tacaagactc ggaggattcc    360

gggaagatgg ttgcgaaacg ccagttcaga atcggcgaca tagcgggcga acatacatct    420

tttgacaagc ttcccaaagg cggcagtgcg acatatcgcg ggacggcgtt cggttcagac    480

gatgctggcg gaaaactgac ctatactata gatttcgccg ccaagcaggg acacggcaaa    540

atcgaacatt tgaaatcgcc cgaactcaat gtcgagcttg ccaccgccta tatcaagccg    600

gatgaaaaac gccatgccgt tatcagcggt tccgtccttt acaaccaaga cgagaaaggc    660

agttactccc tcggtatctt tggcgggcaa gcccaggaag ttgccggcag cgcggaagtg    720

gaaaccgcaa acggcataca ccatatcggt cttgccgcca agcagtaa                 768
```

<210> SEQ ID NO 224
<211> LENGTH: 255
<212> TYPE: PRT
<213> ORGANISM: Neisseria meningitidis

<400> SEQUENCE: 224

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Gly Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190
```

```
Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255
```

<210> SEQ ID NO 225
<211> LENGTH: 771
<212> TYPE: DNA
<213> ORGANISM: Neisseria meningitidis

<400> SEQUENCE: 225

```
tgcggatcca gcggaggggg cggtgtcgcc gccgacatcg gtgcggggct tgccgatgca      60

ctaaccgcac cgctcgacca taaagacaaa ggtttgcagt ctttaacgct ggatcagtcc     120

gtcaggaaaa acgagaaact gaagctggcg gcacaaggtg cggaaaaaac ttatggaaac     180

ggcgacagcc ttaatacggg caaattgaag aacgacaagg tcagccgctt cgactttatc     240

cgtcaaatcg aagtggacgg gaagctcatt accttggaga gcggagagtt ccaagtgtac     300

aaacaaagcc attccgcctt aaccgccctt cagaccgagc aagtacaaga ctcggaggat     360

tccgggaaga tggttgcgaa acgccagttc agaatcggcg acatagcggg cgaacataca     420

tcttttgaca agcttcccaa aggcggcagt gcgacatatc gcgggacggc gttcggttca     480

gacgatgctg gcggaaaact gacctatact atagatttcg ccgccaagca gggacacggc     540

aaaatcgaac atttgaaatc gcccgaactc aatgtcgagc ttgccaccgc ctatatcaag     600

ccggatgaaa aacgccatgc cgttatcagc ggttccgtcc tttacaacca agacgagaaa     660

ggcagttact ccctcggtat ctttggcggg caagcccagg aagttgccgg cagcgcggaa     720

gtggaaaccg caaacggcat acaccatatc ggtcttgccg ccaagcagta a              771
```

<210> SEQ ID NO 226
<211> LENGTH: 256
<212> TYPE: PRT
<213> ORGANISM: Neisseria meningitidis

<400> SEQUENCE: 226

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Gly Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Lys Leu Ile Thr Leu Glu Ser Gly Glu
                85                  90                  95

Phe Gln Val Tyr Lys Gln Ser His Ser Ala Leu Thr Ala Leu Gln Thr
            100                 105                 110

Glu Gln Val Gln Asp Ser Glu Asp Ser Gly Lys Met Val Ala Lys Arg
        115                 120                 125

Gln Phe Arg Ile Gly Asp Ile Ala Gly Glu His Thr Ser Phe Asp Lys
```

-continued 130 135 140

Leu Pro Lys Gly Gly Ser Ala Thr Tyr Arg Gly Thr Ala Phe Gly Ser
145 150 155 160

Asp Asp Ala Gly Gly Lys Leu Thr Tyr Thr Ile Asp Phe Ala Ala Lys
165 170 175

Gln Gly His Gly Lys Ile Glu His Leu Lys Ser Pro Glu Leu Asn Val
180 185 190

Glu Leu Ala Thr Ala Tyr Ile Lys Pro Asp Glu Lys Arg His Ala Val
195 200 205

Ile Ser Gly Ser Val Leu Tyr Asn Gln Asp Glu Lys Gly Ser Tyr Ser
210 215 220

Leu Gly Ile Phe Gly Gly Gln Ala Gln Glu Val Ala Gly Ser Ala Glu
225 230 235 240

Val Glu Thr Ala Asn Gly Ile His His Ile Gly Leu Ala Ala Lys Gln
245 250 255

<210> SEQ ID NO 227
<211> LENGTH: 768
<212> TYPE: DNA
<213> ORGANISM: Neisseria meningitidis

<400> SEQUENCE: 227
atgagcagcg gagggggcgg tgtcgccgcc gacatcggtg cggggcttgc cgatgcacta 60
accgcaccgc tcgaccataa agacaaaggt ttgcagtctt taacgctgga tcagtccgtc 120
aggaaaaacg agaaactgaa gctggcggca caaggtgcgg aaaaaactta tggaaacggc 180
gacagcctta atacgggcaa attgaagaac gacaaggtca gccgcttcga ctttatccgt 240
caaatcgaag tggacgggaa gctcattacc ttggagagcg gagagttcca agtgtacaaa 300
caaagccatt ccgccttaac cgcccttcag accgagcaag tacaagactc ggaggattcc 360
gggaagatgg ttgcgaaacg ccagttcaga atcggcgaca tagcgggcga acatacatct 420
tttgacaagc ttcccaaagg cggcagtgcg acatatcgcg ggacggcgtt cggttcagac 480
gatgctggcg gaaaactgac ctatactata gatttcgccg ccaagcaggg acacggcaaa 540
atcgaacatt tgaaatcgcc cgaactcaat gtcgagcttg ccaccgccta tatcaagccg 600
gatgaaaaac gccatgccgt tatcagcggt tccgtccttt acaaccaaga cgagaaaggc 660
agttactccc tcggtatctt tggcgggcaa gcccaggaag ttgccggcag cgcggaagtg 720
gaaaccgcaa acggcataca ccatatcggt cttgccgcca agcagtaa 768

<210> SEQ ID NO 228
<211> LENGTH: 255
<212> TYPE: PRT
<213> ORGANISM: Neisseria meningitidis

<400> SEQUENCE: 228

Met Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Gly Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

```
Gln Ile Glu Val Asp Gly Lys Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Val Gln Asp Ser Glu Asp Ser Gly Lys Met Val Ala Lys Arg Gln
        115                 120                 125

Phe Arg Ile Gly Asp Ile Ala Gly Glu His Thr Ser Phe Asp Lys Leu
    130                 135                 140

Pro Lys Gly Gly Ser Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys Arg His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255


<210> SEQ ID NO 229
<211> LENGTH: 768
<212> TYPE: DNA
<213> ORGANISM: Neisseria meningitidis

<400> SEQUENCE: 229

tgcagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctta atacgggcaa attgaagaac gacaaggtca gccgtttcga ctttatccgt     240

caaatcgaag tggacgggca gctcattacc ttggagagcg gagagttcca agtgtacaaa     300

caaagccatt ccgccttaac cgcccttcag accgagcaag aacaagatcc agagcattcc     360

gggaagatgg ttgcgaaacg ccggttcaaa atcggcgaca tagcgggcga acatacatct     420

tttgacaagc ttcccaaaga cgtcatggcg acatatcgcg ggacggcgtt cggttcagac     480

gatgccggcg gaaaactgac ctatactata gattttgctg ccaaacaggg acacggcaaa     540

atcgaacatt tgaaatcgcc cgaactcaat gtcgagcttg ccaccgccta tatcaagccg     600

gatgaaaaac accatgccgt catcagcggt tccgtccttt acaatcaaga cgagaaaggc     660

agttactccc tcggtatctt tggcgggcaa gcccaggaag ttgccggcag cgcggaagtg     720

gaaaccgcaa acggcataca ccatatcggt cttgccgcca agcaataa                  768


<210> SEQ ID NO 230
<211> LENGTH: 255
<212> TYPE: PRT
<213> ORGANISM: Neisseria meningitidis

<400> SEQUENCE: 230

Cys Ser Ser Gly Gly Gly Gly Val Ala Ala Asp Ile Gly Ala Gly Leu
1               5                   10                  15
```

-continued

```
Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
        115                 120                 125

Phe Lys Ile Gly Asp Ile Ala Gly Glu His Thr Ser Phe Asp Lys Leu
    130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255
```

<210> SEQ ID NO 231
<211> LENGTH: 771
<212> TYPE: DNA
<213> ORGANISM: Neisseria meningitidis

<400> SEQUENCE: 231

```
tgcggatcca gcggaggcgg cggtgtcgcc gccgacatcg gcgcggggct tgccgatgca     60

ctaaccgcac cgctcgacca taaagacaaa agtttgcagt ctttgacgct ggatcagtcc    120

gtcaggaaaa acgagaaact gaagctggcg gcacaaggtg cggaaaaaac ttatggaaac    180

ggcgacagcc ttaatacggg caaattgaag aacgacaagg tcagccgttt cgactttatc    240

cgtcaaatcg aagtggacgg gcagctcatt accttggaga gcggagagtt ccaagtgtac    300

aaacaaagcc attccgcctt aaccgccctt cagaccgagc aagaacaaga tccagagcat    360

tccgggaaga tggttgcgaa acgccggttc aaaatcggcg acatagcggg cgaacataca    420

tcttttgaca agcttcccaa agacgtcatg gcgacatatc gcgggacggc gttcggttca    480

gacgatgccg gcggaaaact gacctatact atagattttg ctgccaaaca gggacacggc    540

aaaatcgaac atttgaaatc gcccgaactc aatgtcgagc ttgccaccgc ctatatcaag    600

ccggatgaaa aacaccatgc cgtcatcagc ggttccgtcc tttacaatca agacgagaaa    660

ggcagttact ccctcggtat ctttggcggg caagcccagg aagttgccgg cagcgcggaa    720

gtggaaaccg caaacggcat acaccatatc ggtcttgccg ccaagcaata a             771
```

<210> SEQ ID NO 232
<211> LENGTH: 256
<212> TYPE: PRT
<213> ORGANISM: Neisseria meningitidis

<400> SEQUENCE: 232

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Val Tyr Lys Gln Ser His Ser Ala Leu Thr Ala Leu Gln Thr
            100                 105                 110

Glu Gln Glu Gln Asp Pro Glu His Ser Gly Lys Met Val Ala Lys Arg
        115                 120                 125

Arg Phe Lys Ile Gly Asp Ile Ala Gly Glu His Thr Ser Phe Asp Lys
    130                 135                 140

Leu Pro Lys Asp Val Met Ala Thr Tyr Arg Gly Thr Ala Phe Gly Ser
145                 150                 155                 160

Asp Asp Ala Gly Gly Lys Leu Thr Tyr Thr Ile Asp Phe Ala Ala Lys
                165                 170                 175

Gln Gly His Gly Lys Ile Glu His Leu Lys Ser Pro Glu Leu Asn Val
            180                 185                 190

Glu Leu Ala Thr Ala Tyr Ile Lys Pro Asp Glu Lys His His Ala Val
        195                 200                 205

Ile Ser Gly Ser Val Leu Tyr Asn Gln Asp Glu Lys Gly Ser Tyr Ser
    210                 215                 220

Leu Gly Ile Phe Gly Gly Gln Ala Gln Glu Val Ala Gly Ser Ala Glu
225                 230                 235                 240

Val Glu Thr Ala Asn Gly Ile His His Ile Gly Leu Ala Ala Lys Gln
                245                 250                 255
```

<210> SEQ ID NO 233
<211> LENGTH: 768
<212> TYPE: DNA
<213> ORGANISM: Neisseria meningitidis

<400> SEQUENCE: 233

```
atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctta atacgggcaa attgaagaac gacaaggtca gccgtttcga ctttatccgt     240

caaatcgaag tggacgggca gctcattacc ttggagagcg gagagttcca agtgtacaaa     300

caaagccatt ccgccttaac cgcccttcag accgagcaag aacaagatcc agagcattcc     360

gggaagatgg ttgcgaaacg ccggttcaaa atcggcgaca tagcgggcga acatacatct     420

tttgacaagc ttcccaaaga cgtcatggcg acatatcgcg ggacggcgtt cggttcagac     480
```

gatgccggcg gaaaactgac ctatactata gattttgctg ccaaacaggg acacggcaaa 540
atcgaacatt tgaaatcgcc cgaactcaat gtcgagcttg ccaccgccta tatcaagccg 600
gatgaaaaac accatgccgt catcagcggt tccgtccttt acaatcaaga cgagaaaggc 660
agttactccc tcggtatctt tggcgggcaa gcccaggaag ttgccggcag cgcggaagtg 720
gaaaccgcaa acggcataca ccatatcggt cttgccgcca agcaataa 768

<210> SEQ ID NO 234
<211> LENGTH: 255
<212> TYPE: PRT
<213> ORGANISM: Neisseria meningitidis

<400> SEQUENCE: 234

Met Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Val Tyr Lys Gln Ser His Ser Ala Leu Thr Ala Leu Gln Thr Glu
100 105 110

Gln Glu Gln Asp Pro Glu His Ser Gly Lys Met Val Ala Lys Arg Arg
115 120 125

Phe Lys Ile Gly Asp Ile Ala Gly Glu His Thr Ser Phe Asp Lys Leu
130 135 140

Pro Lys Asp Val Met Ala Thr Tyr Arg Gly Thr Ala Phe Gly Ser Asp
145 150 155 160

Asp Ala Gly Gly Lys Leu Thr Tyr Thr Ile Asp Phe Ala Ala Lys Gln
165 170 175

Gly His Gly Lys Ile Glu His Leu Lys Ser Pro Glu Leu Asn Val Glu
180 185 190

Leu Ala Thr Ala Tyr Ile Lys Pro Asp Glu Lys His His Ala Val Ile
195 200 205

Ser Gly Ser Val Leu Tyr Asn Gln Asp Glu Lys Gly Ser Tyr Ser Leu
210 215 220

Gly Ile Phe Gly Gly Gln Ala Gln Glu Val Ala Gly Ser Ala Glu Val
225 230 235 240

Glu Thr Ala Asn Gly Ile His His Ile Gly Leu Ala Ala Lys Gln
245 250 255

<210> SEQ ID NO 235
<211> LENGTH: 768
<212> TYPE: DNA
<213> ORGANISM: Neisseria meningitidis

<400> SEQUENCE: 235
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120

-continued

```
aggaaaaacg agaaactgaa gctggcggca caaggtgcgg aaaaaactta tggaaacggc    180

gacagcctta atacgggcaa attgaagaac gacaaggtca gccgtttcga ctttatccgt    240

caaatcgaag tggacgggca gctcattacc ttggagagcg gagagttcca agtgtacaaa    300

caaagccatt ccgccttaac cgcccttcag accgagcaag aacaagatcc agagcattcc    360

gggaagatgg ttgcgaaacg ccggttcaaa atcggcgaca tagcgggcga acatacatct    420

tttgacaagc ttcccaaaga cgtcatggcg acatatcgcg ggacggcgtt cggttcagac    480

gatgccggcg gaaaactgac ctatactata gattttgctg ccaaacaggg acacggcaaa    540

atcgaacatt tgaaatcgcc cgaactcaat gtcgagcttg ccaccgccta tatcaagccg    600

gatgaaaaac accatgccgt catcagcggt tccgtccttt acaatcaaga cgagaaaggc    660

agttactccc tcggtatctt tggcgggcaa gcccaggaag ttgccggcag cgcggaagtg    720

gaaaccgcaa acggcataca ccatatcggt cttgccgcca agcaataa                 768
```

<210> SEQ ID NO 236
<211> LENGTH: 255
<212> TYPE: PRT
<213> ORGANISM: Neisseria meningitidis

<400> SEQUENCE: 236

```
Cys Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
        115                 120                 125

Phe Lys Ile Gly Asp Ile Ala Gly Glu His Thr Ser Phe Asp Lys Leu
    130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255
```

<210> SEQ ID NO 237
<211> LENGTH: 771
<212> TYPE: DNA
<213> ORGANISM: Neisseria meningitidis

<400> SEQUENCE: 237

```
tgcggatcca gcggaggcgg cggtgtcgcc gccgacatcg gcgcggggct tgccgatgca     60
ctaaccgcac cgctcgacca taaagacaaa agtttgcagt ctttgacgct ggatcagtcc    120
gtcaggaaaa acgagaaact gaagctggcg gcacaaggtg cggaaaaaac ttatggaaac    180
ggcgacagcc ttaatacggg caaattgaag aacgacaagg tcagccgttt cgactttatc    240
cgtcaaatcg aagtggacgg gcagctcatt accttggaga gcggagagtt ccaagtgtac    300
aaacaaagcc attccgcctt aaccgccctt cagaccgagc aagaacaaga tccagagcat    360
tccgggaaga tggttgcgaa acgccggttc aaaatcggcg acatagcggg cgaacataca    420
tcttttgaca agcttcccaa agacgtcatg gcgacatatc gcgggacggc gttcggttca    480
gacgatgccg gcggaaaact gacctatact atagattttg ctgccaaaca gggacacggc    540
aaaatcgaac atttgaaatc gcccgaactc aatgtcgagc ttgccaccgc ctatatcaag    600
ccggatgaaa aacaccatgc cgtcatcagc ggttccgtcc tttacaatca agacgagaaa    660
ggcagttact ccctcggtat ctttggcggg caagcccagg aagttgccgg cagcgcggaa    720
gtggaaaccg caaacggcat acaccatatc ggtcttgccg ccaagcaata a             771
```

<210> SEQ ID NO 238
<211> LENGTH: 256
<212> TYPE: PRT
<213> ORGANISM: Neisseria meningitidis

<400> SEQUENCE: 238

```
Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30

Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Val Tyr Lys Gln Ser His Ser Ala Leu Thr Ala Leu Gln Thr
            100                 105                 110

Glu Gln Glu Gln Asp Pro Glu His Ser Gly Lys Met Val Ala Lys Arg
        115                 120                 125

Arg Phe Lys Ile Gly Asp Ile Ala Gly Glu His Thr Ser Phe Asp Lys
    130                 135                 140

Leu Pro Lys Asp Val Met Ala Thr Tyr Arg Gly Thr Ala Phe Gly Ser
145                 150                 155                 160

Asp Asp Ala Gly Gly Lys Leu Thr Tyr Thr Ile Asp Phe Ala Ala Lys
                165                 170                 175

Gln Gly His Gly Lys Ile Glu His Leu Lys Ser Pro Glu Leu Asn Val
            180                 185                 190

Glu Leu Ala Thr Ala Tyr Ile Lys Pro Asp Glu Lys His His Ala Val
        195                 200                 205
```

Ile Ser Gly Ser Val Leu Tyr Asn Gln Asp Glu Lys Gly Ser Tyr Ser
210 215 220

Leu Gly Ile Phe Gly Gly Gln Ala Gln Glu Val Ala Gly Ser Ala Glu
225 230 235 240

Val Glu Thr Ala Asn Gly Ile His His Ile Gly Leu Ala Ala Lys Gln
245 250 255

<210> SEQ ID NO 239
<211> LENGTH: 768
<212> TYPE: DNA
<213> ORGANISM: Neisseria meningitidis

<400> SEQUENCE: 239
atgagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctta atacgggcaa attgaagaac gacaaggtca gccgtttcga ctttatccgt 240
caaatcgaag tggacgggca gctcattacc ttggagagcg gagagttcca agtgtacaaa 300
caaagccatt ccgccttaac cgcccttcag accgagcaag aacaagatcc agagcattcc 360
gggaagatgg ttgcgaaacg ccggttcaaa atcggcgaca tagcgggcga acatacatct 420
tttgacaagc ttcccaaaga cgtcatggcg acatatcgcg ggacggcgtt cggttcagac 480
gatgccggcg gaaaactgac ctatactata gattttgctg ccaaacaggg acacggcaaa 540
atcgaacatt tgaaatcgcc cgaactcaat gtcgagcttg ccaccgccta tatcaagccg 600
gatgaaaaac accatgccgt catcagcggt tccgtccttt acaatcaaga cgagaaaggc 660
agttactccc tcggtatctt tggcgggcaa gcccaggaag ttgccggcag cgcggaagtg 720
gaaaccgcaa acggcataca ccatatcggt cttgccgcca agcaataa 768

<210> SEQ ID NO 240
<211> LENGTH: 255
<212> TYPE: PRT
<213> ORGANISM: Neisseria meningitidis

<400> SEQUENCE: 240

Met Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe
85 90 95

Gln Val Tyr Lys Gln Ser His Ser Ala Leu Thr Ala Leu Gln Thr Glu
100 105 110

Gln Glu Gln Asp Pro Glu His Ser Gly Lys Met Val Ala Lys Arg Arg
115 120 125

Phe Lys Ile Gly Asp Ile Ala Gly Glu His Thr Ser Phe Asp Lys Leu
130 135 140

Pro Lys Asp Val Met Ala Thr Tyr Arg Gly Thr Ala Phe Gly Ser Asp
145 150 155 160

Asp Ala Gly Gly Lys Leu Thr Tyr Thr Ile Asp Phe Ala Ala Lys Gln
165 170 175

Gly His Gly Lys Ile Glu His Leu Lys Ser Pro Glu Leu Asn Val Glu
180 185 190

Leu Ala Thr Ala Tyr Ile Lys Pro Asp Glu Lys His His Ala Val Ile
195 200 205

Ser Gly Ser Val Leu Tyr Asn Gln Asp Glu Lys Gly Ser Tyr Ser Leu
210 215 220

Gly Ile Phe Gly Gly Gln Ala Gln Glu Val Ala Gly Ser Ala Glu Val
225 230 235 240

Glu Thr Ala Asn Gly Ile His His Ile Gly Leu Ala Ala Lys Gln
245 250 255

<210> SEQ ID NO 241
<211> LENGTH: 765
<212> TYPE: DNA
<213> ORGANISM: Neisseria meningitidis

<400> SEQUENCE: 241
tgcagcagcg gaggcggcgg tgtcgccgcc gacatcggcg cggggcttgc cgatgcacta 60
accgcaccgc tcgaccataa agacaaaagt ttgcagtctt tgacgctgga tcagtccgtc 120
aggaaaaacg agaaactgaa gctggcggca caaggtgcgg aaaaaactta tggaaacggc 180
gacagcctta atacgggcaa attgaagaac gacaaggtca gccgtttcga ctttatccgt 240
caaatcgaag tggacgggca gctcattacc ttggagagcg gagagttcca agtgtacaaa 300
caaagccatt ccgccttaac cgcccttcag accgagcaag aacaagatcc agagcattcc 360
gggaagatgg ttgcgaaacg ccggttcaaa atcggcgaca tagcgggcga acatacatct 420
tttgacaagc ttcccaaaga cgtcatggcg acatatcgcg ggacggcgtt cggttcagac 480
gatgccggcg gaaaactgac ctatactata gattttgctg ccaaacaggg acacggcaaa 540
atcgaacatt tgaaatcgcc cgaactcaat gtcgagcttg ccaccgccta tatcaagccg 600
gatgaaaaac accatgccgt catcagcggt tccgtccttt acaatcaaga cgagaaaggc 660
agttactccc tcggtatctt tggcgggcaa gcccaggaag ttgccggcag cgcggaagtg 720
gaaaccgcaa acggcataca ccatatcggt cttgccgcca agcaa 765

<210> SEQ ID NO 242
<211> LENGTH: 255
<212> TYPE: PRT
<213> ORGANISM: Neisseria meningitidis

<400> SEQUENCE: 242

Cys Ser Ser Gly Gly Gly Gly Val Ala Ala Asp Ile Gly Ala Gly Leu
1 5 10 15

Ala Asp Ala Leu Thr Ala Pro Leu Asp His Lys Asp Lys Ser Leu Gln
20 25 30

Ser Leu Thr Leu Asp Gln Ser Val Arg Lys Asn Glu Lys Leu Lys Leu
35 40 45

Ala Ala Gln Gly Ala Glu Lys Thr Tyr Gly Asn Gly Asp Ser Leu Asn
50 55 60

Thr Gly Lys Leu Lys Asn Asp Lys Val Ser Arg Phe Asp Phe Ile Arg
65 70 75 80

Gln Ile Glu Val Asp Gly Gln Leu Ile Thr Leu Glu Ser Gly Glu Phe

-continued

```
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
        115                 120                 125

Phe Lys Ile Gly Asp Ile Ala Gly Glu His Thr Ser Phe Asp Lys Leu
    130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255
```

```
<210> SEQ ID NO 243
<211> LENGTH: 768
<212> TYPE: DNA
<213> ORGANISM: Neisseria meningitidis

<400> SEQUENCE: 243

tgcggatcca gcggaggcgg cggtgtcgcc gccgacatcg gcgcggggct tgccgatgca      60

ctaaccgcac cgctcgacca taaagacaaa agtttgcagt ctttgacgct ggatcagtcc     120

gtcaggaaaa acgagaaact gaagctggcg gcacaaggtg cggaaaaaac ttatggaaac     180

ggcgacagcc ttaatacggg caaattgaag aacgacaagg tcagccgttt cgactttatc     240

cgtcaaatcg aagtggacgg gcagctcatt accttggaga gcggagagtt ccaagtgtac     300

aaacaaagcc attccgcctt aaccgccctt cagaccgagc aagaacaaga tccagagcat     360

tccgggaaga tggttgcgaa acgccggttc aaaatcggcg acatagcggg cgaacataca     420

tcttttgaca agcttcccaa agacgtcatg gcgacatatc gcgggacggc gttcggttca     480

gacgatgccg gcggaaaact gacctatact atagattttg ctgccaaaca gggacacggc     540

aaaatcgaac atttgaaatc gcccgaactc aatgtcgagc ttgccaccgc ctatatcaag     600

ccggatgaaa aacaccatgc cgtcatcagc ggttccgtcc tttacaatca agacgagaaa     660

ggcagttact ccctcggtat ctttggcggg caagcccagg aagttgccgg cagcgcggaa     720

gtggaaaccg caaacggcat acaccatatc ggtcttgccg ccaagcaa                  768


<210> SEQ ID NO 244
<211> LENGTH: 256
<212> TYPE: PRT
<213> ORGANISM: Neisseria meningitidis

<400> SEQUENCE: 244

Cys Gly Ser Ser Gly Gly Gly Gly Val Ala Ala Asp Ile Gly Ala Gly
1               5                   10                  15

Leu Ala Asp Ala Leu Thr Ala Pro Leu Asp His Lys Asp Lys Ser Leu
            20                  25                  30
```

```
Gln Ser Leu Thr Leu Asp Gln Ser Val Arg Lys Asn Glu Lys Leu Lys
        35                  40                  45

Leu Ala Ala Gln Gly Ala Glu Lys Thr Tyr Gly Asn Gly Asp Ser Leu
    50                  55                  60

Asn Thr Gly Lys Leu Lys Asn Asp Lys Val Ser Arg Phe Asp Phe Ile
65                  70                  75                  80

Arg Gln Ile Glu Val Asp Gly Gln Leu Ile Thr Leu Glu Ser Gly Glu
                85                  90                  95

Phe Gln Val Tyr Lys Gln Ser His Ser Ala Leu Thr Ala Leu Gln Thr
            100                 105                 110

Glu Gln Glu Gln Asp Pro Glu His Ser Gly Lys Met Val Ala Lys Arg
        115                 120                 125

Arg Phe Lys Ile Gly Asp Ile Ala Gly Glu His Thr Ser Phe Asp Lys
    130                 135                 140

Leu Pro Lys Asp Val Met Ala Thr Tyr Arg Gly Thr Ala Phe Gly Ser
145                 150                 155                 160

Asp Asp Ala Gly Gly Lys Leu Thr Tyr Thr Ile Asp Phe Ala Ala Lys
                165                 170                 175

Gln Gly His Gly Lys Ile Glu His Leu Lys Ser Pro Glu Leu Asn Val
            180                 185                 190

Glu Leu Ala Thr Ala Tyr Ile Lys Pro Asp Glu Lys His His Ala Val
        195                 200                 205

Ile Ser Gly Ser Val Leu Tyr Asn Gln Asp Glu Lys Gly Ser Tyr Ser
    210                 215                 220

Leu Gly Ile Phe Gly Gly Gln Ala Gln Glu Val Ala Gly Ser Ala Glu
225                 230                 235                 240

Val Glu Thr Ala Asn Gly Ile His His Ile Gly Leu Ala Ala Lys Gln
                245                 250                 255
```

<210> SEQ ID NO 245
<211> LENGTH: 765
<212> TYPE: DNA
<213> ORGANISM: Neisseria meningitidis

<400> SEQUENCE: 245

```
atgagcagcg gaggcggcgg tgtcgccgcc gacatcggcg cggggcttgc cgatgcacta      60

accgcaccgc tcgaccataa agacaaaagt ttgcagtctt tgacgctgga tcagtccgtc     120

aggaaaaacg agaaactgaa gctggcggca caaggtgcgg aaaaaactta tggaaacggc     180

gacagcctta atacgggcaa attgaagaac gacaaggtca gccgtttcga ctttatccgt     240

caaatcgaag tggacgggca gctcattacc ttggagagcg gagagttcca agtgtacaaa     300

caaagccatt ccgccttaac cgcccttcag accgagcaag aacaagatcc agagcattcc     360

gggaagatgg ttgcgaaacg ccggttcaaa atcggcgaca tagcgggcga acatacatct     420

tttgacaagc ttcccaaaga cgtcatggcg acatatcgcg ggacggcgtt cggttcagac     480

gatgccggcg gaaaactgac ctatactata gattttgctg ccaaacaggg acacggcaaa     540

atcgaacatt tgaaatcgcc cgaactcaat gtcgagcttg ccaccgccta tatcaagccg     600

gatgaaaaac accatgccgt catcagcggt tccgtccttt acaatcaaga cgagaaaggc     660

agttactccc tcggtatctt tggcgggcaa gcccaggaag ttgccggcag cgcggaagtg     720

gaaaccgcaa acggcataca ccatatcggt cttgccgcca agcaa                     765
```

<210> SEQ ID NO 246

<211> LENGTH: 255
<212> TYPE: PRT
<213> ORGANISM: Neisseria meningitidis

<400> SEQUENCE: 246

```
Met Ser Ser Gly Gly Gly Gly Val Ala Ala Asp Ile Gly Ala Gly Leu
1               5                   10                  15

Ala Asp Ala Leu Thr Ala Pro Leu Asp His Lys Asp Lys Ser Leu Gln
            20                  25                  30

Ser Leu Thr Leu Asp Gln Ser Val Arg Lys Asn Glu Lys Leu Lys Leu
        35                  40                  45

Ala Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Glu Gln Asp Pro Glu His Ser Gly Lys Met Val Ala Lys Arg Arg
        115                 120                 125

Phe Lys Ile Gly Asp Ile Ala Gly Glu His Thr Ser Phe Asp Lys Leu
    130                 135                 140

Pro Lys Asp Val Met Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Glu
            180                 185                 190

Leu Ala Thr Ala Tyr Ile Lys Pro Asp Glu Lys His His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Gly Gln Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255
```

<210> SEQ ID NO 247
<211> LENGTH: 783
<212> TYPE: DNA
<213> ORGANISM: Neisseria meningitidis

<400> SEQUENCE: 247

```
tgcagcagcg gaggcggcgg aagcggaggc ggcggtgtca ccgccgacat cggcacgggg     60

cttgccgatg cactaactgc gccgctcgac cataaagaca aaggcttgaa atccctgaca    120

ttggaagact ccatttccca aaacggaaca ctgaccctgt cggcacaagg tgcggaaaaa    180

acttatggaa acggcgacag ccttaatacg ggcaaattga agaacgacaa ggtcagccgt    240

ttcgacttta tccgtcaaat cgaagtggac gggcagctca ttaccttgga gagcggagag    300

ttccaagtgt acaaacaaag ccattccgcc ttaaccgccc ttcagaccga gcaagaacaa    360

gatccagagc attccgagaa gatggttgcg aaacgccggt tcagaatcgg cgacatagcg    420

ggcgaacata catcttttga caagcttccc aaagacgtca tggcgacata tcgcgggacg    480

gcgttcggtt cagacgatgc cggcggaaaa ctgacctata ctatagattt tgctgccaaa    540
```

```
cagggacacg gcaaaatcga acatttgaaa tcgccggaac tcaatgtcga tctggccgtc    600

gcctatatca agccggatga aaaacaccat gccgtcatca gcggttccgt tctttacaac    660

caagacgaga aaggcagtta ctccctcggt atctttggcg aaaaagccca ggaagttgcc    720

ggcagcgcgg aagtggaaac cgcaaacggc atacaccata tcggtcttgc cgccaagcag    780

taa                                                                  783


<210> SEQ ID NO 248
<211> LENGTH: 260
<212> TYPE: PRT
<213> ORGANISM: Neisseria meningitidis

<400> SEQUENCE: 248

Cys Ser Ser Gly Gly Gly Gly Ser Gly Gly Gly Gly Val Thr Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
    130                 135                 140

Ser Phe Asp Lys Leu Pro Lys Asp Val Met Ala Thr Tyr Arg Gly Thr
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
        195                 200                 205

His His Ala Val Ile Ser Gly Ser Val Leu Tyr Asn Gln Asp Glu Lys
    210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260


<210> SEQ ID NO 249
<211> LENGTH: 786
<212> TYPE: DNA
<213> ORGANISM: Neisseria meningitidis

<400> SEQUENCE: 249

tgcggatcca gcggaggcgg cggaagcgga ggcggcggtg tcaccgccga catcggcacg     60
```

```
gggcttgccg atgcactaac tgcgccgctc gaccataaag acaaaggctt gaaatccctg    120

acattggaag actccatttc ccaaaacgga acactgaccc tgtcggcaca aggtgcggaa    180

aaaacttatg gaaacggcga cagccttaat acgggcaaat tgaagaacga caaggtcagc    240

cgtttcgact ttatccgtca aatcgaagtg gacgggcagc tcattacctt ggagagcgga    300

gagttccaag tgtacaaaca aagccattcc gccttaaccg cccttcagac cgagcaagaa    360

caagatccag agcattccga gaagatggtt gcgaaacgcc ggttcagaat cggcgacata    420

gcgggcgaac atacatcttt tgacaagctt cccaaagacg tcatggcgac atatcgcggg    480

acggcgttcg gttcagacga tgccggcgga aaactgacct atactataga ttttgctgcc    540

aaacagggac acggcaaaat cgaacatttg aaatcgccgg aactcaatgt cgatctggcc    600

gtcgcctata tcaagccgga tgaaaaacac catgccgtca tcagcggttc cgttctttac    660

aaccaagacg agaaaggcag ttactccctc ggtatctttg gcgaaaaagc ccaggaagtt    720

gccggcagcg cggaagtgga aaccgcaaac ggcatacacc atatcggtct tgccgccaag    780

cagtaa                                                               786
```

<210> SEQ ID NO 250
<211> LENGTH: 261
<212> TYPE: PRT
<213> ORGANISM: Neisseria meningitidis

<400> SEQUENCE: 250

```
Cys Gly Ser Ser Gly Gly Gly Gly Ser Gly Gly Gly Gly Val Thr Ala
1               5                   10                  15

Asp Ile Gly Thr Gly Leu Ala Asp Ala Leu Thr Ala Pro Leu Asp His
            20                  25                  30

Lys Asp Lys Gly Leu Lys Ser Leu Thr Leu Glu Asp Ser Ile Ser Gln
        35                  40                  45

Asn Gly Thr Leu Thr Leu Ser Ala Gln Gly Ala Glu Lys Thr Tyr Gly
    50                  55                  60

Asn Gly Asp Ser Leu Asn Thr Gly Lys Leu Lys Asn Asp Lys Val Ser
65                  70                  75                  80

Arg Phe Asp Phe Ile Arg Gln Ile Glu Val Asp Gly Gln Leu Ile Thr
                85                  90                  95

Leu Glu Ser Gly Glu Phe Gln Val Tyr Lys Gln Ser His Ser Ala Leu
            100                 105                 110

Thr Ala Leu Gln Thr Glu Gln Glu Gln Asp Pro Glu His Ser Glu Lys
        115                 120                 125

Met Val Ala Lys Arg Arg Phe Arg Ile Gly Asp Ile Ala Gly Glu His
    130                 135                 140

Thr Ser Phe Asp Lys Leu Pro Lys Asp Val Met Ala Thr Tyr Arg Gly
145                 150                 155                 160

Thr Ala Phe Gly Ser Asp Asp Ala Gly Gly Lys Leu Thr Tyr Thr Ile
                165                 170                 175

Asp Phe Ala Ala Lys Gln Gly His Gly Lys Ile Glu His Leu Lys Ser
            180                 185                 190

Pro Glu Leu Asn Val Asp Leu Ala Val Ala Tyr Ile Lys Pro Asp Glu
        195                 200                 205

Lys His His Ala Val Ile Ser Gly Ser Val Leu Tyr Asn Gln Asp Glu
    210                 215                 220

Lys Gly Ser Tyr Ser Leu Gly Ile Phe Gly Glu Lys Ala Gln Glu Val
225                 230                 235                 240
```

```
Ala Gly Ser Ala Glu Val Glu Thr Ala Asn Gly Ile His His Ile Gly
                245                 250                 255

Leu Ala Ala Lys Gln
            260


<210> SEQ ID NO 251
<211> LENGTH: 783
<212> TYPE: DNA
<213> ORGANISM: Neisseria meningitidis

<400> SEQUENCE: 251

atgagcagcg gaggcggcgg aagcggaggc ggcggtgtca ccgccgacat cggcacgggg      60

cttgccgatg cactaactgc gccgctcgac cataaagaca aaggcttgaa atccctgaca     120

ttggaagact ccatttccca aaacggaaca ctgaccctgt cggcacaagg tgcggaaaaa     180

acttatggaa acggcgacag ccttaatacg ggcaaattga agaacgacaa ggtcagccgt     240

ttcgacttta tccgtcaaat cgaagtggac gggcagctca ttaccttgga gagcggagag     300

ttccaagtgt acaaacaaag ccattccgcc ttaaccgccc ttcagaccga gcaagaacaa     360

gatccagagc attccgagaa gatggttgcg aaacgccggt tcagaatcgg cgacatagcg     420

ggcgaacata catcttttga caagcttccc aaagacgtca tggcgacata tcgcgggacg     480

gcgttcggtt cagacgatgc cggcggaaaa ctgacctata ctatagattt tgctgccaaa     540

cagggacacg gcaaaatcga acatttgaaa tcgccggaac tcaatgtcga tctggccgtc     600

gcctatatca agccggatga aaaacaccat gccgtcatca gcggttccgt tctttacaac     660

caagacgaga aaggcagtta ctccctcggt atctttggcg aaaaagccca ggaagttgcc     720

ggcagcgcgg aagtggaaac cgcaaacggc atacaccata tcggtcttgc cgccaagcag     780

taa                                                                   783


<210> SEQ ID NO 252
<211> LENGTH: 260
<212> TYPE: PRT
<213> ORGANISM: Neisseria meningitidis

<400> SEQUENCE: 252

Met Ser Ser Gly Gly Gly Gly Ser Gly Gly Gly Gly Val Thr Ala Asp
1               5                   10                  15

Ile Gly Thr Gly Leu Ala Asp Ala Leu Thr Ala Pro Leu Asp His Lys
            20                  25                  30

Asp Lys Gly Leu Lys Ser Leu Thr Leu Glu Asp Ser Ile Ser Gln Asn
        35                  40                  45

Gly Thr Leu Thr Leu Ser Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Val Tyr Lys Gln Ser His Ser Ala Leu Thr
            100                 105                 110

Ala Leu Gln Thr Glu Gln Glu Gln Asp Pro Glu His Ser Glu Lys Met
        115                 120                 125

Val Ala Lys Arg Arg Phe Arg Ile Gly Asp Ile Ala Gly Glu His Thr
    130                 135                 140

Ser Phe Asp Lys Leu Pro Lys Asp Val Met Ala Thr Tyr Arg Gly Thr
```

```
145                 150                 155                 160

Ala Phe Gly Ser Asp Asp Ala Gly Gly Lys Leu Thr Tyr Thr Ile Asp
                165                 170                 175

Phe Ala Ala Lys Gln Gly His Gly Lys Ile Glu His Leu Lys Ser Pro
            180                 185                 190

Glu Leu Asn Val Asp Leu Ala Val Ala Tyr Ile Lys Pro Asp Glu Lys
        195                 200                 205

His His Ala Val Ile Ser Gly Ser Val Leu Tyr Asn Gln Asp Glu Lys
    210                 215                 220

Gly Ser Tyr Ser Leu Gly Ile Phe Gly Glu Lys Ala Gln Glu Val Ala
225                 230                 235                 240

Gly Ser Ala Glu Val Glu Thr Ala Asn Gly Ile His His Ile Gly Leu
                245                 250                 255

Ala Ala Lys Gln
            260
```

<210> SEQ ID NO 253
<211> LENGTH: 390
<212> TYPE: DNA
<213> ORGANISM: Neisseria meningitidis

<400> SEQUENCE: 253

```
gacagcctga taaaccaacg ctccttcctt gtcagcggtt tgggcggaga acataccgcc     60

ttcaaccaac tgcctgacgg caaagccgag tatcacggca aagcattcag ctccgacgat    120

gctggcggaa aactgaccta taccatagat ttcgccgcca aacagggaca cggcaaaatc    180

gaacacctga aaacacccga gcaaaatgtc gagcttgccg ccgccgaact caaagcagat    240

gaaaaatcac acgccgtcat tttgggcgac acgcgctacg gcagcgaaga aaaaggcact    300

taccacctcg ccctttttcgg cgaccgcgcc caagaaatcg ccggctcggc aaccgtgaag    360

ataggggaaa aggttcacga aatcggcatc                                     390
```

<210> SEQ ID NO 254
<211> LENGTH: 10
<212> TYPE: PRT
<213> ORGANISM: Neisseria meningitidis
<220> FEATURE:
<221> NAME/KEY: MISC_FEATURE
<222> LOCATION: (5)..(5)
<223> OTHER INFORMATION: Xaa equals any of the naturally occurring L-amino acids

<400> SEQUENCE: 254

```
Ala Asp Ile Gly Xaa Gly Leu Ala Asp Ala
1               5                   10
```

<210> SEQ ID NO 255
<211> LENGTH: 10
<212> TYPE: PRT
<213> ORGANISM: Neisseria meningitidis
<220> FEATURE:
<221> NAME/KEY: MISC_FEATURE
<222> LOCATION: (3)..(3)
<223> OTHER INFORMATION: Xaa equals any of the naturally occurring L-amino acids

<400> SEQUENCE: 255

```
Ile Gly Xaa Gly Leu Ala Asp Ala Leu Thr
1               5                   10
```

<210> SEQ ID NO 256

<211> LENGTH: 10
<212> TYPE: PRT
<213> ORGANISM: Neisseria meningitidis

<400> SEQUENCE: 256

Ser Leu Asn Thr Gly Lys Leu Lys Asn Asp
1 5 10

<210> SEQ ID NO 257
<211> LENGTH: 17
<212> TYPE: PRT
<213> ORGANISM: Neisseria meningitidis
<220> FEATURE:
<221> NAME/KEY: MISC_FEATURE
<222> LOCATION: (12)..(12)
<223> OTHER INFORMATION: Xaa equals any of the naturally occurring L-amino acids

<400> SEQUENCE: 257

Ser Leu Asn Thr Gly Lys Leu Lys Asn Asp Lys Xaa Ser Arg Phe Asp
1 5 10 15

Phe

<210> SEQ ID NO 258
<211> LENGTH: 9
<212> TYPE: PRT
<213> ORGANISM: Neisseria meningitidis
<220> FEATURE:
<221> NAME/KEY: MISC_FEATURE
<222> LOCATION: (6)..(6)
<223> OTHER INFORMATION: Xaa equals any of the naturally occurring L-amino acids

<400> SEQUENCE: 258

Ser Gly Glu Phe Gln Xaa Tyr Lys Gln
1 5

<210> SEQ ID NO 259
<211> LENGTH: 8
<212> TYPE: PRT
<213> ORGANISM: Neisseria meningitidis
<220> FEATURE:
<221> NAME/KEY: MISC_FEATURE
<222> LOCATION: (6)..(6)
<223> OTHER INFORMATION: Xaa equals any of the naturally occurring L-amino acids

<400> SEQUENCE: 259

Ile Glu His Leu Lys Xaa Pro Glu
1 5

<210> SEQ ID NO 260
<211> LENGTH: 10
<212> TYPE: PRT
<213> ORGANISM: Neisseria meningitidis
<220> FEATURE:
<221> NAME/KEY: MISC_FEATURE
<222> LOCATION: (10)..(10)
<223> OTHER INFORMATION: Xaa equals any of the naturally occurring L-amino acids

<400> SEQUENCE: 260

Gly Gly Gly Val Ala Ala Asp Ile Gly Xaa
1 5 10

<210> SEQ ID NO 261
<211> LENGTH: 9
<212> TYPE: PRT

<213> ORGANISM: Neisseria meningitidis

<400> SEQUENCE: 261

Ser Gly Glu Phe Gln Ile Tyr Lys Gln
1               5

<210> SEQ ID NO 262
<211> LENGTH: 10
<212> TYPE: PRT
<213> ORGANISM: Neisseria meningitidis

<400> SEQUENCE: 262

His Ser Ala Val Val Ala Leu Gln Ile Glu
1               5                   10

<210> SEQ ID NO 263
<211> LENGTH: 10
<212> TYPE: PRT
<213> ORGANISM: Neisseria meningitidis

<400> SEQUENCE: 263

Glu Lys Ile Asn Asn Pro Asp Lys Ile Asp
1               5                   10

<210> SEQ ID NO 264
<211> LENGTH: 10
<212> TYPE: PRT
<213> ORGANISM: Neisseria meningitidis

<400> SEQUENCE: 264

Ser Leu Ile Asn Gln Arg Ser Phe Leu Val
1               5                   10

<210> SEQ ID NO 265
<211> LENGTH: 10
<212> TYPE: PRT
<213> ORGANISM: Neisseria meningitidis

<400> SEQUENCE: 265

Ser Gly Leu Gly Gly Glu His Thr Ala Phe
1               5                   10

<210> SEQ ID NO 266
<211> LENGTH: 10
<212> TYPE: PRT
<213> ORGANISM: Neisseria meningitidis

<400> SEQUENCE: 266

Gly Glu His Thr Ala Phe Asn Gln Leu Pro
1               5                   10

<210> SEQ ID NO 267
<211> LENGTH: 11
<212> TYPE: PRT
<213> ORGANISM: Neisseria meningitidis

<400> SEQUENCE: 267

Ser Phe Leu Val Ser Gly Leu Gly Gly Glu His
1               5                   10

<210> SEQ ID NO 268
<211> LENGTH: 34
<212> TYPE: PRT
<213> ORGANISM: Neisseria meningitidis

<400> SEQUENCE: 268

Glu Lys Ile Asn Asn Pro Asp Lys Ile Asp Ser Leu Ile Asn Gln Arg
1 5 10 15

Ser Phe Leu Val Ser Gly Leu Gly Gly Glu His Thr Ala Phe Asn Gln
20 25 30

Leu Pro

<210> SEQ ID NO 269
<211> LENGTH: 10
<212> TYPE: PRT
<213> ORGANISM: Neisseria meningitidis

<400> SEQUENCE: 269

Gly Lys Ala Glu Tyr His Gly Lys Ala Phe
1 5 10

<210> SEQ ID NO 270
<211> LENGTH: 10
<212> TYPE: PRT
<213> ORGANISM: Neisseria meningitidis

<400> SEQUENCE: 270

Tyr His Gly Lys Ala Phe Ser Ser Asp Asp
1 5 10

<210> SEQ ID NO 271
<211> LENGTH: 14
<212> TYPE: PRT
<213> ORGANISM: Neisseria meningitidis

<400> SEQUENCE: 271

Gly Lys Ala Glu Tyr His Gly Lys Ala Phe Ser Ser Asp Asp
1 5 10

<210> SEQ ID NO 272
<211> LENGTH: 10
<212> TYPE: PRT
<213> ORGANISM: Neisseria meningitidis

<400> SEQUENCE: 272

Ile Glu His Leu Lys Thr Pro Glu Gln Asn
1 5 10

<210> SEQ ID NO 273
<211> LENGTH: 10
<212> TYPE: PRT
<213> ORGANISM: Neisseria meningitidis

<400> SEQUENCE: 273

Lys Thr Pro Glu Gln Asn Val Glu Leu Ala
1 5 10

<210> SEQ ID NO 274
<211> LENGTH: 14
<212> TYPE: PRT
<213> ORGANISM: Neisseria meningitidis

<400> SEQUENCE: 274

Ile Glu His Leu Lys Thr Pro Glu Gln Asn Val Glu Leu Ala
1 5 10

<210> SEQ ID NO 275
<211> LENGTH: 10

<212> TYPE: PRT
<213> ORGANISM: Neisseria meningitidis

<400> SEQUENCE: 275

Ala Glu Leu Lys Ala Asp Glu Lys Ser His
1 5 10

<210> SEQ ID NO 276
<211> LENGTH: 10
<212> TYPE: PRT
<213> ORGANISM: Neisseria meningitidis

<400> SEQUENCE: 276

Ala Val Ile Leu Gly Asp Thr Arg Tyr Gly
1 5 10

<210> SEQ ID NO 277
<211> LENGTH: 20
<212> TYPE: PRT
<213> ORGANISM: Neisseria meningitidis

<400> SEQUENCE: 277

Ala Glu Leu Lys Ala Asp Glu Lys Ser His Ala Val Ile Leu Gly Asp
1 5 10 15

Thr Arg Tyr Gly
20

<210> SEQ ID NO 278
<211> LENGTH: 10
<212> TYPE: PRT
<213> ORGANISM: Neisseria meningitidis

<400> SEQUENCE: 278

Glu Glu Lys Gly Thr Tyr His Leu Ala Leu
1 5 10

<210> SEQ ID NO 279
<211> LENGTH: 10
<212> TYPE: PRT
<213> ORGANISM: Neisseria meningitidis

<400> SEQUENCE: 279

Leu Ile Thr Leu Glu Ser Gly Glu Phe Gln
1 5 10

<210> SEQ ID NO 280
<211> LENGTH: 10
<212> TYPE: PRT
<213> ORGANISM: Neisseria meningitidis

<400> SEQUENCE: 280

Ser Ala Leu Thr Ala Leu Gln Thr Glu Gln
1 5 10

<210> SEQ ID NO 281
<211> LENGTH: 10
<212> TYPE: PRT
<213> ORGANISM: Neisseria meningitidis

<400> SEQUENCE: 281

Phe Gln Val Tyr Lys Gln Ser His Ser Ala
1 5 10

<210> SEQ ID NO 282

<211> LENGTH: 26
<212> TYPE: PRT
<213> ORGANISM: Neisseria meningitidis

<400> SEQUENCE: 282

Leu Ile Thr Leu Glu Ser Gly Glu Phe Gln Val Tyr Lys Gln Ser His
1               5                   10                  15

Ser Ala Leu Thr Ala Leu Gln Thr Glu Gln
            20                  25

<210> SEQ ID NO 283
<211> LENGTH: 10
<212> TYPE: PRT
<213> ORGANISM: Neisseria meningitidis

<400> SEQUENCE: 283

Ile Gly Asp Ile Ala Gly Glu His Thr Ser
1               5                   10

<210> SEQ ID NO 284
<211> LENGTH: 10
<212> TYPE: PRT
<213> ORGANISM: Neisseria meningitidis

<400> SEQUENCE: 284

Glu His Thr Ser Phe Asp Lys Leu Pro Lys
1               5                   10

<210> SEQ ID NO 285
<211> LENGTH: 16
<212> TYPE: PRT
<213> ORGANISM: Neisseria meningitidis

<400> SEQUENCE: 285

Ile Gly Asp Ile Ala Gly Glu His Thr Ser Phe Asp Lys Leu Pro Lys
1               5                   10                  15

<210> SEQ ID NO 286
<211> LENGTH: 10
<212> TYPE: PRT
<213> ORGANISM: Neisseria meningitidis

<400> SEQUENCE: 286

Ala Thr Tyr Arg Gly Thr Ala Phe Gly Ser
1               5                   10

<210> SEQ ID NO 287
<211> LENGTH: 10
<212> TYPE: PRT
<213> ORGANISM: Neisseria meningitidis

<400> SEQUENCE: 287

Asp Asp Ala Gly Gly Lys Leu Thr Tyr Thr
1               5                   10

<210> SEQ ID NO 288
<211> LENGTH: 10
<212> TYPE: PRT
<213> ORGANISM: Neisseria meningitidis

<400> SEQUENCE: 288

Ile Asp Phe Ala Ala Lys Gln Gly His Gly
1               5                   10

<210> SEQ ID NO 289
<211> LENGTH: 10
<212> TYPE: PRT
<213> ORGANISM: Neisseria meningitidis

<400> SEQUENCE: 289

Lys Ile Glu His Leu Lys Ser Pro Glu Leu
1 5 10

<210> SEQ ID NO 290
<211> LENGTH: 42
<212> TYPE: PRT
<213> ORGANISM: Neisseria meningitidis

<400> SEQUENCE: 290

Ala Thr Tyr Arg Gly Thr Ala Phe Gly Ser Asp Asp Ala Gly Gly Lys
1 5 10 15

Leu Thr Tyr Thr Ile Asp Phe Ala Ala Lys Gln Gly His Gly Lys Ile
20 25 30

Glu His Leu Lys Ser Pro Glu Leu Asn Val
35 40

<210> SEQ ID NO 291
<211> LENGTH: 10
<212> TYPE: PRT
<213> ORGANISM: Neisseria meningitidis

<400> SEQUENCE: 291

His Ala Val Ile Ser Gly Ser Val Leu Tyr
1 5 10

<210> SEQ ID NO 292
<211> LENGTH: 10
<212> TYPE: PRT
<213> ORGANISM: Neisseria meningitidis

<400> SEQUENCE: 292

Lys Gly Ser Tyr Ser Leu Gly Ile Phe Gly
1 5 10

<210> SEQ ID NO 293
<211> LENGTH: 10
<212> TYPE: PRT
<213> ORGANISM: Neisseria meningitidis

<400> SEQUENCE: 293

Val Leu Tyr Asn Gln Asp Glu Lys Gly Ser
1 5 10

<210> SEQ ID NO 294
<211> LENGTH: 24
<212> TYPE: PRT
<213> ORGANISM: Neisseria meningitidis

<400> SEQUENCE: 294

His Ala Val Ile Ser Gly Ser Val Leu Tyr Asn Gln Asp Glu Lys Gly
1 5 10 15

Ser Tyr Ser Leu Gly Ile Phe Gly
20

<210> SEQ ID NO 295
<211> LENGTH: 10
<212> TYPE: PRT
<213> ORGANISM: Neisseria meningitidis

<400> SEQUENCE: 295

Ala Gln Glu Val Ala Gly Ser Ala Glu Val
1 5 10

<210> SEQ ID NO 296
<211> LENGTH: 10
<212> TYPE: PRT
<213> ORGANISM: Neisseria meningitidis

<400> SEQUENCE: 296

Ile His His Ile Gly Leu Ala Ala Lys Gln
1 5 10

<210> SEQ ID NO 297
<211> LENGTH: 10
<212> TYPE: PRT
<213> ORGANISM: Neisseria meningitidis

<400> SEQUENCE: 297

Val Glu Thr Ala Asn Gly Ile His His Ile
1 5 10

<210> SEQ ID NO 298
<211> LENGTH: 25
<212> TYPE: PRT
<213> ORGANISM: Neisseria meningitidis

<400> SEQUENCE: 298

Ala Gln Glu Val Ala Gly Ser Ala Glu Val Glu Thr Ala Asn Gly Ile
1 5 10 15

His His Ile Gly Leu Ala Ala Lys Gln
20 25

<210> SEQ ID NO 299
<211> LENGTH: 22
<212> TYPE: PRT
<213> ORGANISM: Neisseria meningitidis

<400> SEQUENCE: 299

Val Ala Gly Ser Ala Glu Val Glu Thr Ala Asn Gly Ile His His Ile
1 5 10 15

Gly Leu Ala Ala Lys Gln
20

<210> SEQ ID NO 300
<211> LENGTH: 254
<212> TYPE: PRT
<213> ORGANISM: Neisseria meningitidis
<220> FEATURE:
<221> NAME/KEY: MISC_FEATURE
<222> LOCATION: (9)..(9)
<223> OTHER INFORMATION: Xaa equals any of the naturally occurring L-amino acids
<220> FEATURE:
<221> NAME/KEY: MISC_FEATURE
<222> LOCATION: (14)..(14)
<223> OTHER INFORMATION: Xaa equals any of the naturally occurring L-amino acids
<220> FEATURE:
<221> NAME/KEY: MISC_FEATURE
<222> LOCATION: (22)..(22)
<223> OTHER INFORMATION: Xaa equals any of the naturally occurring L-amino acids
<220> FEATURE:
<221> NAME/KEY: MISC_FEATURE
<222> LOCATION: (24)..(24)

<223> OTHER INFORMATION: Xaa equals any of the naturally occurring L-
amino acids
<220> FEATURE:
<221> NAME/KEY: MISC_FEATURE
<222> LOCATION: (26)..(26)
<223> OTHER INFORMATION: Xaa equals any of the naturally occurring L-
amino acids
<220> FEATURE:
<221> NAME/KEY: MISC_FEATURE
<222> LOCATION: (30)..(30)
<223> OTHER INFORMATION: Xaa equals any of the naturally occurring L-
amino acids
<220> FEATURE:
<221> NAME/KEY: MISC_FEATURE
<222> LOCATION: (32)..(32)
<223> OTHER INFORMATION: Xaa equals any of the naturally occurring L-
amino acids
<220> FEATURE:
<221> NAME/KEY: MISC_FEATURE
<222> LOCATION: (37)..(37)
<223> OTHER INFORMATION: Xaa equals any of the naturally occurring L-
amino acids
<220> FEATURE:
<221> NAME/KEY: MISC_FEATURE
<222> LOCATION: (38)..(38)
<223> OTHER INFORMATION: Xaa equals any of the naturally occurring L-
amino acids
<220> FEATURE:
<221> NAME/KEY: MISC_FEATURE
<222> LOCATION: (40)..(40)
<223> OTHER INFORMATION: Xaa equals any of the naturally occurring L-
amino acids
<220> FEATURE:
<221> NAME/KEY: MISC_FEATURE
<222> LOCATION: (41)..(41)
<223> OTHER INFORMATION: Xaa equals any of the naturally occurring L-
amino acids
<220> FEATURE:
<221> NAME/KEY: MISC_FEATURE
<222> LOCATION: (42)..(42)
<223> OTHER INFORMATION: Xaa equals any of the naturally occurring L-
amino acids
<220> FEATURE:
<221> NAME/KEY: MISC_FEATURE
<222> LOCATION: (44)..(44)
<223> OTHER INFORMATION: Xaa equals any of the naturally occurring L-
amino acids
<220> FEATURE:
<221> NAME/KEY: MISC_FEATURE
<222> LOCATION: (45)..(45)
<223> OTHER INFORMATION: Xaa equals any of the naturally occurring L-
amino acids
<220> FEATURE:
<221> NAME/KEY: MISC_FEATURE
<222> LOCATION: (47)..(47)
<223> OTHER INFORMATION: Xaa equals any of the naturally occurring L-
amino acids
<220> FEATURE:
<221> NAME/KEY: MISC_FEATURE
<222> LOCATION: (49)..(49)
<223> OTHER INFORMATION: Xaa equals any of the naturally occurring L-
amino acids
<220> FEATURE:
<221> NAME/KEY: MISC_FEATURE
<222> LOCATION: (57)..(57)
<223> OTHER INFORMATION: Xaa equals any of the naturally occurring L-
amino acids
<220> FEATURE:
<221> NAME/KEY: MISC_FEATURE
<222> LOCATION: (58)..(58)
<223> OTHER INFORMATION: Xaa equals any of the naturally occurring L-
amino acids
<220> FEATURE:
<221> NAME/KEY: MISC_FEATURE
<222> LOCATION: (59)..(59)
<223> OTHER INFORMATION: Xaa equals any of the naturally occurring L-
amino acids
<220> FEATURE:
<221> NAME/KEY: MISC_FEATURE
<222> LOCATION: (73)..(73)
<223> OTHER INFORMATION: Xaa equals any of the naturally occurring L-
amino acids
<220> FEATURE:
<221> NAME/KEY: MISC_FEATURE
<222> LOCATION: (79)..(79)
<223> OTHER INFORMATION: Xaa equals any of the naturally occurring L-
amino acids
<220> FEATURE:
<221> NAME/KEY: MISC_FEATURE
<222> LOCATION: (80)..(80)
<223> OTHER INFORMATION: Xaa equals any of the naturally occurring L-
amino acids
<220> FEATURE:
<221> NAME/KEY: MISC_FEATURE
<222> LOCATION: (81)..(81)
<223> OTHER INFORMATION: Xaa equals any of the naturally occurring L-
amino acids
<220> FEATURE:
<221> NAME/KEY: MISC_FEATURE
<222> LOCATION: (83)..(83)
<223> OTHER INFORMATION: Xaa equals any of the naturally occurring L-
amino acids
<220> FEATURE:
<221> NAME/KEY: MISC_FEATURE
<222> LOCATION: (87)..(87)
<223> OTHER INFORMATION: Xaa equals any of the naturally occurring L-
amino acids
<220> FEATURE:
<221> NAME/KEY: MISC_FEATURE
<222> LOCATION: (88)..(88)
<223> OTHER INFORMATION: Xaa equals any of the naturally occurring L-
amino acids
<220> FEATURE:
<221> NAME/KEY: MISC_FEATURE
<222> LOCATION: (92)..(92)
<223> OTHER INFORMATION: Xaa equals any of the naturally occurring L-
amino acids
<220> FEATURE:
<221> NAME/KEY: MISC_FEATURE
<222> LOCATION: (98)..(98)
<223> OTHER INFORMATION: Xaa equals any of the naturally occurring L-
amino acids
<220> FEATURE:
<221> NAME/KEY: MISC_FEATURE
<222> LOCATION: (102)..(102)
<223> OTHER INFORMATION: Xaa equals any of the naturally occurring L-
amino acids
<220> FEATURE:
<221> NAME/KEY: MISC_FEATURE
<222> LOCATION: (106)..(106)
<223> OTHER INFORMATION: Xaa equals any of the naturally occurring L-
amino acids
<220> FEATURE:
<221> NAME/KEY: MISC_FEATURE
<222> LOCATION: (107)..(107)
<223> OTHER INFORMATION: Xaa equals any of the naturally occurring L-
amino acids
<220> FEATURE:
<221> NAME/KEY: MISC_FEATURE
<222> LOCATION: (111)..(111)
<223> OTHER INFORMATION: Xaa equals any of the naturally occurring L-
amino acids
<220> FEATURE:
<221> NAME/KEY: MISC_FEATURE
<222> LOCATION: (113)..(113)
<223> OTHER INFORMATION: Xaa equals any of the naturally occurring L-
amino acids
<220> FEATURE:
<221> NAME/KEY: MISC_FEATURE
<222> LOCATION: (114)..(114)
<223> OTHER INFORMATION: Xaa equals any of the naturally occurring L-
amino acids
<220> FEATURE:
<221> NAME/KEY: MISC_FEATURE
<222> LOCATION: (115)..(115)
<223> OTHER INFORMATION: Xaa equals any of the naturally occurring L-
amino acids
<220> FEATURE:

<221> NAME/KEY: MISC_FEATURE
<222> LOCATION: (116)..(116)
<223> OTHER INFORMATION: Xaa equals any of the naturally occurring L-amino acids
<220> FEATURE:
<221> NAME/KEY: MISC_FEATURE
<222> LOCATION: (117)..(117)
<223> OTHER INFORMATION: Xaa equals any of the naturally occurring L-amino acids
<220> FEATURE:
<221> NAME/KEY: MISC_FEATURE
<222> LOCATION: (118)..(118)
<223> OTHER INFORMATION: Xaa equals any of the naturally occurring L-amino acids
<220> FEATURE:
<221> NAME/KEY: MISC_FEATURE
<222> LOCATION: (119)..(119)
<223> OTHER INFORMATION: Xaa equals any of the naturally occurring L-amino acids
<220> FEATURE:
<221> NAME/KEY: MISC_FEATURE
<222> LOCATION: (120)..(120)
<223> OTHER INFORMATION: Xaa equals any of the naturally occurring L-amino acids
<220> FEATURE:
<221> NAME/KEY: MISC_FEATURE
<222> LOCATION: (121)..(121)
<223> OTHER INFORMATION: Xaa equals any of the naturally occurring L-amino acids
<220> FEATURE:
<221> NAME/KEY: MISC_FEATURE
<222> LOCATION: (122)..(122)
<223> OTHER INFORMATION: Xaa equals any of the naturally occurring L-amino acids
<220> FEATURE:
<221> NAME/KEY: MISC_FEATURE
<222> LOCATION: (123)..(123)
<223> OTHER INFORMATION: Xaa equals any of the naturally occurring L-amino acids
<220> FEATURE:
<221> NAME/KEY: MISC_FEATURE
<222> LOCATION: (124)..(124)
<223> OTHER INFORMATION: Xaa equals any of the naturally occurring L-amino acids
<220> FEATURE:
<221> NAME/KEY: MISC_FEATURE
<222> LOCATION: (125)..(125)
<223> OTHER INFORMATION: Xaa equals any of the naturally occurring L-amino acids
<220> FEATURE:
<221> NAME/KEY: MISC_FEATURE
<222> LOCATION: (126)..(126)
<223> OTHER INFORMATION: Xaa equals any of the naturally occurring L-amino acids
<220> FEATURE:
<221> NAME/KEY: MISC_FEATURE
<222> LOCATION: (128)..(128)
<223> OTHER INFORMATION: Xaa equals any of the naturally occurring L-amino acids
<220> FEATURE:
<221> NAME/KEY: MISC_FEATURE
<222> LOCATION: (130)..(130)
<223> OTHER INFORMATION: Xaa equals any of the naturally occurring L-amino acids
<220> FEATURE:
<221> NAME/KEY: MISC_FEATURE
<222> LOCATION: (131)..(131)
<223> OTHER INFORMATION: Xaa equals any of the naturally occurring L-amino acids
<220> FEATURE:
<221> NAME/KEY: MISC_FEATURE
<222> LOCATION: (132)..(132)
<223> OTHER INFORMATION: Xaa equals any of the naturally occurring L-amino acids
<220> FEATURE:
<221> NAME/KEY: MISC_FEATURE
<222> LOCATION: (133)..(133)
<223> OTHER INFORMATION: Xaa equals any of the naturally occurring L-amino acids

```
<220> FEATURE:
<221> NAME/KEY: MISC_FEATURE
<222> LOCATION: (134)..(134)
<223> OTHER INFORMATION: Xaa equals any of the naturally occurring L-
      amino acids
<220> FEATURE:
<221> NAME/KEY: MISC_FEATURE
<222> LOCATION: (135)..(135)
<223> OTHER INFORMATION: Xaa equals any of the naturally occurring L-
      amino acids
<220> FEATURE:
<221> NAME/KEY: MISC_FEATURE
<222> LOCATION: (140)..(140)
<223> OTHER INFORMATION: Xaa equals any of the naturally occurring L-
      amino acids
<220> FEATURE:
<221> NAME/KEY: MISC_FEATURE
<222> LOCATION: (142)..(142)
<223> OTHER INFORMATION: Xaa equals any of the naturally occurring L-
      amino acids
<220> FEATURE:
<221> NAME/KEY: MISC_FEATURE
<222> LOCATION: (143)..(143)
<223> OTHER INFORMATION: Xaa equals any of the naturally occurring L-
      amino acids
<220> FEATURE:
<221> NAME/KEY: MISC_FEATURE
<222> LOCATION: (146)..(146)
<223> OTHER INFORMATION: Xaa equals any of the naturally occurring L-
      amino acids
<220> FEATURE:
<221> NAME/KEY: MISC_FEATURE
<222> LOCATION: (147)..(147)
<223> OTHER INFORMATION: Xaa equals any of the naturally occurring L-
      amino acids
<220> FEATURE:
<221> NAME/KEY: MISC_FEATURE
<222> LOCATION: (148)..(148)
<223> OTHER INFORMATION: Xaa equals any of the naturally occurring L-
      amino acids
<220> FEATURE:
<221> NAME/KEY: MISC_FEATURE
<222> LOCATION: (150)..(150)
<223> OTHER INFORMATION: Xaa equals any of the naturally occurring L-
      amino acids
<220> FEATURE:
<221> NAME/KEY: MISC_FEATURE
<222> LOCATION: (152)..(152)
<223> OTHER INFORMATION: Xaa equals any of the naturally occurring L-
      amino acids
<220> FEATURE:
<221> NAME/KEY: MISC_FEATURE
<222> LOCATION: (154)..(154)
<223> OTHER INFORMATION: Xaa equals any of the naturally occurring L-
      amino acids
<220> FEATURE:
<221> NAME/KEY: MISC_FEATURE
<222> LOCATION: (157)..(157)
<223> OTHER INFORMATION: Xaa equals any of the naturally occurring L-
      amino acids
<220> FEATURE:
<221> NAME/KEY: MISC_FEATURE
<222> LOCATION: (161)..(161)
<223> OTHER INFORMATION: Xaa equals any of the naturally occurring L-
      amino acids
<220> FEATURE:
<221> NAME/KEY: MISC_FEATURE
<222> LOCATION: (162)..(162)
<223> OTHER INFORMATION: Xaa equals any of the naturally occurring L-
      amino acids
<220> FEATURE:
<221> NAME/KEY: MISC_FEATURE
<222> LOCATION: (164)..(164)
<223> OTHER INFORMATION: Xaa equals any of the naturally occurring L-
      amino acids
<220> FEATURE:
<221> NAME/KEY: MISC_FEATURE
<222> LOCATION: (166)..(166)
<223> OTHER INFORMATION: Xaa equals any of the naturally occurring L-
```

amino acids
<220> FEATURE:
<221> NAME/KEY: MISC_FEATURE
<222> LOCATION: (168)..(168)
<223> OTHER INFORMATION: Xaa equals any of the naturally occurring L-amino acids
<220> FEATURE:
<221> NAME/KEY: MISC_FEATURE
<222> LOCATION: (172)..(172)
<223> OTHER INFORMATION: Xaa equals any of the naturally occurring L-amino acids
<220> FEATURE:
<221> NAME/KEY: MISC_FEATURE
<222> LOCATION: (173)..(173)
<223> OTHER INFORMATION: Xaa equals any of the naturally occurring L-amino acids
<220> FEATURE:
<221> NAME/KEY: MISC_FEATURE
<222> LOCATION: (177)..(177)
<223> OTHER INFORMATION: Xaa equals any of the naturally occurring L-amino acids
<220> FEATURE:
<221> NAME/KEY: MISC_FEATURE
<222> LOCATION: (179)..(179)
<223> OTHER INFORMATION: Xaa equals any of the naturally occurring L-amino acids
<220> FEATURE:
<221> NAME/KEY: MISC_FEATURE
<222> LOCATION: (185)..(185)
<223> OTHER INFORMATION: Xaa equals any of the naturally occurring L-amino acids
<220> FEATURE:
<221> NAME/KEY: MISC_FEATURE
<222> LOCATION: (188)..(188)
<223> OTHER INFORMATION: Xaa equals any of the naturally occurring L-amino acids
<220> FEATURE:
<221> NAME/KEY: MISC_FEATURE
<222> LOCATION: (191)..(191)
<223> OTHER INFORMATION: Xaa equals any of the naturally occurring L-amino acids
<220> FEATURE:
<221> NAME/KEY: MISC_FEATURE
<222> LOCATION: (194)..(194)
<223> OTHER INFORMATION: Xaa equals any of the naturally occurring L-amino acids
<220> FEATURE:
<221> NAME/KEY: MISC_FEATURE
<222> LOCATION: (195)..(195)
<223> OTHER INFORMATION: Xaa equals any of the naturally occurring L-amino acids
<220> FEATURE:
<221> NAME/KEY: MISC_FEATURE
<222> LOCATION: (196)..(196)
<223> OTHER INFORMATION: Xaa equals any of the naturally occurring L-amino acids
<220> FEATURE:
<221> NAME/KEY: MISC_FEATURE
<222> LOCATION: (197)..(197)
<223> OTHER INFORMATION: Xaa equals any of the naturally occurring L-amino acids
<220> FEATURE:
<221> NAME/KEY: MISC_FEATURE
<222> LOCATION: (199)..(199)
<223> OTHER INFORMATION: Xaa equals any of the naturally occurring L-amino acids
<220> FEATURE:
<221> NAME/KEY: MISC_FEATURE
<222> LOCATION: (203)..(203)
<223> OTHER INFORMATION: Xaa equals any of the naturally occurring L-amino acids
<220> FEATURE:
<221> NAME/KEY: MISC_FEATURE
<222> LOCATION: (208)..(208)
<223> OTHER INFORMATION: Xaa equals any of the naturally occurring L-amino acids
<220> FEATURE:
<221> NAME/KEY: MISC_FEATURE
<222> LOCATION: (210)..(210)

<223> OTHER INFORMATION: Xaa equals any of the naturally occurring L-
amino acids
<220> FEATURE:
<221> NAME/KEY: MISC_FEATURE
<222> LOCATION: (211)..(211)
<223> OTHER INFORMATION: Xaa equals any of the naturally occurring L-
amino acids
<220> FEATURE:
<221> NAME/KEY: MISC_FEATURE
<222> LOCATION: (212)..(212)
<223> OTHER INFORMATION: Xaa equals any of the naturally occurring L-
amino acids
<220> FEATURE:
<221> NAME/KEY: MISC_FEATURE
<222> LOCATION: (214)..(214)
<223> OTHER INFORMATION: Xaa equals any of the naturally occurring L-
amino acids
<220> FEATURE:
<221> NAME/KEY: MISC_FEATURE
<222> LOCATION: (215)..(215)
<223> OTHER INFORMATION: Xaa equals any of the naturally occurring L-
amino acids
<220> FEATURE:
<221> NAME/KEY: MISC_FEATURE
<222> LOCATION: (216)..(216)
<223> OTHER INFORMATION: Xaa equals any of the naturally occurring L-
amino acids
<220> FEATURE:
<221> NAME/KEY: MISC_FEATURE
<222> LOCATION: (220)..(220)
<223> OTHER INFORMATION: Xaa equals any of the naturally occurring L-
amino acids
<220> FEATURE:
<221> NAME/KEY: MISC_FEATURE
<222> LOCATION: (222)..(222)
<223> OTHER INFORMATION: Xaa equals any of the naturally occurring L-
amino acids
<220> FEATURE:
<221> NAME/KEY: MISC_FEATURE
<222> LOCATION: (224)..(224)
<223> OTHER INFORMATION: Xaa equals any of the naturally occurring L-
amino acids
<220> FEATURE:
<221> NAME/KEY: MISC_FEATURE
<222> LOCATION: (225)..(225)
<223> OTHER INFORMATION: Xaa equals any of the naturally occurring L-
amino acids
<220> FEATURE:
<221> NAME/KEY: MISC_FEATURE
<222> LOCATION: (226)..(226)
<223> OTHER INFORMATION: Xaa equals any of the naturally occurring L-
amino acids
<220> FEATURE:
<221> NAME/KEY: MISC_FEATURE
<222> LOCATION: (228)..(228)
<223> OTHER INFORMATION: Xaa equals any of the naturally occurring L-
amino acids
<220> FEATURE:
<221> NAME/KEY: MISC_FEATURE
<222> LOCATION: (229)..(229)
<223> OTHER INFORMATION: Xaa equals any of the naturally occurring L-
amino acids
<220> FEATURE:
<221> NAME/KEY: MISC_FEATURE
<222> LOCATION: (233)..(233)
<223> OTHER INFORMATION: Xaa equals any of the naturally occurring L-
amino acids
<220> FEATURE:
<221> NAME/KEY: MISC_FEATURE
<222> LOCATION: (236)..(236)
<223> OTHER INFORMATION: Xaa equals any of the naturally occurring L-
amino acids
<220> FEATURE:
<221> NAME/KEY: MISC_FEATURE
<222> LOCATION: (238)..(238)
<223> OTHER INFORMATION: Xaa equals any of the naturally occurring L-
amino acids
<220> FEATURE:
<221> NAME/KEY: MISC_FEATURE
<222> LOCATION: (240)..(240)
<223> OTHER INFORMATION: Xaa equals any of the naturally occurring L-amino acids
<220> FEATURE:
<221> NAME/KEY: MISC_FEATURE
<222> LOCATION: (241)..(241)
<223> OTHER INFORMATION: Xaa equals any of the naturally occurring L-amino acids
<220> FEATURE:
<221> NAME/KEY: MISC_FEATURE
<222> LOCATION: (242)..(242)
<223> OTHER INFORMATION: Xaa equals any of the naturally occurring L-amino acids
<220> FEATURE:
<221> NAME/KEY: MISC_FEATURE
<222> LOCATION: (243)..(243)
<223> OTHER INFORMATION: Xaa equals any of the naturally occurring L-amino acids
<220> FEATURE:
<221> NAME/KEY: MISC_FEATURE
<222> LOCATION: (244)..(244)
<223> OTHER INFORMATION: Xaa equals any of the naturally occurring L-amino acids
<220> FEATURE:
<221> NAME/KEY: MISC_FEATURE
<222> LOCATION: (245)..(245)
<223> OTHER INFORMATION: Xaa equals any of the naturally occurring L-amino acids
<220> FEATURE:
<221> NAME/KEY: MISC_FEATURE
<222> LOCATION: (247)..(247)
<223> OTHER INFORMATION: Xaa equals any of the naturally occurring L-amino acids
<220> FEATURE:
<221> NAME/KEY: MISC_FEATURE
<222> LOCATION: (249)..(249)
<223> OTHER INFORMATION: Xaa equals any of the naturally occurring L-amino acids
<220> FEATURE:
<221> NAME/KEY: MISC_FEATURE
<222> LOCATION: (250)..(250)
<223> OTHER INFORMATION: Xaa equals any of the naturally occurring L-amino acids
<220> FEATURE:
<221> NAME/KEY: MISC_FEATURE
<222> LOCATION: (252)..(252)
<223> OTHER INFORMATION: Xaa equals any of the naturally occurring L-amino acids

<400> SEQUENCE: 300

```
Cys Ser Ser Gly Gly Gly Gly Val Xaa Ala Asp Ile Gly Xaa Gly Leu
1               5                   10                  15

Ala Asp Ala Leu Thr Xaa Pro Xaa Asp Xaa Lys Asp Lys Xaa Leu Xaa
            20                  25                  30

Ser Leu Thr Leu Xaa Xaa Ser Xaa Xaa Xaa Asn Xaa Xaa Leu Xaa Leu
        35                  40                  45

Xaa Ala Gln Gly Ala Glu Lys Thr Xaa Xaa Xaa Gly Asp Ser Leu Asn
    50                  55                  60

Thr Gly Lys Leu Lys Asn Asp Lys Xaa Ser Arg Phe Asp Phe Xaa Xaa
65                  70                  75                  80

Xaa Ile Xaa Val Asp Gly Xaa Xaa Ile Thr Leu Xaa Ser Gly Glu Phe
                85                  90                  95

Gln Xaa Tyr Lys Gln Xaa His Ser Ala Xaa Xaa Ala Leu Gln Xaa Glu
            100                 105                 110

Xaa Xaa Xaa Xaa Xaa Xaa Xaa Xaa Xaa Xaa Xaa Xaa Xaa Xaa Arg Xaa
        115                 120                 125

Phe Xaa Xaa Xaa Xaa Xaa Xaa Gly Glu His Thr Xaa Phe Xaa Xaa Leu
    130                 135                 140

Pro Xaa Xaa Xaa Ala Xaa Tyr Xaa Gly Xaa Ala Phe Xaa Ser Asp Asp
```

```
145                 150                 155                 160

Xaa Xaa Gly Xaa Leu Xaa Tyr Xaa Ile Asp Phe Xaa Xaa Lys Gln Gly
                165                 170                 175

Xaa Gly Xaa Ile Glu His Leu Lys Xaa Pro Glu Xaa Asn Val Xaa Leu
            180                 185                 190

Ala Xaa Xaa Xaa Xaa Lys Xaa Asp Glu Lys Xaa His Ala Val Ile Xaa
        195                 200                 205

Gly Xaa Xaa Xaa Tyr Xaa Xaa Xaa Glu Lys Gly Xaa Tyr Xaa Leu Xaa
    210                 215                 220

Xaa Xaa Gly Xaa Xaa Ala Gln Glu Xaa Ala Gly Xaa Ala Xaa Val Xaa
225                 230                 235                 240

Xaa Xaa Xaa Xaa Xaa His Xaa Ile Xaa Xaa Ala Xaa Lys Gln
                245                 250
```

<210> SEQ ID NO 301
<211> LENGTH: 254
<212> TYPE: PRT
<213> ORGANISM: Neisseria meningitidis
<220> FEATURE:
<221> NAME/KEY: MISC_FEATURE
<222> LOCATION: (14)..(14)
<223> OTHER INFORMATION: Xaa equals any of the naturally occurring L-amino acids
<220> FEATURE:
<221> NAME/KEY: MISC_FEATURE
<222> LOCATION: (22)..(22)
<223> OTHER INFORMATION: Xaa equals any of the naturally occurring L-amino acids
<220> FEATURE:
<221> NAME/KEY: MISC_FEATURE
<222> LOCATION: (24)..(24)
<223> OTHER INFORMATION: Xaa equals any of the naturally occurring L-amino acids
<220> FEATURE:
<221> NAME/KEY: MISC_FEATURE
<222> LOCATION: (26)..(26)
<223> OTHER INFORMATION: Xaa equals any of the naturally occurring L-amino acids
<220> FEATURE:
<221> NAME/KEY: MISC_FEATURE
<222> LOCATION: (30)..(30)
<223> OTHER INFORMATION: Xaa equals any of the naturally occurring L-amino acids
<220> FEATURE:
<221> NAME/KEY: MISC_FEATURE
<222> LOCATION: (32)..(32)
<223> OTHER INFORMATION: Xaa equals any of the naturally occurring L-amino acids
<220> FEATURE:
<221> NAME/KEY: MISC_FEATURE
<222> LOCATION: (37)..(37)
<223> OTHER INFORMATION: Xaa equals any of the naturally occurring L-amino acids
<220> FEATURE:
<221> NAME/KEY: MISC_FEATURE
<222> LOCATION: (38)..(38)
<223> OTHER INFORMATION: Xaa equals any of the naturally occurring L-amino acids
<220> FEATURE:
<221> NAME/KEY: MISC_FEATURE
<222> LOCATION: (40)..(40)
<223> OTHER INFORMATION: Xaa equals any of the naturally occurring L-amino acids
<220> FEATURE:
<221> NAME/KEY: MISC_FEATURE
<222> LOCATION: (41)..(41)
<223> OTHER INFORMATION: Xaa equals any of the naturally occurring L-amino acids
<220> FEATURE:
<221> NAME/KEY: MISC_FEATURE
<222> LOCATION: (42)..(42)
<223> OTHER INFORMATION: Xaa equals any of the naturally occurring L- amino acids
<220> FEATURE:
<221> NAME/KEY: MISC_FEATURE
<222> LOCATION: (44)..(44)
<223> OTHER INFORMATION: Xaa equals any of the naturally occurring L-
amino acids
<220> FEATURE:
<221> NAME/KEY: MISC_FEATURE
<222> LOCATION: (45)..(45)
<223> OTHER INFORMATION: Xaa equals any of the naturally occurring L-
amino acids
<220> FEATURE:
<221> NAME/KEY: MISC_FEATURE
<222> LOCATION: (47)..(47)
<223> OTHER INFORMATION: Xaa equals any of the naturally occurring L-
amino acids
<220> FEATURE:
<221> NAME/KEY: MISC_FEATURE
<222> LOCATION: (49)..(49)
<223> OTHER INFORMATION: Xaa equals any of the naturally occurring L-
amino acids
<220> FEATURE:
<221> NAME/KEY: MISC_FEATURE
<222> LOCATION: (57)..(57)
<223> OTHER INFORMATION: Xaa equals any of the naturally occurring L-
amino acids
<220> FEATURE:
<221> NAME/KEY: MISC_FEATURE
<222> LOCATION: (58)..(58)
<223> OTHER INFORMATION: Xaa equals any of the naturally occurring L-
amino acids
<220> FEATURE:
<221> NAME/KEY: MISC_FEATURE
<222> LOCATION: (59)..(59)
<223> OTHER INFORMATION: Xaa equals any of the naturally occurring L-
amino acids
<220> FEATURE:
<221> NAME/KEY: MISC_FEATURE
<222> LOCATION: (73)..(73)
<223> OTHER INFORMATION: Xaa equals any of the naturally occurring L-
amino acids
<220> FEATURE:
<221> NAME/KEY: MISC_FEATURE
<222> LOCATION: (79)..(79)
<223> OTHER INFORMATION: Xaa equals any of the naturally occurring L-
amino acids
<220> FEATURE:
<221> NAME/KEY: MISC_FEATURE
<222> LOCATION: (80)..(80)
<223> OTHER INFORMATION: Xaa equals any of the naturally occurring L-
amino acids
<220> FEATURE:
<221> NAME/KEY: MISC_FEATURE
<222> LOCATION: (81)..(81)
<223> OTHER INFORMATION: Xaa equals any of the naturally occurring L-
amino acids
<220> FEATURE:
<221> NAME/KEY: MISC_FEATURE
<222> LOCATION: (83)..(83)
<223> OTHER INFORMATION: Xaa equals any of the naturally occurring L-
amino acids
<220> FEATURE:
<221> NAME/KEY: MISC_FEATURE
<222> LOCATION: (88)..(88)
<223> OTHER INFORMATION: Xaa equals any of the naturally occurring L-
amino acids
<220> FEATURE:
<221> NAME/KEY: MISC_FEATURE
<222> LOCATION: (92)..(92)
<223> OTHER INFORMATION: Xaa equals any of the naturally occurring L-
amino acids
<220> FEATURE:
<221> NAME/KEY: MISC_FEATURE
<222> LOCATION: (102)..(102)
<223> OTHER INFORMATION: Xaa equals any of the naturally occurring L-
amino acids
<220> FEATURE:
<221> NAME/KEY: MISC_FEATURE
<222> LOCATION: (146)..(146)

```
<223> OTHER INFORMATION: Xaa equals any of the naturally occurring L-
      amino acids
<220> FEATURE:
<221> NAME/KEY: MISC_FEATURE
<222> LOCATION: (161)..(161)
<223> OTHER INFORMATION: Xaa equals any of the naturally occurring L-
      amino acids
<220> FEATURE:
<221> NAME/KEY: MISC_FEATURE
<222> LOCATION: (162)..(162)
<223> OTHER INFORMATION: Xaa equals any of the naturally occurring L-
      amino acids
<220> FEATURE:
<221> NAME/KEY: MISC_FEATURE
<222> LOCATION: (164)..(164)
<223> OTHER INFORMATION: Xaa equals any of the naturally occurring L-
      amino acids
<220> FEATURE:
<221> NAME/KEY: MISC_FEATURE
<222> LOCATION: (166)..(166)
<223> OTHER INFORMATION: Xaa equals any of the naturally occurring L-
      amino acids
<220> FEATURE:
<221> NAME/KEY: MISC_FEATURE
<222> LOCATION: (168)..(168)
<223> OTHER INFORMATION: Xaa equals any of the naturally occurring L-
      amino acids
<220> FEATURE:
<221> NAME/KEY: MISC_FEATURE
<222> LOCATION: (172)..(172)
<223> OTHER INFORMATION: Xaa equals any of the naturally occurring L-
      amino acids
<220> FEATURE:
<221> NAME/KEY: MISC_FEATURE
<222> LOCATION: (173)..(173)
<223> OTHER INFORMATION: Xaa equals any of the naturally occurring L-
      amino acids
<220> FEATURE:
<221> NAME/KEY: MISC_FEATURE
<222> LOCATION: (177)..(177)
<223> OTHER INFORMATION: Xaa equals any of the naturally occurring L-
      amino acids
<220> FEATURE:
<221> NAME/KEY: MISC_FEATURE
<222> LOCATION: (179)..(179)
<223> OTHER INFORMATION: Xaa equals any of the naturally occurring L-
      amino acids
<220> FEATURE:
<221> NAME/KEY: MISC_FEATURE
<222> LOCATION: (194)..(194)
<223> OTHER INFORMATION: Xaa equals any of the naturally occurring L-
      amino acids
<220> FEATURE:
<221> NAME/KEY: MISC_FEATURE
<222> LOCATION: (215)..(215)
<223> OTHER INFORMATION: Xaa equals any of the naturally occurring L-
      amino acids
<220> FEATURE:
<221> NAME/KEY: MISC_FEATURE
<222> LOCATION: (226)..(226)
<223> OTHER INFORMATION: Xaa equals any of the naturally occurring L-
      amino acids
<220> FEATURE:
<221> NAME/KEY: MISC_FEATURE
<222> LOCATION: (236)..(236)
<223> OTHER INFORMATION: Xaa equals any of the naturally occurring L-
      amino acids
<220> FEATURE:
<221> NAME/KEY: MISC_FEATURE
<222> LOCATION: (242)..(242)
<223> OTHER INFORMATION: Xaa equals any of the naturally occurring L-
      amino acids
<220> FEATURE:
<221> NAME/KEY: MISC_FEATURE
<222> LOCATION: (249)..(249)
<223> OTHER INFORMATION: Xaa equals any of the naturally occurring L-
      amino acids
<220> FEATURE:
<221> NAME/KEY: MISC_FEATURE
```

<222> LOCATION: (252)..(252)
<223> OTHER INFORMATION: Xaa equals any of the naturally occurring L-
amino acids

<400> SEQUENCE: 301

```
Cys Ser Ser Gly Gly Gly Gly Val Ala Ala Asp Ile Gly Xaa Gly Leu
1               5                   10                  15

Ala Asp Ala Leu Thr Xaa Pro Xaa Asp Xaa Lys Asp Lys Xaa Leu Xaa
            20                  25                  30

Ser Leu Thr Leu Xaa Xaa Ser Xaa Xaa Xaa Asn Xaa Xaa Leu Xaa Leu
        35                  40                  45

Xaa Ala Gln Gly Ala Glu Lys Thr Xaa Xaa Xaa Gly Asp Ser Leu Asn
    50                  55                  60

Thr Gly Lys Leu Lys Asn Asp Lys Xaa Ser Arg Phe Asp Phe Xaa Xaa
65                  70                  75                  80

Xaa Ile Xaa Val Asp Gly Gln Xaa Ile Thr Leu Xaa Ser Gly Glu Phe
                85                  90                  95

Gln Ile Tyr Lys Gln Xaa His Ser Ala Val Val Ala Leu Gln Ile Glu
            100                 105                 110

Lys Ile Asn Asn Pro Asp Lys Ile Asp Ser Leu Ile Asn Gln Arg Ser
        115                 120                 125

Phe Leu Val Ser Gly Leu Gly Gly Glu His Thr Ala Phe Asn Gln Leu
    130                 135                 140

Pro Xaa Gly Lys Ala Glu Tyr His Gly Lys Ala Phe Ser Ser Asp Asp
145                 150                 155                 160

Xaa Xaa Gly Xaa Leu Xaa Tyr Xaa Ile Asp Phe Xaa Xaa Lys Gln Gly
                165                 170                 175

Xaa Gly Xaa Ile Glu His Leu Lys Thr Pro Glu Gln Asn Val Glu Leu
            180                 185                 190

Ala Xaa Ala Glu Leu Lys Ala Asp Glu Lys Ser His Ala Val Ile Leu
        195                 200                 205

Gly Asp Thr Arg Tyr Gly Xaa Glu Glu Lys Gly Thr Tyr His Leu Ala
    210                 215                 220

Leu Xaa Gly Asp Arg Ala Gln Glu Ile Ala Gly Xaa Ala Thr Val Lys
225                 230                 235                 240

Ile Xaa Glu Lys Val His Glu Ile Xaa Ile Ala Xaa Lys Gln
                245                 250
```

<210> SEQ ID NO 302
<211> LENGTH: 255
<212> TYPE: PRT
<213> ORGANISM: Neisseria meningitidis
<220> FEATURE:
<221> NAME/KEY: MISC_FEATURE
<222> LOCATION: (9)..(9)
<223> OTHER INFORMATION: Xaa equals any of the naturally occurring L-
amino acids
<220> FEATURE:
<221> NAME/KEY: MISC_FEATURE
<222> LOCATION: (14)..(14)
<223> OTHER INFORMATION: Xaa equals any of the naturally occurring L-
amino acids
<220> FEATURE:
<221> NAME/KEY: MISC_FEATURE
<222> LOCATION: (30)..(30)
<223> OTHER INFORMATION: Xaa equals any of the naturally occurring L-
amino acids
<220> FEATURE:
<221> NAME/KEY: MISC_FEATURE
<222> LOCATION: (32)..(32)
<223> OTHER INFORMATION: Xaa equals any of the naturally occurring L-
amino acids <220> FEATURE:
<221> NAME/KEY: MISC_FEATURE
<222> LOCATION: (37)..(37)
<223> OTHER INFORMATION: Xaa equals any of the naturally occurring L-
amino acids
<220> FEATURE:
<221> NAME/KEY: MISC_FEATURE
<222> LOCATION: (38)..(38)
<223> OTHER INFORMATION: Xaa equals any of the naturally occurring L-
amino acids
<220> FEATURE:
<221> NAME/KEY: MISC_FEATURE
<222> LOCATION: (40)..(40)
<223> OTHER INFORMATION: Xaa equals any of the naturally occurring L-
amino acids
<220> FEATURE:
<221> NAME/KEY: MISC_FEATURE
<222> LOCATION: (41)..(41)
<223> OTHER INFORMATION: Xaa equals any of the naturally occurring L-
amino acids
<220> FEATURE:
<221> NAME/KEY: MISC_FEATURE
<222> LOCATION: (42)..(42)
<223> OTHER INFORMATION: Xaa equals any of the naturally occurring L-
amino acids
<220> FEATURE:
<221> NAME/KEY: MISC_FEATURE
<222> LOCATION: (44)..(44)
<223> OTHER INFORMATION: Xaa equals any of the naturally occurring L-
amino acids
<220> FEATURE:
<221> NAME/KEY: MISC_FEATURE
<222> LOCATION: (45)..(45)
<223> OTHER INFORMATION: Xaa equals any of the naturally occurring L-
amino acids
<220> FEATURE:
<221> NAME/KEY: MISC_FEATURE
<222> LOCATION: (47)..(47)
<223> OTHER INFORMATION: Xaa equals any of the naturally occurring L-
amino acids
<220> FEATURE:
<221> NAME/KEY: MISC_FEATURE
<222> LOCATION: (49)..(49)
<223> OTHER INFORMATION: Xaa equals any of the naturally occurring L-
amino acids
<220> FEATURE:
<221> NAME/KEY: MISC_FEATURE
<222> LOCATION: (87)..(87)
<223> OTHER INFORMATION: Xaa equals any of the naturally occurring L-
amino acids
<220> FEATURE:
<221> NAME/KEY: MISC_FEATURE
<222> LOCATION: (114)..(114)
<223> OTHER INFORMATION: Xaa equals any of the naturally occurring L-
amino acids
<220> FEATURE:
<221> NAME/KEY: MISC_FEATURE
<222> LOCATION: (117)..(117)
<223> OTHER INFORMATION: Xaa equals any of the naturally occurring L-
amino acids
<220> FEATURE:
<221> NAME/KEY: MISC_FEATURE
<222> LOCATION: (119)..(119)
<223> OTHER INFORMATION: Xaa equals any of the naturally occurring L-
amino acids
<220> FEATURE:
<221> NAME/KEY: MISC_FEATURE
<222> LOCATION: (121)..(121)
<223> OTHER INFORMATION: Xaa equals any of the naturally occurring L-
amino acids
<220> FEATURE:
<221> NAME/KEY: MISC_FEATURE
<222> LOCATION: (128)..(128)
<223> OTHER INFORMATION: Xaa equals any of the naturally occurring L-
amino acids
<220> FEATURE:
<221> NAME/KEY: MISC_FEATURE
<222> LOCATION: (130)..(130)
<223> OTHER INFORMATION: Xaa equals any of the naturally occurring L- amino acids
<220> FEATURE:
<221> NAME/KEY: MISC_FEATURE
<222> LOCATION: (147)..(147)
<223> OTHER INFORMATION: Xaa equals any of the naturally occurring L-amino acids
<220> FEATURE:
<221> NAME/KEY: MISC_FEATURE
<222> LOCATION: (148)..(148)
<223> OTHER INFORMATION: Xaa equals any of the naturally occurring L-amino acids
<220> FEATURE:
<221> NAME/KEY: MISC_FEATURE
<222> LOCATION: (149)..(149)
<223> OTHER INFORMATION: Xaa equals any of the naturally occurring L-amino acids
<220> FEATURE:
<221> NAME/KEY: MISC_FEATURE
<222> LOCATION: (192)..(192)
<223> OTHER INFORMATION: Xaa equals any of the naturally occurring L-amino acids
<220> FEATURE:
<221> NAME/KEY: MISC_FEATURE
<222> LOCATION: (195)..(195)
<223> OTHER INFORMATION: Xaa equals any of the naturally occurring L-amino acids
<220> FEATURE:
<221> NAME/KEY: MISC_FEATURE
<222> LOCATION: (196)..(196)
<223> OTHER INFORMATION: Xaa equals any of the naturally occurring L-amino acids
<220> FEATURE:
<221> NAME/KEY: MISC_FEATURE
<222> LOCATION: (204)..(204)
<223> OTHER INFORMATION: Xaa equals any of the naturally occurring L-amino acids
<220> FEATURE:
<221> NAME/KEY: MISC_FEATURE
<222> LOCATION: (229)..(229)
<223> OTHER INFORMATION: Xaa equals any of the naturally occurring L-amino acids
<220> FEATURE:
<221> NAME/KEY: MISC_FEATURE
<222> LOCATION: (230)..(230)
<223> OTHER INFORMATION: Xaa equals any of the naturally occurring L-amino acids

<400> SEQUENCE: 302

```
Cys Ser Ser Gly Gly Gly Gly Val Xaa Ala Asp Ile Gly Xaa Gly Leu
1               5                   10                  15

Ala Asp Ala Leu Thr Ala Pro Leu Asp His Lys Asp Lys Xaa Leu Xaa
            20                  25                  30

Ser Leu Thr Leu Xaa Xaa Ser Xaa Xaa Xaa Asn Xaa Xaa Leu Xaa Leu
        35                  40                  45

Xaa Ala Gln Gly Ala Glu Lys Thr Tyr Gly Asn Gly Asp Ser Leu Asn
    50                  55                  60

Thr Gly Lys Leu Lys Asn Asp Lys Val Ser Arg Phe Asp Phe Ile Arg
65                  70                  75                  80

Gln Ile Glu Val Asp Gly Xaa Leu Ile Thr Leu Glu Ser Gly Glu Phe
                85                  90                  95

Gln Val Tyr Lys Gln Ser His Ser Ala Leu Thr Ala Leu Gln Thr Glu
            100                 105                 110

Gln Xaa Gln Asp Xaa Glu Xaa Ser Xaa Lys Met Val Ala Lys Arg Xaa
        115                 120                 125

Phe Xaa Ile Gly Asp Ile Ala Gly Glu His Thr Ser Phe Asp Lys Leu
    130                 135                 140

Pro Lys Xaa Xaa Xaa Ala Thr Tyr Arg Gly Thr Ala Phe Gly Ser Asp
145                 150                 155                 160
```

-continued

```
Asp Ala Gly Gly Lys Leu Thr Tyr Thr Ile Asp Phe Ala Ala Lys Gln
                165                 170                 175

Gly His Gly Lys Ile Glu His Leu Lys Ser Pro Glu Leu Asn Val Xaa
            180                 185                 190

Leu Ala Xaa Xaa Tyr Ile Lys Pro Asp Glu Lys Xaa His Ala Val Ile
        195                 200                 205

Ser Gly Ser Val Leu Tyr Asn Gln Asp Glu Lys Gly Ser Tyr Ser Leu
    210                 215                 220

Gly Ile Phe Gly Xaa Xaa Ala Gln Glu Val Ala Gly Ser Ala Glu Val
225                 230                 235                 240

Glu Thr Ala Asn Gly Ile His His Ile Gly Leu Ala Ala Lys Gln
                245                 250                 255


<210> SEQ ID NO 303
<211> LENGTH: 31
<212> TYPE: DNA
<213> ORGANISM: Artificial Sequence
<220> FEATURE:
<223> OTHER INFORMATION: Primer

<400> SEQUENCE: 303

gcgcggatcc ttactgcttg gcggcaagac c                                  31


<210> SEQ ID NO 304
<211> LENGTH: 23
<212> TYPE: DNA
<213> ORGANISM: Artificial Sequence
<220> FEATURE:
<223> OTHER INFORMATION: Primer

<400> SEQUENCE: 304

ctattctgca tatgactagg agc                                           23


<210> SEQ ID NO 305
<211> LENGTH: 21
<212> TYPE: DNA
<213> ORGANISM: Artificial Sequence
<220> FEATURE:
<223> OTHER INFORMATION: Primer

<400> SEQUENCE: 305

agcagcggag gcggcggtgt c                                             21


<210> SEQ ID NO 306
<211> LENGTH: 21
<212> TYPE: DNA
<213> ORGANISM: Artificial Sequence
<220> FEATURE:
<223> OTHER INFORMATION: Primer

<400> SEQUENCE: 306

tgccgatgca ctaaccgcac c                                             21


<210> SEQ ID NO 307
<211> LENGTH: 21
<212> TYPE: DNA
<213> ORGANISM: Artificial Sequence
<220> FEATURE:
<223> OTHER INFORMATION: Primer

<400> SEQUENCE: 307

cgtttcgcaa ccatcttccc g                                             21
```

<210> SEQ ID NO 308
<211> LENGTH: 44
<212> TYPE: DNA
<213> ORGANISM: Artificial Sequence
<220> FEATURE:
<223> OTHER INFORMATION: Primer

<400> SEQUENCE: 308
gagatctcac tcactcatta ctgcttggcg gcaagaccga tatg 44

<210> SEQ ID NO 309
<211> LENGTH: 29
<212> TYPE: DNA
<213> ORGANISM: Artificial Sequence
<220> FEATURE:
<223> OTHER INFORMATION: Primer

<400> SEQUENCE: 309
gcggatccag cggagggggt ggtgtcgcc 29

<210> SEQ ID NO 310
<211> LENGTH: 35
<212> TYPE: DNA
<213> ORGANISM: Artificial Sequence
<220> FEATURE:
<223> OTHER INFORMATION: Primer

<400> SEQUENCE: 310
gcgcatgctt actgcttggc ggcaagaccg atatg 35

<210> SEQ ID NO 311
<211> LENGTH: 26
<212> TYPE: DNA
<213> ORGANISM: Artificial Sequence
<220> FEATURE:
<223> OTHER INFORMATION: Primer

<400> SEQUENCE: 311
gcggatccag cggaggcggc ggaagc 26

<210> SEQ ID NO 312
<211> LENGTH: 65
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (46)..(46)
<223> OTHER INFORMATION: “Y” equals C or T
<220> FEATURE:
<221> NAME/KEY: misc_feature
<222> LOCATION: (49)..(49)
<223> OTHER INFORMATION: “W” equals A or T

<400> SEQUENCE: 312
gcgcagatct catatgagca gcggaggggg tggtgtcgcc gccgayatwg gtgcggggct 60
tgccg 65

<210> SEQ ID NO 313
<211> LENGTH: 19
<212> TYPE: DNA
<213> ORGANISM: Artificial Sequence
<220> FEATURE:
<223> OTHER INFORMATION: Primer

<400> SEQUENCE: 313

-continued ctattctgcg tatgactag 19

<210> SEQ ID NO 314
<211> LENGTH: 22
<212> TYPE: DNA
<213> ORGANISM: Artificial Sequence
<220> FEATURE:
<223> OTHER INFORMATION: Primer

<400> SEQUENCE: 314
gtccgaacgg taaattatcg tg 22

<210> SEQ ID NO 315
<211> LENGTH: 29
<212> TYPE: DNA
<213> ORGANISM: Artificial Sequence
<220> FEATURE:
<223> OTHER INFORMATION: Primer

<400> SEQUENCE: 315
gcggatccag cggaggcggc ggtgtcgcc 29

<210> SEQ ID NO 316
<211> LENGTH: 34
<212> TYPE: DNA
<213> ORGANISM: Artificial Sequence
<220> FEATURE:
<223> OTHER INFORMATION: Primer

<400> SEQUENCE: 316
gagatctcat atgagcagcg gaggcggcgg aagc 34

<210> SEQ ID NO 317
<211> LENGTH: 16
<212> TYPE: DNA
<213> ORGANISM: Artificial Sequence
<220> FEATURE:
<223> OTHER INFORMATION: Primer

<400> SEQUENCE: 317
gacagcctga taaacc 16

<210> SEQ ID NO 318
<211> LENGTH: 19
<212> TYPE: DNA
<213> ORGANISM: Artificial Sequence
<220> FEATURE:
<223> OTHER INFORMATION: Primer

<400> SEQUENCE: 318
gatgccgatt tcgtgaacc 19

<210> SEQ ID NO 319
<211> LENGTH: 27
<212> TYPE: DNA
<213> ORGANISM: Artificial Sequence
<220> FEATURE:
<223> OTHER INFORMATION: Primer

<400> SEQUENCE: 319
gcgcatgcct actgtttgcc ggcgatg 27

<210> SEQ ID NO 320
<211> LENGTH: 44
<212> TYPE: DNA
<213> ORGANISM: Artificial Sequence
<220> FEATURE:
<223> OTHER INFORMATION: Primer

<400> SEQUENCE: 320
gagatctcac tcactcacta ctgtttgccg gcgatgccga tttc 44

<210> SEQ ID NO 321
<211> LENGTH: 70
<212> TYPE: DNA
<213> ORGANISM: Artificial Sequence
<220> FEATURE:
<223> OTHER INFORMATION: Primer

<400> SEQUENCE: 321
gcgcagatct catatgagca gcggaggcgg cggaagcgga ggcggcggtg tcaccgccga 60
cataggcacg 70

<210> SEQ ID NO 322
<211> LENGTH: 59
<212> TYPE: DNA
<213> ORGANISM: Artificial Sequence
<220> FEATURE:
<223> OTHER INFORMATION: Leader

<400> SEQUENCE: 322
atgaaaacaa cgttaaaaat gaccgcactt gcggctcttt ctgcttttgt tttagctgg 59

<210> SEQ ID NO 323
<211> LENGTH: 75
<212> TYPE: DNA
<213> ORGANISM: Artificial Sequence
<220> FEATURE:
<223> OTHER INFORMATION: Leader

<400> SEQUENCE: 323
atgactagga gcaaacctgt gaaccgaact gccttctgct gcctttccct gaccgccgcc 60
ctgattctga ccgcc 75

<210> SEQ ID NO 324
<211> LENGTH: 75
<212> TYPE: DNA
<213> ORGANISM: Artificial Sequence
<220> FEATURE:
<223> OTHER INFORMATION: Leader

<400> SEQUENCE: 324
atgactagga gcaaacctgt gaaccgaact gccttctgct gcttttctct gaccgccgcc 60
ctgattctga ccgcc 75

<210> SEQ ID NO 325
<211> LENGTH: 75
<212> TYPE: DNA
<213> ORGANISM: Artificial Sequence
<220> FEATURE:
<223> OTHER INFORMATION: Leader

<400> SEQUENCE: 325
atgactagga gcaaacctgt gaaccgaact accttctgtt gcctttctct gaccgccgcc 60
ctgattctga ccgcc 75

<210> SEQ ID NO 326
<211> LENGTH: 75
<212> TYPE: DNA

<213> ORGANISM: Artificial Sequence
<220> FEATURE:
<223> OTHER INFORMATION: Leader

<400> SEQUENCE: 326
atgactagga gtaaacctgt gaatcgaact gccttctgct gcctttctct gaccactgcc 60
ctgattctga ccgcc 75

<210> SEQ ID NO 327
<211> LENGTH: 335
<212> TYPE: PRT
<213> ORGANISM: Neisseria meningitidis

<400> SEQUENCE: 327

Cys Ser Pro Ala Ala Asp Ser Asn His Pro Ser Gly Gln Asn Ala Pro
1 5 10 15

Ala Asn Thr Glu Ser Asp Gly Lys Asn Ile Thr Leu Leu Asn Ala Ser
20 25 30

Tyr Asp Val Ala Arg Asp Phe Tyr Lys Glu Tyr Asn Pro Leu Phe Ile
35 40 45

Lys Thr Tyr Gln Ser Glu His Pro Gly Thr Ser Val Ser Ile Gln Gln
50 55 60

Ser His Gly Gly Ser Ser Lys Gln Ala Leu Ser Val Ala Asn Gly Leu
65 70 75 80

Gln Ala Asp Val Val Thr Met Asn Gln Ser Ser Asp Ile Asp Leu Leu
85 90 95

Glu Lys Lys Gly Leu Val Glu Lys Gly Trp Gln Gln Ala Leu Pro Asp
100 105 110

His Ala Ala Pro Tyr Thr Ser Thr Met Val Phe Leu Val Arg Lys Asn
115 120 125

Asn Pro Lys Gln Ile Arg Asp Trp Asn Asp Leu Ala Lys Asp Gly Val
130 135 140

Asn Ile Val Ile Ala Asn Pro Lys Thr Ser Gly Asn Gly Arg Tyr Ala
145 150 155 160

Phe Leu Gly Ala Tyr Gly Tyr Gly Leu Lys Thr Thr Asn Gly Asn Glu
165 170 175

Gln Glu Ala Gln Lys Leu Val Ala Ser Ile Leu Lys Asn Thr Pro Val
180 185 190

Phe Glu Asn Gly Gly Arg Ala Ala Thr Thr Thr Phe Thr Gln Arg Asn
195 200 205

Ile Gly Asp Val Leu Ile Thr Phe Glu Asn Glu Ala Asn Tyr Val Ser
210 215 220

Lys Lys Leu Thr Gln Gly Gln Phe Glu Ile Val Tyr Pro Ser Tyr Thr
225 230 235 240

Ile Ser Ala Glu Ser Pro Val Ala Val Val Asn Ser Val Val Ala Lys
245 250 255

Lys Gly Thr Gln Lys Thr Ala Arg Ala Tyr Leu Glu Tyr Leu Trp Ser
260 265 270

Glu Pro Ala Gln Glu Leu Ala Ala Ser Leu Tyr Leu Arg Pro Arg Asn
275 280 285

Pro Glu Val Leu Ala Arg His Lys Ala Asp Phe Pro Asp Leu Asp Thr
290 295 300

Phe Ser Pro Glu Glu Lys Phe Gly Gly Trp Asp Asn Ile Met Lys Thr
305 310 315 320

Tyr Phe Ala Asp Gly Gly Ile Phe Asp Arg Leu Thr Ala Gln Lys

-continued

```
            325                 330                 335


<210> SEQ ID NO 328
<211> LENGTH: 68
<212> TYPE: PRT
<213> ORGANISM: Neisseria meningitidis

<400> SEQUENCE: 328

Cys Ala Gly Thr Trp Glu Gly Ala Lys Gln Asp Thr Ala Arg Asn Leu
1               5                   10                  15

Asp Lys Thr Gln Ala Ala Ala Glu Arg Ala Ala Glu Gln Thr Gly Asn
            20                  25                  30

Ala Val Glu Lys Gly Trp Asp Lys Thr Lys Glu Ala Val Lys Lys Gly
        35                  40                  45

Gly Asn Ala Val Gly Arg Gly Ile Ser His Leu Gly Gly Lys Ile Glu
    50                  55                  60

Asn Ala Thr Glu
65


<210> SEQ ID NO 329
<211> LENGTH: 21
<212> TYPE: PRT
<213> ORGANISM: Neisseria meningitidis

<400> SEQUENCE: 329

Cys Met Lys Thr Thr Leu Lys Met Thr Ala Leu Ala Ala Leu Ser Ala
1               5                   10                  15

Phe Val Leu Ala Gly
            20
```